United States Patent

Kamigauchi et al.

[11] Patent Number: 5,876,984
[45] Date of Patent: Mar. 2, 1999

[54] SEQUITERPENE DERIVATIVES HAVING ANTIVIRAL ACTIVITY

[75] Inventors: Toshiyuki Kamigauchi, Toyonaka; Tamio Fujiwara, Kobe; Hiroyoshi Tani, Ibaraki; Yoshimi Kawamura, Minoo; Isao Horibe, Hirakata, all of Japan

[73] Assignee: Shionogi & Co., Ltd, Osaka, Japan

[21] Appl. No.: 43,449

[22] PCT Filed: Sep. 25, 1996

[86] PCT No.: PCT/JP96/02749

§ 371 Date: Mar. 20, 1998

§ 102(e) Date: Mar. 20, 1998

[87] PCT Pub. No.: WO97/11947

PCT Pub. Date: Apr. 3, 1997

[51] Int. Cl.[6] .......... A61K 00/00; C07D 209/56; C07D 311/79; C12P 1/02
[52] U.S. Cl. .......... 435/119; 435/171; 514/280; 548/418; 549/382
[58] Field of Search .......... 548/418; 435/119, 435/171

[56] References Cited

FOREIGN PATENT DOCUMENTS 9711947  4/1977  WIPO .

*Primary Examiner*—Johann Richter
*Assistant Examiner*—Taofiq A. Solola
*Attorney, Agent, or Firm*—Foley & Lardner

[57] ABSTRACT

A compound of the formula (I):

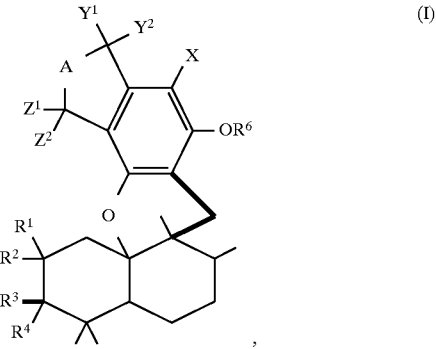

or a pharmaceutically acceptable salt, or a hydrate thereof, a process for preparing said compound, and a pharmaceutical composition having antiviral activity which comprise said compound.

14 Claims, No Drawings

SEQUITERPENE DERIVATIVES HAVING ANTIVIRAL ACTIVITY

TECHNICAL FIELD

The present invention relates to novel compounds having antiviral activities. In particular, the invention relates to sesquiterpene derivatives having inhibitory activities against influenza A and B, a process for preparing the same and pharmaceutical compositions containing such derivatives.

BACKGROUND ART

The development of effective therapeutic agents for viral disease is one of the most important subject matters in the field of medicine and pharmacy. As in the case of other virus diseases, there have been no established method for treating the commonest viral disease, influenza. Human influenza viruses are classified into types A, B and C, depending on their internal antigens, among which types A and B are known to cause intensive symptoms. Amantadine has been known for more than 20 years as a chemotherapeutic agent though, efficiency thereof has not been evaluated yet. Accordingly, there has been a strong demand for the development of novel and effective anti-influenza agents.

It has been known that microorganisms can produce various useful compounds. For example, Stachybotrys, a fungus, was known to produce compounds having pyran fused ring [(1) Japanese Patent Publication (KOKAI) 176782/1993; (2) Japanese Patent Publication (KOKAI) 128266/1994; (3) Japanese Patent Publication (KOKAI) 239869/1994; (4) Japanese Patent Publication (KOKAI) 256350 1994; (5) J. Org. Chem. 57 6700–03 (1992)].

These references, however, merely describe that such compounds have nerve growth factor (NGF) activating effects and are useful for treatment of Alzheimer's disease (References 1–4) or that such compounds have antibacterial and antifungal effects (Reference 5). Thus, it has not been known that Stachybotrys produces compounds having antiviral activities.

Further, the following references describe compounds having spiro-type fused ring of tetrahydrofuran ring: (6) Japanese Patent Publication (KOKOKU) 11634/1982 (U.S. Pat. No. 4,229,466); (7) Japanese Patent Publication (KOKOKU) 32170/1987 (U.S. Pat. No. 4,831,053); (8) Japanese Patent Publication (KOKAI) 145161/1995; (9) WO 95 26344. Among these references, References (6), (7) and (9) merely show that their compounds are useful in the testament of anti-complement activity/nephritis, hepatitis, and depression/mania, respectively, and Reference (8) merely shows that the compounds have retrovirus protease inhibitory effects. Although a neuraminic acid derivative (4-guanidino-Neu5Ac2en; a neuraminidase inhibitor) (Japan Glaxo) has been proposed as a compound having an antiviral activity so far, the said compound, when administered orally or intraperitoneally, has not a satisfactory activity against influenza A and B (Antimicrob. Agent Chemother. 37 (7) 1473–1479 (93.7); Antimicrob. Agent Chemother. 38(10) 2270–2275 (91.10); ICAAC (34th) 265 (94.10). Therefore, the development of novel and effective antivirus agents, in particular, those effective against influenza orally or parenterally has long been demanded.

The present inventors have found that, when cultivated in an appropriate medium, fungus strains belonging to the Stachybotrys genus produce a substance(s) having a strong inhibitory activity against virus. The substance has been isolated, purified, structurally elucidated, and characterized. As a result, the substance was revealed that it is a sesquiterpene derivative having a novel structure containing a fused ring with a 5-membered ring and a pyran ring and that it has remarkable activity against virus, in particular, influenza A and B viruses. Furthermore, the present inventors have succeeded in preparing a series of useful compounds having an antiviral activity through the chemical modification of the compound derived from microorganisms.

DISCLOSURE OF INVENTION

Thus, the present invention provides a compound of the formula (I):

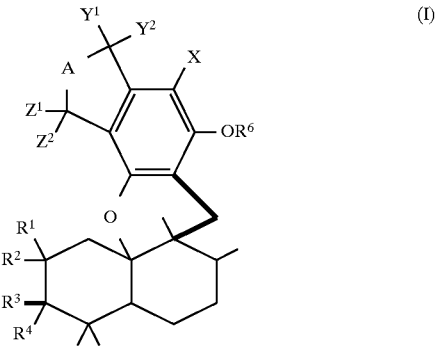

wherein $R^1$ is hydrogen; and $R^2$ is hydrogen, a halogen, azido, an optionally substituted lower alkyl, an optionally substituted lower alkylcarbonyl, an optionally substituted arylcarbonyl, an optionally substituted heteroarylcarbonyl, —$OR^7$ (wherein $R^7$ is hydrogen, an optionally substituted lower alkyl, an optionally substituted lower alkylcarbonyl, an optionally substituted arylcarbonyl, an optionally substituted heteroarylcarbonyl, an optionally substituted lower alkylsulfonyl, an optionally substituted arylsulfonyl, an optionally substituted heteroarylsulfonyl, —$SO_3H$, an optionally substituted aryl, an optionally substituted aralkyl, a carbamoyl, or —$PO_3H_2$), $S(O)_nR^{13}$ (wherein $R^{13}$ is hydrogen, an optionally substituted lower alkyl, or an optionally substituted aryl, and n is 0, 1, or 2), or —$NHR^8$ (wherein $R^8$ is hydrogen, an optionally substituted lower alkyl, an optionally substituted lower alkylcarbonyl, an optionally substituted lower alkylsulfonyl, an optionally substituted arylcarbonyl, an optionally substituted aralkyloxycarbonyl, an optionally substituted arylsulfonyl, an optionally substituted heteroarylsulfonyl, or an optionally substituted carbamoyl); or $R^1$ and $R^2$ taken together may form oxo or =$NR^9$ (wherein $R^9$ is hydroxy, a lower alkoxy, an optionally substituted aralkyl, an optionally substituted arylsulfonylamino, or —$NHCONH_2$);

$R^3$ is hydrogen; and $R^4$ is hydrogen, a halogen, —$OR^{10}$ (wherein $R^{10}$ is hydrogen, an optionally substituted lower alkyl, an optionally substituted lower alkylcarbonyl, an optionally substituted arylcarbonyl, an optionally substituted heteroarylcarbonyl, an optionally substituted lower alkylsulfonyl, an optionally substituted arylsulfonyl, an optionally substituted heteroarylsulfonyl, —$SO_3H$, or —$PO_3H_2$), $SR^{14}$ (wherein $R^{14}$ is hydrogen, an optionally substituted lower alkyl, or an optionally substituted aryl), or —$NHR^{11}$ (wherein $R^{11}$ is hydrogen, an optionally substituted lower alkyl, an optionally substituted lower alkylcarbonyl, an optionally substituted lower alkylsulfonyl, an optionally substituted arylsulfonyl, an optionally substituted heteroarylsulfonyl, or an optionally substituted carbamoyl); or $R^3$ and $R^4$ taken together may form oxo or =$NR^{12}$ (wherein $R^{12}$ is hydroxy, cyano, amino, an optionally substituted lower alkoxy, an optionally substituted aralkyl, an optionally substituted arylsulfonylamino, an optionally substituted aliphatic heterocyclic group, or —NHCONH$_2$);

or $R^2$ and $R^4$ taken together may form a single bond or —O—;

A is =NR$^5$ or O (wherein R$^5$ is hydrogen, an optionally substituted lower alkyl, an optionally substituted lower alkylcarbonyl, an optionally substituted lower alkylsulfonyl, or an optionally substituted arylsulfonyl;

R$^6$ is hydrogen, an optionally substituted lower alkyl, an optionally substituted lower alkylcarbonyl, or —PO$_3$H$_2$;

X is hydrogen or a halogen;

Y$^1$ and Y$^2$ are both hydrogens, or taken together may form oxo or an optionally substituted imino;

Z$^1$ and Z$^2$ are both hydrogens, or taken together may form oxo, or Z$^1$ is hydrogen and Z$^2$ is hydroxy, an optionally substituted lower alkyl, or an optionally substituted lower alkoxy, or a pharmaceutically acceptable salt or a hydrate thereof.

The present invention also provides a pharmaceutical composition which comprises a compound(s) (I).

The present invention further provides an antivirus agent which comprises a compound(s) (I).

Furthermore, the present invention provides a process for preparing the compound (I) which comprises cultivating in a medium a microorganism belonging to the Stachybotrys genus capable of producing a compound of the above formula (I), separating and purifying the produced compound from the resultant culture, and, if desired, chemically modifying the same.

Terms used herein are defined below.

The term "lower alkyl" refers to a straight or branched alkyl group of 1–8 carbons, and includes, for example, methyl, ethyl, n-propyl, isopropyl, n-butyl, isobutyl, sec-butyl, tert-butyl, n-pentyl, isopentyl, neopentyl, tert-pentyl, hexyl, heptyl, octyl, and the like.

The term "lower alkoxy" refers to a straight or branched alkoxy group, and includes, for example, methoxy, ethoxy, n-propoxy, isopropoxy, n-butoxy, isobutoxy, s-butoxy, t-butoxy, n-pentyloxy, isopentyloxy, n-hexyloxy, isohexyloxy, and the like.

The term "aryl" includes, for example, phenyl, naphthyl, or polycyclic aromatic hydrocarbon groups.

The term "arylcarbonyl" refers to a carbonyl group which is substituted by one of the above aryls, and is exemplified by benzoyl, naphthylcarbonyl, or the like.

The term "heteroaryl" refers to a 5–6 membered aromatic ring which contains 1–4 heteroatom(s) selected from a group consisting of N, O and S, such as furan, thiophene, pyrrole, oxazole, thiazole, imidazole, pyrazole, triazole, pyridine, pyridazine, pyrimidine, pyrazine, triazine, among which a cyclic group containing N atom(s) such as pyridine or pyrazine is preferred.

The term "aralkyl" refers to a group in which one of the above lower alkyls is substituted by one or more of the above aryls, and is exemplified by benzyl, methylbenzyl, or naphthylmethyl.

The term "aralkyloxycarbonyl" refers to a carbonyl group to which one of the above aralkyls is attached through O atom and is exemplified by benzyloxycarbonyl, or the like.

A "halogen" may include fluoro, chloro, iodo, and bromo.

The terms "lower alkylcarbonyl", "arylcarbonyl" and "heteroarylcarbonyl" refer to carbonyl groups substituted by one of the above lower alkyls, aryls, or hieteroaryls, respectively.

The terms "lower alkylsulfonyl", "arylsulfonyl", and "heteroarylsulfonyl" refer to carbonyl groups substituted by one of the above lower alkyls, aryls or heteroaryls, respectively.

The term "aliphatic heterocyclic group" refers to a 5–6 membered heterocyclic group containing 1–4 heteroatom(s) selected from a group consisting of N, O and S, and includes, for example, pyrrolidinyl, thiazolidinyl, oxazolidinyl, imidazolidinyl, piperidinyl, piperazinyl, morpholinyl, thiomorpholinyl, and the like.

In the definitions of $R^2$, $R^7$ and $R^{13}$, the substituent(s) on the "optionally substituted lower alkyl", "optionally substituted lower alkylcarbonyl" or "optionally substituted lower alkylsulfonyl" may include a lower alkoxy group as described above, a carboxyl group, a hydroxy group, a halogen atom, an amino group, a substituted amino group, a cyano group, a nitro group, a lower alkoxycarbonyl group, a carbamoyl group, an aliphatic heterocyclic group (N-methylpiperidine, N-methylmorpholine, N-methylpiperazine) substituted by a lower alkyl, and the like.

Similarly, examples of the substituent(s) on the "optionally substituted aryl", "optionally substituted aralkyl", "optionally substituted arylcarbonyl", "optionally substituted heteroarylcarbonyl", "optionally substituted arylsulfonyl", or "optionally substituted heteroarylsulfonyl" may include a lower alkyl group as described above, a lower alkoxy group as described above, a hydroxy group, a halogen atom, a haloalkyl group, an amino group, a substituted amino group, a cyano group, a nitro group, a carbamoyl group, and the like.

In the definition of R$^8$, the substituent(s) on the "optionally substituted lower alkyl", "optionally substituted lower alkylcarbonyl", or "optionally substituted lower alkylsulfonyl" may includes a lower alkoxy group as described above, a carboxy group, a hydroxy group, a halogen atom, an amino group, a substituted amino group, a cyano group, a nitro group, a lower alkoxycarbonyl group, a carbamoyl group, an aliphatic heterocyclic group (N-methylpiperidine, N-methylmorpholine, N-methylpiperazine) substituted by a lower alkyl, and the like.

Examples of the substituent(s) on the "optionally substituted arylcarbonyl", "optionally substituted aralkyloxycarbonyl", "optionally substituted arylsulfonyl", or "optionally substituted heteroarylsulfonyl" may include a lower alkyl group as described above, a lower alkoxy group as described above, a hydroxy group, a halogen atom, a haloalkyl group, an amino group, a substituted amino group, a cyano group, a nitro group, a carbamoyl group, and the like.

In the definitions of R$^7$ and R$^8$, the substituent(s) on the "optionally substituted carbamoyl" may includes a lower alkyl group and an aryl group as defined above.

In the definition of R$^9$, the substituent(s) on the "optionally substituted aralkyl" or "optionally substituted arylsulfonylamino" may include a lower alkyl group as described above, a lower alkoxy group as described above, a hydroxy group, a halogen atom, an amino group, a substituted amino group, and the like.

In the definition of R$^{10}$ or R$^{14}$, the substituent(s) on the "optionally substituted lower alkyl", "optionally substituted lower alkylcarbonyl", or "optionally substituted lower alkylsulfonyl" may include a lower alkoxy group as described above, a carboxy group, a hydroxy group, a halogen atom, an amino group, a substituted amino group, a cyano group, a nitro group, a lower alkoxycarbonyl group, a carbamoyl group, an aliphatic heterocyclic group (N-methylpiperidine, N-methylmorpholine, N-methylpiperazine) substituted by a lower alkyl, and the like.

Examples of the substituent(s) on the "optionally substituted aryl", "optionally substituted arylcarbonyl", "optionally substituted heteroarylcarbonyl", "optionally substituted arylsulfonyl" or "optionally substituted heteroarylsulfonyl" may include a lower alkyl group as described above, a lower alkoxy group as described above, a hydroxy group, a halogen atom, a haloalkyl group, an amino group, a substituted amino group, a carboxyl group, a lower alkoxycarbonyl group, a lower alkylcarbonyl group, a cyano group, a nitro group, a carbamoyl group, and the like.

In the definition of $R^{11}$, the substituent(s) on the "optionally substituted lower alkyl", "optionally substituted lower alkylcarbonyl", or "optionally substituted lower alkylsulfonyl" may include a lower alkoxy group as described above, a carboxy group, a hydroxy group, a halogen atom, an amino group, a substituted amino group, a cyano group, a nitro group, a lower alkoxycarbonyl group, a carbamoyl group, an aliphatic heterocyclic group (N-methylpiperidine, N-methylmorpholine, N-methylpiperazine) substituted by a lower alkyl, and the like.

Examples of the substituent(s) on the "optionally substituted arylsulfonyl" or "optionally substituted heteroarylsulfonyl" may include a lower alkyl group as described above, a lower alkoxy group as described above, a hydroxy group, a halogen atom, a haloalkyl group, an amino group, a substituted amino group, a cyano group, a nitro group, a carbamoyl group, and the like.

Examples of the substituent(s) on the "optionally substituted carbamoyl" may include a lower alkyl group as described above, an aryl group, and the like.

In the definition of $R^{12}$, the substituent(s) on the "optionally substituted lower alkoxy", "optionally substituted aralkyl", "optionally substituted arylsulfonylamino", or "optionally substituted aliphatic heterocyclic group" may include a lower alkyl group as described above, a lower alkoxy group as described above, a hydroxy group, a halogen atom, an amino group, a substituted amino group, and the like.

In the definition of $R^5$, the substituent(s) on the "optionally substituted lower alkyl", "optionally substituted lower alkylcarbonyl", or "optionally substituted lower alkylsulfonyl" may include a hydroxy group, an alkoxy group as described above, a carboxy group, a lower alkoxycarbonyl group, an amino group, a substituted amino group, a carbamoyl group, a guanidino group and the like.

Examples of the substituent(s) on the "optionally substituted arylsulfonyl" may include a lower alkyl group as described above, a lower alkoxy group as described group, a hydroxy group, a carboxyl group, a substituted amino group, and the like.

In the definition of $R^6$, the substituent(s) on the "optionally substituted lower alkyl" or "optionally substituted lower alkylcarbonyl" may include a carboxy group, an aryl group as described above, a heteroaryl group as described above, and the like.

The substituent(s) on the "optionally substituted imino" formed by $Y^1$ and $Y^2$ may include any of the above lower alkyl groups which may be optionally substituted.

As a salt of the compound of the general formula (I), any of pharmaceutically acceptable salts can be used, including base addition salts, for example, alkali metal salts such as sodium or potassium salts; alkaline-earth metal salts such as calcium or magnesium salts; ammonium salts; aliphatic amine salts such as trimethylamine, triethylamine dicyclohexylamine, ethanolamine, diethanolamine, triethanolamine, or procaine salts; aralkylamine salts such as N,N-dibenzylethylenediamine salts; heterocyclic aromatic amine salts such as pyridine, picoline, quinoline, or isoquinoline salts; quaternary ammonium salts such as tetramethylammonium, tetraethylammonium, benzyltrimethylammonium, benzyltriethylammonium, benzyltributylammonium, methyltrioctylammonium or tetrabutylammonium salts; and basic amino acid salts such as arginine or lysine salts.

Acid addition salts include, for example, mineral acid salts such as hydrochlorides, sulfates, nitrate, phosphates, carbonates, hydrogen carbonates or perchlorates; organic acid salts such as acetates, propionates, lactates, maleates, fumarates, tartrates, malates, succinates, or ascorbates; sulfonates such as methanesulfonates, isethionates, benzenesulfonates, or p-toluenesulfonates; and acidic amino acid salts such as aspartates or glutamates.

Some of the compounds of the present invention or the salts thereof may exist in the form of hydrates, and such hydrates are also encompassed by the present invention. Although the number of water molecules per molecule of the compound or salt varies depending on the method for synthesis and purification, or crystallization condition, it is usually in the range of 1 to 5 molecules.

The present invention includes all of the stereoisomers (such as diastereomers, epimers and enantiomers) of the compound represented by the general formula (I).

Although all the compounds represented by the general formula (J) are suitable for the purpose of the present invention, preferable ones are those wherein, in the formula (I), A is =N H; $Y^1$ and $Y^2$ taken together form oxo; $Z^1$ and $Z^2$ are both hydrogens; $R^1$ is hydrogen; $R^3$ is hydrogen, $R^4$ is $OR^{10}$; $R^3$ and $R^4$ taken together form =$NR^{12}$ or oxo; $R^2$ is —$OR^7$ or —$NHR^8$; $Z^1$ is hydrogen, $Z^2$ is hydroxy, an optionally substituted lower alkyl, or an optionally substituted lower alkoxy; and/or $R^6$ is hydrogen or —$PO_3H_2$, and particularly preferable ones are those wherein A is NH, $R^1$, X, and $Z^1$ are both hydrogens, $R^2$ is —$OR^7$ or —$NHR^8$, $R^3$ and $R^4$ taken together form oxo or =$NR^{12}$, $R^6$ is hydrogen or —$PO_3H_2$, and $Y^1$ and $Y^2$ taken together form oxo.

The compound (I) of the present invention can be prepared by cultivating a fungus strain of Stachybotrys capable of producing a compound of the formula (I), in an appropriate medium such as a solid medium containing brown rice as a principal ingredient or a liquid medium supplemented by amino acids. The compound having an antiviral activity can be then recovered from the medium, isolated, purified, and chemically modified appropriately by conventional methods so as to provide other compounds (I) which also have an antiviral activity.

Although any fungus strains of Stachybotrys which are capable of producing a compound represented by the formula (I) can be used for production of Compound (I) by microorganism fermentation, a particularly preferred strain is Stachybotrys sp. RF-7260 strain which has been deposited at the National Institute of Bioscience and Human Technology, Ministry of International Trade and Industry (1-1-3 Higashi, Tsukuba shi, Ibaraki) under Accession No. FERM P-14383 on Jun. 24, 1994, and transferred into the International Deposition under Budapest Treaty as FERM BP-5545 on May 20, 1996. The said strain has been disclosed in Japanese Patent Publication (KOKAI) 151385/1996, wherein it was cultivated to give a compound different from the compound (I) of the present invention in both of structure and pharmaceutical effects.

Among the compounds (1) obtained by cultivating Stachybotrys sp. RF-7260, the present inventors have determined the relative stereostructures of compounds including SQ-02-S3(1) and SQ-02-S5(2) which are shown by the following formulae:

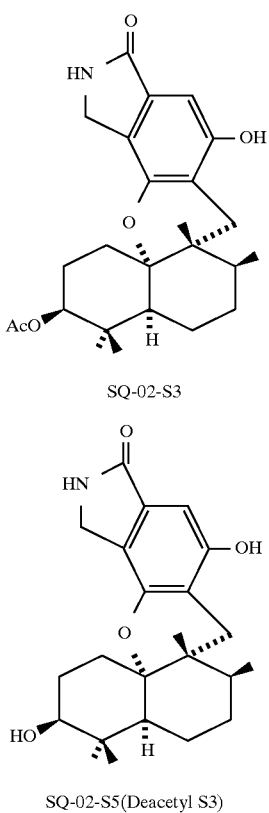

SQ-02-S3 (1)

SQ-02-S5(Deacetyl S3) (2)

based on their LSIMS, IR, UV, $^1$H NMR and $^{13}$C NMR. In addition, the structure of Compound SQ-02-S3(1) has been determined by X-ray crystallography analysis too. The relationships among these compounds have then been elucidated on the basis of the fact that the deacylated form of Compound SQ-02-S3(1) corresponds to Compound SQ-02-S5 (2). As a result, it has been established that Compounds SQ-02-S3(1) and SQ-02-S5(2) are novel sesquiterpene-type compounds represented by the above formulae.

To cultivate a fungus strain of Stachybotrys for the purpose of producing a compound (I) of the present invention, a solid or liquid medium used for a similar purpose in zymology can be used under an appropriate condition. Separation and purification of the compound of interest from the culture can also be achieved according to the known methods in zymology. The Examples below describe the preferred methods and conditions for preparation, but the present invention is not limited to those examples. Alternatively, compounds (I) are also obtainable by chemical synthesis, and those obtained by such additional methods are also fall within the scope of the present invention.

BEST MODE FOR CARRYING OUT THE INVENTION

A general method for preparing the present compounds will be explained below.

A fungus strain belonging to the Stachybotrys genus, such as Stachybotrys sp. RF-7260 described above, is cultivated in a solid or liquid medium of suited compositions under appropriate conditions. In principle, the medium can be an usual synthetic or natural medium containing nutrition sources required for growth of Stachybotrys, including a carbon source, a nitrogen source, inorganic salts, etc. Additional ingredients such as vitamins or precursor substances can also be added, if necessary. For instance, as a carbon source, glucose, sucrose, soluble starch, dextrin, glycerin, fatty acids, organic acids, and the like are used alone or in combination. As a nitrogen source, soy flour, peanuts meal, cornsteep liqueur, meat extract, yeast extract, cottonseed flour, polypeptone, wheat germ, sodium nitrate, ammonium sulfate, ammonium nitrate and the like are used alone or in combination, for example. Inorganic salts include, for example, calcium carbonate, sodium chloride, potassium chloride, magnesium sulfate, copper sulfate, manganese chloride, zinc sulfate, cobalt chloride, various phosphates etc., and are added as needed. A preferred solid medium is that comprising brown rice, glucose and yeast extract, and a preferred liquid medium is that comprising glycerin, potato starch, peanut powder, polypeptone, sodium nitrate, and those supplemented by amino acids are also preferable. Amino acids to be added include L-glutamic acid, D-lysine, DL-valine, General Amino Acids Powder F (Ajinomoto) and the like.

The cultivation can be done at about 15°–40° C., preferably at 18°–28° C. The pH of the medium can be in the range of 5–9, preferably 6–8. Duration of the cultivation may substantially vary depending on the medium and the cultivation condition, and it takes about 9–14 days. These conditions are, however, adjusted as appropriate according to the state of each cultivation, and not limited to those described above. If the culture foams intensively, an antifoam agent such as vegetable oil, lard or polypropylene glycol can be added as appropriate, before or during the cultivation.

To separate and isolate the compound of the present invention from the culture after the completion of the cultivation, usual methods for separation and isolation of fermentation products can be used in combination as appropriate.

Since active substances are typically accumulated in the cell body, they can be extracted by adding a solvent such as acetone, ethyl acetate or methanol to the culture itself or a concentrate of the culture obtained, for example, by ultrafiltration. Alternatively, the culture may be subjected to filtration or centrifugation to collect solid materials including the cell body, to which the above solvent can be added for extraction, for instance The extract so obtained is further subjected to isolation and purification by an appropriate combination of, for example, extraction with an appropriate solvent, crystallization, adsorption chromatography, high performance liquid chromatography, and the like.

The given compound (I) thus obtained can be then chemically modified (for example, through oxidization, reduction, protection, deprotection, dehydration, epoxidation, phosphorylation, halogenation, O-alkylation, O-acylation, N-alkylation, amination, imination, thiolation, etc.) by procedures known in the art such as those described in the working Examples and Reaction Schemes below to convert into other sesquiterpene derivatives. Such derivatization can be made to a compound (I) after isolating from the culture or in situ without isolation.

Since the sesquiterpene derivatives of the present invention exert strong inhibitory activities against influenza A and B viruses as shown in the Examples below, they are useful antivirus agents.

The compounds of the present invention can be administered orally or parenterally. For oral administration, the compounds of the present invention can be used in any form of usual formulations, for example, solid formulations such as tablets, powders, granules, capsules; aqueous formulations; oleaginous suspensions; solutions such as syrup or elixir. For parenteral administration, the compounds of the present invention can be used as an aqueous or oleaginous suspension injection, or nose drops. In the preparation of such formulations, conventional excipients, binding agents, lubricants, aqueous solvents, oleaginous solvents, emulsifying agents, preservatives, stabilizers, and the like can be optionally used.

Although the dosage of the compounds of the present invention vary depending on the administration route, age, weight and conditions of the patient, and the disease to be treated, the daily dose for adult can generally be about 0.05 mg–2 g, preferably about 0.1 mg–500 mg, which is administered in one to five divisions, for oral administration. For parenteral administration, the daily dose can be about 0.01 mg–1 g, preferably about 0.05 mg–300 mg, which is administered in one to five divisions.

The following examples are provided to further illustrate the present invention and are not to be construed as limiting the scope of the invention.

EXAMPLES

Example 1

Preparation of SQ-02-S3(1) and SQ-02-S5(2) in a solid medium

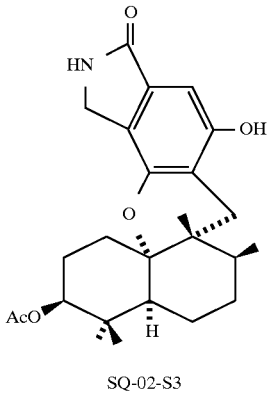

SQ-02-S3

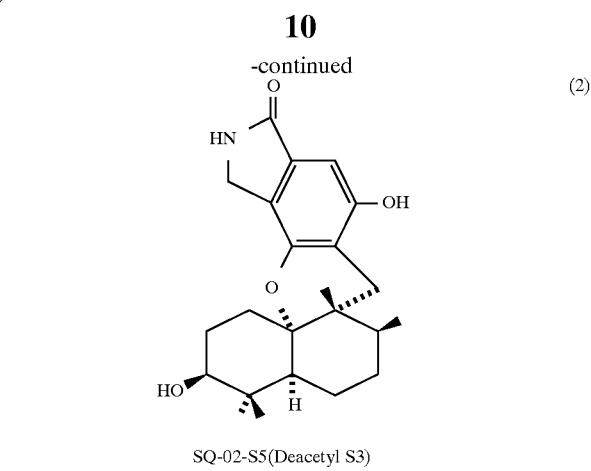

SQ-02-S5(Deacetyl S3)

(1) Fermentation Step

Spores of Stachybotrys sp. RF-7260 slant-cultured in 5 test tubes were scraped with a platinum loop, and suspended into 50 ml of physiological saline. Two ml each of this suspension was then inoculated to each of 25 Erlenmeyer flasks (500 ml volume) containing brown rice mediums (25 g of brown rice, 0.5 g of glucose, 0.1 g of yeast extract (Difco), 50 ml of tap water) which have been sterilized at 121° C. for 30 minutes in an autoclave, and statically cultured at 28° C. for 14 days.

(2) Separation Step

The fermented materials in each Erlenmeyer flask from the fermentation step were harvested, which was followed by extraction with 2 L of acetone with stirring. After suction-filtration, the filtrate containing acetone was evaporated under reduced pressure, and the residual aqueous layer was adjusted to pH 4.0 with 1N HCl, followed by extraction with ethyl acetate. The ethyl acetate layer was concentrated to dryness, and partitioned into 0.5 L of 10% water/methanol and 0.5 L of n-hexane. The methanol layer so obtained was concentrated to dryness to give 24 g of crude fraction. This crude faction was recrystallized from toluene-ethyl acetate and ethyl acetate-acetone, successively, to give 3.0 g of SQ-02-S3(1) as colorless needle crystals. The recrystallization mother liquid was then concentrated under reduced pressure, and subjected to a silica gel chromatography (Pre-packed column size B (310–25), LiChroprep Si60 (40–63 μm), E. Merck) eluting with a mixed solvent of toluene:ethyl acetate=1:2. The eluate was then concentrated to dryness and recrystallized in ethyl acetate-acetone to give 1.2 g of SQ-02-S3(1).

The column was then eluted with a mixed solvent of toluene : ethyl acetate=1:4 to give 19 g of a SQ-02-S5 containing fraction. This SQ-02-S5 containing fraction was separated and isolated by a preparative HPLC (LiChroprep RP-18, 25–40 μm, 2 cm i.d.×50 cm, acetonitrile:0.1% trifluoroacetic acid-water=50:50) to give a SQ-02-S5 fraction, which was neutralized with 1N NaOH, and evaporated under reduced pressure to remove acetonitrile. The residue was extracted with ethyl acetate. After the evaporation of solvent, SQ-02-S5(2) was recrystallized from acetone as colorless needle crystals (0.017 g).

SQ-02-S3(1)

Compound name: (6aR,7S,9aS,11S,13a S)-11-acetoxy-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole Physicochemical properties
Appearance: colorless needle crystals
Solubility: soluble in acetone, ethyl acetate, tetrahydrofuran, methanol; slightly soluble in chloroform; insoluble in n-hexane, water.
Melting point: >300° C.
$[\alpha]_D^{24.5}$=+136.4±1.7° (c=1.03, methanol)
Molecular formula: $C_{25}H_{33}NO_5$
Elemental Analysis for $C_2,H_{33}NO_5 \cdot H_2O$ Calcd.; C: 67.39%, H: 7.91%, N: 3.14% Found; C: 67.84%, H: 7.68%, N: 3.18%
LSIMS, m/z: 428 (MH)$^+$
HR-LSIMS, m/z (for $C_{25}H_{34}NO_5$)
Calcd.; 428.2435
Found; 428.2445 (MH)$^+$
IR $\nu_{max}$ KBr cm$^{-1}$: 3405, 2962, 2875, 1735, 1689, 1627, 1613, 1466, 1369, 1245, 1196, 1167, 1073, 960, 773.
UV (methanol), nm($\epsilon$): 215 (45,700), 256 (7,000), 301 (3,200).
$^1$H NMR (DMSO-d$_6$, 600 MHz) δ: 0.81 (3H, s), 0.84 (3H, s), 1.03 (3H, s), 1.11 (3H, d, J=7.3 Hz), 1.77 (1H, m), 2.05 (3H, s), 2.13 (1H, d, J=17.8 Hz), 3.09 (1H, d, J=17.8 Hz), 4.09 (1H, d-like, J=16.9 Hz), 4.17 (1H, d-like, J=16.9 Hz), 4.65 (1H, t-like), 6.63 (1H, s-like), 8.31 (1H, s-like), 9.73 (1H, s).
$^{13}$C NMR (DMSO-d$_6$, 150 MHz) δ: 16.73 (q), 19.62 (q), 20.92 (q), 22.46 (t), 22.77 (t), 23.82 (t), 25.87 (q), 27.14 (t), 29.41 (q), 31.63 (t), 36.53 (s), 36.95 (s), 38.66 (d), 42.34 (t), 43.76 (d), 75.24 (d), 82.43 (s), 99.13 (d), 111.81 (s), 120.59 (s), 131.62 (s), 146.78 (s), 155.81 (s), 169.62 (s), 170.27 (s).
TLC Rf value (detected with a conc. $H_2SO_4$ reagent): 0.46 ($CH_2Cl_2$: methanol=10:1)
HPLC analysis: retention time; 5.96 min.
Column: YMC-Pack ODS-AM, AM-302, 4.6 i.d.×150 mm (YMC).
Mobile phase: 0.1% trifluoroacetic acid-acetonitrile: 0.1% trifluoroacetic acid-water=55:45.
Flow rate: 1 ml/min.
Detection: 254 nm (UV).
SQ-02-S5(2)
Compound name: (6a R,7S,9a S,11S,13a S)-2,3,6,6a,7,8,9,9a,10,11,12,13-dodecahydro-5,11-dihydroxy-6a,7,10,10-tetramethyl-3-oxo-1H-benzo[8,8a][1]benzopyrano[2,3-e]isoindole
Physicochemical properties:
Appearance: colorless needle crystals
Solubility: soluble in acetone, tetrahydrofuran, methanol; slightly soluble in chloroform, ethyl acetate; insoluble in n-hexane, water.
Melting point: >300° C.
$[\alpha]_D^{24}$=+138.7±1.8° (c=1.00, methanol)
Molecular formula: $C_{23}H_{31}NO_4$
Elemental analysis for $C_{23}H_{31}NO_4 \cdot H_2O$ Calcd.; C: 68.46%, H: 7.99%, N: 3.47% Found; C: 68.82%, H: 8.13%, N: 3.53%
LSIMS, m/z: 386 (MH)$^+$
HR-LSIMS, m/z for $C_{23}H_{32}NO_4$
Calcd.; 386.2329
Found; 386.2328 (MH)$^+$
IR $\nu_{max}$ KBr cm$^{-1}$: 3410, 2960, 2872, 1684, 1625, 1465, 1364, 1168, 1072, 974, 774.
UV (methanol), nm ($\epsilon$): 216 (42,700), 257 (6,600), 302 (3,000).
$^1$H NMR (DMSO-d$_6$, 600 MHz) δ: 0.83 (3H, s), 0.89 (3H, s), 0.92 (3H, s), 1.09 (3H, d, J=7.2 Hz), 1.25 (1H, m), 1.46 (1H, dd, J=3.0, 13.0 Hz), 1.54 (1H, m), 1.57 (1H, m), 1.64 (1H, m), 1.73 (1H, m), 1.97 (1H, m), 2.09 (1H, d, J=17.9 Hz), 2.12 (1H, m), 2.21 (1H, m), 2.34 (1H, m), 3.07 (1H, d, J=17.9 Hz), 3.34(1H, m), 4.06 (1H, d like, J=16.8 Hz), 4.16 (1H, d like, J=16.8 Hz), 4.46 (1H, d, J=3.0 Hz), 6.61 (1H, s), 8.29 (1H, s like), 9.70 (1H, s).
$^{13}$C NMR (DMSO-d$_6$,150 MHz) δ: 16.88 (q), 19.84 (q), 23.34 (t), 23.39 (t), 25.63 (t), 26.94 (q), 27.50 (t), 29.99 (q), 31.83 (t), 37.02 (s), 37.34 (s), 38.95 (d), 42.44 (t), 44.23 (d), 72.08 (d), 83.16 (s), 98.95 (d), 111.94 (s), 120.67 (s), 131.46(s), 147.10 (s), 155.80 (s), 170.36 (s).
TLC Rf value (detected with a conc. $H_2SO_4$ reagent): 0.31 ($CH_2Cl_2$: methanol=10:1).
HPLC analysis: retention time; 3.22 min.
Column: YMC-Pack ODS-AM, AM-302, 4.6 i.d.×150 mm (YMC).
Mobile phase: 0.1% trifluoroacetic acid-acetonitrile : 0.1% trifluoroacetic acid-water=55:45.
Flow rate: 1 ml/min.
Detection: 254 nm (UV).

Example 2

Preparation of SQ-02-S3(1) and SQ-02-S5(2) in liquid fermentation (1) Fermentation Step To infusion obtained by boiling 200 g of potato per 1 liter were added 20 g of maltose and 4 g of polypeptone (Nippon Seiyaku), and the medium so obtained was divided into 48 Erlenmeyer flasks (500 ml volume) at 100 ml per flask. They were then sterilized at 121° C. for 20 min to provide flask mediums. To each of the flask mediums was inoculated 1 ml of a spore suspension prepared by adding 10 ml per tube of physiological saline to test tube slants of Stachybotrys sp. RF-7260. These flasks were then cultured at 28° C. for 15 days on a rotary shaker at 180 rpm.

(2) Isolation of SQ-02-S3(1)

After the cultivation, 5 L of ethyl acetate was added to 4 liter of the combined culture. The mixture was stirred for 30 min and filtrated using a centrifugal filter to give an extraction filtrate. The filtrate was allowed to stand. The ethyl acetate layer was separated, washed with 1 L of water, and concentrated to dryness to give 4.4 g of the crude material. The crude material was then dissolved in a small amount of ethyl acetate and allowed to adsorb onto a silica gel column (adsorbent: Merck Silica Gel 60 (80 g)) pre-equilibrated with toluene, which was eluted with a mixed solvent of toluene-ethyl acetate (7:3–3:7, V/V) while collecting 50 ml fractions.

The factions containing SQ-02-S3(1) were combined, and concentrated to dryness to give 340 mg of crude SQ-02-S3. The solid was recrystallized from a mixed solvent of methanol: ethyl acetate (2:8, V/V) to give 302 mg of SQ-02-S3(1) as colorless crystals.

(3) Isolation of SQ-02-S5(2)

The fractions eluted after SQ-02-S3(1) were combined, and concentrated to dryness to give 72 mg of powder. This material was dissolved in 0.2 ml of methanol and subjected to a preparative high performance liquid chromatography (column: Shinwa Kako ULTRON VX-ODS 20×250 mm; eluent: 48% (V/V) aqueous acetonitrile (supplemented by 0.1% trifluoroacetic acid); flow rate: 6 ml/min; detector: UV detector). Fractions eluting around 15 min of retention time, which correspond to SQ-02-S5, were combined, and concentrated under reduced pressure. The residual aqueous layer was then extracted with ethyl acetate, and concentrated to dryness to give 9.4 mg of SQ-02-S5(2) as colorless powder.

Example 3

Conversion of SQ-02-S3(1) into SQ-02-S5(2)

SQ-02-S3(1) (1.2 g, 2.8 mmol) obtained in Example 1 or 2 was dissolved in dry methanol (50 ml) and 1M sodium

Example 4

Synthesis of SQ-02-S3-Ac(3) from S1-02-S3(1)

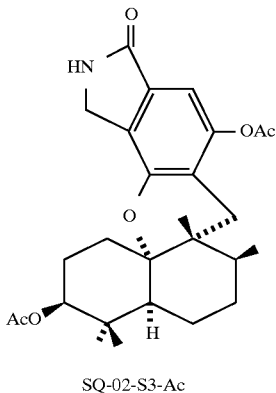

SQ-02-S3-Ac

To a solution of SQ-02-S3(1) (50 mg, 0.12 mmol) in dry pyridine (2 ml) was added acetic anhydride (0.3 ml), followed by stirring at room temperature for 20 hours. After addition of methanol (5 ml) to the reaction, solvent was evaporated under reduced pressure. The residue was partitioned into ethyl acetate (40 ml) and water (30 ml), and the ethyl acetate layer was washed with water, dried over anhydrous sodium sulfate, and evaporated under reduced pressure to give SQ-02-S3-Ac(3) (50 mg, 92% yield) as a colorless solid.

SQ-02-S3-Ac(3)

Compound name: (6aR,7S,9aS,11S,13aS)-5,11-diacetoxy-2,3,6,6a,7,8,9,9a,10,11,12,13-dodecahydro-6a,7,10,10-tetramethyl-3-oxo-1H-benzo[8,8a][1]benzopyrano[2,3-e]isoindole Physicochemical properties:

LSIMS, m/z: 470 (MH)$^+$

IR $v_{max}$ KBr cm$^{-1}$: 3422, 3219, 2966, 2939, 1763, 1734, 1701, 1655, 1600, 1458, 1372, 1242, 1199, 1064, 1053, 960.

$^1$H NMR (CDCl$_3$, 200 MHz) δ: 0.87 (3H, s), 0.91 (3H, s), 1.11 (3H, s), 1.16 (3H, d, J=7.4 Hz), 2.02 (1H, d, J=17.4 Hz), 2.10 (3H, s), 2.34 (3H, s), 3.21 (1H, d, J=17.4 Hz), 4.32 (1H, d, J=16.8 Hz), 4.41 (1H, d, J=16.8 Hz), 4.78 (1H, m), 6.60 (1H, br.s), 7.12 (1H, s).

$^{13}$C NMR(CDCl$_3$, 75 MHz) δ: 17.07, 19.90, 21.47, 23.00, 23.40, 24.48, 26.27, 27.76, 30.06, 30.95, 32.20, 37.26, 37.63, 39.45, 43.42, 45.02, 76.26, 84.11, 108.22, 118.16, 127.56, 131.51, 147.56, 149.72, 168.87, 170.37, 170.91.

Example 5

Synthesis of SQ-02-S3-Me(4) from SQ-02-03(1)

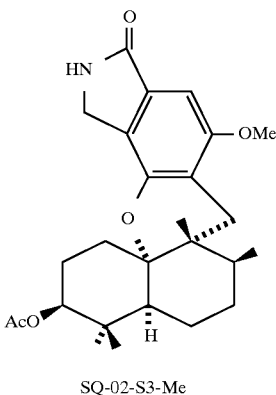

SQ-02-S3-Me

To a solution of SQ-02-S3(1) (45 mg, 0.105 mmol) in acetone (4 ml) were added methyl iodide (2 ml) and potassium carbonate (100 mg), and the mixture heated to reflux for 8 hours. The reaction mixture was filtered. The filtrate was concentrated and the resultant products were separated by TLC (Pre-Coated TLC Plates, SILICA GEL F-254, E. Merck, CH$_2$Cl$_2$: methanol 10:1) to give SQ-02-S3-Me(4) (37 mg, 80% yield).

SQ-02-S3-Me(4)

Compound name: (6aR,7S,9aS,11S,13aS)-11-acetoxy-2,3,6,6a,7,8,9,9a,10,11,12,13-dodecahydro-5-methoxy-6a,7,10,10-tetramethyl-3-oxo-1H-benzo[8,8a][1]benzopyrano[2,3-e]isoindole Physicochemical properties:

LSIMS, m/z: 442 (MH)$^+$

IR $v_{max}$ KBr cm$^{-1}$: 3422, 2960, 2874, 1736, 1698, 1625, 1601, 1472, 1435, 1369, 1244, 1194, 1169, 1121, 1102, 960.

$^1$H NMR (CDCl$_3$, 300 MHz) δ: 0.86 (3H, s), 0.91 (3H, s), 1.08 (3H, s), 1.15 (3H, d, J=7.5 Hz), 2.10 (3H, s), 2.23 (1H, d, J=18.0 Hz), 3.17 (1H, d, J=18.0 Hz), 4.30 (1H, d, J=16.5 Hz), 4.36 (1H, d, J=16.5 Hz), 4.78 (1H, m), 6.58 (1H, br.s), 6.90 (1H, s).

$^{13}$C NMR (CDCl$_3$, 50 MHz) δ: 17.15, 20.17, 21.49, 23.09, 23.46, 24.49, 26.33, 27.88, 30.01, 32.16, 37.22, 37.60, 39.48, 43.41, 44.61, 55.78, 77.22, 83.41, 95.72, 114.07, 123.25, 131.07, 147.10, 158.49, 170.42, 172.06.

Example 6

Synthesis of SQ-02-S3-Bn(5) from SQ-02-S3(1)

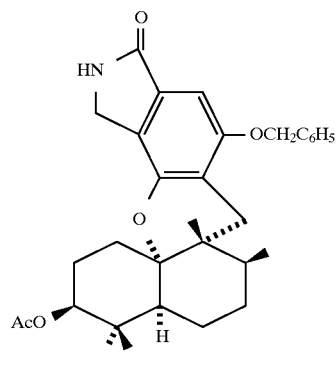

SQ-02-S3-Bn

To a solution of SQ-02-S3(1) (500 mg, 1.17 mmol) in acetone (30 ml) were added benzyl bromide (1.52 g) and

--- methylate/methanol solution (57 ml), and heated to reflux for 12 hours. To cooled reaction mixture was added water (50 ml), and methanol was evaporated under reduced pressure. To the residual aqueous layer was added 1N HCl to adjust pH to 1.0, followed by extraction with ethyl acetate (500 ml). The ethyl acetate layer was washed with water and dried over anhydrous sodium sulfate. The solvent was then evaporated under reduced pressure. The residue was crystallized from methanol to give SQ-02-S5(2) (720 mg, 67% yield).

potassium carbonate (500 mg), and the mixture heated to reflux for 6 hours. The reaction mixture was filtered and the filtrate was concentrated. The resultant product (1.89 g) was subjected to a silica gel column chromatography (Silica gel 60, 70–230 mesh, 70 g, E. Merck) and separated and purified with a mixed solvent of acetone:n-hexane=1:1 to give SQ-02-S3-Bn(5) (600 mg, 99% yield).

SQ-02-S3-Bn(5)

Compound name: (6aR,7S,9aS,11S,13aS)-11-acetoxy-5-benzyloxy-2,3,6,6a,7,8,9,9a,10,11,12,13-dodecahydro-6a,7,10,10-tetramethyl-3-oxo-1H-benzo[8,8a][1]benzopyrano[2,3-e]isoindole Physicochemical properties:

LSIMS, m/z: 518 (MH)$^+$

IR $\nu_{max}$ KBr cm$^{-1}$: 3421, 3246, 2961, 2874, 1735, 1697, 1625, 1601, 1467, 1450, 1371, 1300, 1244, 1195, 1170, 1118, 1091, 1016, 959, 768, 753.

$^1$H NMR (CDCl$_3$, 300 MHz) δ: 0.86 (3H, s), 0.92 (3H, s), 1.09 (3H, s), 1.15(3H, d, J=7.5 Hz), 2.10 (3H, s), 2.30 (1H, d, J=18.3 Hz), 3.20 (1H, d, J=18.3Hz), 4.32 (1H, ABq, A part, J=16.5 Hz), 4.36 (1H, ABq, B part, J=16.5 Hz), 4.78(1H, t-like), 5.13 (1H, ABq, A part, J=12.3 Hz), 5.17 (1H, ABq, B part, J=12.3 Hz), 6.44 (1H, br.s), 6.99 (1H, s), 7.30–7.47 (5H, m).

$^{13}$C NMR (CDCl$_3$, 75 MHz) δ: 17.12, 20.16, 21.48, 23.08, 23.45, 24.48, 26.32, 27.88, 30.01, 32.23, 37.23, 37.63, 39.33, 43.38, 44.67, 70.31, 76.40, 83.46, 96.98, 114.56, 123.44, 127.44, 127.96, 128.55, 131.04, 136.86, 147.25, 157.62, 170.42, 171.93.

Example 7

Synthesis of SQ-02-S3-Cl(6) from SQ-02-S3(1)

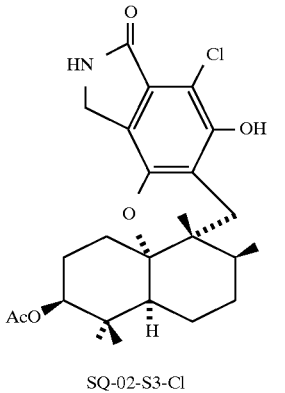

SQ-02-S3-Cl

To an ice-cooled solution of SQ-02-S3(1) (22 mg, 0.051 mmol) in tetrahydrofuran (4 ml) was added N-chlorosuccinimide (12.3 mg) with stirring. Two hours later, the reaction was returned to room temperature and stirred for another 3 hours. To the reaction was added 10% aqueous sodium hydrogen sulfite (2 ml). The mixture was stirred for 10 min and partitioned into organic and aqueous layers. The organic layer was washed with water, dried over anhydrous sodium sulfate, and the solvent was evaporated to give 27 mg of crude product. The crude product was separated by TLC (Pre-Coated TLC Plates, SILICA GEL F-254, E. Merck, acetone:n-hexane=1:1) to give SQ-02-S3-Cl(6) (7.6 mg, 32% yield) and the starting compound (SQ-02-S3, 14 mg, 64% yield).

SQ-02-S3-Cl(6)

Compound name: (6aR,7S,9aS,11S,13aS)-11-acetoxy-4-chloro-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole Physicochemical properties:

LSIMS, m/z: 462 (MH)$^+$

IR $\nu_{max}$ KBr cm$^{-1}$: 3350, 2957, 1773, 1700, 1478, 1362, 1249, 1187.

$^1$H NMR (CDCl$_3$, 300 MHz) δ: 0.87 (3H, s), 0.92 (3H, s), 1.07 (3H, s), 1.16 (3H, d, J=7.8 Hz), 2.10 (3H, s), 2.29 (1H, d, J=18.0 Hz), 3.27 (1H, d, J=18.0 Hz), 4.28 (1H, ABq, J=18.0 Hz), 4.30 (1H, ABq, J=18.0 Hz), 4.78 (1H, t-like), 5.96 (1H, br.s), 6.63 (1H, s).

$^{13}$C NMR (CDCl$_3$, 75 MHz) δ: 17.08, 20.09, 21.48, 23.03, 23.48, 24.48, 26.32, 27.82, 29.99, 32.42, 37.24, 37.59, 39.38, 42.37, 44.83, 76.24, 84.18, 105.99, 113.69, 124.20, 126.13, 146.01, 150.00, 169.69, 170.42.

Example 8

Synthesis of SQ-02-S3-Br(7) from SQ-02-S3(1)

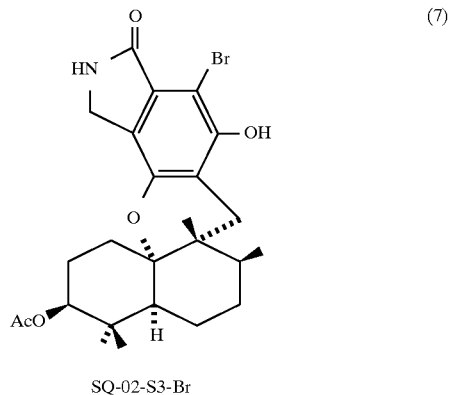

SQ-02-S3-Br

To an ice-cooled solution of SQ-02-S3(1) (42 mg, 0.10 mmol) in tetrahydrofuran (6 ml) was added N-bromosuccinimide (26 mg). Three hours later, 10% aqueous sodium hydrogen sulfite (2 ml) was added to the reaction. The reaction mixture was stirred for 10 min and partitioned into organic and aqueous layers. The organic layer was washed with water, dried over anhydrous sodium sulfate, and the solvent was evaporated to give 59 mg of crude product. The crude product was separated by TLC (Pre-Coated TLC Plates, SILICA GEL F-254, E. Merck, acetone:n-hexane=1:1) to give SQ-02-S3-Br(7) (49 mg, 98% yield).

SQ-02-S3-Br(7)

Compound name: (6aR,7S,9aS,11S,13aS)-11-acetoxy-4-bromo-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole Physicochemical properties:

LSIMS, m/z: 506 (MH)$^+$

IR $\nu_{max}$ KBr cm$^{-1}$: 3391, 2992, 2961, 2875, 1735, 1697, 1591, 1474, 1435, 1359, 1243, 1194, 1082, 1017, 960, 754.

$^1$H NMR (CDCl$_3$, 300 MHz) δ: 0.87 (3H, s), 0.92 (3H, s), 1.07 (3H, s), 1.16 (3H, d, J=7.8 Hz), 2.10 (3H, s), 2.30 (1H, d, J=18.3 Hz), 3.29 (1H, d, J=18.3 Hz), 4.25 (1H, ABq, J=17.6 Hz), 4.28 (1H, ABq, J=17.6 Hz), 4.78 (1H, t-like), 6.00 (1H, s), 6.36 (1H, br.s).

$^{13}$C NMR (DMSO-d$_6$, 75 MHz) δ: 17.08, 20.09, 21.48, 23.03, 23.48, 24.48, 26.32, 27.82, 29.99, 32.63, 37.24, 37.66, 39.38, 42.01, 44.84, 76.23, 84.23, 94.84, 113.61, 124.84, 127.38, 146.80, 150.83, 169.74, 170.40.

Example 9

Synthesis of SQ-02-S3-OX(8) from SQ-02-S3-Bn(5)

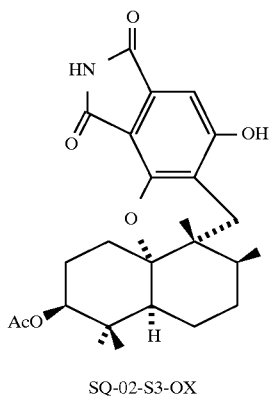

SQ-02-S3-OX

To a solution of SQ-02-S3-Bn(5) (50 mg, 0.097 mmol) in water-saturated dichloromethane (2 ml) was added 2,3-dichloro-5,6-dicyanobenzoquinone (90 mg) and the mixture allowed to stand for 5 days at room temperature. The insoluble materials in the reaction were filtered off. The filtrate was concentrated and separated by TLC (Pre-Coated TLC Plates, SILICA GEL F-254, E.Merck, dichloromethane:methanol=95:5) to give the oxidation product (17 mg, 33% yield) as a pale yellow powder. To a solution of the oxidation product in ethanol (1.5 ml) was added 10% Pd-C (8 mg), and the mixture subjected to a catalytic reduction under atomospheric pressure. After the completion of the reaction, the catalyst was filtered off and the filtrate evaporated to give SQ-02-S3-OX(8) (8 mg).

SQ-02-S3-OX(8)

Compound name: (6aR,7S,9aS,11S,13aS)-11-acetoxy-2,3,6,6a,7,8,9,9a,10,11,12,13-dodecahydro-5-hydroxy-6a,7,10,10-tetramethyl-1,3-dioxo-1H-benzo[8,8a][1]benzopyrano[2,3-e]isoindole Physicochemical properties:

LSIMS, m/z: 442 (MH)$^+$

IR $\nu_{max}$ KBr cm$^{-1}$: 3411, 3315, 2961, 1756, 1715, 1610, 1455, 1372, 1338, 1265, 1196, 1069, 960, 757.

$^1$H NMR (DMSO-d$_6$, 300 MHz) δ: 0.80 (3H, s), 0.85 (3H, s), 1.04 (3H, s), 1.11 (3H, d, J=5.0 Hz), 2.13 (1H, d, J=12 Hz), 3.05 (1H, d, J=12 Hz), 4.62 (1H, s), 10.64 (1H, br.s).

$^{13}$C NMR (DMSO-d$_6$, 75 MHz) δ: 16.73, 19.73, 21.03, 22.60, 22.96, 23.85, 26.13, 27.22, 28.94, 31.49, 36.62, 36.77, 38.69, 44.27, 75.44, 83.57, 101.26, 107.26, 114.11, 133.39, 149.96, 162.05, 167.90, 169.03, 169.62.

Example 10

Synthesis of SQ-02-S5-Bn(9) from SQ-02-S3-Bn(5)

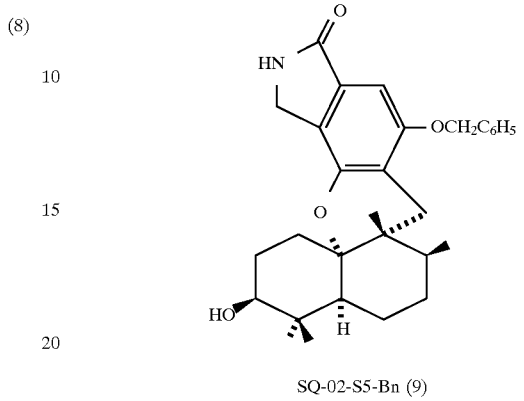

SQ-02-S5-Bn (9)

SQ-02-S3-Bn(5) (102 mg, 0.24 mmol) was dissolved in dry methanol (1 ml) and 1M sodium methylate solution (4.8 ml), and heated to reflux for 5 hours. After cooling, water (3 ml) was added to the reaction and methanol was removed under reduced pressure. The pH of the residual aqueous layer was adjusted to 1.0 with 1N HCl, followed by extraction with ethyl acetate (50 ml). The ethyl acetate layer was washed with water, dried over anhydrous sodium sulfate, and concentrated. The residue was crystallized from methanol to give SQ-02-S5-Bn(9) (76 mg, 83% yield).

SQ-02-S5-Bn(9)

Compound name: (6aR,7S,9aS,11S,13aS)-5-benzyloxy-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole.

Physicochemical properties:

LSIMS, m/z: 476 (MH)$^+$

IR $\nu_{max}$ KBr cm$^{-1}$: 3423, 2957, 2871, 1682, 1625, 1601, 1465, 1452, 1366, 1343, 1300, 1172, 1116, 1098, 974.

$^1$H NMR (CDCl$_3$, 200 MHz) δ: 0.92 (3H, s), 0.98 (3H, s), 1.02 (3H, s), 1.14 (3H, d, J=7.4 Hz), 2.28 (1H, d, J=18.0 Hz), 3.20 (1H, d, J=18.0 Hz), 3.56 (1H, m), 4.36 (2H, s), 5.11 (2H, s), 6.29 (1H, br.s), 6.98 (1H, s), 7.34–7.47 (5H, m).

$^{13}$C NMR (CDCl$_3$, 50 MHz) δ: 17.10, 20.21, 23.76, 24.13, 25.83, 26.39, 28.08, 30.30, 32.30, 37.64, 37.94, 39.44, 43.38, 44.72, 70.28, 74.57, 83.93, 96.82, 114.74, 123.49, 127.42 (x2), 127.94, 128.55 (x2), 130.85, 136.90, 147.44, 157.62, 171.97.

Example 11

Synthesis of SQ-02-S5-OA(10) from SQ-02-S3(1)

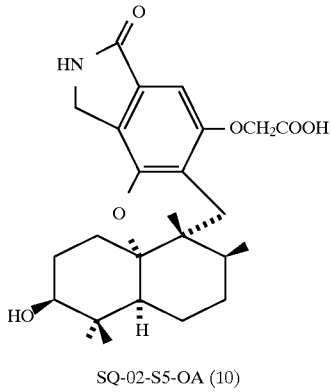

SQ-02-S5-OA (10)

To a solution of SQ-02-S3(1) (50 mg, 0.12 mmol) in acetone (10 ml) were added potassium carbonate (50 mg) and ethyl bromoacetate (145 mg), and the mixture heated to reflux for 16 hours. The insoluble materials were filtered off. The filtrate was subjected to the concentration under reduced pressure and separation by TLC (Pre-Coated TLC Plates, SILICA GEL F-254, E.Merck, acetone: n-hexane=1:1) to give the product (60 mg). The product was dissolved in 1N sodium methylate-methanol (3 ml) and heated to reflux for 2 hours. The reaction was then concentrated, and the residue partitioned into ethyl acetate (3 ml) and water (3 ml). The aqueous layer was adjusted to pH 3.0 with 1N HCl, and extracted with ethyl acetate (3 ml). The ethyl acetate layer was washed with water, dried over anhydrous sodium sulfate, and concentrated to dryness to give SQ-02-S5-OA (10) (35 mg, 93% yield).

SQ-02-S5-OA(10)

Compound name: (6aR,7S,9aS,11S,13aS)-5-carboxymethyloxy-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole Physicochemical properties:

LSIMS, m/z: 444 (MH)$^+$

IR $\nu_{max}$ KBr cm$^{-1}$: 3421, 2960, 2873, 1684, 1625, 1604, 1466, 1413, 1369, 1302, 1258, 1224, 1178, 1128, 1105, 1049, 973, 769.

$^1$H NMR (DMSO-d$_6$, 300 MHz) δ: 0.85 (3H, s), 0.89 (3H, s), 0.93 (3H, s), 1.10 (3H, d, J=7.2 Hz), 3.13 (1H, d, J=18.3 Hz), 4.15 (1H, ABq, A part, J=17.4 Hz), 4.22 (1H, ABq, B part, J=17.4 Hz), 4.47 (1H, br.s), 4.72 (1H, ABq, A part, J=16.8 Hz), 4.77 (1H, ABq, B part, J=16.8 Hz), 6.56 (1H, s), 8.40 (1H, br.s).

$^{13}$C NMR (DMSO-d$_6$, 75 MHz) δ: 16.86, 19.85, 23.38, 25.59, 26.86, 27.48, 29.99, 31.75, 36.96, 37.37, 42.48, 44.27, 65.08, 72.05, 83.50, 95.88, 113.21, 123.07, 131.49, 147.01, 156.40, 170.02, 170.12.

Example 12

Synthesis of SQ-02-S5-OX1(11) from SQ-02-S5-Bn(9)

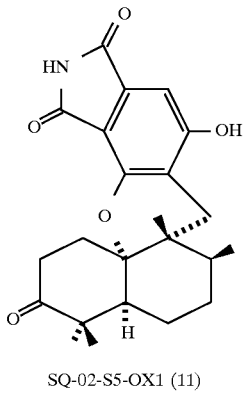

SQ-02-S5-OX1 (11)

To a solution of SQ-02-S5-Bn(9) (24 mg, 0.05 mmol) in acetone (2 ml) was added the Jones reagent (8 eq.mol), and the mixture stirred at room temperature for 3 hours. After the addition of 2 drops of isopropanol and the termination of the reaction, the reaction mixture was neutralized with 10% aqueous sodium hydrogen carbonate. The solvent was evaporated under reduced pressure. The residue was partitioned into ethyl acetate (20 ml) and water (20 ml). The ethyl acetate layer was concentrated and separated by TLC (Pre-Coated TLC Plates, SILICA GEL F-254, E.Merck, dichloromethane:methanol=10:1) to give the oxidation product (8.4 mg, 34% yield). To a solution of the oxidation product (8.4 mg) in ethanol (2 ml) was added 10% Pd-C (10 mg), and the mixture subjected to a catalytic reduction under atomospheric pressure. After completion of the reaction, the catalyst was filtered off and the filtrate was evaporated to obtain SQ-02-S5-OX1(11) (5.6 mg, 28% yield).

SQ-02-S5-OX1(11)

Compound name: (6aR,7S,9aS,13aS)-2,3,6,6a,7,8,9,9a,10,11,12,13-dodecahydro-5-hydroxy-6a,7,10,10-tetramethyl-1,3,11-trioxo-1H-benzo[8,8a][1]benzopyrano[2,3-e]isoindole.

Physicochemical properties:

LSIMS, m/z: 398 (MH)$^+$

IR $\nu_{max}$ KBr cm$^{-1}$: 3450, 3340, 2967, 2933, 2883, 1752, 1706, 1620, 1603, 1482, 1457, 1425, 1389, 1370, 1340, 1310, 1226, 1204, 1185, 1167, 1144, 1113, 1095, 1067, 1037, 994.

$^1$H NMR (DMSO-d$_6$, 300 MHz) δ: 0.86 (3H, s), 0.89 (3H, s), 1.07 (3H, d, J=7.2 Hz), 1.22 (3H, s), 2.19 (1H, d, J=18 Hz), 3.05 (1H, d, J=18 Hz), 6.77 (1H, s), 10.73 (1H, s).

$^{13}$C NMR (DMSO-d$_6$, 75 MHz) δ: 16.83, 19.86, 23.68, 24.01, 27.03, 28.50, 30.21, 31.89, 33.39, 36.64, 47.45, 48.45, 82.74, 101.42, 107.72, 114.25, 133.49, 149.78, 161.77, 167.94, 168.91, 214.81.

Example 13

Synthesis of SQ-02-S5-OX2(12) from SQ-02-S5-Bn(9)

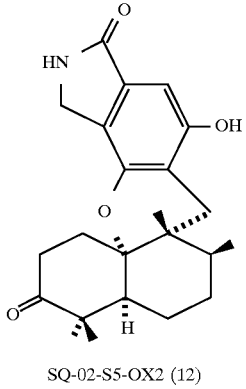

SQ-02-S5-OX2 (12)

To a solution of SQ-02-S5-Bn(9) (47 mg, 0.1 mmol) in acetone (4 ml) was added the Jones reagent (2 eq.mol), and the mixture stirred for 1.5 hours under ice-cooling. After the addition of 3 drops of isopropanol and the termination of the reaction, solvent was evaporated under reduced pressure. The residue was then partitioned into ethyl acetate (5 ml) and water (2 ml). The ethyl acetate layer was concentrated and separated by TLC (Pre-Coated TLC Plates, SILICA GEL F-254, E.Merck, dichloromethane:methanol=10:1) to give the oxidation product (42 mg, 89% yield). To a solution of the oxidation product (13 mg) in ethyl acetate (1 ml) was added 10% Pd-C (14 mg), and the mixture subjected to a catalytic reduction under atmospheric pressure. After completion of the reaction, the catalyst was filtered off, and the filtrate was evaporated to give SQ-02-S5-OX2(12) (8.8 mg, 84% yield).

SQ-02-S5-OX2(12)

Compound name: (6aR,7S,9aS,13aS)-2,3,6,6a,7,8,9,9a,10,11,12,13-dodecahydro-5-hydroxy-6a,7,10,10-tetramethyl-3,11-dioxo-1H-benzo[8,8a][1]benzopyrano[2,3-e]isoindole.

Physicochemical properties:

LSIMS, m/z: 384 (MH)$^+$

IR $\nu_{max}$ KBr cm$^{-1}$: 3396, 2966, 2928, 2875, 1692, 1628, 1611, 1465, 1385, 1363, 1281, 1243, 1205, 1168, 1147, 1110, 1078, 1070, 1038, 993, 960, 942, 910, 880, 850, 774.

$^1$H NMR (DMSO-d$_6$, 300 MHz) δ: 0.88 (3H, s), 0.90 (3H, s), 1.02 (3H, s), 1.09 (3H, d, J=7.4 Hz), 2.18 (1H, d, J=18 Hz), 3.04 (1H, d, J=18 Hz), 4.04 (1H, d, J=17.4 Hz), 4.16 (1H, d, J=17.4 Hz), 6.66 (1H, s), 8.34 (1H, s), 9.82 (1H, s).

$^{13}$C NMR(DMSO-d$_6$, 75 MHz) δ: 16.83, 20.02, 23.27, 23.82, 27.18, 28.45, 29.01, 32.13, 32.83, 36.80, 42.33, 46.14, 47.52, 81.57, 99.58, 111.83, 120.88, 131.68, 146.61, 155.93, 170.18, 214.93.

Example 14

Synthesis of SQ-02-S5-Epi(13) from SQ-02-S5-Bn(9)

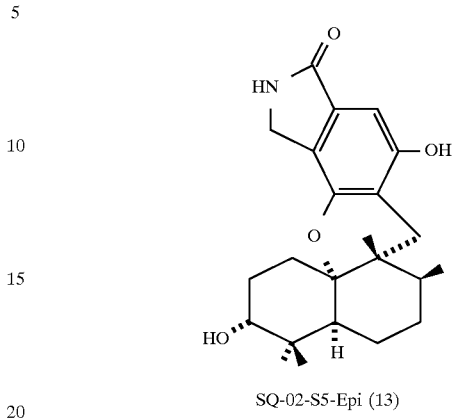

SQ-02-S5-Epi (13)

To a solution of SQ-02-S5-Bn(9) (47 mg, 0.1 mmol) in acetone (4 ml) was added the Jones reagent (2 eq.mol), and the mixture stirred for 1.5 hours under ice-cooling. After addition of 3 drops of isopropanol and termination of the reaction, the solvent was evaporated under reduced pressure. The residue was partitioned into ethyl acetate (5 ml) and water (2 ml). The ethyl acetate layer was concentrated, and then separated by TLC (Pre-Coated TLC Plates, SILICA GEL F-254, E.Merck, dichloromethane:methanol=10:1) to give the oxidation product (42 mg, 89% yield). To an ice-cooled solution of this oxidation product (16 mg) in methanol (1.5 ml) was added sodium borohydride (2.3 mg), and the mixture stirred for 1.5 hours under ice-cooling. Water (0.5 ml) was then added to the reaction, stirred for 0.5 hours, and evaporated under reduced pressure. The residue was partitioned into ethyl acetate (4 ml) and water (2 ml). The ethyl acetate was concentrated and separated by TLC (Pre-Coated TLC Plates, SILICA GEL F-254, E.Merck, dichloromethane:methanol=10:1) to give SQ-02-S5-Bn (6 mg, 37% yield) and the reduction product (10 mg, 62% yield). To a solution of the reduction product (10 mg) in ethanol (1 ml) was added 10% Pd-C (10 mg), and the mixture subjected to a catalytic reduction for 3 hours under atmospheric pressure. After completion of the reaction, the catalyst was filtered off. The filtrate was evaporated under reduced pressure to give SQ-02-S5-Epi(13) (7.2 mg, 89% yield).

SQ-02-S5-Epi(13)

Compound name: (6aR,7S,9aS,11R,13aS)-2,3,6,6a,7,8,9,9a,10,11,12,13-dodecahydro-5,11-dihydroxy-6a,7,10,10-tetramethyl-3-oxo-1H-benzo[8,8a][1]benzopyrano[2,3-e]isoindole.

Physicochemical properties:

LSIMS, m/z : 386 (MH)$^+$

IR $\nu_{max}$ KBr cm$^{-1}$: 3422, 2960, 2874, 1684, 1622, 1463, 1365, 1283, 1244, 1214, 1168, 1121, 1096, 1074, 1016, 981, 947, 912, 878, 847, 774, 754.

$^1$H NMR (DMSO-d$_6$, 300 MHz) δ: 0.80 (3H, s), 0.85 (3H, s), 0.88 (3H, s), 1.08 (3H, d, J=7.5 Hz), 2.09 (1H, d, J=17.4 Hz), 3.03 (1H, d, J=17.4 Hz), 3.53(1H, m), 4.11 (1H, d, J=16.8 Hz), 4.18 (1H, d, J=16.8 Hz), 4.25 (1H, br.s), 6.62 (1H, s), 8.28 (1H, br.s), 9.89 (1H, br.s).

$^{13}$C NMR (DMSO-d$_6$, 75 MHz) δ: 16.89, 19.88, 21.80, 23.29, 27.10, 27.33, 28.16, 28.95, 32.22, 36.84, 37.97, 42.46, 46.22, 71.25, 82.45, 99.03, 111.82, 120.60, 131.51, 147.15, 155.91, 170.32.

Example 15

Preparation in an amino acids-supplemented medium (1)

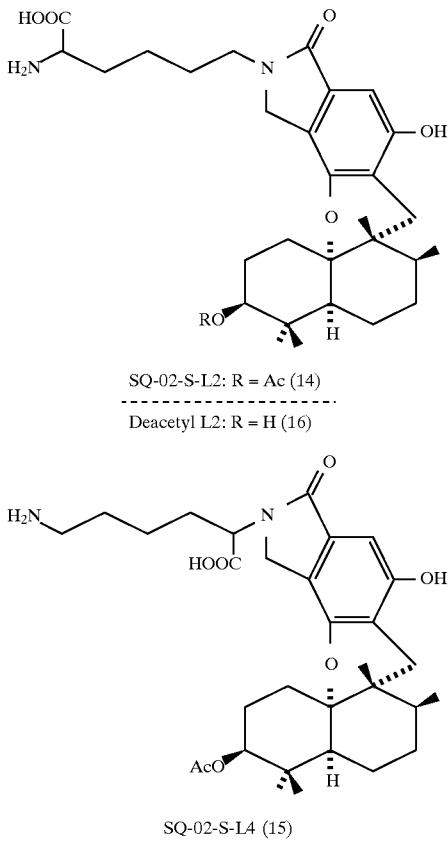

SQ-02-S-L2: R = Ac (14)

Deacetyl L2: R = H (16)

SQ-02-S-L4 (15)

(1) Fermentation step

One hundred ml of medium consisting of 2.0% glucose, 2.0% soluble starch, 1.0% polypeptone (Nippon Seiyaku), 0.3% meat extract (Difco), 0.1% yeast extract (Difco) and 0.1% sodium chloride was put into each of 500 ml Erlenmeyer flasks, sterilized, and seeded with one platinum loop of Stachybotrys sp. RF-7260 from the slant culture. The flasks were then cultured at 28° C. for 72 hours on a rotary shaker at 180 rpm. One hundred ml of medium consisting of 6.0% glycerol, 3.0% potato starch, 3.0% peanut powder, 0.5% polypeptone (Nippon Seiyaku), 0.1% sodium nitrate and 0.2% D-lysine hydrochloride were put into each of 233 Erlenmeyer flasks (500 ml volume), and sterilized at 121° C. for 20 min to provide the production medium. Four ml each of the seed culture cultivated in the foregoing Erlenmeyer flasks was inoculated into each of the production medium in the above flasks. The flasks were then cultured at 18° C. for 14 days on a rotary shaker at 180 rpm.

(2) Separation and Purification step

After completion of the cultivation, 23 L of the combined medium was centrifuged. To the resultant cell body part was added 18 L of acetone, and the mixture stirred for 1 hour, and centrifuged to give an extracted filtrate. The filtrate was then concentrated under reduced pressure to remove acetone. To the residual aqueous solution was added 10 L of ethyl acetate to partition between aqueous and ethyl acetate layers. To the aqueous layer was added 7 L of n-butanol, and the mixture stirred for 30 min. After still standing, the separated butanol layer was washed with 2 L of water and concentrated to dryness to give 14.5 g of the crude material. The crude material was dissolved in a small amount of methanol and allowed to adsorb onto a silica gel column (adsorbent: Merck Silica Gel 60 (600 g)) pre-equilibrated with a mixed solvent of ethyl acetate:methanol (10:1), eluting with a mixed solvent of ethyl acetate:methanol:water (16:8:2, V/V) while collecting 80 ml fractions. The fractions containing SQ-02-S-L2, SQ-02-S-L4 were combined, and concentrated to dryness to obtain 833 mg of a crude fraction. This fraction was then subjected to a preparative high performance liquid chromatography (column: Develosil ODS 15/30ϕ50×500 mm from Nomura Kagaku; eluent:acetonitrile: 0.1% phosphoric acid=50:50; flow rate: 50 ml/min). Fractions eluting around 15 min of retention time corresponding to the SQ-02-S-L2 peak were collected, and concentrated under reduced pressure. The residual aqueous layer was extracted with n-butanol, and concentrated under reduced pressure to give 304 mg of SQ-02-S-L2(14) as a colorless powder. The fractions around 11 min of retention time corresponding to the SQ-02-S-L4 peak were collected, and concentrated under reduced pressure. The residual aqueous layer was extracted with n-butanol, and concentrated under reduced pressure to give 7.5 mg of SQ-02-S-L4(15) as a colorless powder.

(3) Preparation of Deacetyl L2(16)

To SQ-02-S-L2(14) (15 mg, 0.027 mM) were added dry methanol (0.5 ml) and 1M sodium methylate-methanol solution (0.54 ml), and the mixture heated to reflux for 5 hours. After cooling, 0.5 ml of water was added to the reaction and the pH was adjusted to 2.0 with diluted hydrochloric acid. Methanol was evaporated under reduced pressure, and the residue was extracted with n-butanol. The butanol layer was washed with water, and concentrated to dryness to give Deacetyl L2(16) (10 mg).

SQ-02-S-L2(14)

Compound name: 2-(5-amino-5-carboxypentyl)-(6aR,7S,9aS,11S,13aS)-11-acetoxy-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole Physicochemical properties:

$[\lambda]_D^{24}$=+96.6±2.4° (c=0.56, MeOH)

LSIMS, m/z: 557 (MH)$^+$

IR $\nu_{max}$ KBr cm$^{-1}$: 3423, 2962, 2876, 1734, 1671, 1626, 1466, 1376, 1337, 1249, 1199, 1143, 1073.

$^1$H NMR (DMSO-d$_6$, 300 MHz) δ: 0.82 (3H, s), 0.84 (3H, s), 1.04 (3H, s), 1.11 (3H, d, J=7.2 Hz), 2.05 (3H, s), 2.13 (1H, d, J=18.0 Hz), 3.10 (1H, d, J=18.0 Hz), 3.35 (1H, m), 3.55 (1H, m), 3.91 (1H, m), 4.16 (1H, d, J=17.1 Hz), 4.33 (1H, d, J=17.1 Hz), 4.66 (1H, m), 6.31 (1H, s), 8.20 (2H, s), 9.78 (1H, s).

$^{13}$C NMR (DMSO-d$_6$, 50 MHz) δ: 16.84, 19.71, 21.05, 21.63, 22.58, 22.92, 23.98, 26.01, 27.23, 29.60, 29.67, 31.72, 36.67, 37.08, 41.19, 43.93, 47.07, 51.74, 75.29, 82.61, 99.31, 111.83, 118.32, 131.48, 146.56, 155.93, 167.56, 169.65, 171.03.

SQ-02-S-L4(15)

Compound name: 2-(5-amino-1-carboxypentyl)-(6aR,7S,9aS,11S,13aS)-11-acetoxy-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole Physicochemical properties:

LSIMS, m/z: 557 (MH)$^+$ $^1$H NMR (DMSO-d$_6$, 300 MHz) δ: 0.82 (3H, s), 0.85 (3H, s), 1.03 (3H, s), 1.11 (3H, d, J=7.2 Hz), 2.05 (3H, s), 2.15 (1H, d, J=18.0 Hz), 2.76 (2H, m), 3.12 (1H, d, J=18.0 Hz), 4.24 (1H, d, J=17.1 Hz), 4.32 (1H, d, J=17.1 Hz), 4.66 (1H, m), 4.72 (1H, m), 6.66 (1H, s), 7.61 (2H, s), 9.32(1H, s).

$^{13}$C NMR (DMSO-d$_6$, 50 MHz) δ: 6.84, 19.76, 21.05, 22.56, 22.81, 23.94, 26.00, 26.35, 27.21, 28.15, 29.45, 31.75, 36.63, 37.05, 38.20, 43.85, 44.25, 53.03, 75.30, 82.73, 99.08, 112.39, 118.98, 130.65, 146.38, 155.97, 168.47, 169.65, 172.47.

Deacetyl L2(16)

Compound name: 2-(5-amino-5-carboxypentyl)-(6aR,7S,9aS,11S,13aS)-2,3,6,6a,7,8,9,9a,10,11,12,13-dodecahydro-5,11-dihydroxy-6a,7,10,10-tetramethyl-3-oxo-1H-benzo[8,8a][1]benzopyrano[2,3-e]isoindole Physicochemical properties:

$[\alpha]_D^{24} = +116.3 \pm 3.8°$ (c=0.41, MeOH)

LSIMS, m/z: 515 (MH)$^+$

IR $v_{max}$ Br cm$^{-1}$: 3427, 2932, 2870, 1734, 1655, 1464, 1381, 1363, 1336, 1284, 1251, 1216, 1180, 1070, 972.

$^1$H NMR (DMSO-d$_6$, 300 MHz) δ: 0.83 (3H, s), 0.89 (3H, s), 0.93 (3H, s), 1.09 (3H, d, J=7.2 Hz), 2.10 (1H, d, J=17.7 Hz), 3.07 (1H, d, J=17.7 Hz), 3.55 (1H, m), 3.90 (1H, t-like), 4.12 (1H, d, J=17.1 Hz), 4.32 (1H, d, J=17.1 Hz), 4.64 (1H, m), 6.61 (1H, s), 8.21 (2H, s), 9.74 (1H, s).

$^{13}$C NMR (DMSO-d$_6$, 75 MHz) δ: 17.37, 20.31, 22.10, 23.84, 23.91, 26.11, 27.42, 27.70, 27.98, 30.08, 30.64, 32.29, 37.51, 37.86, 41.63, 44.80, 47.55, 52.21, 72.58, 83.76, 99.56, 112.38, 118.82, 131.83, 147.41, 156.35, 168.08, 171.50.

Example 16

Preparation in an amino acids-supplemented medium (2)

(1) Fermentation step

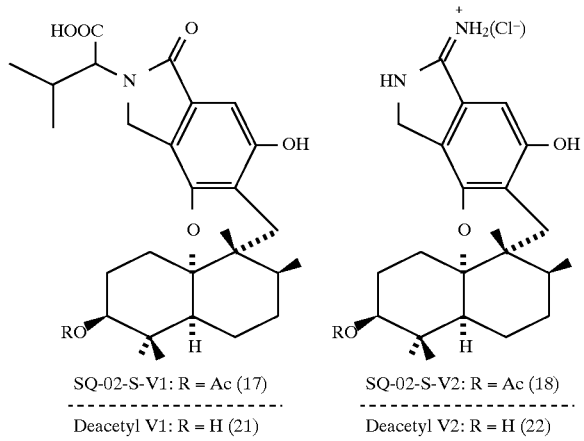

SQ-02-S-V1: R = Ac (17)
Deacetyl V1: R = H (21)

SQ-02-S-V2: R = Ac (18)
Deacetyl V2: R = H (22)

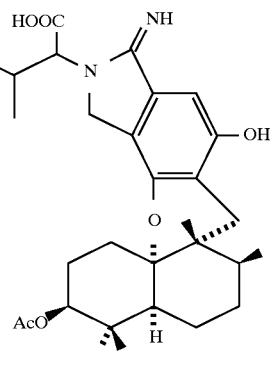

SQ-02-S-V3 (19)

-continued

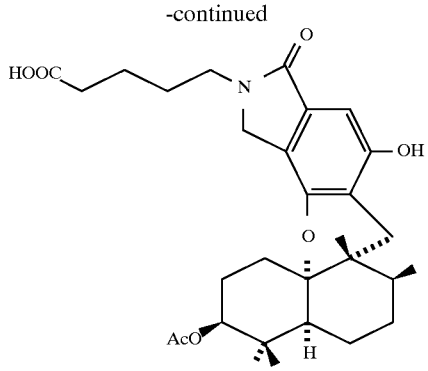

SQ-02-S-V7 (20)

One hundred ml of a medium consisting of 2.0% glucose, 2.0% soluble starch, 1.0% polypeptone (Nippon Seiyaku), 0.3% meat extract (Difco), 0.1% yeast extract (Difco) and 0.1% sodium chloride was put into each of 5 Erlenmeyer flasks (each 500 ml volume), and sterilized. To each of the flasks was added one platinum loop of Stachybotrys sp. RF-7260, followed by cultivation at 28° C. for 72 hours on a rotary shaker at 180 rpm. Brown rice valine medium (25 g of brown rice, 0.5 g of glucose, 0.1 g of Difco yeast extract, 0.5 g DL-valine, 50 ml of tap water per flask) sterilized at 120° C. for 30 min was introduced into one hundred Erlenmeyer flasks (each 500 ml volume). Each flask was inoculated with 4 ml of the above culture and cultivated statically at 28° C. for 14 days.

(2) Separation and Purification step

After completion of the cultivation, 100 ml per flask of acetone was added to the culture flasks. The flasks were allowed to stand overnight, and filtered through 0.1 mm wire gauze to give 10 L of extract. The extract was concentrated under reduced pressure to 3 L of aqueous solution. To the solution were added 100 g of sodium chloride and 5 L of ethyl acetate. The mixture was stirred and separated into an aqueous and ethyl acetate layers. The ethyl acetate layer was concentrated under reduced pressure to 300 ml volume. The resultant solid was filtered off, and the filtrate was concentrated to give 38 g of an oil.

The oil was dissolved in a small amount of methanol and allowed to adsorb onto a silica gel column (adsorbent: Merck Silica Gel 60 (1.5 Kg)) pre-equilibrated with ethyl acetate and eluted with a mixed solvent of ethyl acetate: methanol (9:1–8:2, V/V). The fractions containing SQ-02-S-V1 and SQ-02-S-V7 were combined, and concentrated to dryness to give 7.5 g of a crude fraction. The faction was decolorized with 17.5 g of activated charcoal (Norit "SX-3" from Wako Junyaku Kogyo) and subjected to a preparative high performance liquid chromatography (column: YMC-PACK ODS-AP S-15/30,300 angstrom, φ50×500 mm, eluent:acetonitrile: 0.1% phosphoric acid=6:4, flow rate: 50 ml/min). The fractions eluting around 31 min of retention time corresponding to the SQ-02-S-V1 peak were collected, and concentrated under reduced pressure. The residual aqueous layer was extracted with ethyl acetate, and concentrated under reduced pressure to give 3.1 g of SQ-02-S-V1(17) as a colorless powder. Furthermore, the fractions eluting around 25 min of retention time corresponding to the SQ-02-S-V7 peak were collected, and concentrated under reduced pressure. The residual aqueous layer was extracted with ethyl acetate, and concentrated under reduced pressure to give 68 mg of SQ-02-S-V7(20) as a colorless powder.

Separately, the fractions containing SQ-02-S-V2, SQ-02-S-V3 which were eluted with a mixed solvent of ethyl acetate:methanol (8:2–1:1, V/V) were combined, and concentrated to dryness to give 4.5 g of a crude fraction. This fraction was then subjected to a preparative high performance liquid chromatography (column: YMC-PACK, ODS-AP S-15/30, 300 angstrom, φ50×500 mm, eluent:acetonitrile: 0.1% phosphoric acid=48:52, flow rate: 50 ml/min). The fractions eluting around 24 min of retention time corresponding to the SQ-02-S-V2 peak were collected, and concentrated under reduced pressure. The residual aqueous layer was extracted with ethyl acetate, and concentrated under reduced pressure to give 102 mg of SQ-02-S-V2(18) as a colorless powder. The fractions eluting around 30 min of retention time corresponding to the SQ-02-S-V3 peak were collected, and concentrated under reduced pressure. The residual aqueous layer was then extracted with ethyl acetate, and concentrated under reduced pressure to give 7 mg of SQ-02-S-V3(19) as a colorless powder.

(4) Preparation of Deacetyl V1(21)

To SQ-02-S-V1(17) (15 mg, 0.028 mM) were added dry methanol (0.5 ml) and 1M sodium methylate/methanol solution (0.55 ml), and the mixture heated to reflux for 5 hours. After cooling, 0.5 ml of water was added to the reaction and the pH was adjusted to 2.0 with diluted hydrochloric acid. After evaporation of methanol under reduced pressure, the residue was extracted with ethyl acetate. The ethyl acetate layer was washed with water, and concentrated to dryness under reduced pressure to give Deacetyl V1(21) (11 mg).

(5) Preparation of Deacetyl V2(22)

To SQ-02-S-V2(18) (30 mg, 0.070 mM) was added 1M sodium methylate/methanol solution (1.5 ml), and the mixture heated to reflux for 4 hours. After cooling, 1.5 ml of water was added to the reaction and the pH was adjusted to pH 1.0 with diluted hydrochloric acid. After evaporation of methanol under reduced pressure, the residue was dissolved in water. The solution was then allowed to adsorbed onto MCI GEL CHP20P (Mitsubishi Kasei) column, washed with water, eluted with 50% water-containing acetone, and concentrated under reduced pressure. To the residue dissolved in methanol (0.5 ml) was added diluted hydrochloric acid to adjust pH to 2.0. Deacetyl V2 hydrochloride (22) (19.5 mg) was then precipitated with an excess of diethyl ether.

SQ-02-S-V1(17)

Compound name: 2-(1-carboxy-2-methylpropyl)-(6aR,7S,9aS,11S,13aS)-11-acetoxy-2,3,6,6a,7,8,9,9a,10,11,12,13-dodecahydro-5-hydroxy-6a, 7, 10, 10-tetramethyl-3-oxo-1H-benzo[8,8a][1]benzopyrano[2,3-e]isoindole Physicochemical properties:

$[\alpha]_D^{24}$+113.5±4.5° (c=0.34, MeOH)

LSIMS, m/z: 528 (MH)$^+$

IR $\nu_{max}$ KBr cm$^{-1}$: 3424, 2963, 2876, 1737, 1708, 1668, 1626, 1467, 1374, 1246, 1214, 1196, 1169, 1073.

$^1$H NMR (DMSO-d$_6$, 300 MHz) δ: 0.79 (3H, d, J=6.9 Hz), 0.81 (3H, s), 0.86 (3H, s), 0.99 (3H, d, J=6.3 Hz), 1.02 (3H, s), 1.11 (3H, d, J=7.5 Hz), 2.05 (3H, s), 2.15 (1H, d, J=18.0 Hz), 3.11 (1H, d, J=18.0 Hz), 4.28 (1H, d, J=17.1 Hz), 4.41 (1H; d, J=10.2 Hz), 4.44 (1H, d, J=17.1 Hz), 4.65 (1H, m), 6.66 (1H, s), 9.82 (1H, s).

$^{13}$C NMR (DMSO-d$_6$, 75 MHz) δ: 16.84, 19.14, 19.33, 19.80, 21.03, 22.56, 22.87, 23.92, 25.95, 27.22, 27.78, 29.40, 31.73, 36.62, 37.05, 43.89, 44.60, 59.72, 75.27, 82.77, 99.36, 112.42, 118.79, 130.31, 146.73, 155.99, 168.16, 169.62, 171.83.

Deacetyl V1(21)

Compound name: 2-(1-carboxy-2-methylpropyl)-(6aR,7S,9aS,11S,13aS)-2,3,6,6a,7,8,9,9a,10,11,12,13-dodecahydro-5,11-dihydroxy-6a,7,10,10-tetramethyl-3-oxo-1H-benzo[8,8a][1]benzopyrano[2,3-e]isoindole Physicochemical properties:

$[\alpha]_D^{24}$=+131.8±6.1° (c=0.28, MeOH)

LSIMS, m/z: 486 (MH)$^+$

IR $\nu_{max}$ KBr cm$^{-1}$: 3428, 2963, 2874, 1722, 1669, 1624, 1466, 1363, 1215, 1170, 1069.

$^1$H NMR (DMSO-d$_6$, 300 MHz) δ: 0.78 (3H, d, J=6.6 Hz), 0.84 (3H, s), 0.89 (3H, s), 0.91(3H, s), 0.98 (3H, d, J=6.3 Hz), 1.09 (3H, d, J=7.5 Hz), 2.10 (1H, d, J=18.0 Hz), 3.08 (1H, d, J=18.0 Hz), 4.25 (1H, d, J=16.8 Hz), 4.42 (1H, d, J=16.8 Hz), 4.40 (1H, d, J=10.2 Hz), 6.42 (1H, s), 9.77 (1H, s).

$^{13}$C NMR (DMSO-d$_6$, 75 MHz) δ: 16.89, 19.10, 19.33, 19.92, 23.36, 23.41, 25.68, 26.89, 27.52, 27.83, 29.95, 31.85, 37.05, 37.35, 44.31, 44.58, 59.80, 72.07, 8,3.43, 99.17, 112.49, 118.83, 130.20, 147.02, 155.96, 168.19, 168.19, 171.83.

SQ-02-S-V2(18)

Compound name: (6aR,7S,9aS,11S,13aS)-11-acetoxy-2,3,6,6a,7,8,9,9a,10,11,12,13-dodecahydro-5-hydroxy-3-imino-6a,7,10,10-tetramethyl-1H-benzo[8,8a][1]benzopyrano[2,3-e]isoindole hydrochloride Physicochemical properties:

$[\alpha]D^{24}$=+113.6±3.3° (c=0.47, MeOH)

LSIMS, m/z: 427 (MH)$^+$

HR-LSIMS, m/z for $C_{24}H_{35}N_2O_4$:

Calcd.; 427.2594

Found; 427.2585 (MH)$^+$

IR $\nu_{max}$ KBr cm$^{-1}$: 3380, 3271, 2963, 2877, 1735, 1698, 1624, 1510, 1464, 1438, 1376, 1333, 1249, 1200, 1137, 1078.

$^1$H NMR (DMSO-d$_6$, 600 MHz) δ: 0.82 (3H, s), 0.84 (3H, s), 1.01 (3H, s), 1.11 (3H, d, J=7.2 Hz), 1.32 (1H, m), 1.59 (1H, m), 1.61 (1H, m), 1.69 (1H, m), 1.72 (1H, m), 1.79 (1H, m), 1.93 (1H, m), 2.03 (1H, m), 2.05 (3H, s), 2.08 (1H, m), 2.19 (1H, d, J=17.8 Hz), 2.24 (1H, m), 3.13 (1H, d, J=17.8 Hz), 4.47 (1H, d, J=18.9 Hz), 4.65 (1H, d, J=18.9 Hz), 4.66 (1H, t-like), 7.10 (1H, s), 9.06 (1H, s), 9.48 (1H, s), 10.20 (1H, s), 10.24 (1H, s).

$^{13}$C NMR (DMSO-d$_6$, 125 MHz) δ: 16.77 (q), 19.65 (q), 21.03 (q), 22.52 (t), 22.92 (t), 23.87 (t), 25.96 (q), 27.16 (t), 29.68 (q), 31.79 (t), 36.64 (s), 37.07 (s), 38.68 (d), 44.03 (d), 48.71 (t), 75.18 (d), 83.41 (s), 99.70 (d), 115.11 (s), 121.53 (s), 126.73 (s), 147.05 (s), 156.66 (s), 163.70 (s), 169.76 (s).

Deacetyl V2(22)

Compound name: (6aR,7S,9aS,11S,13aS)-2,3,6,6a,7,8,9,9a,10,11,12,13-dodecahydro-5,11-dihydroxy-3-imino-6a,7,10,10-tetramethyl-1H-benzo[8,8a][1]benzopyrano[2,3-e]isoindole hydrochloride Physicochemical properties:

$[\alpha]_D^{24}$=+123.5±6.3° (c=0.26, MeOH)

LSIMS, m/z: 385(MH)$^+$

IR $\nu_{max}$ KBr cm$^{-1}$: 3426, 2960, 2872, 1685, 1622, 1463, 1382, 1332, 1183, 1076, 973.

$^1$H NMR (DMSO-d$_6$, 300 MHz) δ: 0.83 (3H, s), 0.89 (3H, s), 0.90 (3H, s), 1.09 (3H, d, J=7.2 Hz), 2.15 (1H, d, J=18.3 Hz), 3.11 (1H, d, J=18.3 Hz), 4.42 (1H, d, J=19.2 Hz), 4.51 (1H, m), 4.63 (1H, d, J=19.2 Hz), 7.14 (1H, s), 9.20 (1H, s), 9.60 (1H, s), 10.26 (2H, s).

$^{13}$C NMR (DMSO-d$_6$, 75 MHz) δ: 15.66, 18.61, 22.20, 24.42, 25.73, 26.27, 28.98, 30.75, 35.87, 36.18, 43.26, 47.51, 70.80, 82.87, 98.49, 113.97, 120.22, 125.42, 146.01, 155.41, 162.52.

SQ-02-S-V3(19)

Compound name: 2-(1-carboxy-2-methylpropyl)-(6aR,7S,9aS,11S,13aS)-11-acetoxy-2,3,6,6a,7,8,9,9a,10,11,12,13-dodecahydro-5-hydroxy-3-imino-6a,7,10,10-tetramethyl-1H-benzo[8,8a][1]benzopyrano[2,3-e]isoindole Physicochemical properties:

$[\alpha]_D^{24} = +82.2 \pm 3.8°$ (c=0.32, MeOH)

LSIMS, m/z: 527 (MH)$^+$

IR $v_{max}$ KBr cm$^{-1}$: 3427, 2964, 2877, 1734, 1674, 1624, 1467, 1375, 1247, 1199, 1138, 1078.

$^1$H NMR (DMSO-d$_6$, 300 MHz) δ: 0.83 (3H, d, J=7.2 Hz), 0.85 (3H, s), 0.87 (3H, s), 1.01 (3H, d, J=6.6 Hz), 1.02 (3H, s), 1.12 (3H, d, J=7.5 Hz), 2.05 (3H, s), 2.20 (1H, d, J=18.6 Hz), 3.16 (1H, d, J=18.6 Hz), 4.39 (1H, m), 4.51 (1H, d, J=19.5 Hz), 4.67 (1H, m), 4.74 (1H, d, J=19.5 Hz), 7.44 (1H, s), 10.00 (1H, d, J=9.3 Hz), 10.26 (1H, s), 10.67 (1H, s).

$^{13}$C NMR (DMSO-d$_6$, 75 MHz) δ: 16.79, 18.33, 18.80, 19.55, 21.03, 22.54, 22.93, 23.88, 25.97, 27.15, 29.80, 29.99, 31.75, 36.65, 37.05, 44.08, 48.85, 61.89, 75.15, 83.44, 100.27, 115.16, 121.35, 126.51, 146.95, 156.56, 162.45, 169.67, 170.78.

SQ-02-S-V7(20)

Compound name: 2-(4-carboxybutyl)-(6aR,7S,9aS,11S,13aS)-11-acetoxy-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole Physicochemical properties:

$[\alpha]_D^{24} = +131.3 \pm 7.5°$ (c=0.23, MeOH)

LSIMS, m/z: 528 (MH)$^+$

IR $v_{max}$ KBr cm$^{-1}$: 3420, 2960, 2875, 1735, 1708, 1662, 1626, 1465, 1375, 1337, 1247, 1194, 1073.

$^1$H NMR (DMSO-d$_6$, 300 MHz) δ: 0.81 (3H, s), 0.84 (3H, s), 1.04 (3H, s), 1.11 (3H, d, J=7.2 Hz), 2.05 (3H, s), 2.14 (1H, d, J=18.3 Hz), 2.24 (2H, m), 3.10 (1H, d, J=18.3 Hz), 3.38 (1H, m), 3.53 (1H, m), 4.16 (1H, d, J=17.0 Hz), 4.30 (1H, d, J=17.0 Hz), 4.65 (1H, m), 6.63 (1H, s), 9.77 (1H, s).

$^{13}$C NMR (DMSO-d$_6$, 75 MHz) δ: 16.82, 19.73, 21.03, 21.61, 22.58, 22.89, 23.94, 26.01, 27.03, 27.24, 29.62, 31.69, 32.93, 36.65, 37.07, 41.02, 43.92, 46.98, 75.34, 82.64, 99.22, 111.82, 118.37, 131.40, 146.68, 155.77, 167.65, 169.74, 174.21.

Example 17

Preparation in an amino acids-supplemented medium (3)

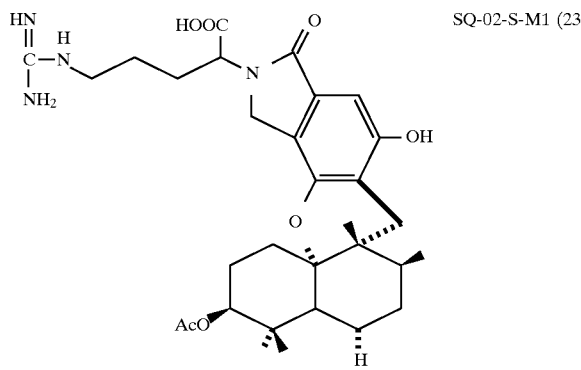

SQ-02-S-M1 (23)

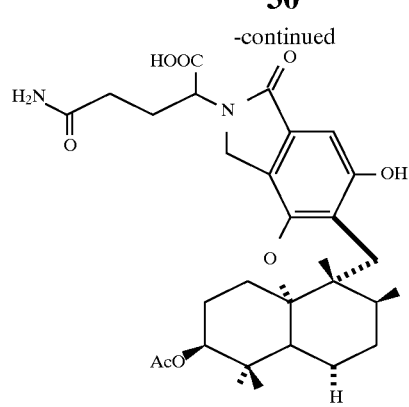

SQ-02-S-M2 (24)

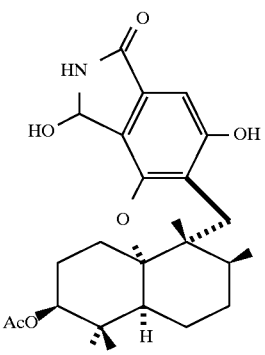

SQ-02-S-M3 (25)

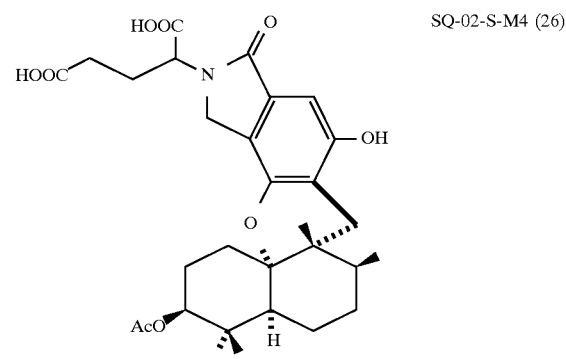

SQ-02-S-M4 (26)

(1) Fermentation step

Spores of Stachybotrys sp. RF-7260 cultured on slants in 20 test tubes were scraped with a platinum loop, and suspended in 500 ml of physiological saline. Four ml aliquots of this suspension were seeded into 120 Erlenmeyer flasks (each 500 ml volume) containing the brown rice AA medium (25 g of brown rice, 0.5 g of glucose, 0.1 g of yeast extract (Difco), 0.1 g of General Amino Acids powder F (Ajinomoto) and 50 ml of tap water per flask), and cultured statically at 28° C. for 14 days.

(2) Separation and purification

After completion of the fermentation, the cultures in the 120 flasks were combined, and 8 L of acetone was added thereto. After stirring, centrifugation was performed to give an extraction filtrate. The filtrate was then concentrated under reduced pressure to remove acetone. To the resultant aqueous solution was added 7 L of n-butanol, and the mixture stirred and separated into an aqueous layer and a n-butanol layer. The separated n-butanol layer was washed with 2 L of water and concentrated to dryness to give 82 g of a crude material. This was dissolved in a small amount of methanol, allowed to adsorb onto a silica gel column (adsorbent: Merck Silica Gel 60 (800 g)) pre-equilibrated with ethyl acetate, and eluted with a mixed solvent of ethyl acetate:methanol (20:1, V/V). The fractions containing SQ-02-S-M3 were combined, and concentrated to dryness to give 0.3 g of a residue. This was dissolved in a small amount of methanol, cooled to 4° C. to give 60 mg of SQ-02-S-M3 (25) as needle crystals. The above column was then eluted with a mixed solvent of ethyl acetate: methanol: water (8:4:1, V/V). The fractions containing SQ-02-S-M1, SQ-02-S-M2 and SQ-02-S-M4 were combined, and concentrated to dryness to give 580 mg of a crude fraction. This fraction was subjected to a preparative high performance liquid chromatography (column: Develosil ODS 15/30φ50×500 mm from Nomura Kagaku, eluent:acetonitrile: 0.1% phosphoric acid= 46:54, flow rate: 50 ml/min). The fractions eluting around 32 min of retention time corresponding to the SQ-02-S-M1 peak were collected, and concentrated under reduced pressure. The residual aqueous layer was then extracted with n-butanol, and concentrated under reduced pressure to give 270 mg of SQ-02-S-M1(23) as a colorless powder. The fractions eluting around 47 min of retention time corresponding to the SQ-02-S-M2 peak were collected, and concentrated under reduced pressure. The residual aqueous layer was then extracted with n-butanol, and concentrated under reduced pressure to give 60 mg of SQ-02-S-M2(24) as a colorless powder. The fractions eluting around 62 min of retention time corresponding to the SQ-02-S-M4 peak were collected, and concentrated under reduced pressure. The residual aqueous layer was then extracted with n-butanol, and concentrated under reduced pressure to give 60 mg of SQ-02-S-M4(26) as a colorless power.

SQ-02-S-M1(23)

Compound name: 2-(4-guanidino-1-carboxybutyl)-(6aR,7S,9aS,11S,13aS)-11-acetoxy-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole Physicochemical properties:

LSIMS, m/z: 585 (MH)$^+$

IR $v_{max}$ KBr cm$^{-1}$: 3423, 2961, 2876, 1735 (sh), 1671, 1465, 1375, 1249, 1200, 1137, 1074.

$^1$H NMR (DMSO-d$_6$, 300 MHz) δ: 0.82 (3H, s), 0.86 (3H, s), 1.02 (3H, s), 1.11 (3H, d, J=7.2 Hz), 2.05 (3H, s), 2.15 (1H, d, J=18.0 Hz), 4.67–4.74 (3H, m), 4.16 (1H, d, J=16.5 Hz), 4.32 (1H, d, J=16.5 Hz), 4.67 (1H, m), 4.71 (1H, m), 6.67 (1H, s), 7.59 (1H, t-like), 9.87 (1H, s).

$^{13}$C NMR (DMSO-d$_6$, 75 MHz) δ: 16.84, 19.73, 21.03, 22.61, 22.91, 23.94, 25.57, 25.78, 25.95, 27.26, 29.31, 31.73, 36.62, 37.07, 43.94, 44.48, 48.48, 53.02, 75.25, 82.73, 99.38, 112.44, 118.69, 130.50, 146.76, 156.10, 156.52, 168.38, 169.71, 172.33.

SQ-02-S-M2(24)

Compound name: 2-(4-amino-1-carboxy-4-oxobutyl)-(6aR,7S,9aS,11S,13aS)-11-acetoxy-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole Physicochemical properties:

$[α]_D^{24}$=+97.6±5.5° (c=0.25, MeOH)

LSIMS, m/z: 557(MH)$^+$

IR $v_{max}$ KBr cm$^{-1}$: 3430, 2962, 2878, 1735, 1710, 1669, 1465, 1417, 1374, 1249, 1196, 1073.

$^1$H NMR (DMSO-d$_6$, 300 MHz) δ: 0.82 (3H, s), 0.85 (3H, s), 1.04 (3H, s), 1.11 (3H, d, J=7.8 Hz), 2.05 (3H, s), 2.16 (1H, d, J=18.9 Hz), 3.10 (1H, d, J=18.9 Hz), 4.18 (1H, d, J=17.0 Hz), 4.30 (1H, d, J=17.0 Hz), 4.66 (2H, m), 6.65 (1H, s),6.75 (1H, s), 7.24 ( 1H, s), 9.81 (1H, s).

$^{13}$C NMR (DMSO-d$_6$, 75 MHz) δ: 16.86, 19.74, 21.04, 22.60, 22.91, 23.94, 24.39, 26.02 27.26, 29.55, 31.24, 31.71, 36.62, 37.05, 43.98, 44.64, 53.23, 75.30, 82.70, 99.33, 112.30, 118.88, 130.72, 146.76, 156.00, 168.40, 169.44, 172.40, 172.82.

SQ-02-S-M3(25)

Compound name: (6aR,7S,9aS,11S,13aS)-11-acetoxy-2,3,6,6a,7,8,9,9a,10,11,12,13-dodecahydro-1,5-dihydroxy-6a,7,10,10-tetramethyl-3-oxo-1H-benzo[8,8a][1]benzopyrano[2,3-e]isoindole Physicochemical properties:

$[α]_D^{24}$=+164.0±20.4° (c=0.1, MeOH)

LSIMS, m/z: 444 (MH)$^+$

IR $v_{max}$ KBr cm$^{-1}$: 3362, 2963, 2930, 2868, 1728, 1693, 1626, 1494, 1460, 1373, 1359, 1249, 1080.

$^1$H NMR (DMSO-d$_6$, 300 MHz) δ: 0.80 (3H, s), 0.86 (3H, s), 1.08 (3H, s), 1.10 (3H, d, J=7.1 Hz), 2.04 (3H, s), 2.10 (1H, d, J=17.7 Hz), 3.05 (1H, d, J=17.7 Hz), 4.64 (1H, m) 5.73(1H, d, J=9.3 Hz), 5.93 (1H, d, J=9.3 Hz), 6.55 (1H, s), 8.52 (1H, s), 9.83 (1H, s).

$^{13}$C NMR (DMSO-d$_6$, 75 MHz) δ: 16.86, 19.78, 21.03, 22.58, 22.88, 23.95, 26.04, 27.31, 29.59, 31.80, 36.69, 36.90, 43.00, 75.49, 77.10, 82.17, 98.87, 112.27, 122.84, 131.33, 147.79, 156.76, 168.70, 169.64.

SQ-02-S-M4(26)

Compound name: 2-(1,3-dicarboxypropyl)-(6aR,7S,9aS,11S,13aS)-11-acetoxy-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole Physicochemical properties:

$[α]_D^{24}$=+96.7±6.5° (c=0.21, MeOH)

LSIMS, m/z: 558 (MH)$^+$

IR $v_{max}$ KBr cm$^{-1}$: 3428, 2962, 2878, 1735 (sh), 1715, 1669, 1545, 1466, 1417, 1375, 1248, 1196, 1073, 1021, 900, 772.

$^1$H NMR (DMSO-d$_6$, 200 MHz) δ: 0.81 (3H, s), 0.85 (3H, s), 1.03 (3H, s), 1.11 (3H, d, J=7.0 Hz), 2.05 (3H, s), 3.12 (1H, d, J=18.0 Hz), 4.17 (1H, d, J=17.0 Hz), 4.30 (1H, d, J=17.0 Hz), 4.66 (1H, m), 4.70 (1H, m), 6.65 (1H, s), 9.82 (1H, s).

$^{13}$C NMR (DMSO-d$_6$, 75 MHz) δ: 17.33, 20.22, 21.53, 23.06, 23.39, 24.48, 26.47, 27.74, 29.93, 30.61, 32.21, 37.10, 37.55, 44.42, 45.08, 53.36, 75.78, 83.17, 99.80, 112.87, 119.34, 131.01, 147.24, 156.49, 168.91, 170.13, 172.69, 173.78.

In the following examples, the Compounds (I) of the present invention obtained in the above examples are used to prepare additional sesquiterpene derivatives of the present invention. The representative examples for such reactions are shown below.

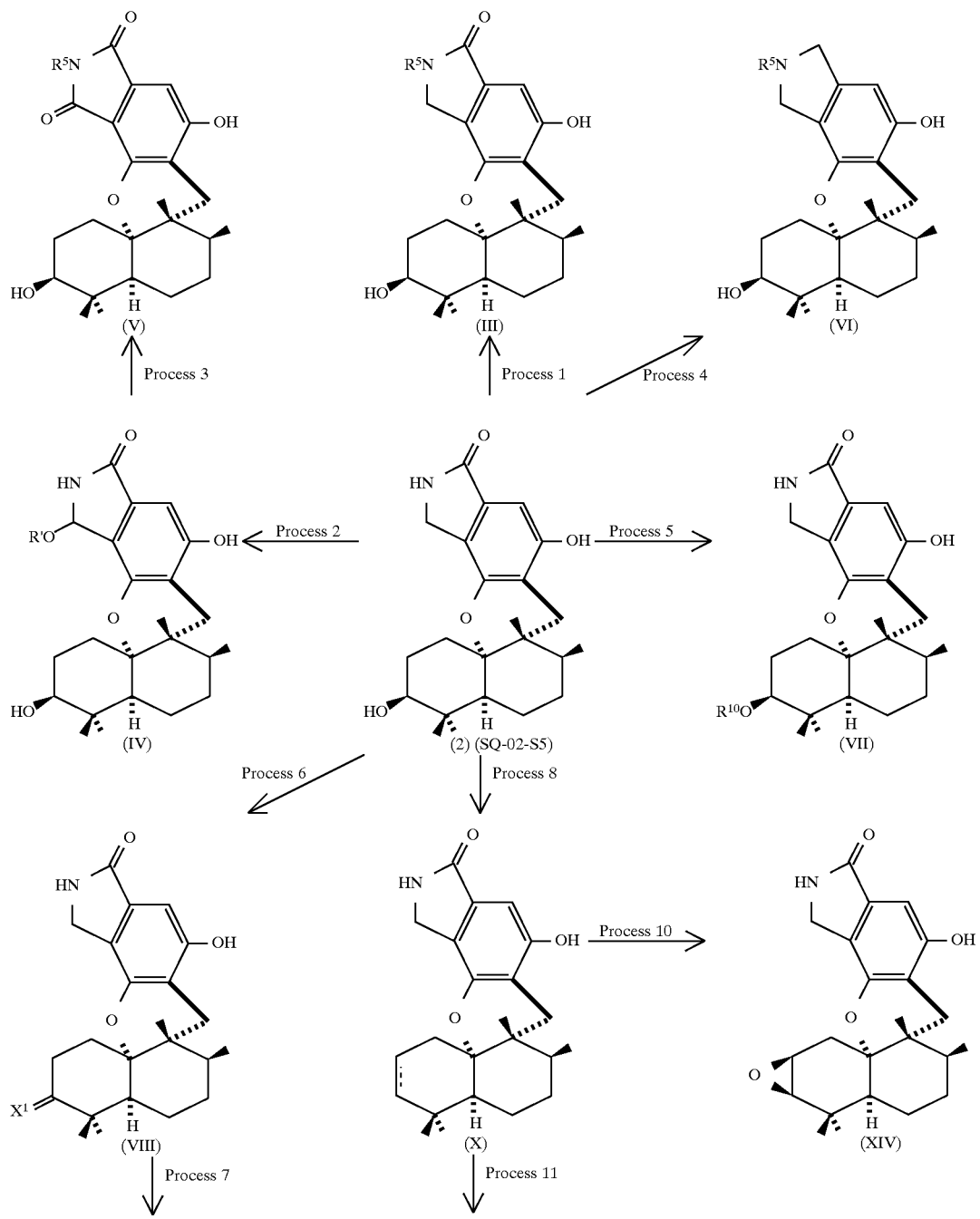

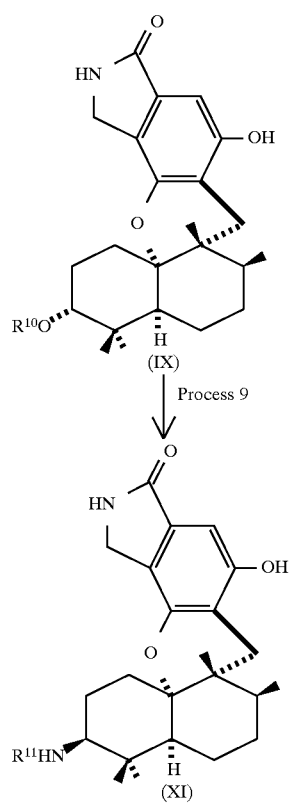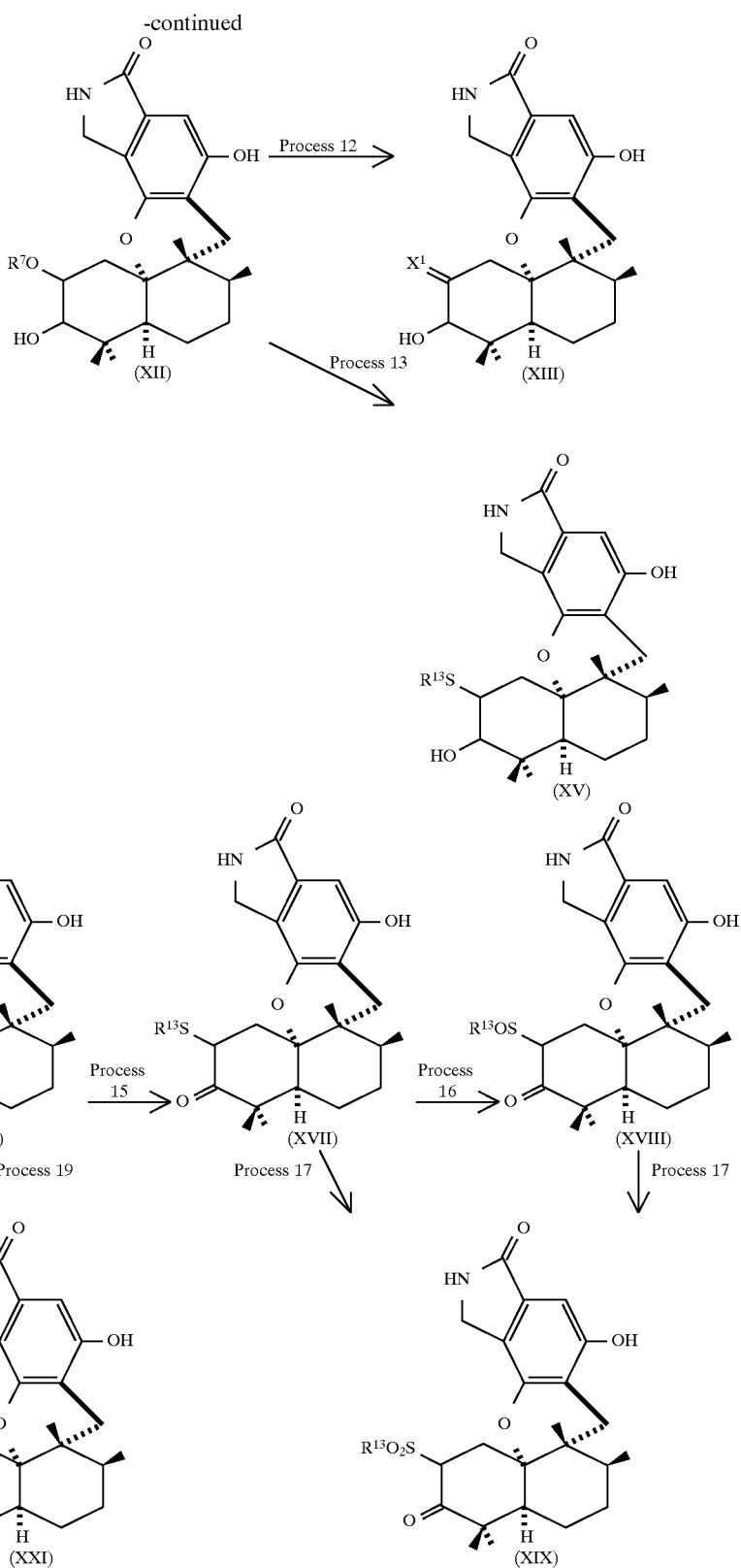

Although Compound (2) is shown as the starting material in the above reaction scheme, it is readily realized by those skilled in the art that other compounds can be also used in similar reactions to prepare a variety of corresponding derivatives.

Each process in the above reaction scheme is described below in more detail. Throughout the reaction scheme, the hydroxy group at the 5-position is protected by an easily displaceable protecting group such as, for example, benzyl, t-butyldimethylsilyl, or t-butoxycarbonyl in advance, and deprotected after the completion of the reaction. These protecting groups can be chosen considering the reaction condition of each process. Displacement of the protecting group varies depending on the type of the protecting group used, and is readily achieved under known reaction conditions for, for example, hydrolysis, reduction or the like. In addition, a 5-hydroxy derivative can also be phosphorylated.

Process 1

Compound (2) is reacted with, for example, an alkyl halide, chloride of lower fatty acid, or sulfonyl chloride compound in the presence of a strong base to give Compound (III). This reaction can be achieved in the presence of a base such as sodium hydride, sodium amide, or potassium t-butoxide, under cooling or heating, according to the usual reaction conditions for amide.

Process 2

The active methylene at the 1-position of Compound (2) is oxidized using, for example, 2,3-dichloro-5,6-dicyanobenzoquinone (DDQ), to give Compound (IV) in which an alkoxy or hydroxy group (OR') has been introduced.

The oxidation reaction is typically achieved using 2- to 10-fold equivalents of the reagent, in an alcoholic solvent such as methanol, ethanol, propanol, at room temperature or an elevated temperature. Preferably, the reaction can be done using 4-fold equivalents of DDQ at 40°–50° C. for 20 and several hours. The product of this reaction is a 1-methoxy compound. Although this compound can be directly substituted to give a desired alkoxy derivative, it is preferably converted to its hydroxy form, and then subjected to a substitution reaction with an alcohol. The reaction is achieved by a treatment with an acidic aqueous solution such as diluted hydrochloric or sulfuric acid, in a water-miscible solvent such as dioxane, tetrahydrofuran, acetone or acetonitrile at room temperature.

The substitution reaction of the alkoxy group can be achieved by stirring at room temperature for several tens of minutes in the alcohol solvent corresponding to the desired alkoxy group, in the presence of p-toluenesulfonic acid, benzenesulfonic acid and pyridinium salts thereof.

Process 3

The 1-hydroxy group (OR') of Compound (IV) is oxidized to the oxo compound, and then any of various substituents is introduced at the 2-nitrogen atom to give a N-alkyl derivative (V).

The oxidation reaction can be achieved in a solvent, for example, acetone, ethyl acetate, acetonitrile, tetrahydrofuran or a halogenated hydrocarbon such as dichloromethane, dichloroethane, chloroform, or carbon tetrachloride, by adding a corresponding amount or excess of active manganese dioxide, and stirring with cooling or at room temperature.

The substitution reaction at the 2-position can be achieved according to the procedure described for Process 1, or more preferably, by a reaction with a desired alkyl halide in the presence of a carbonate such as potassium, sodium or lithium salt, as a base.

Process 4

The 3-carbonyl group of Compound (2) is reduced, and then any of various substituents is introduced at the 2-imino group to give Compound (VI).

The deoxygenation reaction is achieved using, for example, an excess of borane-tetrahydrofuran complex, borane-dimethyl sulfide complex, or the like, in a solvent such as tetrahydrofuran, dioxane, dimethoxyethane, benzene or toluene, with heating at reflux. The reaction time is several hours to several tens of hours.

The substitution reaction of the imino group can be achieved by reacting with, for example, an acid anhydride or chloride of aliphatic lower carboxylic acid, or a sulfonyl chloride, in the presence of a base such as triethylamine, diisopropylethylamine, pyridine or collidine, in an aprotic solvent, for example, dichloromethane, chloroform, diethyl ether, tetrahydrofuran, benzene, toluene, N,N-dimethylformamide or a mixture thereof, with cooling, preferably at a temperature from −20° C. to room temperature.

Process 5

A substituent corresponding to the $R^{10}$ of the general formula (I) is introduced at the 11-hydroxy group of Compound (2) to give an ester derivative (VII).

The esterification reaction can be achieved by reacting with, for example, a corresponding aliphatic lower carboxylic acid, an aromatic carboxylic acid, or an acid anhydride, chloride, or activated ester of an aromatic carboxylic acid containing heteroatom(s), according to the conventional methods.

Process 6

The 11-hydroxy group of Compound (2) is oxidized to give the 11-oxo compound (VIII). It is farther subjected to a reaction with any of various substituted amino compounds to give the imino derivative (VIII) ($X^1$=$NR^{12}$).

The oxidation reaction is preferably achieved by reacting with chromic acid/pyridine, chromic acid/aqueous acetic acid, pyridinium chlorochromate, pyridinium dichromate, chromic acid/acetone/sulfuric acid (the Jones reagent), or the like.

The imination reaction of the 11-oxo compound is achieved by reacting a substituted amino compound or hydrochloride thereof according to a known method.

Process 7

The 11-oxo compound (VIII) ($X^1$=O) is reduced to its hydroxy form, and then a substituent corresponding to the $R^{10}$ of the general formula (I) is introduced to give an ester derivative (IX).

The reduction reaction is achieved using sodium or potassium borohydride, sodium cyanoborohydride, or the like. The reaction is done in a solvent such as methanol, ethanol, tetrahydrofuran, dioxane, dimethoxyethane or a mixture thereof, with cooling or at room temperature.

The esterification can be done similarly to that in Process 5.

Process 8

Compound (2) is subjected to a dehydration reaction, and if desired, further to a hydrogenation reaction, to give Compound (X) (the waved line represents a presence or absence of a double bond).

The dehydration reaction can be directly achieved in the presence of a base such as pyridine, collidine, lutidine, triethylamine, diisopropylethylamine, using, for example, thionyl chloride, thionyl bromide, oxalyl chloride, methanesulfonyl chloride, or p-toluenesulfonyl chloride, or more preferably, can be achieved by reacting with triphenylphosphine and azodicarboxylic acid diester. The reaction will be typically completed in an aromatic hydrocarbon solvent such as benzene, toluene, or xylene, by heating at a temperature in the range from room temperature to 150° C., preferably at 50°–130° C., for several tens of minutes to several hours.

The hydrogenation reaction can be achieved by reducing catalytically in the presence of a catalyst such as palladium-carbon, palladium black, or platinum oxide, in a solvent such as methanol, ethanol, ethyl acetate, dioxane, or tetrahydrofuran.

Process 9

The 11-hydroxy group (OR') of Compound (IX) is converted to an amino group, and then a substituent corresponding to the $R^{11}$ of the general formula (I) is introduced into that amino group to give Compound (XI).

In order to convert the hydroxy group to an amino group, hydrazoic acid is firstly used under conditions for Mitsunobu reaction to give an azide compound. This reaction can be achieved according to the known method. The 11-azido group of the azide compound formed is in the β coordination.

The reduction reaction of the azide group can be achieved by a hydride reduction using a reducing agent such as sodium or lithium borohydride, a reduction through active hydrogen using an alkaline-earth metal, for example, magnesium, or calcium in methanol, or a catalytic reduction in the presence of, for example, palladium, platinum, Raney nickel, or Lindlar catalyst, and more preferably, by a reduction using triphenylphosphine. In the latter case, about 1- to 5-fold equivalents of triphenylphosphine and a solvent such as tetrahydrofuran, dioxane, or dimethoxyethane are used. The reaction time will be several hours to several tens of hours at a temperature in the range from 50° C. to 110° C.

The substitution reaction of the amino group can be done as in that for the imino group in the Process 4.

Process 10

The double bond between the 11- and 12-position of Compound (X) is oxidized using an appropriate oxidizing agent to give Compound (XIV).

The oxidation of Compound (X) can be done according to a conventional method, using an oxidizing agent such as perbenzoic acid, m-chloroperbenzoic acid, or peracetic acid in a solvent such as tetrahydrofuran, dioxane, acetonitrile or a halogenated hydrocarbon such as dichloromethane, dichloroethane, chloroform, or carbon tetrachloride.

Process 11

The double bond of Compound (X) is oxidized to its dihydroxy form (XII) ($R^7$=H), and then a substituent corresponding to the $R^7$ of the general formula (I) is introduced thereto to give an ester derivative (XII).

The oxidation reaction is achieved by the osmium tetroxide oxidation, or by using an amine oxide, for example, trimethylamine oxide, or N-methylmorpholine oxide, in the presence of a catalytic amount of osmium tetroxide. As a reaction solvent, halogenated hydrocarbons such as dichloromethane, chloroform, and dichloroethane, ketones such as methyl ethyl ketone, or ethers such as tetrahydrofuran, dioxane, and dimethoxyethane are used alone or in combination. The reaction time varies as needed according to the reaction conditions such as the oxidizing agent used, and is usually several hours to several tens of hours.

The esterification step is done similarly to that in Process 5.

Process 12

In this process, the dihydroxy compound (XII) ($R^7$=H) is oxidized to the 12-oxo compound ($X^1$=O), and further subjected to a reaction with a substituted amino compound to give the imino derivative (XIII) ($X^1$=$NR^9$).

The oxidation and imination reactions can be done similarly to those in Process 6.

Process 13

The 12-hydroxy group ($OR^7$) of Compound (XII) is substituted with hydrogen sulfide or a thiol corresponding to the $R^{13}$ of the general formula (I) to give a mercapto derivative (XV) ($R^{13}$=H) or a substituted thio derivative (XV).

The substitution reaction with hydrogen sulfide is done using sodium or potassium hydrogensulfide. The reaction is achieved by stirring with cooling or heating in a solvent such as methanol, ethanol, N,N-dimethylformamide, or dimethylsulfoxide. Alternatively, this reaction can be achieved by reacting with potassium thioacetate to give a thioacetate ester which is then hydrolyzed according to a conventional method.

The substitution reaction with a thiol can be done by using an alkali metal salt of a desired thiol in place of the above hydrogensulfide salt. The alkali metal salt in this process can be prepared in solution by reacting the thiol compound with a base such as sodium or potassium hydroxide, sodium methoxide or ethoxide, sodium hydride, or potassium t-butoxide.

Process 14

Compound (XIV) is halogenated with a concomitant opening of the epoxy ring, and then the 11-hydroxy group is oxidized to give Compound (XVI) ($X^2$-halogen).

In the halogenation reaction, hydrogen fluoride-pyridine complex, hydrochloric acid-dioxane solution, diethylalminium chloride, bromotrimethylsilane, magnesium bromide-diethyl ether complex, or iodotrimethylsilane, for example, is reacted in a solvent such as tetrahydrofuran, dioxane, dimethoxyethane, acetonitrile, or ethyl acetate, with cooling or at room temperature.

The oxidation reaction can be done similarly to that in Process 6, or more preferably, by the Swern oxidation according to a convention method.

Process 15

The 12-halogen of Compound (XVI) is subjected to a substitution reaction with hydrogen sulfide or a thiol corresponding to the $R^{13}$ of the general formula (I) to give a mercapto derivative (XVII) ($R^{13}$=H) or a substituted thio derivative (XVII).

The substitution reaction with hydrogen sulfide or a thiol is done similarly to those in Process 13.

Process 16

The 12-sulfenyl group of Compound (XVII) is oxidized to give a sulfinyl compound (XVIII).

The oxidation reaction is typically achieved by using an equivalent of an oxidizing agent such as chromic acid, potassium permanganate, perbenzoic acid, m-chloroperbenzoic acid, or Oxone™ in a solvent such as tetrahydrofuran, dioxane, acetonitrile, or a halogenated hydrocarbon such as dichloromethane, dichloroethane, or chloroform, according to a known method.

Process 17

The sulfenyl group on Compound (XVII) or the sulfinyl group of Compound (XVIII) is oxidized using an appropriate oxidizing agent to a sulfonyl compound (XIX).

Although the oxidation reaction can be done through an oxidation using 30% hydrogen peroxide in a solvent such as acetone, or acetic acid, it can be achieved, more preferably, by using 2- to 5-fold equivalents of oxidizing agent as in Process 16.

Process 18

Concomitant with opening of the epoxy ring of Compound (XIV), various alkyl group is introduced thereto to give 12-alkyl derivatives (XX). Typically, this reaction can be achieved in the presence or absence of copper iodide by a reaction with a Grignard reagent or an alkyl lithium with cooling or at room temperature.

Process 19

The 12-halogen of Compound (XVI) is substituted with a functional group corresponding to the $R^2$ of the general formula (I) to give Compound (XXI).

In the substitution reaction, the 2-nitrogen atom may be protected with an appropriate protective group such as t-butoxycarbonyl, in advance. Next, a strong base such as lithium or sodium amide, sodium hydride, lithium diisopropylamide, lithium or sodium bistrimethylsilylamide can be applied to generate an enolate which is then reacted with, for example, a desired alkyl halide, a chloride or anhydride of aliphatic lower carboxylic acid, aromatic carboxylic acid, or aromatic carboxylic acid containing heteroatom(s). The reaction will be completed by stirring for several tens of minutes to several hours in a solvent such as tetrahydrofuran, dioxane, dimethoxyethane, dimethylsulfoxide, with cooling or at room temperature.

The following Examples show specific examples according to the above processes for derivatizing Compound (I), to which the scope of the present invention is not limited.

The reactions in the following Example 18–23 are illustrated by the following reaction scheme.

Process 1

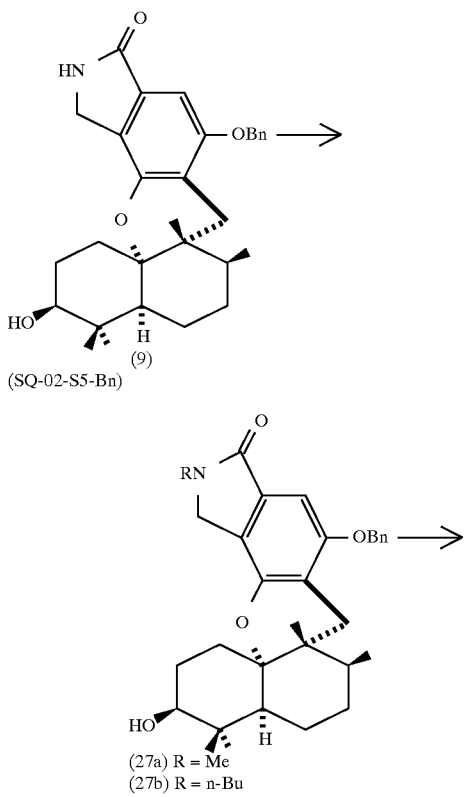

(9)
(SQ-02-S5-Bn)

(27a) R = Me
(27b) R = n-Bu
(27c) R = CH$_2$CO$_2$H
(27d) R = CH$_2$(CH$_2$)$_4$CO$_2$Me
(27e) R = SO$_2$Me
(27f) R = COMe

-continued
Process 1

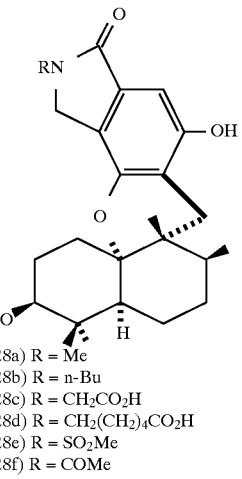

(28a) R = Me
(28b) R = n-Bu
(28c) R = CH$_2$CO$_2$H
(28d) R = CH$_2$(CH$_2$)$_4$CO$_2$H
(28e) R = SO$_2$Me
(28f) R = COMe

Example 18

Synthesis of (6aR,7S,9aS,11S,13aS)-2,3,6,6a,7,8,9,9a,10,11,12,13-dodecahydro-5,11-dihydroxy-2,6a,7,10,10-pentamethyl-3-oxo-1H-benzo[8,8a][1]benzopyrano[2,3-e]isoindole (28a)

Step-1: Synthesis of (6aR,7S,9aS,11S,13aS)-5-benzyloxy-2,3,6,6a,7,8,9,9a,10,11,12,13-dodecahydro-11-hydroxy-2,6a,7,10,10-pentamethyl-3-oxo-1H-benzo[8,8a][1]benzopyrano[2,3-e]isoindole (27a)

Under nitrogen, 13 mg (0.315 mmol) of sodium hydride (ca. 60% in oil) was added to a solution of Compound (9) (Example 10) (50 mg, 0.105 mmol) in dry DMF (0.7 ml), and the mixture stirred for 1 hour at room temperature. To the mixture was added dropwise 26 μl (0.42 mmol) of methyl iodide, followed by stirring for additional 2 hours at the same temperature. After addition of saturated ammonium chloride solution (1 ml) and water (1 ml) under cooling, the mixture was extracted with ethyl acetate. The extract was washed with saturated brine, and dried over anhydrous sodium sulfate. After evaporation of the solvent, the residue was purified by a column chromatography (Merck, Lobar column, size A; toluene:ethyl acetate=1:1) to give 30 mg (60%) of Compound (27a).

$^1$H NMR (CDCl$_3$) δ: 0.90(3H, s), 0.98(3H, s), 1.03(3H, s), 1.14(3H, d, J=7.8 Hz), 2.27(1H, d, J=18.0 Hz), 3.17(3H, s), 3.19(1H, d, J=18.0 Hz), 3.57(1H, br.s), 4.24(1H, ABq, A part, J=16.8 Hz), 4.27(1H, ABq, B part, J=16.8 Hz), 5.11 (2H, s), 6.96(1H, s), 7.30–7.50(5H, m) ppm Step-2: Synthesis of (28a)

To Compound (27a) (54 mg, 0.11 mmol) dissolved in 6.0 ml of methanol was added 15 mg of 10% palladium-carbon, followed by stirring at room temperature for 2 hours under hydrogen atmosphere. The palladium-carbon was then filtered off, and the filtrate concentrated under reduced pressure. The residue was purified by a column chromatography (Merck, Lobar column, size A; ethyl acetate) to give 44 mg (100%) of Compound (28a).

Melting point: 205°–210° C. (ethyl acetate)
LSIMS: m/z 400 [M+H]$^+$

Other physical properties of the compound are shown in Table 1.

Example 19

Synthesis of (6aR,7S,9aS,11S,13aS)-2-butyl-2,3,6,6a,7,8,9,9a,10,11,12,13-dodecahydro-5,11-dihydroxy-6a,7,10,10-tetramethyl-3-oxo-1H-benzo[8,8a][1]benzopyrano[2,3-e]isoindole (28b)

Step-1: Synthesis of (6aR,7S,9aS,11S,13aS)-5-benzyloxy-2-butyl-2,3,6,6a,7,8,9,9a,10,11,12,13-dodecahydro-11- hydroxy-6a,7,10,10-tetramethyl-3-oxo-1H-benzo[8,8a][1]benzopyrano[2,3-e]isoindole (27b)

According to the procedure of Step-1 in Example 18 except that n-butyl bromide was used, a crude product was obtained from Compound (9) (50 mg, 0.105 mmol). This was purified by a column chromatography (Merck, Lobar column, size A: toluene:ethyl acetate=2:1) to give 54 mg (97%) of Compound (27b).

$^1$H NMR (CDCl$_3$) δ: 0.91(3H, s), 0.95(3H, t, J=7.2 Hz), 0.98(3H, s), 1.03(3H, s), 1.14(3H, d, J=7.6 Hz), 2.27(1H, d, J=18.0 Hz), 3.19(1H, d, J=18.0 Hz), 3.46(1H, m), 3.57(1H, br.s), 3.70(1H, m), 4.19(1H, ABq, A part, J=16.8 Hz), 4.30(1H, ABq, B part, J=16.8 Hz), 5.11(2H, s), 6.97(1H, s), 7.35–7.50(5H, m) ppm Step-2: Synthesis of (28b)

Compound (27b) (74 mg, 0.14 mmol) was catalytically reduced as in the Step-2 of Example 18. The resultant crude product was then purified by a column chromatography (Merck, Lobar column, size A; toluene:ethyl acetate=1:1) to give 61 mg (100%) of Compound (28b).

LSIMS: m/z 442 [M+H]$^+$

Other physical properties of the compound are shown in Table 1.

Example 20

Synthesis of (6aR,7S,9aS,11S,13aS)-2-carboxymethyl-2,3,6,6a,7,8,9,9a,10,11,12,13-dodecahydro-5,11-dihydroxy-6a,7,10,10-tetramethyl-3-oxo-1H-benzo[8,8a][1]benzopyrano[2,3-e]isoindole (28c)

Step-1: Synthesis of (6aR,7S,9aS,11S,13aS)-5-benzyloxy-2-carboxymethyl-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole (27c)

i) According to the procedure of Step-1 in Example 18 except that methyl bromoacetate was used, 34 mg of the methyl ester was obtained as an oil from Compound (9) (27 mg, 0.057 mmol). This product was used in the next reaction without further purification.

ii) The methyl ester obtained above was dissolved in 2.0 ml of methanol, and a lithium hydroxide aqueous solution (prepared from 30 mg of lithium hydroxide monohydrate and 0.3 ml of water) was added thereto, and the mixture stirred at 50° C. for 3 hours. After cooling, water was added to the reaction, and extracted with ethyl acetate to remove neutral materials. The aqueous layer was acidified with 1N HCl, and extracted with ethyl acetate. The acidic extract was washed with saturated brine, and dried over anhydrous sodium sulfate. The solvent was evaporated to give 21 mg (70%) of Compound (27c).

$^1$H NMR (CDCl$_3$) δ: 0.90(3H, s), 0.97(3H, s), 1.01(3H, s), 1.13(3H, d, J=7.4 Hz), 2.27(1H, d, J=18.0 Hz), 3.19(1H, d, J=18.0 Hz), 3.57(1H, br.s), 4.31(1H, ABq, A part, J=18.0 Hz), 4.37(1H, ABq, A part, J=16.8 Hz), 4.48(1H, ABq, B part, J=16.8 Hz), 4.52(1H, ABq, B part, J=18.0 Hz), 5.09 (2H, s), 6.99(1H, s), 7.33–7.50(5H, m) ppm Step-2: Synthesis of (28c)

Compound (27c) (21 mg, 0.04 mmol) was catalytically reduced as in Step-2 of Example 18, and the crude product was purified by a preparative thin layer chromatography (Merck, Kieselgel 60 F254, 0.5 mm; chloroform:methanol:water=7:3:0.3) to give 14 mg (91%) of Compound (28c).

LSIMS: m/z 444 [M+H]$^+$

Other physical properties are shown in Table 1.

Example 21

Synthesis of (6aR,7S,9aS,11S,13aS)-2,3,6,6a,7,8,9,9a,10,11,12,13-dodecahydro-5,11-dihydroxy-2-(5-carboxylpentyl)-6a,7,10,10-tetramethyl-3-oxo-1H-benzo[8,8a][1]benzopyrano[2,3-e]isoindole (28d)

Step 1: Synthesis of (6aR,7S,9aS,11S,13aS)-5-benzyloxy-2,3,6,6a,7,8,9,9a,10,11,12,13-dodecahydro-11-hydroxy-2-(5-methoxycarbonylpentyl)-6a,7,10,10-tetramethyl-3-oxo-1H-benzo[8,8a][1]benzopyrano[2,3-e]isoindole (27d)

According to the procedure of Step-1 in Example 18 except that methyl 6-bromohexanoate is used, the crude product was obtained from Compound (9) (40 mg, 0.08 mmol). This product was purified by a column chromatography (Merck, Lobar column, size A; toluene:ethyl acetate= 2:1) to give 32 mg (63%) of Compound (27d).

$^1$H NMR (CDCl$_3$) δ: 0.91(3H, s), 0.98(3H, s), 1.03(3H, s), 1.14(3H, d, J=7.5 Hz), 2.27(1H, d, J=18.0 Hz), 3.19(1H, d, J=18.0 Hz), 3.45(1H, m), 3.57(1H, br.s), 3.65(3H, s), 3.70 (1H, m), 4.19(1H, ABq, A part, J=16.8 Hz), 4.31(1H, ABq, B part, J=16.8 Hz), 5.11(2H, s), 6.96(1H, s), 7.33–7.48(5H, m) ppm Step-2: Synthesis of (28d)

To Compound (27d) (32 mg, 0.053 mmol) dissolved in 2.0 ml of methanol was added a lithium hydroxide aqueous solution (prepared from 20 mg of lithium hydroxide monohydrate and 0.3 ml of water), and the mixture stirred at 50° C. for one hour under nitrogen. After cooling, the reaction was acidified with 1N HCl, and then extracted with ethyl acetate. The extract was washed with water, dried over anhydrous sodium sulfate, and concentrated under reduced pressure to give 32 mg of residue. To this residue dissolved in 3.0 ml of ethanol was added 10 mg of 10% palladium-carbon, and the mixture stirred at room temperature for 1.5 hours under hydrogen atmosphere. After the removal of palladium-carbon by filtration, the filtrate was evaporated to give a crude product. The crude product was then purified by a silica gel column chromatography (chloroform:methanol:water=9:1:0.1) to give 25 mg (96%) of Compound (28d).

LSIMS: m/z 500 [M+H]$^+$

Other physical properties are shown in Table 1.

Example 22

Synthesis of(6aR,7S,9aS,11S,13aS)-2,3,6,6a,7,8,9,9a,10,11,12,13-dodecahydro-5,11-dihydroxy-6a,7,10,10-tetramethyl-2-methanesulfonyl-3-oxo-1H-benzo[8,8a][1]benzopyrano[2,3-e]isoindole (28e)

Step-1: Synthesis of (6aR,7S,9aS,11S,13aS)-5-benzyloxy-2,3,6,6a,7,8,9,9a,10,11,12,13-dodecahydro-11-hydroxy-6a,7,10,10-tetramethyl-2-methanesulfonyl-3-oxo-1H-benzo[8,8a][1]benzopyrano[2,3-e]isoindole (27e)

According to the procedure of Step-1 in Example 18 except that methanesulfonyl chloride is used, the crude product was obtained from Compound (9) (50 mg, 0.105 mmol). This crude product was purified by a column chromatography (Merck, Lobar column, size A; toluene:ethyl acetate=2:1) to give 22 mg (38%) of Compound (27e).

$^1$H NMR (CDCl$_3$) δ: 0.89(3H, s), 0.99(3H, s), 1.01(3H, s), 1.14(3H, d, J=7.8 Hz), 2.29(1H, d, J=18.0 Hz), 3.21(1H, d, J=18.0 Hz), 3.39(3H, s), 3.58(1H, br.s), 4.73(1H, ABq, A part, J=13 Hz), 4.78(1H, ABq, B part, J=13 Hz), 5.11(2H, s), 7.30–7.50(5H, m) ppm Step-2: Synthesis of (28e)

Compound (27e) (25 mg, 0.045 mmol) was catalytically reduced as in Step-2 of Example 18, the resultant crude product was purified by a column chromatography (Merck, Lobar column, size A; toluene:ethyl acetate=4:1) to give 16 mg (76%) of Compound (28e). The physical properties of the compound are shown in Table 1.

Example 23

Synthesis of (6aR,7S,9aS,11S,13aS)-2-acetyl-2,3,6,6a,7,8,9,9a,10,11,12,13-dodecahydro-5,11-dihydroxy-6a,7,10,10-tetramethyl-3-oxo-1H-benzo[8,8a][1]benzopyrano[2,3-e]isoindole (28f)

Step-1: Synthesis of (6aR,7S,9aS,11S,13aS)-2-acetyl-5-benzyloxy-2,3,6,6a,7,8,9,9a,10,11,12,13-dodecahydro-11- hydroxy-6a,7,10,10-tetramethyl-3-oxo-1H-benzo[8,8a][1]benzopyrano[2,3-e]isoindole (27f)

According to the procedure of Step-1 in Example 18 except that acetyl chloride is used, the crude product was obtained from Compound (9) (70 mg, 0.15 mmol). This crude product was purified by a silica gel column chromatography (silica gel 2.5 g; chloroform), and by crystallization from diethyl ether to give 57 mg (75%) of Compound (27f).

$^1$H NMR (CDCl$_3$) δ: 0.91(3H, s), 0.99(3H, s), 1.02(3H, s), 1.15(3H, d, J=7.4 Hz), 2.30(1H, d, J=18.0 Hz), 2.67(3H, s), 3.21(1H, d, J=18.0 Hz), 3.58(1H, br.s), 4.67(1H, ABq, A part, J=13 Hz), 4.72(1H, ABq, B part, J=13 Hz), 5.12(2H, s), 6.95(1H, s), 7.35–7.50(5H, m) ppm Step-2: Synthesis of (28f)

Compound (27f) (57 mg, 0.11 mmol) was catalytically reduced as in Step-2 of Example 18, the resulting crude product was purified by a column chromatography (Merck, Lobar column, size A; toluene:ethyl acetate=2:1) to give 39 mg (82%) of Compound (28f). The physical properties are shown in Table 1.

The reactions in the following Examples 24–26 are illustrated by the following reaction scheme.

Process 2

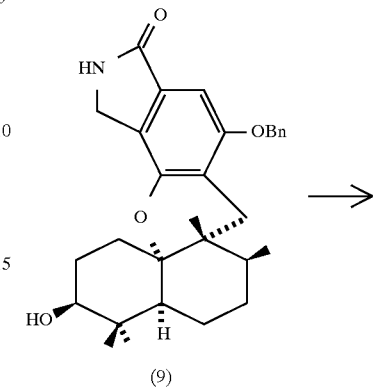

(9)

TABLE 1

| Ex. No. | Compd. | $^1$H-NMR δ (DMSO-d$_6$) ppm | IR ν max (Nujol) cm$^{-1}$ |
|---|---|---|---|
| 18 | 28a | 0.83(3H, s), 0.89(3H, s), 0.94(3H, s), 1.09(3H, d, J=7.5Hz), 2.09(1H, d, J=18 Hz), 3.00(3H, s), 3.07(1H, d, J=18Hz), 3.33(1H, br.s), 4.16(1H, ABq, A part, J=17.4Hz), 4.26(1H, ABq, B part, J=17.4Hz), 6.60(1H, s) | 3321, 3197, 1670, 1630, 1612, 1500, 1267, 1249, 1233, 1066, 983, 968 |
| 19 | 28b | 0.92(3H, s), 0.95(3H, t, J=7.5Hz), 0.98 (3H, s), 1.02(3H, s), 1.17(3H, d, J=7.2 Hz), 2.24(1H, d, J=18Hz), 3.23(1H, d, J=18Hz), 3.46(1H, dt, J=13.5, 7.5Hz), 3 57(1H, br.s), 3.70(1H, dt, J=13.5, 7.5Hz), 4.19(1H, ABq, A part, J=16.8Hz), 4.31 (1H, ABq, B part, J=16.8Hz), 7.20(1H, s) (CDCl$_3$) | 3257, 1668, 1625, 1611, 1071, 977 |
| 20 | 28c | 0.83(3H, s), 0.89(3H, s), 0.93(3H, s), 1.09(3H, d, J=7.5Hz), 2.10(1H, d, J=18 Hz), 3.07(1H, d, J=18Hz), 3.74(1H, ABq, A part, J=16.8Hz), 3.85(1H, ABq, B part, J=16.8Hz), 4.24(1H, ABq, A part, J=17.1Hz), 4.34(1H, ABq, B part, J=17.1 Hz), 6.60(1H, s) | 3395, 1656, 1606, 1072, 976 |
| 21 | 28d | 0.83(3H, s), 0.89(3H, s), 0.93(3H, s), 1.09(3H, d, J=7.5Hz), 2.09(1H, d, J=18 Hz), 3.07(1H, d, J=18Hz), 3.30–3.42(2H, m), 3.50(1H, br.s), 4.13(1H, ABq, A part, J=16.8Hz), 4.29(1H, ABq, B part, J=16.8Hz), 6.60(1H, s) | 3206, 1732, 1673, 1626, 1612, 1179, 1093, 1074, 972 |
| 22 | 28e | 0.91(3H, s), 1.01(3H, s), 1.16(3H, d, J=7.8Hz), 1.59(3H, s) 2.22(1H, d, J=18 Hz), 3.24(1H, d, J=18Hz), 3.39(3H, s), 3.58(1H, br.s), 4.70(1H, ABq, A part, J=13Hz), 4.78(1H, ABq, B part, J=13 Hz), 5.46(1H, s), 6.85(1H, s) | 3483, 3233, 1720, 1623, 1169, 1136, 1068, 972, 769 |
| 23 | 28f | 0.84(3H, s), 0.89(3H, s), 0.93(3H, s), 1.09(3H, d, J=7.4Hz), 2.13(1H, d, J=7.4 Hz), 2.13(1H, d, J=18Hz), 2.49(3H, s), 3.10(1H, d, J=18Hz), 3.36(1H, br.s), 4.46 (1H, ABq, A part, J=17.0Hz), 4.55(1H, ABq, B part, J=17.0Hz), 6.72(1H, s) | 3442, 3192, 1738, 1680, 1621, 1062, 984, 972 |

-continued
Process 2

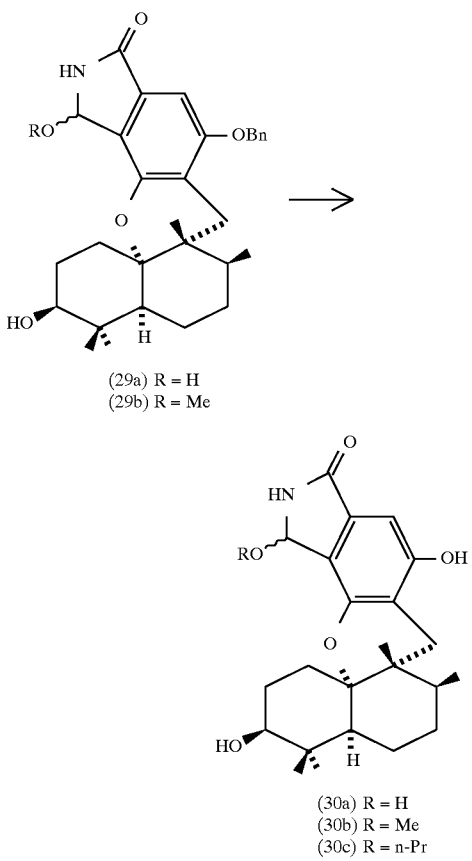

(29a) R = H
(29b) R = Me (30a) R = H
(30b) R = Me
(30c) R = n-Pr

Example 24

Synthesis of (6aR,7S,9aS,11S,13aS)-2,3,6,6a,7,8,9,
9a,10,11,12,13-dodecahydro-1,5,11-trihydroxy-6a,7,
10,10-tetramethyl-3-oxo-1H-benzo[8,8a][1]
benzopyrano[2,3-e]isoindole (30a)

Step-1: Synthesis of (6aR,7S,9aS,11S,13aS)-5-benzyloxy-2,
3,6,6a,7,8,9,9a,10,11,12,13-dodecahydro-11-hydroxy-1-
methoxy-6a,7,10,10-tetramethyl-3-oxo-1H-benzo[8,8a][1]
benzopyrano[2,3-e]isoindole (29b)

To a solution of Compound (9) (500 mg, 1.05 mmol) in methanol (50 ml) was added 0.95 g (4.2 mmol) of 2,3-dicyano-1,4-benzoquinone-5,6-diquinone (DDQ), and the mixture stirred at 45° C. for 25 hours. After cooling, methanol was evaporated under reduced pressure to about a half volume. Water (50 ml) was added to the residue, and extracted with ethyl acetate. The extract was washed with 1N sodium hydroxide aqueous solution and saturated brine, and dried over anhydrous sodium sulfate. After concentration under reduced pressure, the residue was purified by a column chromatography (Merck, Lobar column, size B; toluene:ethyl acetate=1:1) to give 439 mg (83%) of Compound (29b).

$^1$H NMR (CDCl$_3$) δ: 0.92(3H, s), 0.99(3H, s), 1.07(3H, s), 1.14(3H, d, J=7.4 Hz), 2.28(1H, d, J=18.0 Hz), 3.08(3H, s), 3.19(1H, d, J=18.0 Hz), 3.57(1H, br.s), 5.11(2H, s), 6.04(1H, s), 6.32(1H, m), 6.95(1H, s), 7.35–7.50(5H, m) ppm Step-2: Synthesis of (6aR,7S,9aS,11S,13aS)-5-benzyloxy-2,
3,6,6a,7,8,9,9a,10,11,12,13-dodecahydro-1,11-dihydroxy-6a,7,10,10-tetramethyl-3-oxo-1H-benzo[8,8a][1]
benzopyrano[2,3-e]isoindole (29a)

To a solution of the above Compound (29b) (439 mg, 0.87 mmol) in dioxane (15 ml) was added 0.15 ml of 0.1N HCl, and the mixture stirred at room temperature for 2 hours. Water was added to the reaction, and extracted with ethyl acetate. The extract was washed with 5% sodium carbonate aqueous solution and saturated brine, and dried over anhydrous sodium sulfate. After concentration under reduced pressure, the residue was purified by a silica gel column chromatography (silica gel 15 g; toluene:ethyl acetate=1:2) to give 276 mg (62%) of Compound (29a).

Melting point: 150°–156° C. (ethyl acetate-ether)

$^1$H NMR (CDCl$_3$) δ: 0.93(3H, s), 0.99(3H, s), 1.07(3H, s), 1.13(3H, d, J=7.4 Hz), 2.27(1H, d, J=18.0 Hz), 3.17(1H, d, J=18.0 Hz), 3.58(1H, br.s), 5.07(2H, s), 6.01(1H, d, J=7.4 Hz), 6.66(1H, m), 6.83(1H, s), 7.35–7.50(5H, m) ppm IR $v_{max}$ (CHCl$_3$): 3438, 1706, 1620, 1168, 1115, 1099, 969 cm$^{-1}$ Step-3: Synthesis of (30a)

To the above Compound (29a) (100 mg, 0.20 mmol) dissolved in 5.0 ml of THF and 2.0 ml of ethyl acetate was added 45 mg of 10% palladium-carbon, and the mixture stirred at room temperature for 3 hours under hydrogen atmosphere. The palladium-carbon was filtered off, and the filtrate concentrated under reduced pressure. The residue was then purified by a silica gel column chromatography (silica gel 5.2 g; ethyl acetate) to give 78 mg (96%) of Compound (30a).

LSIMS: m/z 402 [M+H]$^+$

Other physical properties are shown in Table 2.

Example 25

Synthesis of (6aR,7S,9aS,11S,13aS)-2,3,6,6a,7,8,9,
9a,10,11,12,13-dodecahydro-5,11-dihydroxy-1-
methoxy-6a,7,10,10-tetramethyl-3-oxo-1H-benzo[8,
8a][1]benzopyrano[2,3-e]isoindole (30b)

Compound (29b) (36.5 mg, 0.07 mmol) was catalytically reduced as in Step-3 of Example 24, and the product was crystallized from ethyl acetate-methanol to give 20 mg (67%) of Compound (30b).

LSIMS: m/z 416 [M+H]$^+$

Other physical properties are shown in Table 2.

Example 26

Synthesis of (6aR,7S,9aS,11S,13aS)-2,3,6,6a,7,8,9,
9a,10,11,12,13-dodecahydro-5,11-dihydroxy-1-
propoxy-6a,7,10,10-tetramethyl-3-oxo-1H-benzo[8,
8a][1]benzopyrano[2,3-e]isoindole (30c)

To a solution of Compound (30a) (33 mg, 0.08 mmol) in 3.0 ml of 1-propanol was added 6 mg of pyridinium p-toluenesulfonate, and the mixture stirred at room temperature for one hour. To the reaction was added 20 ml of ethyl acetate. The mixture was washed with saturated brine, and dried over anhydrous sodium sulfate. After concentration under reduced pressure, the residue was purified by a column chromatography (Merck, Lobar column, size A; ethyl acetate), and by crystallization from ethyl acetate to give 22 mg (60%) of Compound (30c).

LSIMS: m/z 444 [M+H]$^+$

Other physical properties are shown in Table 2.

TABLE 2

| Ex. No. | Compd. | $^1$H-NMR δ (DMSO-$d_6$) ppm | IR ν max (Nujol) cm$^{-1}$ |
|---|---|---|---|
| 24 | 30a | 0.83(3H, s), 0.88(3H, s), 0.97(3H, s), 1.09(3H, d, J=7.4Hz), 2.10(1H, d, J=18 Hz), 3.03(1H, d, J=18Hz), 4.41(1H, d, J=3.4Hz), 5.70(1H, s), 6.53(1H, s), 8.50(1H, s) | 3317, 1693, 1619, 1246, 1074, 1046, 973 |
| 25 | 30b | 0.83(3H, s), 0.89(3H, s), 0.97(3H, s), 1.09 (3H, d, J=7.4Hz), 2.10(1H, d, J=18Hz), 3.03(3H, s), 3.05(1H, d, J=18Hz), 4.44(1H, d, J=3.4Hz), 5.69(1H, s), 6.58(1H, s), 8.67(1H, s) | 3504, 3242, 1685, 1623, 1497, 1244, 1097, 1075, 1045, 971 |
| 26 | 30c | 0.83(3H, s), 0.85(3H, t, J=7.5Hz), 0.90 (3H, s), 0.99(3H, s), 1.09(3H, d, J=7.4Hz), 2.08(1H, d, J=18Hz), 3.06(1H, d, J=18 Hz), 4.34(1H, d, J=3.6Hz), 5.75(1H, s), 6.58(1H, s), 8.66(1H, s) | 3336, 1738, 1686, 1615, 1240, 1077, 1047, 972 |

The reactions in Examples 27–30 are illustrated by the following scheme.

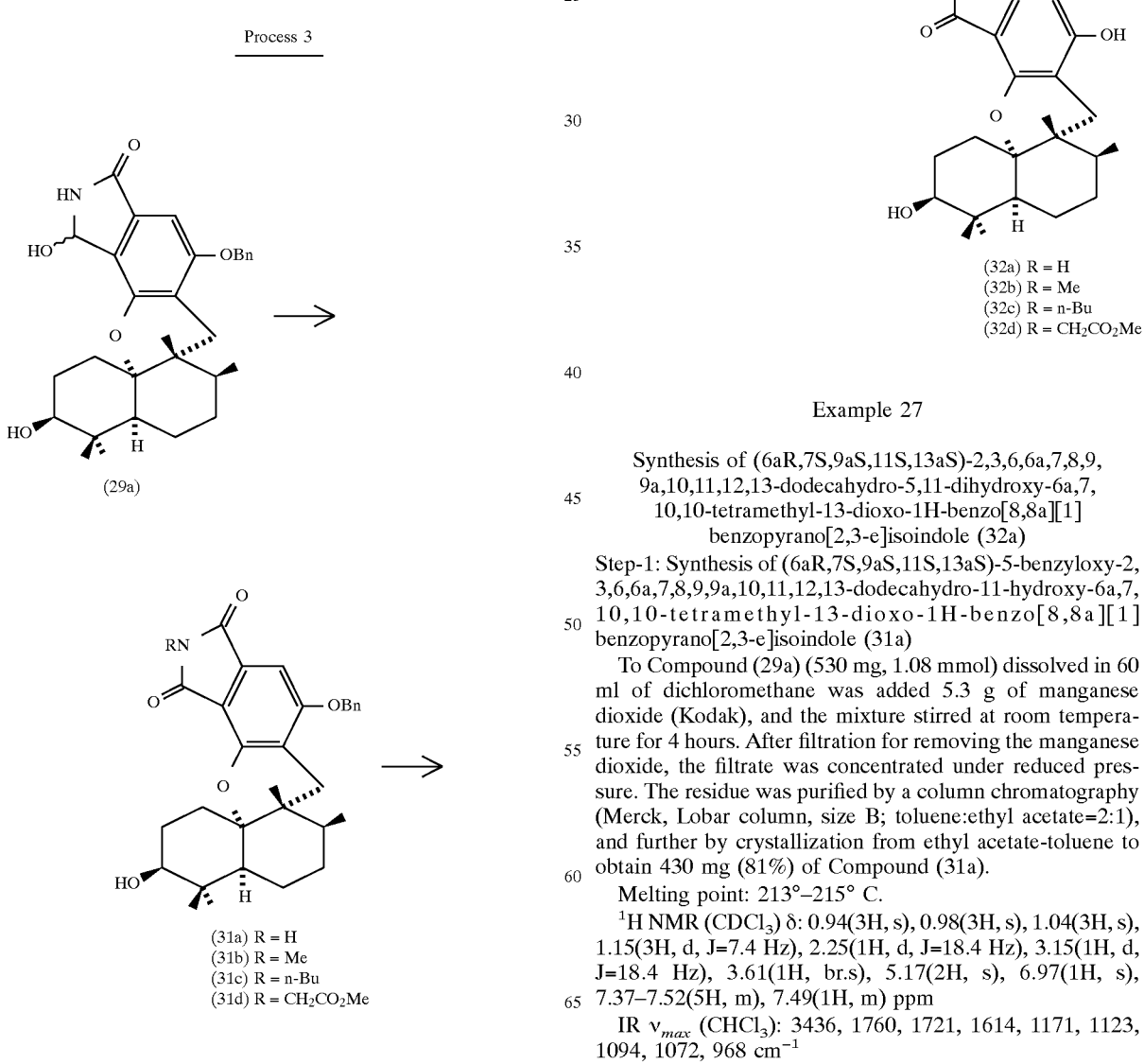

Example 27

Synthesis of (6aR,7S,9aS,11S,13aS)-2,3,6,6a,7,8,9, 9a,10,11,12,13-dodecahydro-5,11-dihydroxy-6a,7, 10,10-tetramethyl-13-dioxo-1H-benzo[8,8a][1] benzopyrano[2,3-e]isoindole (32a)

Step-1: Synthesis of (6aR,7S,9aS,11S,13aS)-5-benzyloxy-2, 3,6,6a,7,8,9,9a,10,11,12,13-dodecahydro-11-hydroxy-6a,7, 10,10-tetramethyl-13-dioxo-1H-benzo[8,8a][1] benzopyrano[2,3-e]isoindole (31a)

To Compound (29a) (530 mg, 1.08 mmol) dissolved in 60 ml of dichloromethane was added 5.3 g of manganese dioxide (Kodak), and the mixture stirred at room temperature for 4 hours. After filtration for removing the manganese dioxide, the filtrate was concentrated under reduced pressure. The residue was purified by a column chromatography (Merck, Lobar column, size B; toluene:ethyl acetate=2:1), and further by crystallization from ethyl acetate-toluene to obtain 430 mg (81%) of Compound (31a).

Melting point: 213°–215° C.

$^1$H NMR (CDCl$_3$) δ: 0.94(3H, s), 0.98(3H, s), 1.04(3H, s), 1.15(3H, d, J=7.4 Hz), 2.25(1H, d, J=18.4 Hz), 3.15(1H, d, J=18.4 Hz), 3.61(1H, br.s), 5.17(2H, s), 6.97(1H, s), 7.37–7.52(5H, m), 7.49(1H, m) ppm IR ν$_{max}$ (CHCl$_3$): 3436, 1760, 1721, 1614, 1171, 1123, 1094, 1072, 968 cm$^{-1}$ Step-2: Synthesis of (32a)

To Compound (31a) (45 mg, 0.09 mmol) dissolved in 3.0 ml of methanol was added 10 mg of 10% palladium-carbon, and the mixture stirred at room temperature for 2 hours under hydrogen atmosphere. After filtration for removing the palladium-carbon, the filtrate was concentrated under reduced pressure. The residue was purified by a column chromatography (Merck, Lobar column, size A; toluene:ethyl acetate=1:1) to give 33 mg (90%) of Compound 32 (a).

LSIMS: m/z 400 [M+H]$^+$

Other physical properties are shown in Table 3

Example 28

Synthesis of (6aR,7S,9aS,11S,13aS)-2,3,6,6a,7,8,9, 9a,10,11,12,13-dodecahydro-5,11-dihydroxy-2,6a,7, 10,10-pentamethyl-13-dioxo-1H-benzo[8,8a][1] benzopyrano[2,3-e]isoindole (32b)

Step-1: Synthesis of (6aR,7S,9aS,11S,13aS)-5-benzyloxy-2, 3,6,6a,7,8,9,9a,10,11,12,13-dodecahydro-11-hydroxy-2,6a, 7,10,10-pentamethyl-13-dioxo-1H-benzo[8,8a][1] benzopyrano[2,3-e]isoindole (31b)

Under nitrogen, 41 mg (0.4 mmol) of potassium carbonate and 26 μl (0.4 mmol) of methyl iodide was added to a solution of Compound (31a) (50 mg, 0.1 mmol) in 0.7 ml of dry DMF, and the mixture stirred at room temperature for one hour. After addition of water, the reaction was extracted with ethyl acetate. The extract was washed with saturated brine, dried over anhydrous sodium sulfate, and concentrated under reduced pressure to give 46 mg (90%) of Compound (31b).

$^1$H NMR (CDCl$_3$) δ: 0.93(3H, s), 0.98(3H, s), 1.06(3H, s), 1.15(3H, d, J=7.4 Hz), 2.25(1H, d, J=18.4 Hz), 3.09(3H, s), 3.15(1H, d, J=18.4 Hz), 3.62(1H, br.s), 5.17(2H, s), 6.98(1H, s), 7.37–7.48(5H, m) ppm Step-2: Synthesis of (32b)

Compound (31b) (46 mg, 0.09 mmol) was catalytically reduced as in Step-2 of Example 27, and the product was purified by a column chromatography (Merck, Lobar column, size A; toluene:ethyl acetate=1:1), and by crystallization from ethyl acetate to give 25 mg (66%) of Compound (32b).

Melting point: 283°–284° C.

LSIMS: m/z 414 [M+H]$^+$

Other physical properties are shown in Table 3.

Example 29

Synthesis of (6aR,7S,9aS,11S,13aS)-2-butyl-2,3,6, 6a,7,8,9,9a,10,11,12,13-dodecahydro-5,11- dihydroxy-6a,7,10,10-tetramethyl-13-dioxo-1H- benzo[8,8a] [1]benzopyrano[2,3-e]isoindole (32c)

Step-1: Synthesis of (6aR,7S,9aS,11S,13aS)-5-benzyloxy-2-butyl-2,3,6,6a,7,8,9,9a,10,11,12,13-dodecahydro-11-hydroxy-6a,7,10,10-tetramethyl-13-dioxo-1H-benzo[8,8a][1]benzopyrano[2,3-e]isoindole (31c)

According to the procedure of Step-1 in Example 28 except that n-butyl bromide is used, the crude product was obtained from Compound (31a) (43 mg, 0.088 mmol). This product was purified by a column chromatography (Merck, Lobar column, size A; toluene:ethyl acetate=2:1) to give 45 mg (94%) of Compound (31c).

$^1$H NMR (CDCl$_3$) δ: 0.92(3H, t, J=7.2 Hz), 0.94(3H, s), 0.98(3H, s), 1.05(3H, s), 1.15(3H, d, J=7.4 Hz), 2.25(1H, d, J=18.4 Hz), 3.14(1H, d, J=18.4 Hz), 3.59(2H, t, J=7.4 Hz), 3.62(1H, br.s), 5.17(2H, s), 6.97(1H, s), 7.37–7.48(5H, m) ppm Step-2: Synthesis of (32c)

Compound (31c) (45 mg, 0.08 mmol) was catalytically reduced as in Step-2 of Example 27 to give 28 mg (76%) of Compound (32c).

Melting point: 276°–279° C.

LSIMS: m/z 456 [M+H]$^+$

Other physical properties are shown in Table 3.

Example 30

Synthesis of (6aR,7S,9aS,11S,13aS)-2,3,6,6a,7,8,9, 9a,10,11,12,13-dodecahydro-5,11-dihydroxy-2- methoxycarbonylmethyl-6a,7,10,10-tetramethyl-13- dioxo-1H-benzo[8,8a][1]benzopyrano[2,3-e] isoindole (32d)

Step-1: Synthesis of (6aR,7S,9aS,11S,13aS)-5-benzyloxy-2, 3,6,6a,7,8,9,9a,10,11,12,13-dodecahydro-11-hydroxy-2-methoxycarbonylmethyl-6a,7,10,10-tetramethyl-13-dioxo-1H-benzo[8,8a][1]benzopyrano[2,3-e]isoindole (31d)

According to the procedure of Step-1 in Example 28 except that methyl bromoacetate is used, the crude product was obtained from Compound (31a) (35 mg, 0.07 mmol). This product was purified by a column chromatography (Merck, Lobar column, size A; toluene:ethyl acetate=4:1) to give 38 mg (95%) of Compound (31d).

$^1$H NMR (CDCl$_3$) δ: 0.94(3H, s), 0.97(3H, s), 1.04(3H, s), 1.15(3H, d, J=7.4 Hz), 2.26(1H, d, J=18.0 Hz), 3.15(1H, d, J=18.0 Hz), 3.60(1H, br.s), 3.73(3H, s), 4.36(2H, s), 5.18 (2H, s), 7.01(1H, s), 7.37–7.48(5H, m) ppm Step-2: Synthesis of (32d)

Compound (31d) (38 mg, 0.068 mmol) was catalytically reduced as in Step-2 of Example 27, and the product was purified by a column chromatography (Merck, Lobar column, size A; toluene:ethyl acetate=2:1), and by crystallization from ethyl acetate-ether to give 26.5 mg (83%) of Compound (32d).

Melting point: 297°–299° C.

LSIMS: m/z 472 [M+H]$^+$

Other physical properties are shown in Table 3.

TABLE 3

| Ex. No. | Compd. | $^1$H-NMR δ (DMSO-d$_6$) ppm | R ν max (Nujol) cm$^{-1}$ |
|---|---|---|---|
| 27 | 32a | 0.84(3H, s), 0.87(3H, s), 0.92(3H, s),1.09(3H, d, J=7.5Hz), 2.08(1H, d, J=18Hz), 3.04(1H, d, J=18Hz), 4.41(1H, br.s), 6.69(1H, s), 10.62(1H, s) | 3541, 3329, 3086, 1764,1745, 1717, 1607, 1495, 1060, 965 |
| 28 | 32b | 0.84(3H, s), 0.87(3H, s), 0.92(3H, s), 1.09(3H, d, J=7.5Hz), 2.11(1H, d, J=18Hz), 2.90(3H, s), 3.05(1H, d, J=18Hz), 6.74,(1H, s) | 3455, 3079, 1753, 1701,1619, 1602, 1489, 1235,1073, 962 |
| 29 | 32c | 0.85(3H, s), 0.86(3H, t, J=7.5Hz), 0.87(3H, s), | 3545, 3175, 1754, |

TABLE 3-continued

| Ex. No. | Compd. | $^1$H-NMR δ (DMSO-$d_6$) ppm | R ν max (Nujol) cm$^{-1}$ |
|---|---|---|---|
| | | 0.91(3H, s), 1.09(3H, d, J=7.5Hz), 2.10(1H, d, J=18Hz), 3.03(1H, d, J=18Hz), 3.43(2H, t, J=6.9Hz), 6.73(1H, s) | 1687,1620, 1603, 1488, 1232, 1064, 964 |
| 30 | 32d | 0.85(3H, s), 0.87(3H, s), 0.91(3H, s), 1.09(3H, d, J=7.2Hz), 2.12(1H, d, J=18Hz), 3.06(1H, d, J=18Hz), 3.66(3H, s), 4.28(2H, s), 6.79(1H, s) | 3524, 3081, 1747, 1712,1617, 1604, 1491, 1227, 1051, 968 |

The reactions in Examples 31–36 are illustrated by the following reaction scheme.

Process 4

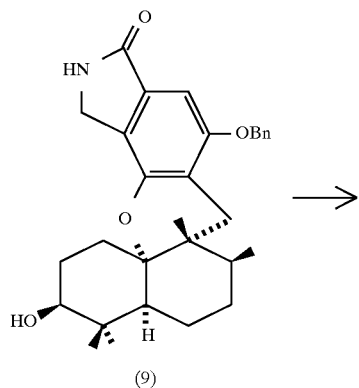

(9)

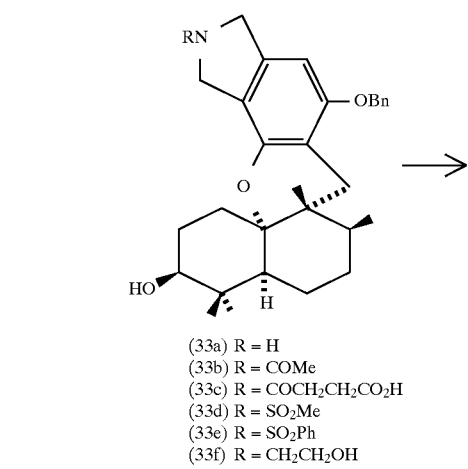

(33a) R = H
(33b) R = COMe
(33c) R = COCH$_2$CH$_2$CO$_2$H
(33d) R = SO$_2$Me
(33e) R = SO$_2$Ph
(33f) R = CH$_2$CH$_2$OH

-continued
Process 4

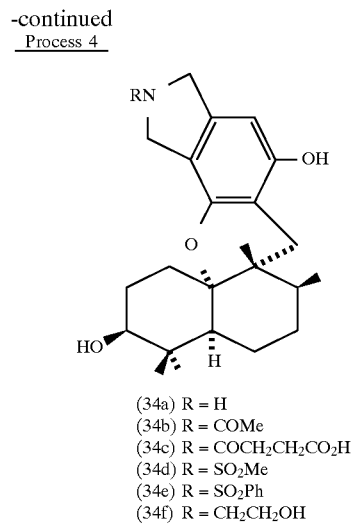

(34a) R = H
(34b) R = COMe
(34c) R = COCH$_2$CH$_2$CO$_2$H
(34d) R = SO$_2$Me
(34e) R = SO$_2$Ph
(34f) R = CH$_2$CH$_2$OH

Example 31

Synthesis of (6aR,7S,9aS,11S,13aS)-2,3,6,6a,7,8,9, 9a,10,11,12,13-dodecahydro-5,11-dihydroxy-6a,7, 10,10-tetramethyl-1H-benzo[8,8a][1]benzopyrano[2, 3-e]isoindole (34a)

Step-1: Synthesis of (6aR,7S,9aS,11S,13aS)-5-benzyloxy-2, 3,6,6a,7,8,9,9a,10,11,12,13-dodecahydro-11-hydroxy-6a,7, 10,10-tetramethyl-1H-benzo[8,8a][1]benzopyrano[2,3-e] isoindole (33a)

Under nitrogen, 4.20 ml (4.2 mmol) of 1M diborane-THF solution was added dropwise to a solution of Compound (9) (Example 10) (500 mg, 1.05 mmol) in 15 ml of dry THF over 10 min under ice-cooling. The reaction was stirred at room temperature for 2 hours, and heated to reflux for additional 24 hours. After cooling, 6.0 ml of 2N sodium carbonate aqueous solution was added to the reaction, and the mixture stirred for one hour. The reaction was poured into ice-water, and extracted with ethyl acetate. The extract was washed with saturated brine, and dried over anhydrous sodium sulfate. After concentration under reduced pressure, the residue was dissolved in 20 ml of THF. To the solution was added 5.0 ml of 1N HCl, and the mixture heated to reflux for 1.5 hours. The reaction was made basic with 2N sodium carbonate. After evaporation of THF under reduced pressure, the residue was extracted with ethyl acetate. The extract was washed with water, dried over anhydrous sodium sulfate, and concentrated under reduced pressure. The residue was purified by a silica gel column chromatography (silica gel log; chloroform:methanol:water=9:1:0.1) to give 246 mg (51%) of Compound (33a).

$^1$H NMR (CDCl$_3$) δ: 0.91(3H, s), 0.97(3H, s), 1.02(3H, s), 1.13(3H, d, J=7.6 Hz), 2.19(1H, d, J=18 Hz), 3.13(1H, d, J=18 Hz), 3.55(1H, br.s), 4.18(4H, s), 5.04(2H, s), 6.39(1H, s), 7.30–7.50(5H, m) ppm IR ν$_{max}$(CHCl$_3$) 1618, 1594, 1180, 1115, 1099, 1061, 970 cm$^{-1}$ Step-2: Synthesis of (34a)

To Compound (33a) (40 mg, 0.087 mmol) dissolved in 4.0 ml of ethanol was added 12 mg of 10% palladium-carbon, and the mixture stirred at room temperature for 2 hours under hydrogen atmosphere. After filtration for removing palladium-carbon, the reaction was concentrated under reduced pressure. The residue was purified by a silica gel column chromatography (silica gel 2.0 g; chloroform:methanol:water=9:1:0.1–7:3:0.3). The fraction containing the desired compound was concentrated under reduced pressure. The residue was dissolved in a small amount of THF. To the solution was added ether gradually, and the precipitate formed was filtered to give Compound (34a) (17 mg, 53%) as a powder.

LSIMS: m/z 372 [M+H]$^+$

Other physical properties are shown in Table 4.

Example 32

Synthesis of (6aR,7S,9aS,11S,13aS)-2-acetyl-2,3,6,6a,7,8,9,9a,10,11,12,13-dodecahydro-5,11-dihydroxy-6a,7,10,10-tetramethyl-1H-benzo[8,8a][1]benzopyrano[2,3-e]isoindole (34b)

Step-1: Synthesis of (6aR,7S,9aS,11S,13aS)-2-acetyl-5-benzyloxy-2,3,6,6a,7,8,9,9a,10,11,12,13-dodecahydro-11-hydroxy-6a,7,10,10-tetramethyl-1H-benzo[8,8a][1]benzopyrano[2,3-e]isoindole (33b)

To a solution of Compound (33a) (47 mg, 0.10 mmol) in 5.0 ml of chloroform was added a sodium carbonate aqueous solution (prepared from 14 mg (0.10 mmol) of sodium carbonate and 5.0 ml of water). Under ice-cooling, to the mixture was added 8 μl (0.12 mmol) of acetyl chloride dissolved in 0.3 ml of chloroform in a single portion with vigorous stirring. After the reaction mixture was stirred for 30 min and warmed up to room temperature, it was extracted with chloroform. The extract was washed with water, dried over anhydrous sodium sulfate, and concentrated under reduced pressure. The residue was purified by a column chromatography (Merck, Lobar column, size A; ethyl acetate) to give 47 mg (92%) of Compound (33b).

$^1$H NMR (CDCl$_3$) δ: 0.89(3H, s), 0.97(3H, s), 1.02(3H, s), 1.13(3H, .d, J=7.4 Hz).2.14(3H, s), 2.18(1H, d, J=18 Hz), 3.12(1H, d, J=18 Hz), 3.54(1H, br.s), 4.60–4.77(4H, m), 5.04(2H, s), 6.33(1H, s), 7.33–7.46(5H, m) ppm Step-2: Synthesis of (34b)

Compound (33b) (39 mg, 0.078 mmol) was catalytically reduced as in Step-2 of Example 31, and the product was crystallized from ethyl acetate-THF to give 25 mg (78%) of Compound (34b).

LSIMS: m/z 414 [M+H]$^+$

Other physical properties are shown in Table 4.

Example 33

Synthesis of(6aR,7S,9aS,11S,13aS)-2-(3-carboxy-1-oxopropyl)-2,3,6,6a,7,8,9,9a,10,11,12,13-dodecahydro-5,11-dihydroxy-6a,7,10,10-tetramethyl-1H-benzo[8,8a][1]benzopyrano[2,3-e]isoindole (34c)

Step-1: Synthesis of (6aR,7S,9aS,11S,13aS)-5-benzyloxy-2-(3-carboxy-1-oxopropyl)-2,3,6,6a,7,8,9,9a,10,11,12,13-dodecahydro-11-hydroxy-6a,7,10,10-tetramethyl-1H-benzo[8,8a][1]benzopyrano[2,3-e]isoindole (33c)

To a solution of Compound (33a) (38 mg, 0.08 mmol) in dry pyridine (0.4 ml) was added 16 mg (0.16 mmol) of succinic anhydride, and the mixture stirred for 1 hour at room temperature. Ice-water was added to the reaction, followed by extraction with ethyl acetate. The extract was washed with saturated brine, and dried over anhydrous sodium sulfate. After concentration under reduced pressure, the resulting residue was purified by silica gel column chromatography (silica gel 2.0 g; chloroform:methanol:water=9:1:0.1) to give 46 mg (100%) of Compound (33c).

Melting point: 195°–197° C. (decomp.) (ethyl acetate-chloroform)

$^1$H NMR (CDCl$_3$) δ: 0.88 (3H, s), 0.98 (3H, s), 1.01 (3H, s), 1.12 (3H, d, J=7.4 Hz), 2.18 (1H, d, J=18 Hz), 2.76 (4H, br.s), 3.12 (1H, d, J=18 Hz), 3.58 (1H, br.s), 4.60–4.80(4H, m), 5.03(2H, s), 6.39(1H, s), 7.30–7.48(5H, m) ppm IR ν$_{max}$ (CHCl$_3$): 1732, 1623, 1598, 1181, 1115, 1099, 1074, 969, 907 cm$^{-1}$ Step-2: Synthesis of (34c)

Compound (33c) (42 mg, 0.075 mmol) was catalytically reduced as in the Step-2 of Example 31. The product was purified by a silica gel column chromatography (silica gel 1.5 g; chloroform:methanol:water=9:1:0.1–8:2:0.2) and by crystallization from ethyl acetate-methanol to give 21.3 mg (61%) of Compound (34c).

LSIMS: m/z 472 [M+H]$^+$

Other physical properties are shown in Table 4.

Example 34

Synthesis of (6aR,7S,9aS,11S,13aS)-2,3,6,6a,7,8,9,9a,10,11,12,13-dodecahydro-5,11-dihydroxy-6a,7,10,10-tetramethyl-2-methanesulfonyl-1H-benzo[8,8a][1]benzopyrano[2,3-e]isoindole (34d)

Step-1: Synthesis of (6aR,7S,9aS,11S,13aS)-5-benzyloxy-2,3,6,6a,7,8,9,9a,10,11,12,13-dodecahydro-11-hydroxy-6a,7,10,10-tetramethyl-2-methanesulfonyl-1H-benzo[8,8a][1]benzopyrano[2,3-e]isoindole (33d)

According to the Step-1 in Example 32 except that methanesulfonyl chloride is used, a crude product was obtained from Compound (33a) (40 mg, 0.087 mmol). This product was then purified by a column chromatography (Merck, Lobar column, size A; toluene:ethyl acetate=1:1) to give 46 mg (98%) of Compound (33d).

Melting point: 257°–259° C. (decomp.) (ethyl acetate)

$^1$H NMR (CDCl$_3$) δ: 0.89 (3H, s), 0.98 (3H, s), 1.02 (3H, s), 1.13 (3H, d, J=7.4 Hz), 2.19 (1H, d, J=18 Hz), 2.82 (3H, s), 3.12 (1H, d, J=18 Hz), 3.55 (1H, br.s), 4.55–4.70 (4H, m), 5.03 (2H, s), 6.34 (1H, s), 7.34–7.47 (5H, m) ppm IR ν$_{max}$ (CHCl$_3$) 1621, 1600, 1181, 1154, 1114, 1097, 1072, 969 cm$^{-1}$ Step-2: Synthesis of (34d)

Compound (33d) (43 mg, 0.08 mmol) was catalytically reduced as in the Step-2 of Example 31, and the product was purified by a column chromatography (Merck, Lobar column, size A; toluene:ethyl acetate=1:1) and by crystallization from ethyl acetate to give 24.6 mg (68%) of Compound (34d).

Melting point: 159°–162° C. (decomp.)

LSIMS: m/z 450 [M+H]$^+$

Other physical properties are shown in Table 4.

Example 35

Synthesis of (6aR,7S,9aS,11S,13aS)-2,3,6,6a,7,8,9,9a,10,11,12,13-dodecahydro-5,11-dihydroxy-6a,7,10,10-tetramethyl-2-phenylsulfonyl-1H-benzo[8,8a][1]benzopyrano[2,3-e]isoindole (34e)

Step-1: Synthesis of (6aR,7S,9aS,11S,13aS)-5-benzyloxy-2,3,6,6a,7,8,9,9a,10,11,12,13-dodecahydro-11-hydroxy-6a,7, 10,10-tetramethyl-2-phenylsulfonyl-1H-benzo[8,8a][1]benzopyrano[2,3-e]isoindole (33e)

According to the procedure of Step-1 in Example 32 except that benzenesulfonyl chloride is used, a crude product was obtained from Compound (33a) (35 mg, 0.076 mmol). This product was then purified by a column chromatography (Merck, Lobar column, size A; toluene:ethyl acetate=2: 1) to give 45 mg (100%) of Compound (33e).

Melting point: 248°–250° C. (decomp.) (ethyl acetate)

$^1$H NMR (CDCl$_3$) δ: 0.75 (3H, s), 0.82 (3H, s), 0.86 (3H, s), 1.04 (3H, d, J=7.4 Hz), 2.00 (1H, d, J=18 Hz), 2.96 (1H, d, J=18 Hz), 3.35 (1H, br.s), 4.34–4.58 (4H, m), 4.99 (2H, s), 6.46 (1H, s), 7.31–7.43 (5H, m), 7.56–7.86 (5H, m) ppm Step-2: Synthesis of (34e)

Compound (33e) (39 mg, 0.065 mmol) was catalytically reduced as in the Step-2 of Example 31. The product was then purified by a column chromatography (Merck, Lobar column, size A; toluene:ethyl acetate=1:1) and by crystallization from acetone-n-hexane to give 24.8 mg (75%) of Compound (34e).

Melting point: 150°–153° C.

LSIMS: m/z 512 [M+H]$^+$

Other physical properties are shown in Table 4.

Example 36

Synthesis of (6aR,7S,9aS,11S,13aS)-2,3,6,6a,7,8,9,9a,10,11,12,13-dodecahydro-5,11-dihydroxy-2-(2-hydroxyethyl)-6a,7,10,10-tetramethyl-1H-benzo[8,8a][1]benzopyrano[2,3-e]isoindole (34f)

Step-1: Synthesis of (6aR,7S,9aS,11S,13aS)-5-benzyloxy-2,3,6,6a,7,8,9,9a,10,11,12,13-dodecahydro-11-hydroxy-2-(2-hydroxyethyl)-6a,7,10,10-tetramethyl-1H-benzo[8,8a][1]benzopyrano[2,3-e]isoindole (33f)

Under nitrogen, 35 mg (0.25 mmol) of sodium carbonate and 23 μl (0.33 mmol) of 2-chloroethanol were added to a solution of Compound (33a) (40 mg, 0.087 mmol) in dry DMF (0.5 ml). The mixture was stirred for 3 hours at 50° C. and then for 18 hours at 65° C. After cooling, water was added to the reaction, and extracted with ethyl acetate. The extract was washed with water, saturated brine, and dried over anhydrous sodium sulfate. After concentration under reduced pressure, the resulting residue was purified by a silica gel column chromatography (silica gel 1.5 g; chloroform:methanol=19: 1) to give 25 mg (57%) of Compound (33f).

$^1$H NMR (CDCl$_3$) δ: 0.90 (3H, s), 0.97 (3H, s), 1.02 (3H, s), 1.12 (3H, d, J=7.4 Hz), 2.19 (1H, d, J=18 Hz), 2.92 (2H, t, J=5.6 Hz), 3.11 (1H, d, J=18 Hz), 3.55 (1H, br.s), 3.70 (2H, t, J=5.6 Hz), 3.78–4.09 (4H, m), 5.03 (2H, s), 6.36 (1H, s), 7.30–7.47 (5H, m) ppm IR ν$_{max}$ (CHCl$_3$) 3426, 1621, 1597, 1181, 1115, 1098, 1073, 1055, 970 cm$^{-1}$ Synthesis of (34f)

Compound (33f) (44 mg, 0.087 mmol) was catalytically reduced as in the Step-2 of Example 31, and the product was purified by a silica gel column chromatography (silica gel 2.0 g; chloroform:methanol:water=9:1:0.1–8:2:0.2). Fractions containing the desired material were concentrated under reduced pressure. The residue was dissolved in a small amount of methanol. To the solution was added ether. The precipitate formed was filtered off to give Compound (34f) (27 mg, 75%) as a powder.

LSIMS: m/z 416 [M+H]$^+$

Other physical properties are shown in Table 4.

TABLE 4

| Ex. No. | Comp. | $^1$H-NMR δ (DMSO-d$_6$) ppm | IR ν max (Nujol) cm$^{-1}$ |
|---|---|---|---|
| 31 | 34a | 0.81(3H, s), 0.90(3H, s), 0.92(3H, s), 1.08 (3H, d, J=7.4Hz), 2.01( 1H, d, J=18Hz), 2.99 (1H, d, J=18Hz), 4.14(1H, ABq, A part, J=14 Hz), 4.26(1H, ABq, B part, J=14Hz), 4.28(2H, s), 4.44(1H, d, J=3.6Hz), 6.32(1H, s) | 3384, 3295, 2732, 1625, 1608, 1184, 1075, 975, 879, 829 |
| 32 | 34b | 0.81(3H, s), 0.89(3H, s), 0.93(3H, s), 1.08 (3H, d, J=7.5Hz), 2.00(1H, d, J=18Hz), 2.01 (3H, s), 2.99(1H, d, J=18Hz), 3.34(1H, br.s), 4.35–4.73(4H, m), 6.25(1H, s) | 3409, 3102, 1619, 1187,1072, 980, 846 |
| 33 | 34c | 0.81(3H, s), 0.88(3H, s), 0.93(3H, s), 1.08 (3H, d, J=7.5Hz), 1.99(1H, d, J=18Hz), 2.45 (4H, br.s), 3.00(1H, d, J=18Hz), 4.35–4.75 (4H, m), 6.26(1H, s) | 3189, 1712, 1620, 1185, 1071, 976, 840 |
| 34 | 34d | 0.81(3H, s), 0.89(3H, s), 0.94(3H, s), 1.08 (3H, d, J=7.4Hz), 2.00(1H, d, J=18Hz), 2.92 (3H, s), 2.99(1H, d, J=18Hz), 4.30–4.50(4H, m), 6.25(1H, s) | 3450, 3200, 1623, 1607, 1145, 1065, 974, 964, 821 |
| 35 | 34e | 0.87(3H, s), 0.96(3H, s), 0.98(3H, s), 1.14 (3H, d, J=7.4Hz), 2.02(1H, d, J=18Hz), 3.11 (1H, d, J=18Hz), 3.57(1H, br.s), 4.46–4.65 (4H, m), 6.14(1H, s)(CDCl$_3$) | 3467, 3212, 1627, 1611,1183, 1167, 1099, 973, 820 |
| 36 | 34f | 0.81(3H, s), 0.90(3H, s), 0.92(3H, s), 1.08(3H, d, J=7.4Hz), 2.01(1H, d, J=18Hz), 2.98(1H, d, J=18Hz), 3.72(2H, m), 4.20–4.50(6H, m), 6.32(1H, s) | 3365, 2685, 1626, 1610, 1184, 1075, 975, 897, 830 |

Reactions in Examples 37–40 are illustrated by the following reaction scheme.

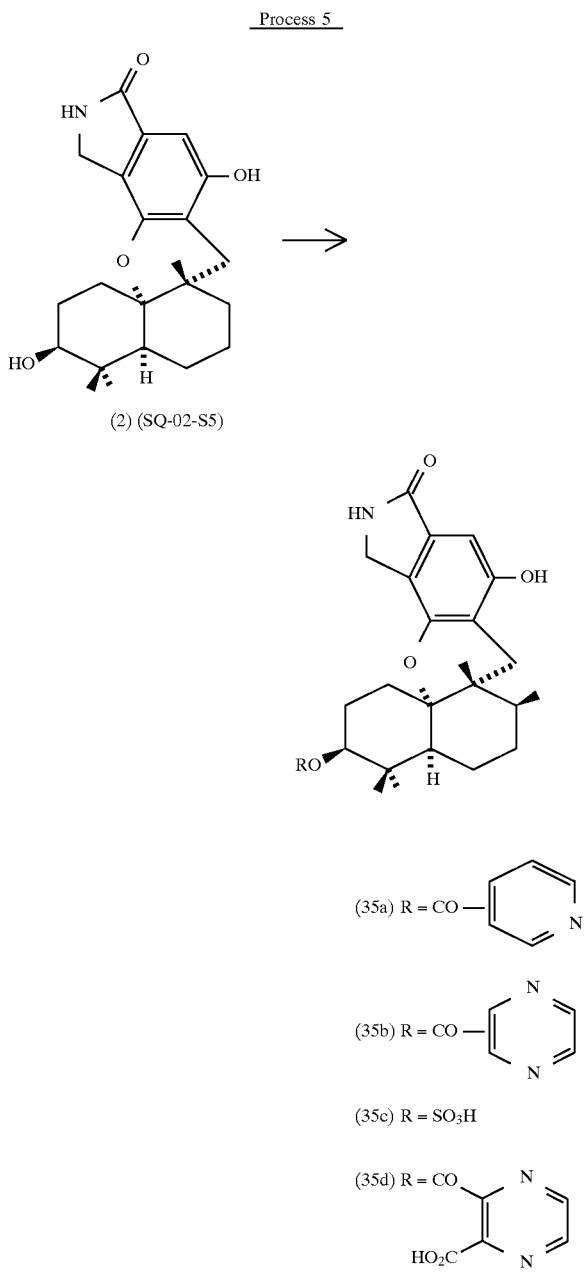

Example 37

Synthesis of (6aR,7S,9aS,11S,13aS)-2,3,6,6a,7,8,9, 9a,10,11,12,13-dodecahydro-5-hydroxy-6a,7,10,10-tetramethyl-3-oxo-11-[(3-pyridyl)carbonyloxy]-1H-benzo[8,8a][1]benzopyrano[2,3-e]isoindole (35a)

Under nitrogen, 0.15 ml (1.07 mmol) of triethylamine, 130 mg (1.06 mmol) of dimethylaminopyridine, and 185 mg (1.04 mmol) of nicotinoyl chloride hydrochloride were added sequentially to a solution of Compound (2) (50 mg, 0.13 mmol) in dry DMF (5.0 ml), and the mixture stirred for 3 days at room temperature. After addition of ice-water, the reaction was extracted with ethyl acetate. The extract was washed with an aqueous saturated sodium hydrogen carbonate solution and water, and dried over anhydrous magnesium sulfate. After concentration under reduced pressure, the un-purified residue so obtained was dissolved in 5.0 ml of dry methanol. To the solution was added 20 µl (0.02 mmol) of 1M sodium methoxide/methanol solution, followed by stirring for 1.5 hours. To the reaction was added 20 mg of ion-exchange resin (Amberlite, IRC-50), and the mixture stirred for additional 30 min. The ion-exchange resin was filtered away. The filtrate was concentrated under reduced pressure. The residue was purified by a preparative thin layer chromatography (Merck, Kieselgel 60 F254, 0.5 mm; chloroform:methanol=10: 1) to give 45 mg (71%) of Compound (35a).

Melting point: 289°–291° C. (decomp.) (acetone-n-hexane)

LSIMS: m/z 491 $[M+H]^+$

Other physical properties are shown in Table 5.

Example 38

Synthesis of (6aR,7S,9aS,11S,13aS)-2,3,6,6a,7,8,9, 9a,10,11,12,13-dodecahydro-5-hydroxy-6a,7,10,10-tetramethyl-3-oxo-11-[(2-pyrazyl)carbonyloxy]-1H-benzo[8,8a][1]benzopyrano[2,3-e]isoindole (35b)

Under nitrogen, 0.20 ml (1.43 mmol) of triethylamine, 175 mg (1.43 mmol) of dimethylaminopyridine, 162 mg (1.30 mmol) of 2-pyrazine carboxylic acid and 250 mg (1.30 mmol) of 1-(3-dimethylaminopropyl)-3-ethylcarbodiimide hydrochloride were added sequentially to a solution of Compound (2) (50 mg, 0.13 mmol) in dry DMF (5.0 ml), and the mixture stirred for 3 days at room temperature. After addition of ice-water, the reaction was extracted with ethyl acetate. The extract was washed with an aqueous saturated sodium hydrogen carbonate solution and water, dried over anhydrous magnesium sulfate, and concentrated under reduced pressure. The residue was purified by a preparative thin layer chromatography (Merck, Kieselgel 60 F254, 0.5 mm; chloroform:methanol=10:1) to give 24 mg (38%) of Compound (35b).

Melting point: 271°–274° C. (decomp.) (diethyl ether)

LSIMS: m/z 492 $[M+H]^+$

Other physical properties are shown in Table 5.

Example 39

Synthesis of (6aR,7S,9aS,11S,13aS)-2,3,6,6a,7,8,9, 9a,10,11,12,13-dodecahydro-5-hydroxy-6a,7,10,10-tetramethyl-3-oxo-11-sulfoxy-1H-benzo[8,8a][1] benzopyrano[2,3-e]isoindole (35c)

Under nitrogen, 134 mg (0.84 mmol) of sulfur trioxide-pyridine complex was added to a solution of Compound (9) (Example 10) (400 mg, 0.84 mmol) in 5.0 ml of pyridine, and the mixture stirred for one hour at 100° C. The reaction was continued for additional 3 hours at the same temperature while adding the same amount of sulfur trioxide-pyridine complex at every one hour. The reaction mixture was then concentrated under reduced pressure. The residue was run through an ion-exchange resin (Dowex 50W×8; 160–200 mesh; 5 g) to remove pyridine. The eluate was adjusted to pH 8 with an aqueous saturated sodium hydrogen carbonate solution and desalted using HP-20 (50 g) to give 450 mg of crude intermediate. The crude material was dissolved in 50 ml of methanol and 1 ml of water. After the addition of 80 mg of 10% palladium-carbon, the solution was catalytically reduced under atomospheric pressure for 3 hours. The palladium-carbon was then filtered off. The filtrate was concentrated under reduced pressure. The residue was run through the above resin (Dowex 50W×8; 5 g), and purified by a reverse phase chromatography (YMC-GEL ODS-AM 120-S50; 1.0 L; acetonitrile:water=1:4) followed by crystallization from ethyl acetate to give 230 mg (50%) of Compound (35c).

Melting point: 205°–209° C. (decomp.)

due was purified by a silica gel column chromatography (silica gel 4.0 g; chloroform:methanol:water=8:2:0.2) to give 20 mg (27%) of Compound (35d).

LSIMS: m/z 535 [M+H]$^+$

Other physical properties are shown in Table 5.

TABLE 5

| Ex. No. | Comp. | $^1$H-NMR δ (DMSO-d$_6$) ppm | IR ν max (Nujol) cm$^{-1}$ |
|---|---|---|---|
| 37 | 35a | 0.95(6H, s), 1.17(3H, d, J=7.5Hz), 1.18(3H, s), 2.31(1H, d, J=18.0Hz), 3.27(1H, d, J=18.0Hz), 4.33(1H, ABq, A part, J=16.8Hz), 4.39(1H, ABq, B part, J=16.8Hz), 5.09(1H, br.s), 6.41(1H, s), 7.11(1H, s), 7.46(1H, dd, J=8.1, 4.8Hz), 8.33(1H, dt, J=8.1, 1.8Hz), 8.81(1H, dd, J=4.8, 1.8Hz), 9.25(1H, d, J=1.8 Hz) (CDCl$_3$) | 3248, 1725, 1698, 1652, 1626, 1602, 1505, 1278, 1133, 1110, 1075 |
| 38 | 35b | 0.96(3H, s), 0.99(3H, s), 1.23(3H, d, J=8.1 Hz), 1.24(3H, s), 2.29(1H, d, J=18Hz), 3.29 (1H, d, J=18Hz), 4.34(2H, s), 5.08(1H, br.s), 6.80(1H, s), 7.35(1H, s), 8.82(1H, dd, J=2.4, 1.5), 8.86(1H, d, J=2.4Hz), 9.25(1H, d, J=1.5 Hz) (Acetone-d$_6$) | 3234, 1705, 1628, 1139, 1075, 952 |
| 39 | 35c | 0.83(3H, s), 0.87(3H, s), 0.97(3H, s), 1.10 (3H, d, J=7.2Hz), 1.20–2.20(11H, m), 3.06 (1H, d, J=18Hz), 3.88(1H, s), 4.07(1H, ABq, Apart, J=16.8Hz), 4.17(1H, ABq, B part, J=16.8Hz), 6.60(1H, s), 8.23(1H, s), 9.50(1H, br.s) | 3399, 1677, 1629 |
| 40 | 35d | 0.84(3H, s), 0.87(3H, s), 1.05(3H, d, J=7.5 Hz), 1.08(3H, s), 2.11(1H, d, J=18Hz), 3.06 (1H, d, J=18Hz), 4.12(1H, ABq, A part, J=16.5 Hz), 4.22(1H, ABq, B part, J=16.5Hz), 4.82 (1H, br.s), 6.63(1H, s), 8.32(1H, s), 8.53(1H, s), 8.63(1H, s) 9.75(1H, s) | 3374, 1721, 1678, 1627, 1560, 1183, 1162, 1097, 1074, 951 |

Elemental Analysis for C$_{23}$H$_{31}$NO$_7$S .19/4 H$_2$O Calcd.: C, 50.12%; H, 6.68%; N, 2.54%; S, 5.82% Found: C, 50.02%; H, 6.65%; N, 2.81%; S, 6.05%

Other physical properties are shown in Table 5

Example 40

Synthesis of (6aR,7S,9aS,11S, 13aS)-11-(3-carboxy-2-pyrazyl)carbonyloxy-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole (35d)

i) To a solution of Compound (9b) (70 mg, 0.14 mmol) in 3 ml of dry DMF were added 51 mg (0.42 mmol) of 4-dimethylaminopyridine and 63 mg (0.42 mmol) of pyrazine 2,3-dicarboxylic acid anhydride, and the mixture stirred for 2 hours at room temperature. After addition of ice-water, the reaction mixture was extracted with ethyl acetate. The extract was washed with 1N HCl and saturated brine, dried over anhydrous magnesium sulfate, and concentrated under reduced pressure. The residue was purified by a silica gel column chromatography (silica gel 4.0 g; chloroform:methanol=19:1–9:1) to give 37 mg of a powdery material.

ii) The product from the above step i) was dissolved in 4 ml of dry THF. To the solution was added dropwise 0.11 ml (0.11 mmol) of 1M tetrabutylammonium fluoride/THF solution under ice-cooling, and the mixture stirred for one hour at the same temperature. After addition of ice-water, the reaction mixture was extracted with ethyl acetate. The extract was concentrated under reduced pressure. The resi-

Example 41

Synthesis of (6aR,7S,9aS,11R,13aS)-2,3,6,6a,7,8,9,9a,10,11,12,13-dodecahydro-5-hydroxy-6a,7,10,10-tetramethyl-11-methanesulfonyloxy-3-oxo-1H-benzo[8,8a][1]benzopyrano[2,3-e]isoindole (13b)

The reactions in this Example are illustrated by the following reaction scheme.

Process 7

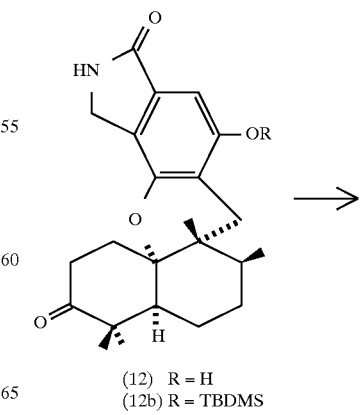

(12) R = H
(12b) R = TBDMS

-continued
Process 7

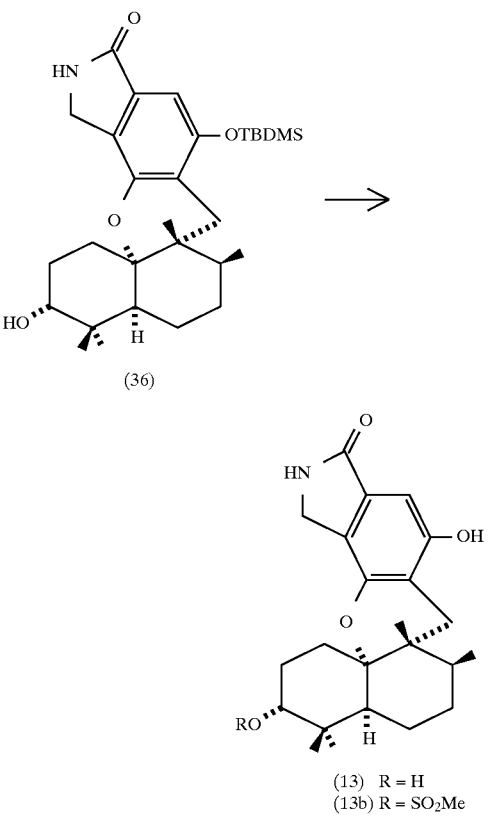

Step-1: Synthesis of (6aR,7S,9aS,13aS)-5-(t-butyldimethylsilyloxy)-2,3,6,6a,7,8,9,9a,10,11,12,13-dodecahydro-6a,7,10,10-tetramethyl-3,11-dioxo-1H-benzo[8,8a][1]benzopyrano[2,3-e]isoindole (12b)

To a solution of Compound (12) (132 mg, 0.345 mmol) in 5 ml of dry DMF were added 155 mg (2.28 mmol) of imidazole and 157 mg (1.04 mmol) of t-butyl(chloro)dimethylsilane, and the mixture stirred for 3 hours at room temperature. After addition of ice-water, the reaction mixture was extracted with ethyl acetate. The extract was washed with water and saturated brine, dried over anhydrous magnesium sulfate, and concentrated under reduced pressure. The residue was purified by a column chromatography (Merck, Lobar column, size A; toluene:ethyl acetate=1:1) to give 159 mg (93%) of Compound (12b).

$^1$H NMR (CDCl$_3$) δ: 0.26 (3H, s), 0.29 (3H, s), 0.96 (3H, s), 1.00 (3H, s), 1.02 (9H, s), 1.13 (3H, d, J=7.5 Hz), 1.18 (3H, s), 2.27 (1H, d, J=18 Hz), 3.11 (1H, d, J=18 Hz), 4.31 (1H, ABq, A part, J=16.8 Hz), 4.34 (1H, ABq, B part, J=16.8 Hz), 6.66 (1H, s), 6.87 (1H, s) ppm Step-2: Synthesis of (6aR, 7S,9aS, 11R,13aS)-5-(t-butyldimethylsilyloxy)-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole (36)

To a solution of the above Compound (12b) (175 mg, 0.35 mmol) in 2 ml of methanol was added 17 mg (0.45 mmol) of sodium borohydride under ice-cooling, and the mixture stirred for 30 min. After addition of water, the reaction mixture was extracted with ethyl acetate. The extract was washed with water and saturated brine, dried over anhydrous magnesium sulfate, and concentrated under reduced pressure. The residue was purified by a column chromatography (Merck, Lobar column, size A; chloroform:methanol=50:1) to give 106 mg (60%) of Compound (36).

$^1$H NMR (CDCl$_3$) δ: 0.24 (3H, s), 0.28 (3H, s), 0.87 (3H, s), 0.98 (3H, s), 1.01 (3H, s), 1.02 (9H, s), 1.13 (3H, d, J=7.8 Hz), 2.19 (1H, d, J=18 Hz), 3.12 (1H, d, J=18 Hz), 3.73 (1H, br.s), 4.35 (2H, s), 6.62 (1H, s), 6.83 (1H, s) ppm Step-3: Synthesis of (13b)

To a solution of the above Compound (36) (42 mg, 0.084 mmol) in 5 ml of dry dichloromethane were added 34 μl (0.244 mmol) of triethylamine and 14 μl (0.181 mmol) of methanesulfonyl chloride under ice-cooling, and the mixture stirred for 15 min at the same temperature. After addition of water, the reaction mixture was extracted with ethyl acetate. The extract was washed with saturated brine, dried over anhydrous magnesium sulfate, and concentrated under reduced pressure to give an oil. This oil was dissolved in 2 ml of dry THF. To the solution was added 0.11 ml (0.11 mmol) of 1M tetrabutylammonium fluoride/THF solution under ice-cooling, and the mixture stirred for 20 min at the same temperature. After addition of ice-water, the reaction mixture was extracted with ethyl acetate. The extract was washed with 1N HCl, water, an aqueous saturated sodium hydrogen carbonate solution, and saturated brine, dried over anhydrous magnesium sulfate, and concentrated under reduced pressure. The residue was purified by a preparative thin layer chromatography (Merck, Kieselgel 60 F254, 0.5 mm; chloroform:methanol=15:1) to give 38 mg (98%) of Compound (13b).

Melting point: 170°–173° C. (diethyl ether)

LSIMS: m/z 464 [M+H]$^+$

Other physical properties are shown in Table 6.

Reactions in Examples 42 and 43 are illustrated by the following reaction scheme.

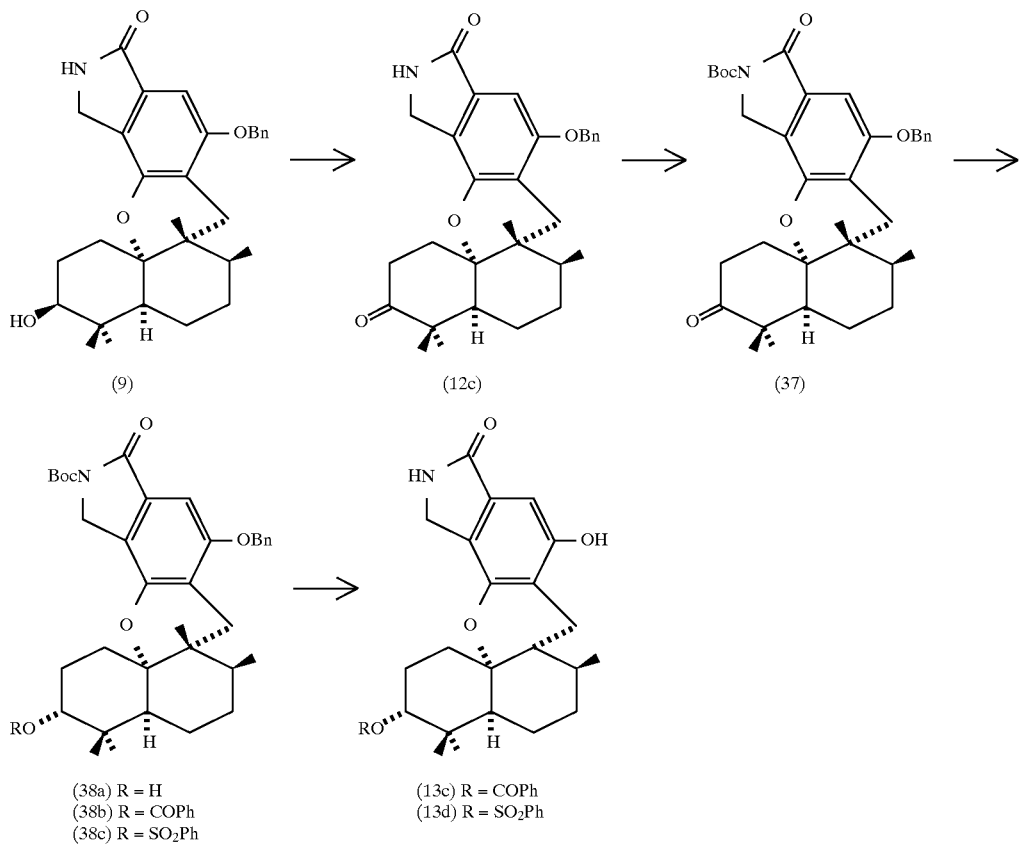

(9) (12c) (37)

(38a) R = H
(38b) R = COPh
(38c) R = SO₂Ph (13c) R = COPh
(13d) R = SO₂Ph

Example 42

Synthesis of (6aR,7S,9aS,11R,13aS)-11-benzoyloxy-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole (13c)

Step-1: Synthesis of (6aR,7S,9aS,13aS)-5-benzyloxy-2,3,6,6a,7,8,9,9a,10,11,12,13-dodecahydro-6a,7,10,10-tetramethyl-3,11-dioxo-1H-benzo[8,8a][1]benzopyrano[2,3-e]isoindole (12c)

To a solution of Compound (9) (Example 10) (2.00 g, 4.21 mmol) in 200 ml of acetone was added dropwise 1.30 ml (5.2 mmol) of the Jones reagent, and the mixture stirred for 10 min at the same temperature. The reaction was neutralized with an aqueous saturated sodium hydrogen carbonate solution, and acetone was evaporated under reduced pressure. Water was added to the residue, and extracted with ethyl acetate. The extract was washed with water and saturated brine, dried over anhydrous magnesium sulfate, and concentrated under reduced pressure. The residue was purified by a silica gel column chromatography (silica gel 150 g; chloroform:methanol=100:1–50: 1) to give 1.746 g (89%) of Compound (12c).

¹H NMR (CDCl₃) δ: 0.96 (3H, s), 0.99 (3H, s), 1.12 (3H, d, J=7.5 Hz), 1.18 (3H, s), 2.36 (1H, d, J=18.3 Hz), 3.13 (1H, d, J=18.3 Hz), 4.31 (1H, ABq, A part, J=17.4 Hz), 4.38 (1H, ABq, B part, J=17.4 Hz), 5.12 (2H, s), 6.51 (1H, s), 7.03 (1H, s), 7.30–7.50 (5H, m) ppm Step-2: Synthesis of (6aR,7S,9aS,13aS)-5-benzyloxy-2-(t-butoxycarbonyl)-2,3,6,6a,7,8,9,9a,10,11,12,13-dodecahydro-6a,7,10,10-tetramethyl-3, 11-dioxo-1H-benzo[8,8a][1]benzopyrano[2,3-e]isoindole (37)

To a solution of the above Compound (12c) (974 mg, 2.06 mmol) in 30 ml of dry THF were added 277 mg (2.27 mmol) of dimethylaminopyridine and 0.95 ml (4.13 mmol) of di-t-butyl dicarbonate, and the mixture stirred for 1 hour and 20 min at room temperature. After addition of water, the reaction mixture was extracted with ethyl acetate. The extract was washed with 1N HCl, water, an aqueous saturated sodium hydrogen carbonate solution, and saturated brine, dried over anhydrous magnesium sulfate, and concentrated under reduced pressure. The residue was purified by a silica gel column chromatography (silica gel 40 g; n-hexane:ethyl acetate=6:1–1:1) and by crystallization from diisopropyl ether to give 1.12 g (95%) of Compound (37).

Melting point: 188°–190° C.

Elemental Analysis for C₃₅H₄₃NO₆ Calcd.: C, 73.27%; H, 7.56%; N, 2.44% Found: C, 73.21%; H, 7.56%; N, 2.45%

¹H NMR (CDCl₃) δ: 0.95 (3H, s), 0.99 (3H, s), 1.11 (3H, d, J=7.5 Hz), 1.25 (3H, s), 1.60 (9H, s), 2.35 (1H, d, J=18.3 Hz), 3.14 (1H, d, J=18.3 Hz), 4.60 (1H, ABq, A part, J=16.8 Hz), 4.70 (1H, ABq, B part, J=16.8 Hz), 5.11 (2H, s), 7.03 (1H, s), 7.32–7.48 (5H, m) ppm IR ν$_{max}$ (CHCl₃): 1773, 1729, 1707, 1626, 1609 cm⁻¹

Step-3: Synthesis of (6aR,7S,9aS,11R,13aS)-5-benzyloxy-2-(t-butoxycarbonyl)-2,3,6,6a,7,8,9,9a,10,11,12,13-dodecahydro-11-hydroxy-6a,7, 10, 10-tetramethyl-3-oxo-1H-benzo[8,8a][1]benzopyrano[2,3-e]isoindole (38a)

The above Compound (37 ) (1.119 g, 1.95 mmol) was subjected to a reaction similar to that of Step-2 in Example 41, and the product was purified by a column chromatography (Merck, Lobar column, size B; n-hexane:ethyl acetate=2:1) and by crystallization from diisopropyl ether to give 721 mg (64%) of Compound (38a).

Melting point: 138°–140° C.

Elemental analysis for $C_{35}H_{45}NO_6 \cdot 1/2H_2O$ Calcd.: C, 71.89%; H, 7.93%; N, 2.40% Found: C, 71.86%; H, 8.23%; N, 2.27%

$^1$H NMR (CDCl$_3$) δ: 0.87 (3H, s), 0.98 (3H, s), 1.03 (3H, s), 1.12 (3H, d, J=7.5 Hz), 1.60 (9H, s), 2.27 (1H, d, J=18.3 Hz), 3.14 (1H, d, J=18.3 Hz), 3.72 (1H, m), 4.64 (1H, ABq, A part, J=16.8 Hz), 4.68 (1H, ABq, B part, J=16.8 Hz), 5.09 (1H, ABq, A part, J=12.0 Hz), 5.10 (1H, ABq, B part, J=12.0 Hz), 6.98 (1H, s), 7.30–7.48 (5H, m) ppm IR ν$_{max}$ (CHCl$_3$): 3610, 3026, 1771, 1728, 1625, 1607 cm$^{-1}$ Step-4: Synthesis of (6aR,7S,9aS,11R,13aS)-11-benzoyloxy-5-benzyloxy-2-(t-butoxycarbonyl)-2,3,6,6a,7,8,9,9a,10,11,12,13-dodecahydro-6a,7,10,10-tetramethyl-3-oxo-1H-benzo[8,8a][1]benzopyrano[2,3-e]isoindole (38b)

To a solution of Compound (38a) (40 mg, 0.07 mmol) in 1 ml of dry dichloromethane were added 13 mg (0.106 mmol) of dimethylaminopyridine and 10 μl (0.086 mmol) of benzoyl chloride under ice-cooling, and the mixture stirred for 3 hours at the same temperature. After addition of water, the reaction mixture was extracted with ethyl acetate. The extract was washed sequentially with 1N HCl, water, an aqueous saturated sodium hydrogen carbonate solution, and saturated brine, dried over anhydrous magnesium sulfate, and concentrated under reduced pressure. The residue was purified by a preparative thin layer chromatography (Merck, Kieselgel 60 F254, 0.5 mm; n-hexane:ethyl acetate=3:1) to give 43 mg (91%) of Compound (38b).

$^1$H NMR (CDCl$_3$) δ: 0.90 (3H, s), 0.94 (3H, s), 1.15 (3H, d, J=7.5 Hz), 1.26 (3H, s), 1.62 (9H, s), 2.30 (1H, d, J=18.3 Hz), 3.17 (1H, d, J=18.3 Hz), 4.72 (2H, s), 5.11 (2H, s), 5.20 (1H, m), 6.99 (1H, s), 7.30–7.62 (8H, m), 8.05–8.12 (2H, m) ppm Step-5: Synthesis of (13c)

To a solution of Compound (38b) (42 mg, 0.062 mmol) in 2 ml of dry dichloromethane were added 20 μl (0.18 mmol) of anisole and 11 μl (0.14 mmol) of trifluoroacetic acid under ice-cooling, and the mixture stirred for 21 hours at room temperature. Under ice-cooling, to the reaction mixture was added an aqueous saturated sodium hydrogen carbonate solution, followed by extraction with ethyl acetate. The extract was washed with saturated brine, dried over anhydrous magnesium sulfate, and concentrated under reduced pressure to give a powdery material.

$^1$H NMR (CDCl$_3$) δ: 0.92 (3H, s), 0.94 (3H, s), 1.16 (3H, d, J=7.2 Hz), 1.26 (3H, s), 2.32 (1H, d, J=18.0 Hz), 3.17 (1H, d, J=18.0 Hz), 4.41 (1H, ABq, A part, J=16.2 Hz), 4.47 (1H, ABq, B part, J=16.2 Hz), 5.13 (2H, s), 5.18 (1H, m), 6.63 (1H, s), 7.12 (1H, s), 7.31–7.62 (8H, m), 8.02–8.10 (2H, m) ppm This material was then catalytically reduced as in Step-2 of Example 31, and the product was purified by a preparative thin layer chromatography (Merck, Kieselgel 60 F254, 0.5 mm; chloroform: methanol =15: 1) to give 26 mg (88%) of Compound (13c).

EIMS: m/z 489 [M]$^+$

Other physical properties are shown in Table 6.

Example 43

Synthesis of (6aR,7S,9aS,11R,13aS)-2,3,6,6a,7,8,9,9a,10,11,12,13-dodecahydro-5-hydroxy-6a,7,10,10-tetramethyl-3-oxo-11-phenylsulfonyloxy-1H-benzo[8,8a][1]benzopyrano[2,3-e]isoindole (13d)

Step-1: Synthesis of (6aR,7S,9aS,11R,13aS)-5-benzyloxy-2-(t-butoxycarbonyl)-2,3,6,6a,7,8,9,9a,10,11,12,13-dodecahydro-6a,7,10,10-tetramethyl-3-oxo-11-phenylsulfonyloxy-1H-benzo[8,8a][1]benzopyrano[2,3-e]isoindole (38c)

The crude product was obtained from Compound (38a) (40 mg, 0.07 mmol) as in Step-4 of Example 42 except that benzenesulfonyl chloride is used. The product was purified by a preparative thin layer chromatography (Merck, Kieselgel 60 F254, 0.5 mm; n-hexane:ethyl acetate=2:1) to give 48 mg (97%) of Compound (38c).

$^1$H NMR (CDCl$_3$) δ: 0.75 (3H, s), 0.85 (3H, s), 1.04 (3H, s), 1.11 (3H, d, J=7.2 Hz), 1.61 (9H, s), 2.24 (1H, d, J=18.3 Hz), 3.08 (1H, d, J=18.3 Hz), 4.60 (1H, ABq, A part, J=17.1 Hz), 4.65 (1H, ABq, B part, J=17.1 Hz), 4.71 (1H, dd, J=12.0, 4.8 Hz), 5.08 (2H, s), 6.97 (1H, s), 7.30–7.45 (5H, m), 7.53–7.70 (3H, m), 7.93–7.98 (2H, m) ppm Step-2: Synthesis of (13d)

Compound (38c) (47 mg, 0.066 mmol) was reacted according to the procedure of Step-5 in Example 42, and the product was purified by a preparative thin layer chromatography (Merck, Kieselgel 60 F254, 0.5 mm; chloroform:methanol=15:1) to give 30 mg (88%) of Compound (13d).

Melting point: 160°–162° C. (diethyl ether-pentane)

LSIMS: m/z 526 [M+H]$^+$

Other physical properties are shown in Table 6.

TABLE 6

| Ex. No. | Comp. | $^1$H-NMR δ (DMSO-d$_6$) ppm | IR ν max (Nujol) cm$^{-1}$ |
|---|---|---|---|
| 41 | 13b | 0.81 (3H, s), 0.93 (3H, s), 1.00 (3H, s), 1.10 (3H, d, J = 7.2 Hz), 2.11 (1H, d, J = 18 Hz), 3.04 (1H, d, J = 18 Hz), 3.20 (3H, s), 4.12 (1H, ABq, A part, J = 16.8 Hz), 4.21 (1H, ABq, B part, J = 16.8 Hz), 4.74 (1H, m), 6.64 (1H, s), 8.33(1H, s) | 3579, 3286, 1677, 1629, 1610, 1173, 1076, 937, 874 |
| 42 | 13c | 0.84 (3H, s), 0.87 (3H, s), 1.14 (3H, d, J = 7.2 Hz), 1.19 (3H, s), 2.14 (1H, d, J = 18 Hz), 3.08 (1H, d, J = 18 Hz), 4.19 (1H, ABq, A part, J = 16.8 Hz), 4.23 (1H, ABq, B part, J = 16.8 Hz), 5.15 (1H, m), 6.65 (1H, s), 7.50–7.72 (3H, m), 7.95–8.05 (2H, m), 8.33 (1H, s) | 3370, 3237, 1706, 1618, 1500, 1277, 1071 |
| 43 | 13d | 0.56 (3H, s), 0.77 (3H, s), 0.95 (3H, s), 1.09 (3H, d, J = 7.5 Hz), 2.08 (1H, d, J = 18 Hz), 3.00 (1H, d, J = 18 Hz), 4.09 (1H, ABq, A part, J = 16.8 Hz), 4.17 (1H, ABq, B part, J = 16.8 Hz), 4.70 (1H, m), 6.62 (1H, s), 7.63–7.82 (3H, m), 7.93–8.03 (2H, m), 8.31 (1H, s) | 3311, 1692, 1628, 1613, 1183, 1098, 1073, 934, 872 |

Reactions in Examples 44–47 are illustrated by the following reaction scheme.

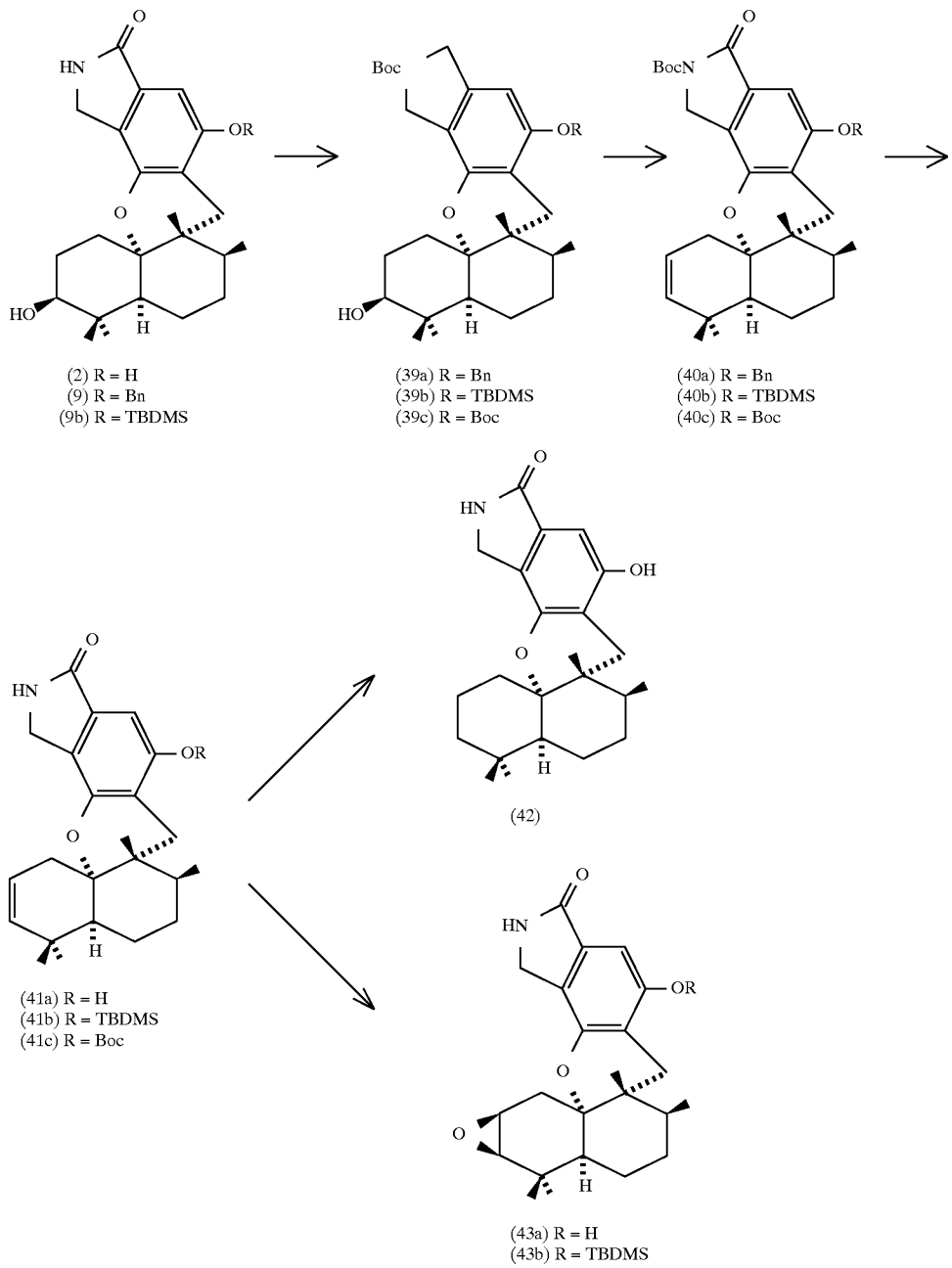

Example 44

Synthesis of (6aR,7S,9aS,13aS)-5-benzyloxy-2-(t-butoxycarbonyl)-2,3,6,6a,7,8,9,9a,10,13-decahydro-6a,7,10,10-tetramethyl-3-oxo-1H-benzo[8,8a][1]benzopyrano[2,3-e]isoindole (40a)

Step-1: Synthesis of (6aR,7S,9aS,11S,13aS)-5-benzyloxy-2-(t-butoxycarbonyl)-2,3,6,6a,7,8,9,9a,10,11,12,13-dodecahydro-11-hydroxy-6a,7, 10, 10-tetramethyl-3-oxo-1H-benzo[8,8a][1]benzopyrano[2,3-e]isoindole (39a)

Compound (9) (Example 10) (500 mg, 1.05 mmol) was reacted as in Step-2 of Example 42, and the crude product was purified by a column chromatography (Merck, Lobar column, size B; n-hexane:ethyl acetate=3:1) to give 510 mg (84%) of Compound (39a).

Melting point: 138°–140° C.

Elemental analysis for $C_{35}H_{45}NO_6 \cdot 1/4H_2O$ Calcd.: C, 72.45%; H, 7.90%; N, 2.41% Found: C, 72.21%; H, 7.98%; N, 2.66%

$^1$H NMR (CDCl$_3$) δ: 0.90 (3H, s), 0.98 (3H, s), 1.02 (3H, s), 1.14 (3H, d, J=7.5 Hz), 1.60 (9H, s), 2.27 (1H, d, J=18.3 Hz), 3.19 (1H, d, J=18.3 Hz), 3.58 (1H, br.s), 4.58 (1H, ABq, A part, J=16.8 Hz), 4.67 (1H, ABq, B part, J=16.8 Hz), 5.10 (2H, s), 6.96 (1H, s), 7.31–7.49 (5H, m) ppm Step-2: Synthesis of (40a)

Under nitrogen, 344 mg (1.31 mmol) of triphenylphosphine and 170 μl (1.08 mmol) of diethyl azodicarboxylate were added to a solution of Compound (39a) (503 mg, 0.875 mmol) in 35 ml of dry benzene, and the mixture heated to reflux for 25 min. After cooling to room temperature, the same amounts of triphenylphosphine and diethyl azodicarboxylate were added to the reaction mixture. The mixture was then heated to reflux for 25 min, and concentrated under reduced pressure to a half volume. The residue was purified by a silica gel column chromatography (silica gel 55 g; n-hexane:ethyl acetate=6:1) to give 434 mg (89%) of Compound (40a).

$^1$H NMR (CDCl$_3$) δ: 0.91 (6H, s), 0.96 (3H, s), 1.14 (3H, d, J=7.5 Hz), 1.59 (9H, s), 2.30 (1H, d, J=18 Hz), 3.18 (1H, d, J=18 Hz), 4.52 (1H, ABq, A part, J=17.1 Hz), 4.58 (1H, d, ABq, J=17.1 Hz), 5.09 (1H, ABq, A part, J=11.7 Hz), 5.11 (1H, ABq, B part, J=11.7 Hz), 5.37–5.56 (2H, m), 6.96 (1H, s), 7.31–7.48 (5H, m) ppm Example 45

Synthesis of (6aR,7S,9aS,11R,12S,13aS)-11,12-epoxy-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole (43a)

Step-1: Synthesis of (6aR,7S,9aS,11S,13aS)-5-(t-butyldimethylsilyloxy)-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole (9b)

Compound (2) (Example 3) (385 mg, 1.0 mmol) was reacted as in Step-1 of Example 41, and the crystalline crude product was recrystallized from ethyl acetate-diethyl ether to give 469 mg (94%) of Compound (9).

$^1$H NMR (CDCl$_3$) δ: 0.24 (3H, s), 0.27 (3H, s), 0.90 (3H, s), 0.98 (3H, s), 1.01 (3H, s), 1.02 (9H, s), 1.15 (3H, d, J=7.5 Hz), 2.19 (1H, d, J=18 Hz), 3.17 (1H, d, J=18 Hz), 3.56 (1H, br.s), 4.31 (2H, s), 6.55 (1H, s), 6.82 (1H, s) ppm Step-2: Synthesis of (6aR,7S,9aS,11S,13aS)-2-(t-butoxycarbonyl)-5-(t-butyldimethylsilyloxy)-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole (39b)

Compound (9b) (10 mg, 0.02 mmol) was reacted as in Step-2 of Example 42, and the crude product was purified by a preparative thin layer chromatography (Merck, Kieselgel 60 F254, 0.5 mm; n-hexane:ethyl acetate=2:1) to give 11 mg (92%) of Compound (39b).

$^1$H NMR (CDCl$_3$) δ: 0.23 (3H, s), 0.26 (3H, s), 0.89 (3H, s), 0.99 (3H, s), 1.01 (9H, s), 1.02 (3H, s), 1.15 (3H, d, J=7.2 Hz), 1.59 (9H, s), 2.18 (1H, d, J=18 Hz), 3.16 (1H, d, J=18 Hz), 3.57 (1H, br.s), 4.57 (1H, ABq, A part, J=17.1 Hz), 4.64 (1H, ABq, B part, J=17.1 Hz), 6.81(1H, s) ppm Step-3: Synthesis of (6aR,7S,9aS,13aS)-2-(t-butoxycarbonyl)-5-(t-butyldimethylsilyloxy)-2,3,6,6a,7,8,9,9a,10,13-decahydro-6a,7,10,10-tetramethyl-3-oxo-1H-benzo[8,8a][1]benzopyrano[2,3-e]isoindole (40b)

Compound (39b) (152 mg, 0.254 mmol) was reacted as in Step-2 of Example 44, and the crude product was purified by a silica gel column chromatography (silica gel 25 g; n-hexane:ethyl acetate=10:1) to give 116 mg (79%) of Compound (40b).

$^1$H NMR (CDCl$_3$) δ: 0.23 (3H, s), 0.26 (3H, s), 0.90 (3H, s), 0.92 (3H, s), 0.95 (3H, s), 1.01 (9H, s), 1.15 (3H, d, J=7.2 Hz), 1.59 (9H, s), 2.21 (1H, d, J=18 Hz), 3.15 (1H, d, J=18 Hz), 4.51 (1H, ABq, A part, J=17.1 Hz), 4.56 (1H, ABq, B part, J=17.1 Hz), 5.35–5.55 (2H, m), 6.81(1H, s) ppm Step-4: Synthesis of (6aR,7S,9aS,13aS)-5-(t-butyldimethylsilyloxy)-2,3,6,6a,7,8,9,9a,10,13-decahydro-6a,7,10,10-tetramethyl-3-oxo-1H-benzo[8,8a][1]benzopyrano[2,3-e]isoindole (41b)

To a solution of Compound (40b) (115 mg, 0.20 mmol) in 10 ml of dry dichloromethane were added 50 μl (0.46 mmol) of anisole and 32 μl (0.42 mmol) of trifluoroacetic acid under ice-cooling, and the mixture stirred for 4 hours at room temperature and allowed to stand over night. To the reaction mixture was added an aqueous saturated sodium hydrogen carbonate solution under ice-cooling, followed by extraction with ethyl acetate. The extract was washed with water and saturated brine, dried over anhydrous magnesium sulfate, and concentrated under reduced pressure. The residue was purified by a column chromatography (Merck, Lobar column, size A; n-hexane:ethyl acetate=3:2) to give 94 mg (98%) of Compound (41b).

$^1$H NMR (CDCl$_3$) δ: 0.25 (3H, s), 0.27 (3H, s), 0.91 (3H, s), 0.95 (3H, s), 1.02 (9H, s), 1.15 (3H, d, J=7.5 Hz), 2.22 (1H, d, J=18 Hz), 3.15 (1H, d, J=18 Hz), 4.24 (2H, s), 5.35–5.55 (2H, m), 6.32 (1H, s), 6.81 (1H, s) ppm Step-5: Synthesis of (6aR,7S,9aS,11R,12S,13aS)-5-(t-butyldimethylsilyloxy)-11,12-epoxy-2,3,6,6a,7,8,9,9a,10,11,12,13-dodecahydro-6a,7,10,10-tetramethyl-3-oxo-1H-benzo[8,8a][1]benzopyrano[2,3-e]isoindole (43b)

To a solution of Compound (41b) (40 mg, 0.08 mmol) in 4 ml of dichloromethane was added 15 mg (0.18 mmol) of sodium hydrogen carbonate under ice-cooling. To the resulting suspension was added 25 mg (0.116 mmol) of 80% m-chloroperbenzoic acid, and the mixture stirred for 18.5 hours at room temperature. To the reaction mixture were added 0.5N aqueous sodium thiosulfate solution and an aqueous saturated sodium hydrogen carbonate solution, followed by extraction with ethyl acetate. The extract was washed with water and saturated brine, dried over anhydrous magnesium sulfate, and concentrated under reduced pressure. The residue was purified by a column chromatography (Merck, Lobar column, size A; chloroform:methanol=100:1) to give 28 mg (85%) of Compound (43b).

$^1$H NMR (CDCl$_3$) δ: 0.24 (3H, s), 0.27 (3H, s), 0.89 (3H, s), 0.99 (3H, s), 1.01 (9H, s), 1.08 (3H, s), 1.13 (3H, d, J=7.4 Hz), 2.20 (1H, d, J=18 Hz), 2.87 (1H, d, J=4.2 Hz), 3.08 (1H, d, J=18 Hz), 3.40 (1H, dd, J=5.7, 4.2 Hz), 4.28 (2H, s), 6.82 (1H, s), 6.94 (1H, s) ppm Step-6: Synthesis of (43a)

To a solution of the above Compound (43b) (28 mg, 0.056 mmol) in 2.0 ml of THF was added dropwise 75 μl (0.075 mmol) of 1M tetrabutylammonium fluoride under ice-cooling, and the mixture stirred for 2 hours at the same temperature. After addition of water, the reaction mixture was extracted with ethyl acetate. The extract was washed sequentially with 1N HCl, water, an aqueous saturated sodium hydrogen carbonate solution, and water, dried over anhydrous magnesium sulfate, and concentrated under reduced pressure. The residue was purified by a preparative thin layer chromatography (Merck, Kieselgel 60 F254, 0.5 mm; chloroform:methanol=10:1) to give 16 mg (74%) of Compound (43a).

EIMS: m/z 383 [M]$^+$

Other physical properties are shown in Table 7.

Example 46

Synthesis of (6aR,7S,9aS,13aS)-2,3,6,6a,7,8,9,9a,10,13-decahydro-5-hydroxy-6a,7,10,10-tetramethyl-3-oxo-1H-benzo[8,8a][1]benzopyrano[2,3-e]isoindole (41a)

Step-1: Synthesis of (6aR,7S,9aS,11S,13aS)-2-(t-butoxycarbonyl)-5-(t-butoxycarbonyloxy)-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole (39c)

The crude product was obtained from Compound (2) (10 mg, 0.026 mmol) substantially according to the procedure of Step-2 in Example 42 except that 4-fold equivalents of di-t-butyl dicarbonate and dimethylaminopyridine are used. The crude product was then purified by a preparative thin layer chromatography (Merck, Kieselgel 60 F254, 0.5 mm; n-hexane:ethyl acetate=2:1) to give 10 mg (70%) of Compound (39c).

$^1$H NMR (CDCl$_3$) δ: 0.89 (3H, s), 1.00 (3H, s), 1.04 (3H, s), 1.15 (3H, d, J=7.5 Hz), 1.56 (9H, s), 1.60 (9H, s), 2.10 (1H, d, J=18 Hz), 3.25 (1H, d, J=18 Hz), 3.58 (1H, br.s), 4.62 (1H, ABq, A part, J=17.1 Hz), 4.69 (1H, ABq, B part, J=17.1 Hz), 7.21 (1H, s) ppm Step-2: Synthesis of (6aR,7S,9aS,13aS)-2-(t-butoxycarbonyl)-5-(t-butoxycarbonyloxy)-2,3,6,6a,7,8,9,9a,10,13-decahydro-6a,7,10,10-tetramethyl-3-oxo-1H-benzo[8,8a][1]benzopyrano[2,3-e]isoindole (40c)

Compound (39c) (131 mg, 0.224 mmol) was subjected to a reaction similar to that in Step-2 of Example 44, and the crude product was purified by a silica gel column chromatography (silica gel 20 g; n-hexane:ethyl acetate=6:1) to give 88 mg (69%) of Compound (40c).

$^1$H NMR (CDCl$_3$) δ: 0.90 (3H, s), 0.93 (3H, s), 0.97 (3H, s), 1.15 (3H, d, J=7.2 Hz), 1.56 (9H, s), 1.59 (9H, s), 2.13 (1H, d, J=18 Hz), 3.23 (1H, d, J=18 Hz), 4.56 (1H, ABq, A part, J=17.4 Hz), 4.61 (1H, ABq, B part, J=17.4 Hz), 5.37–5.55 (2H, m), 7.20 (1H, s) ppm Step-3: Synthesis of (6aR,7S,9aS, 13aS)-5-(t-butoxycarbonyloxy)-2,3,6,6a,7,8,9,9a,10,13-decahydro-6a,7,10,10-tetramethyl-3-oxo-1H-benzo[8,8a][1]benzopyrano[2,3-e]isoindole (41c)

Compound (40c) (88 mg, 0.16 mmol) was subjected to a reaction similar to that in Step-4 of Example 45, and the crude product was purified by a column chromatography (Merck, Lobar column, size A; n-hexane:ethyl acetate=1:1) to give 68 mg (94%) of Compound (41c).

$^1$H NMR (CDCl$_3$) δ: 0.91 (3H, s), 0.92 (3H, s), 0.97 (3H, s), 1.15 (3H, d, J=7.2 Hz), 1.56 (9H, s), 2.14 (1H, d, J=18 Hz), 3.24 (1H, d, J=18 Hz), 4.29 (2H, s), 5.36–5.55 (2H, m), 6.27 (1H, s), 7.19 (1H, s) ppm Step-4: Synthesis of (41a)

The crude product was obtained from the above Compound (41c) according to the procedure in Step-4 of Example 45 except that 30-fold equivalents of trifluoroacetic acid are used. This material was crystallized from diethyl ether to give 38 mg (71%) of Compound (41a).

EIMS: m/z 367 [M]$^+$

Other physical properties are shown in Table 7.

Example 47

Synthesis of (6aR,7S,9aS,13aS)-2,3,6,6a,7,8,9,9a,10,11,12,13-dodecahydro-5-hydroxy-6a,7,10,10-tetramethyl-3-oxo-1H-benzo [8,8a] [1] benzopyrano [2,3-e]isoindole (42)

To the above Compound (41a) (35 mg, 0.095 mmol) dissolved in 5 ml of methanol was added 7 mg of 10% palladium-carbon, and the mixture stirred under hydrogen atmosphere for 7.5 hours at room temperature. After removing palladium-carbon by filtration, the filtrate was concentrated under reduced pressure. The residue was purified by a preparative thin layer chromatography (Merck, Kieselgel 60 F254, 0.5 mm; chloroform:methanol 15:1) to give 30 mg (85%) of Compound (42).

EIMS: m/z 369 [M]$^+$

Other physical properties are shown in Table 7.

TABLE 7

| Ex. No. | Comp. | $^1$H-NMR δ (DMSO-d$_6$) ppm | IR ν max (Nujol) cm$^{-1}$ |
|---|---|---|---|
| 46 | 41a | 0.85 (3H,s), 0.88 (3H, s), 0.90 (3H, s), 1.10 (3H, d, J = 7.5 Hz), 2.14 (1H, d, J = 18 Hz), 3.07 (1H, d, J = 18 Hz), 3.94 (1H, ABq, A part, J = 16.8 Hz), 4.08 (1H, ABq, B part, J = 16.8 Hz), 5.34–5.54(2H, m), 6.62 (1H, s), 8.26 (1H, s) | 3339, 3235, 1703, 1628, 1617, 1498, 1078 |
| 47 | 42 | 0.78 (3H, s), 0.80 (3H, s), 1.00 (3H, s), 1.09 (3H, d, J = 7.8 Hz), 2.09 (1H, d, J = 18 Hz), 3.06 (1H, d, J = 18 Hz), 4.11 (1H, ABq, A part, J = 17.1 Hz), 4.18 (1H, ABq, B part, J = 17.1 Hz), 6.61 (1H, s), 8.29 (1H, s) | 3327, 3228, 1704, 1686, 1628, 1617, 1497, 1071, 953 |
| 45 | 43a | 0.82 (3H, s), 0.93 (3H, s), 1.00 (3H, s), 1.06 (3H, d, J = 7.2 Hz), 2.12 (1H, d, J = 18 Hz,), 2.84 (1H, d, J = 3.9 Hz), 3.00 (1H, d, J = 18 Hz), 4.02 (1H, ABq, A part, J = 17.1 Hz), 4.12 (1H, ABq, B part, J = 17.1 Hz), 6.62 (1H, s), 8.31 (1H, s) | 3248, 2953, 1706, 1692, 1626, 1611, 1499, 1083, 1074 |

Reactions in Examples 48–53 are illustrated by the following reaction scheme.

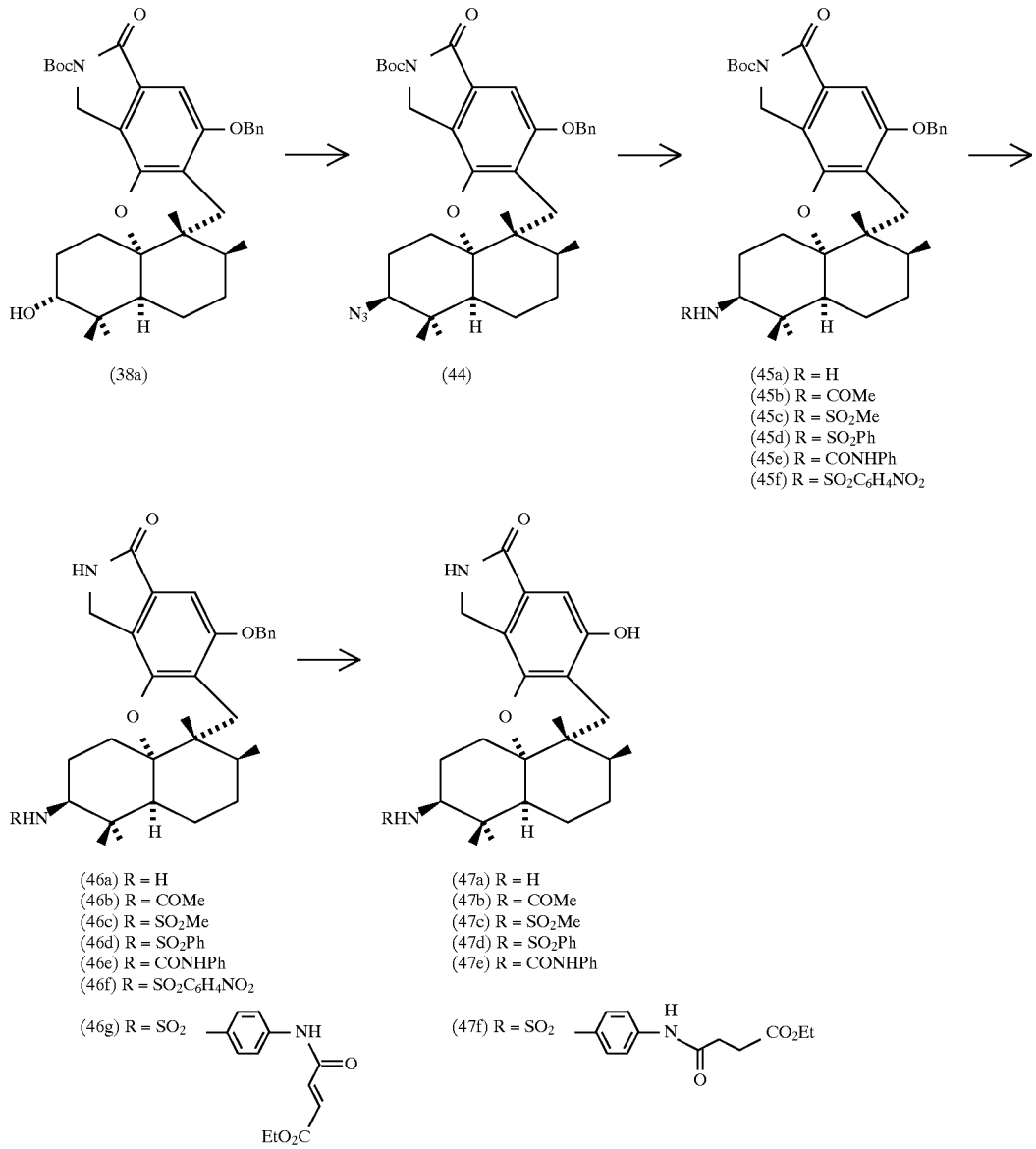

(38a)

(44)

(45a) R = H
(45b) R = COMe
(45c) R = SO$_2$Me
(45d) R = SO$_2$Ph
(45e) R = CONHPh
(45f) R = SO$_2$C$_6$H$_4$NO$_2$ (46a) R = H
(46b) R = COMe
(46c) R = SO$_2$Me
(46d) R = SO$_2$Ph
(46e) R = CONHPh
(46f) R = SO$_2$C$_6$H$_4$NO$_2$ (46g) R = SO$_2$—⟨C$_6$H$_4$⟩—NH—C(=O)—CH=CH—CO$_2$Et (47a) R = H
(47b) R = COMe
(47c) R = SO$_2$Me
(47d) R = SO$_2$Ph
(47e) R = CONHPh (47f) R = SO$_2$—⟨C$_6$H$_4$⟩—NH—C(=O)—CH$_2$CH$_2$—CO$_2$Et

Example 48

Synthesis of (6aR,7S,9aS,11S,13aS)-11-amino-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole (47a)

Step-1: Synthesis of (6aR,7S,9aS,11S,13aS)-11-azido-5-benzyloxy-2-(t-butoxycarbonyl)-2,3,6,6a,7,8,9,9a,10,11,12,13-dodecahydro-6a,7,10,10-tetramethyl-3-oxo-1H-benzo[8,8a][1]benzopyrano[2,3-e]isoindole (44)

To a solution of Compound (38a) (Step-3 in Example 42) (690 mg, 1.20 mmol) in 35 ml of dry benzene were added dropwise 480 mg (1.83 mmol) of triphenylphosphine and 1.0 ml (1.88 mmol) of 1.9M hydrazoic acid/benzene solution at room temperature with stirring, followed by the addition of 290 μl (1.84 mmol) of diethyl azodicarboxylate and stirring at 80° C. for 20 min. After cooling to room temperature, the solvent was evaporated under reduced pressure. The residue was purified by a column chromatography (Merck, Lobar column, size C; toluene:ethyl acetate=9:1) to give 474 mg (66%) of Compound (44).

$^1$H NMR (CDCl$_3$) δ: 0.89 (3H, s), 1.01 (3H, s), 1.10 (3H, s), 1.13 (3H, d, J=7.5 Hz), 1.60 (9H, s), 2.27 (1H, d, J=18 Hz), 3.16 (1H, d, J=18 Hz), 3.41 (1H, br.s), 4.58 (1H, ABq, A part, J=16.8 Hz), 4.67 (1H, ABq, B part, J=16.8 Hz), 5.09 (2H, s), 6.96 (1H, s), 7.30–7.50 (5H, m) ppm IR ν$_{max}$ (CHCl$_3$) 2090, 1770, 1727, 1623, 1610, 1297, 1280, 1255, 1153, 1115, 1078 cm$^{-1}$ Step-2: Synthesis of (6aR,7S,9aS,11S,13aS)-11-amino-5-benzyloxy-2-(t-butoxycarbonyl)-2,3,6,6a,7,8,9,9a,10,11,12,13-dodecahydro-6a,7,10,10-tetramethyl-3-oxo-1H-benzo[8,8a][1]benzopyrano[2,3-e]isoindole (45a)

To the above Compound (44) (300 mg, 0.50 mmol) dissolved in 10 ml of THF were added 1.0 ml of water and 270 mg (1.03 mmol) of triphenylphosphine. The mixture was heated to reflux for 24 hours. After the addition of ethyl acetate, it was dried over anhydrous magnesium sulfate, and concentrated under reduced pressure. The residue was loaded onto a silica gel column (silica gel 20 g), followed by elution with 60 ml of ethyl acetate to remove nonpolar fractions. The polar fractions eluted with 120 ml of ethyl acetate and 80 ml of chloroform-methanol (20:1) mixture were combined, and concentrated under reduced pressure. The residue was further purified by a column chromatography (Merck, Lobar column, size B; chloroform:methanol= 20:1–10:1) to give 262 mg (83%) of Compound (45a) as a powdery material.

$^1$H NMR (CDCl$_3$) δ: 0.91 (3H, s), 0.94 (3H, s), 1.03 (3H, s), 1.13 (3H, d, J=7.6 Hz), 1.60 (9H, s), 2.27 (1H, d, J=18.3 Hz), 2.86 (1H, br.s), 3.17 (1H, d, J=18.3Hz), 4.60 (1H, ABq, A part, J=17.1 Hz), 4.66 (1H, ABq, B part, J=17.1 Hz), 5.10 (2H, s), 6.95 (1H, s), 7.30–7.52 (5H, m) ppm Step-3: Synthesis of (6aR,7S,9aS,11S,13aS)-11-amino-5-benzyloxy-2,3,6,6a,7,8,9,9a,10,11,12,13-dodecahydro-6a,7,10,10-tetramethyl-3-oxo-1H-benzo[8,8a][1]benzopyrano[2,3-e]isoindole (46a)

To a solution of Compound (45a) (50 mg, 0.087 mmol) in 5 ml of dry dichloromethane were added 30 μl (0.28 mmol) of anisole and 35 μl (0.45 mmol) of trifluoroacetic acid, and the mixture stirred for 3 hours at room temperature. Under ice-cooling, to the reaction mixture was added an aqueous saturated sodium hydrogen carbonate solution, followed by extraction with ethyl acetate. The extract was washed with water and an aqueous saturated sodium hydrogen carbonate solution, dried over anhydrous magnesium sulfate, and concentrated under reduced pressure to give 30 mg (73%) of the crude Compound (46a) as a powdery material.

$^1$H NMR (CDCl$_3$) δ: 0.92 (3H, s), 0.93 (3H, s), 1.03 (3H, s), 1.13 (3H, d, J=7.5 Hz), 2.28 (1H, d, J=18.0 Hz), 2.87 (1H, m), 3.17 (1H, d, J=18.0 Hz), 3.45 (2H, s), 5.11 (2H, s), 6.52 (1H, s), 6.97 (1H, s), 7.30–7.48 (5H, m) ppm Step-4: Synthesis of (47a)

To Compound (46a) (30 mg, 0.063 mmol) dissolved in 4.0 ml of methanol was added 6 mg of 10% palladium-carbon, and the mixture stirred under hydrogen atmosphere for 1 hour at room temperature. After the palladium-carbon was removed by filtration, the filtrate was concentrated under reduced pressure. The residue was crystallized from diethyl ether, and recrystallized from diethyl ether-methanol to give 16 mg (48%) of Compound (47a).

MASS: m/z 384 [M]$^+$

Other physical properties are shown in Table 8.

Example 49

Synthesis of (6aR,7S,9aS,11S,13aS)-11-acetylamino-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole (47b)

Step-1: Synthesis of (6aR,7S,9aS,11S,13aS)-11-acetylamino-5-benzyloxy-2-(t-butoxycarbonyl)-2,3,6,6a,7,8,9,9a,10,11,12,13-dodecahydro-6a,7,10,10-tetramethyl-3-oxo-1H-benzo[8,8a][1]benzopyrano [2,3-e] isoindole (45b)

Under nitrogen, 25 μl (0.18 mmol) of triethylamine and 8 μl (0.11 mmol) of acetyl chloride was added to a solution of Compound (45a) (50 mg, 0.087 mmol) in 2.0 ml of dry dichloromethane under ice-cooling, and the mixture stirred for 40 min at the same temperature. After addition of ice-water, the reaction was extracted with ethyl acetate. The extract was washed with aqueous saturated sodium hydrogen carbonate and water, dried over anhydrous magnesium sulfate, and concentrated under reduced pressure. The residue was purified by a preparative thin layer chromatography (Merck, Kieselgel 60 F254, 0.5 mm; chloroform:methanol= 30:1) to give 44 mg (82%) of Compound (45b).

$^1$H NMR (CDCl$_3$) δ: 0.91 (3H, s), 0.92 (3H, s), 1.13 (3H, s), 1.13 (3H, d, J=7.5 Hz), 1.60 (9H, s), 2.03 (3H, s), 2.31 (1H, d, J=18.3Hz), 3.13 (1H, d, J=18.3 Hz), 4.00 (1H, m), 4.62 (1H, ABq, A part, J=17.1 Hz), 4.66 (1H, ABq, B part, J=17.1 Hz), 5.09 (2H, s), 5.61 (1H, d, J=9.0 Hz), 6.99 (1H, s), 7.30–7.48 (5H, m) ppm Step-2: Synthesis of (6aR,7S,9aS,11S,13aS)-11-acetylamino-5-benzyloxy-2,3,6,6a,7,8,9,9a,10,11,12,13-dodecahydro-6a,7,10,10-tetramethyl-3-oxo-1H-benzo[8,8a][1]benzopyrano[2,3-e]isoindole (46b)

Compound (45b) (89 mg, 0.14 mmol) was subjected to a reaction similar to that of Step-3 in Example 48, and the crude product was purified by a preparative thin layer chromatography (Merck, Kieselgel 60 F254, 0.5 mm; chloroform:methanol=10:1) to give 76 mg (99%) of Compound (46b).

$^1$H NMR (CDCl$_3$) δ: 0.89 (3H, s), 0.94 (3H, s), 1.05 (3H, s), 1.12 (3H, d, J=7.8 Hz), 2.03 (3H, s), 2.31 (1H, d, J=18 Hz), 3.12 (1H, d, J=18 Hz), 4.14 (1H, m), 4.38 (1H, ABq, A part, J=16.8 Hz), 4.50 (1H, ABq, B part, J=16.8 Hz), 5.11 (2H, s), 5.57 (1H, d, J=9.0 Hz), 6.46 (1H, s), 6.99 (1H, s), 7.30–7.48 (5H, m) ppm Step-3: Synthesis of (47b)

Compound (46b) (76 mg, 0.15 mmol) was catalytically reduced as in Step-4 of Example 48, and the crude product was purified by a preparative thin layer chromatography (Merck, Kieselgel 60 F254, 0.5 mm; chloroform:methanol= 10:1) and further by crystallization from diethyl ether-pentane to give 50 mg (80%) of Compound (47b).

EIMS: m/z 426 [M]$^+$

Other physical properties are shown in Table 8.

Example 50

Synthesis of (6aR,7S,9aS,11S,13aS)-2,3,6,6a,7,8,9,9a,10,11,12,13-dodecahydro-5-hydroxy-6a,7,10,10-tetramethyl-1 1-methanesulfonylamino-3-oxo-1H-benzo[8,8a][1]benzopyrano[2,3-e]isoindole (47c)

Step-1: Synthesis of (6aR,7S,9aS,11S,13aS)-5-benzyloxy-2-(t-butoxycarbonyl)-2,3,6,6a,7,8,9,9a,10,11,12,13-dodecahydro-6a,7,10,10-tetramethyl-11-methanesulfonylamino-3-oxo-1H-benzo[8,8a][1]benzopyrano[2,3-e]isoindole (45c)

The crude product was obtained from Compound (45a) (22 mg, 0.038 mmol) substantially in accordance with the procedure in Step-1 of Example 49 except that methanesulfonyl chloride was used. This material was purified by a preparative thin layer chromatography (Merck, Kieselgel 60 F254, 0.5 mm; n-hexane:ethyl acetate=1:1) to give 24 mg (96%) of Compound (45c).

$^1$H NMR (CDCl$_3$) δ: 0.91 (3H, s), 1.00 (3H, s), 1.13 (3H, d, J=7.0 Hz), 1.14 (3H, s), 1.60 (9H, s), 2.30 (1H, d, J=18.3 Hz), 2.99 (3H, s), 3.13 (1H, d, J=18.3 Hz), 3.80 (1H, m), 4.59 (1H, ABq, A part, J=16.8 Hz), 4.67 (1H, ABq, B part, J=16.8 Hz), 4.72 (1H, d, J=8.7 Hz), 5.09 (2H, s), 6.99 (1H, s), 7.30–7.48 (5H, m) ppm Step-2: Synthesis of (6aR,7S,9aS,11S,13aS)-5-benzyloxy-2,3,6,6a,7,8,9,9a,10,11,12,13-dodecahydro-6a,7,10,10-tetramethyl-11-methanesulfonylamino-3-oxo-1H-benzo[8,8a][1]benzopyrano[2,3-e]isoindole (46c)

Compound (45c) (37 mg, 0.057 mmol) was subjected to a reaction similar to that of Step-3 in Example 48, and the crude product was purified by a preparative thin layer chromatography (Merck, Kieselgel 60 F254, 0.5 mm; chloroform:methanol=20:1) to give 31 mg (99%) of Compound (46c).

$^1$H NMR (CDCl$_3$) δ: 0.93 (3H, s), 0.99 (3H, s), 1.12 (3H, s), 1.13 (3H, d, J=7.0 Hz), 2.30 (1H, d, J=18.3 Hz), 2.99 (3H, s), 3.13 (1H, d, J=18.3 Hz), 3.41 (1H, m), 4.35 (2H, s), 4.92 (1H, d, J=8.7 Hz), 5.11 (2H, s), 6.73 (1H, s), 6.99 (1H, s), 7.30–7.48 (5H, m) ppm Step-3: Synthesis of (47c)

Compound (46c) (31 mg, 0.056 mmol) was catalytically reduced as in Step-4 of Example 48, and the crude product was purified by a preparative thin layer chromatography (Merck, Kieselgel 60 F254, 0.5 mm; chloroform:methanol= 10:1) and by crystallization from diethyl ether-pentane to give 19 mg (73%) of Compound (47c).

EIMS: m/z 462 [M]$^+$

Other physical properties are shown in Table 8.

Example 51

Synthesis of (6aR,7S,9aS,11S,13aS)-2,3,6,6a,7,8,9, 9a,10,11,12,13-dodecahydro-5-hydroxy-6a,7,10,10-tetramethyl-11-phenylsulfonylamino-3-oxo-1H-benzo[8,8a][1]benzopyrano[2,3-e]isoindole (47d)

Step-1: Synthesis of (6aR,7S,9aS,11S,13aS)-5-benzyloxy-2-(t-butoxycarbonyl)-2,3,6,6a,7,8,9,9a,10,11,12,13-dodecahydro-6a,7,10,10-tetramethyl-11-phenylsulfonylamino-3-oxo-1H-benzo[8,8a][1]benzopyrano[2,3-e]isoindole (45d)

The crude product was obtained from Compound (45a) (50 mg, 0.087 mmol) substantially in accordance with the procedure of Step-1 in Example 49 except that benzenesulfonyl chloride was used. This material was purified by a preparative thin layer chromatography (Merck, Kieselgel 60 F254, 0.5 mm; chloroform:methanol=60:1) to give 30 mg (48%) of Compound (45d).

$^1$H NMR (CDCl$_3$) δ: 0.81 (3H, s), 0.85 (3H, s), 0.99 (3H, s), 1.09 (3H, d, J=7.4 Hz), 1.59 (9H, s), 2.25 (1H, d, J=18.3 Hz), 3.09 (1H, d, J=18.3 Hz), 3.19 (1H, m), 4.58 (1H, ABq, A part, J=17.1 Hz), 4.63 (1H, ABq, B part, J=17.1 Hz), 4.93 (1H, d, J=8.1 Hz), 5.08 (2H, s), 6.96 (1H, s), 7.28–7.46 (5H, m), 7.52–7.66 (3H, m), 7.93–7.99 (2H, m) ppm Step-2: Synthesis of (6aR,7S,9aS,11S,13aS)-5-benzyloxy-2,3,6,6a,7,8,9,9a,10,11,12,13-dodecahydro-6a,7,10,10-tetramethyl-11-phenylsulfonylamino-3-oxo-1H-benzo[8,8a][1]benzopyrano[2,3-e]isoindole (46d)

Compound (45d) (29 mg, 0.041 mmol) was subjected to a reaction similar to that of Step-3 in Example 48, and the crude product was purified by a preparative thin layer chromatography (Merck, Kieselgel 60 F254, 0.5 mm; chloroform:methanol=20:1) to give 23 mg (92%) of Compound (46d).

$^1$H NMR (CDCl$_3$) δ: 0.82 (3H, s), 0.87 (3H, s), 0.99 (3H, s), 1.09 (3H, d, J=7.5 Hz), 2.26 (1H, d, J=18.3 Hz), 3.09 (1H, d, J=18.3 Hz), 3.19 (1H, m), 4.29 (2H, s), 5.09 (2H, s), 5.24 (1H, d, J=8.4 Hz), 6.64 (1H, s), 6.96 (1H, s), 7.30–7.64 (8H, m), 7.92–8.00 (2H, m) ppm Step-3: Synthesis of (47d)

Compound (46d) (23 mg, 0.037 mmol) was catalytically reduced as in Step-4 of Example 48, and the crude product was purified by a preparative thin layer chromatography (Merck, Kieselgel 60 F254, 0.5 mm; chloroform:methanol= 10:1) and by crystallization from diethyl ether-pentane to give 14 mg (71%) of Compound (47d).

EIMS: m/z 524 [M]$^+$

Other physical properties are shown in Table 8.

Example 52

Synthesis of (6aR,7S,9aS,11S,13aS)-2,3,6,6a,7,8,9, 9a,10,11,12,13-dodecahydro-5-hydroxy-6a,7,10,10-tetramethyl-11-(3-phenylureido)-3-oxo-1H-benzo[8, 8a][1]benzopyrano[2,3-e]isoindole (47e)

Step-1: Synthesis of (6aR,7S,9aS,11S,13aS)-5-benzyloxy-2-(t-butoxycarbonyl)-2,3,6,6a,7,8,9,9a,10,11,12,13-dodecahydro-6a,7,10,10-tetramethyl-11-(3-phenylureido)-3-oxo-1H-benzo[8,8a][1]benzopyrano[2,3-e]isoindole (45e)

Under nitrogen, 2 mg (0.017 mmol) of dimethylaminopyridine and 12 μl (0.11 mmol) of phenyl isocyanate were added to a solution of Compound (45a) (50 mg, 0.087 mmol) in 2.0 ml of dry THF, and the mixture stirred at room temperature for 30 min. The reaction mixture was then concentrated under reduced pressure. The residue was purified by a preparative thin layer chromatography (Merck, Kieselgel 60 F254, 0.5 mm; chloroform:methanol=40:1) to give 49 mg (81%) of Compound (45e).

$^1$H NMR (CDCl$_3$) δ: 0.87 (3H, s), 0.91 (3H, s), 0.98 (3H, d, J=7.5 Hz), 1.13 (3H, s), 1.60 (9H, s), 2.26 (1H, d, J=18.6 Hz), 3.10 (1H, d, J=18.6 Hz), 3.87 (1H, m), 4.61 (1H, ABq, A part, J=17.1 Hz), 4.67 (1H, ABq, B part, J=17.1 Hz), 5.06 (2H, s), 5.13 (1H, d, J=8.1 Hz), 6.67 (1H, s), 6.97 (1H, s), 7.28–7.45 (10H, m) ppm Step-2: Synthesis of (6aR,7S,9aS, 11S, 13aS)-5-benzyloxy-2,3,6,6a,7,8,9,9a,10,11,12,13-dodecahydro-6a,7,10,10-tetramethyl-11-(3-phenylureido)-3-oxo-1H-benzo[8,8a][1]benzopyrano[2,3-e]isoindole (46e)

Compound (45e) (49 mg, 0.071 mmol) was subjected to a reaction similar to that of Step-3 in Example 48, and the crude product was purified by a preparative thin layer chromatography (Merck, Kieselgel 60 F254, 0.5 mm; chloroform:methanol=20:1) to give 40 mg (95%) of Compound (46e).

$^1$H NMR (CDCl$_3$) δ: 0.86 (3H, s), 0.89 (3H, s), 1.00 (3H, d, J=7.5 Hz), 1.05 (3H, s), 2.26 (1H, d, J=18.3 Hz), 3.09 (1H, d, J=18.3 Hz), 4.08 (1H, m), 4.39 (1H, ABq, A part, J=17.1 Hz), 4.44 (1H, ABq, B part, J=17.1 Hz), 5.03 (2H, s), 5.25 (1H, d, J=9.3 Hz), 6.97 (1H, s), 7.09 (1H, br.s), 7.25–7.45 (10H, m), 7.62 (1H, br.s) ppm Step-3: Synthesis of (47e)

Compound (46e) (40 mg, 0.067 mmol) was catalytically reduced as in Step-4 of Example 48, and the crude product was purified by a preparative thin layer chromatography (Merck, Kieselgel 60 F254, 0.5 mm; chloroform:methanol= 7:1), and by crystallization from diethyl ether-pentane to give 29 mg (86%) of Compound (47e). Physical properties of Compound (47e) are shown in Table 8.

Example 53

Synthesis of (6aR,7S,9aS,11S,13aS)-11-[4(3-ethoxycarbonyl-1-oxopropyl)amino] phenylsulfonylamino-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole (47f)

Step-1: Synthesis of (6aR,7S,9aS,11S,13aS)-5-benzyloxy-2-(t-butoxycarbonyl)-2,3,6,6a,7,8,9,9a,10,11,12,13-dodecahydro-6a,7,10,10-tetramethyl-11-(4-nitrophenylsulfonyl)amino-3-oxo-1H-benzo[8, 8a][1]benzopyrano[2,3-e]isoindole (45f)

The crude product was obtained from Compound (45a) (120 mg, 0.21 mmol) substantially according to the procedure of Step-1 in Example 49 except that p-nitrobenzenesulfonyl chloride. This material was purified by a silica gel column chromatography (silica gel 6.0 g; toluene:ethyl acetate 4:1) to give 151 mg (96%) of Compound (45f).

$^1$H NMR (CDCl$_3$) δ: 0.82 (3H, s), 0.86 (3H, s), 0.99 (3H, s), 1.08 (3H, d, J=7.4 Hz), 1.60 (9H, s), 2.27 (1H, d, J=18.0 Hz), 3.08 (1H, d, J=18.0 Hz), 3.31 (1H, m), 4.58 (1H, ABq, A part, J=17.0 Hz), 4.63 (1H, ABq, B part, J=17.0 Hz), 5.08 (2H, s), 5.15 (1H, d, J=9.0 Hz), 6.97 (1H, s), 7.30–7.50 (5H, m), 8.14 (2H, d, J=9.0 Hz), 8.41 (2H, d, J=9.0 Hz) ppm Step-2: Synthesis of (6aR,7S,9aS,11S,13aS)-5-benzyloxy-2,3,6,6a,7, 8, 9, 9a,10,11,12,13-dodecahydro-6a,7,10,10- tetramethyl-11-(4-nitrophenylsulfonyl)amino-3-oxo-1H-benzo[8,8a][1]benzopyrano[2,3-e]isoindole (46f)

The above Compound (45f) (150 mg, 0.20 mmol) was subjected to a reaction similar to that of Step-3 in Example 48, and the crude product was purified by a silica gel column chromatography (silica gel 3.0 g; toluene:ethyl acetate=1:1) to give 120 mg (92%) of Compound (46f).

$^1$H NMR (CDCl$_3$) δ: 0.83 (3H, s), 0.88 (3H, s), 1.02 (3H, s), 1.10 (3H, d, J=7.6 Hz), 2.27 (1H, d, J=18.0 Hz), 3.10 (1H, d, J=18.0 Hz), 3.30 (1H, br.d, J=9.0 Hz), 4.32 (2H, s), 5.09 (2H, s), 5.44 (1H, d, J=9.0 Hz), 6.59 (1H, s), 6.97 (1H, s), 7.30–7.50 (5H, m), 8.12 (2H, d, J=9.0 Hz), 8.38 (2H, d, J=9.0 Hz) ppm Step-3: Synthesis of (6aR,7S,9aS,11S,13aS)-5-benzyloxy-11-[4(3-ethoxycarbonyl-1-oxo-2-propenyl)amino]phenylsulfonylamino-2,3,6,6a,7,8,9,9a,10,11,12,13-dodecahydro-6a,7,10,10-tetramethyl-3-oxo-1H-benzo[8,8a][1]benzopyrano[2,3-e]isoindole (46g)

i) To the above Compound (46f) (120 mg, 0.18 mmol) dissolved in 12 ml of THF-methanol (1:1) mixture was added 40 mg of 10% palladium-carbon, and the mixture stirred under hydrogen atmosphere for 3.5 hours at room temperature. After the palladium-carbon was removed by filtration, the filtrate was concentrated under reduced pressure to give 100 mg (88%) of the amino compound. This material was used in the next reaction without further purification.

ii) To a solution of the above amino compound in 8 ml of THF-ethyl acetate (1:1) mixture was added an aqueous sodium carbonate solution (prepared from 25 mg (0.18 mmol) of sodium carbonate and 6.0 ml of water), which was followed by addition of 30 μl (0.22 mmol) of ethyl 3-chlorocarbonylacrylate with vigorous stirring under ice-cooling. The reaction was stirred for 30 min while allowing to warm up to room temperature. The reaction mixture was then extracted with ethyl acetate. The extract was washed with water, dried over anhydrous sodium sulfate, and concentrated under reduced pressure. The residue was purified by a silica gel column chromatography (silica gel 6.0 g; chloroform:methanol=49:1–19:1) to give 113 mg (94%) of Compound (46g)

$^1$H NMR (DMSO-d$_6$) δ: 0.78 (3H, s), 0.89 (3H, s), 0.92 (3H, s), 1.12 (3H, d, J=7.2 Hz), 1.27 (3H, t, J=7.2 Hz), 2.19 (1H, d, J=18.0 Hz), 3.07 (1H, d, J=18.0 Hz), 3.12 (1H, br.s), 4.16 (2H, s), 4.23 (2H, q, J=7.2 Hz), 5.15 (2H, s), 6.77 (1H, d, J=15.8 Hz), 6.81 (1H, s), 7.30–7.60 (6H, m), 7.68 (1H, d, J=15.8 Hz), 7.89 (2H, ABq, A part, J=9.2 Hz), 7.97 (2H, ABq, B part, J=9.2 Hz), 8.40 (1H, s) ppm Step-4: Synthesis of (47f)

A solution of Compound (46g) (110 mg, 0.145 mmol) in 12 ml of THF-ethanol (1:1) mixture was catalytically reduced as in Step-4 of Example 48, and the crude product was purified by a silica gel column chromatography (silica gel 6.0 g; chloroform:methanol=97:3) to give 76.mg (79%) of Compound (47f). Physical properties of Compound (47f) are shown in Table 8.

TABLE 8

| Ex. No. | Comp. | $^1$H-NMR δ (DMSO-d$_6$) ppm | IR ν max (Nujol) cm$^{-1}$ |
|---|---|---|---|
| 48 | 47a | 0.85 (3H, s), 0.92 (3H, s), 0.97 (3H, s), 1.10 (3H, d, J = 7.0 Hz), 2.14 (1H, d, J = 18 Hz), 3.00 (1H, d, J = 18 Hz), 3.18 (1H, br.s), 4.08 (1H, ABq, A part, J = 16.8 Hz), 4.16 (1H, ABq, B part, J = 16.8 Hz), 6.64 (1H, s), 8.35 (1H, s), 9.76 (1H, s) | 3239, 1670, 1627, 1610, 1519, 1079 |
| 49 | 47b | 0.76 (3H, s), 0.85 (3H, s), 0.95 (3H, s), 1.15 (3H, d, J = 7.2 Hz), 1.88 (3H, s), 2.12 (1H, d, J = 18.0Hz), 3.03 (1H, d, J = 18.0Hz), 3.19 (1H, m), 4.16 (2H, s), 6.61 (1H, s), 7.55 (1H, d, J = 9.3 Hz), 8.29 (1H, s), 9.97 (1H, br.s) | 3287, 1676, 1542, 1077 |
| 50 | 47c | 0.83 (3H, s), 0.87 (3H, s), 0.98 (3H, s), 1.13 (3H, d, J = 7.8 Hz), 2.11 (1H, d, J = 18.0 Hz), 2.89 (3H, s), 3.03 (1H, d, J = 18.0Hz), 3.21 (1H, m), 4.10 (1H, ABq, A part, J = 17.1 Hz), 4.15 (1H, ABq, B part, J = 17.1 Hz), 6.61 (1H, s), 6.92 (1H, d, J = 9.0 Hz), 8.28 (1H, s), 9.78 (1H, br.s) | 3276, 1677, 1627, 1611, 1151, 1074, 996 |
| 51 | 47d | 0.76 (3H, s), 0.88 (3H, s), 0.90 (3H, s), 1.11 (3H, d, J = 7.5 Hz), 2.08 (1H, d, J = 18.0Hz), 2.99 (1H, d, J = 18.0Hz), 3.10 (1H, m), 4.08 (2H, s), 6.60 (1H, s), 7.48 (1H, d, J = 8.7 Hz), 7.56–7.65 (3H, m), 7.84–7.95 (2H, m), 8.28 (1H, s), 9.73 (1H, br.s) | 3278, 1678, 1627, 1611, 1158, 1092, 1074 |
| 52 | 47e | 0.85 (3H, s), 0.86 (3H, s), 1.03 (3H, s), 1.17 (3H, d, J = 7.2 Hz), 2.13 (1H, d, J = 18.0Hz), 3.07 (1H, d, J = 18.0Hz), 4.73 (1H, m), 4.15 (1H, ABq, A part, J = 17.1 Hz), 4.19 (1H, ABq, B part, J = 17.1 Hz), 6.22 (1H, d, J = 8.7 Hz), 6.63 (1H, s), 6.87 (1H, m), 7.17-7.26 (2H, m), 7.37–7.44 (2H, m), 8.30 (1H, s), 8.64 (1H, s), 9.74 (1H, s) | 3313, 1663, 1598, 1551, 1498, 1076 |
| 53 | 47f | 0.76 (3H, s), 0.87 (3H, s), 0.90 (3H, s), 1.11(3H, d, J = 7.2 Hz), 1.19 (3H, d, J = 7.2 Hz), 2.08 (1H, d, J = 18.0Hz), 2.99 (1H, d, J = 18.0 Hz), 3.07 (1H, br.s), 4.07 (2H, q, J = 7.2 Hz), 4.08 (1H, ABq, A part, J = 17.0 Hz), 4.12 (1H, ABq, B part, J = 17.0 Hz), 6.60 (1H, s), 7.77 (1H, s), 7.84 (2H, ABq, A part, J = 9.0 Hz), 7.79 (1H, ABq, B part, J = 9.0 Hz), 8.28 (1H, s), 9.67 (1H, s) | 3269, 1736, 1718, 1663, 1609, 1592, 1156, 1092, 1075 |

Reactions in Examples 54–59 are illustrated by the following reaction scheme.

Process 11

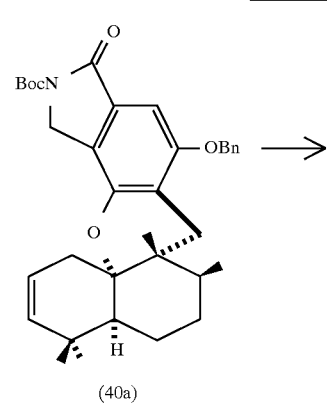

(40a)

Process 11

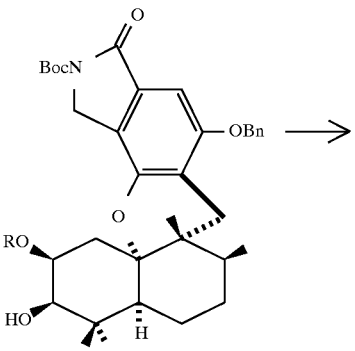

(48a) R = H
(48b) R = COMe
(48c) R = COPh
(48d) R = SO₂Me
(48e) R = SO₂Ph
(48f) R = SO₂C₆H₄NO₂

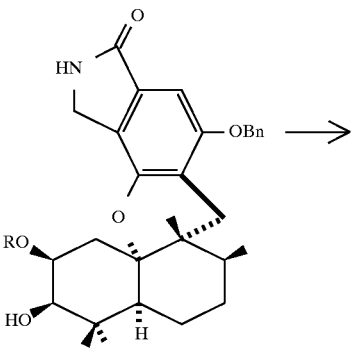

(49a) R = H
(49b) R = COMe
(49c) R = COPh
(49d) R = SO₂Me
(49e) R = SO₂Ph
(49f) R = SO₂C₆H₄NO₂

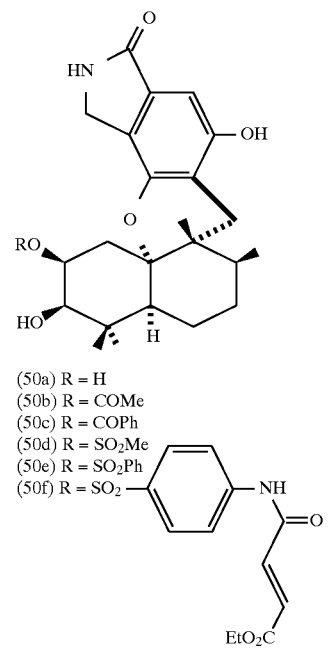

(50a) R = H
(50b) R = COMe
(50c) R = COPh
(50d) R = SO₂Me
(50e) R = SO₂Ph
(50f) R = SO₂—

Example 54

Synthesis of (6aR,7S,9aS, 11R,12S,13aS)-2,3,6,6a,7,8,9,9a,10,11,12,13-dodecahydro-5,11,12-trihydroxy-6a,7,10,10-tetramethyl-3-oxo-1H-benzo[8,8a][1]benzopyrano[2,3-e]isoindole (50a)

Step-1: Synthesis of (6aR,7S,9aS,11R,12S,13aS)-5-benzyloxy-2-(t-butoxycarbonyl)-2,3,6,6a,7,8,9,9a,10,11,12,13-dodecahydro-11,12-dihydroxy-6a,7,10,10-tetramethyl-3-oxo-1H-benzo[8,8a][1]benzopyrano[2,3-e]isoindole (48a)

To a solution of Compound (40a) (Step-2 in Example 44) (40 mg, 0.072 mmol) in 2.0 ml of acetone were added 12 mg (0.108 mmol) of trimethylamine oxide dihydrate and 0.50 ml (0.1 mmol) of 0.2M osmium tetroxide aqueous solution, and the mixture stirred at room temperature for 15 hours. After addition of 8 mg (0.072 mmol) of trimethylamine oxide dihydrate, the mixture was stirred for 5 hours. To the reaction mixture were added 236 mg (2.8 mmol) of sodium hydrogen carbonate and 146 mg (1.4 mmol) of sodium hydrogen sulfite, and the mixture stirred for 1.5 hours. After addition of water, the mixture was extracted with ethyl acetate. The extract was washed with water and saturated brine, dried over anhydrous magnesium sulfate, and concentrated under reduced pressure. The residue was purified by a column chromatography (Merck, Lobar column, size A; n-hexane:ethyl acetate=2:1) to give 28 mg (66%) of Compound (48a).

¹H NMR (CDCl₃) δ: 0.93 (3H, s), 1.03 (3H, s), 1.06 (3H, s), 1.13 (3H, d, J=7.2 Hz), 1.60 (9H, s), 2.28 (1H, d, J=18.3 Hz), 3.17 (1H, d, J=18.3 Hz), 3.58 (1H, br.s), 4.52 (1H, ABq, A part, J=17.1 Hz), 4.56 (1H, m), 4.64 (1H, ABq, B part, J=17.1 Hz), 5.09 (2H, s), 6.98 (1H, s), 7.30–7.48 (5H, m) ppm Step-2: Synthesis of (6aR,7S,9aS, 11R,12S,13aS)-5-benzyloxy-2,3,6,6a,7,8,9,9a,10,11,12,13-dodecahydro-11,12-dihydroxy-6a,7,10,10-tetramethyl-3-oxo-1H-benzo[8,8a][1]benzopyrano[2,3-e]isoindole (49a)

To a solution of Compound (48a) (30 mg, 0.051 mmol) in 2.0 ml of dry dichloromethane were added 17 μl (0.156 mmol) of anisole and 40 μl (0.51 mmol) of trifluoroacetic acid under ice-cooling, and the mixture stirred for 1 hours at room temperature. Under ice-cooling, an aqueous saturated sodium hydrogen carbonate solution was added to the reaction mixture, which was followed by extraction with ethyl acetate. The extract was washed with water and saturated brine, dried over anhydrous magnesium sulfate, and concentrated under reduced pressure. The residue was purified by a preparative thin layer chromatography (Merck, Kieselgel 60 F254, 0.5 mm; chloroform:methanol=10:1) to give 24 mg (96%) of Compound (49a).

¹H NMR (CDCl₃) δ: 0.94 (3H, s), 1.02 (3H, s), 1.05 (3H, s), 1.13 (3H, d, J=7.5 Hz), 2.29 (1H, d, J=18.3 Hz), 3.17 (1H, d, J=18.3 Hz), 3.57 (1H, d, J=2.4 Hz), 4.27 (1H, ABq, A part, J=17.1 Hz), 4.33 (1H, ABq, B part, J=17.1 Hz), 4.54 (1H, m), 5.11 (2H, s), 6.79 (1H, s), 6.99 (1H, s), 7.30–7.50 (5H, m) ppm Step-3: Synthesis of (50a)

To Compound (49a) (43 mg, 0.088 mmol) dissolved in 3.0 ml of methanol was added 9 mg of palladium-carbon, and the mixture stirred under hydrogen atmosphere for 2 hours at room temperature. After the palladium-carbon was removed by filtration, the filtrate was concentrated under reduced pressure. The residue was purified by a preparative thin layer chromatography (Merck, Kieselgel 60 F254, 0.5 mm; chloroform:methanol=10:1) and further by crystallization from diethyl ether to give 32 mg (91%) of Compound (50a).

EIMS: m/z 401 [M]+
Other physical properties are shown in Table 9.

Example 55

Synthesis of (6aR,7S,9aS,11R,12S,13aS)-12-acetoxy-2,3,6,6a,7,8,9,9a,10,11,12,13-dodecahydro-5,11-dihydroxy-6a,7,10,10-tetramethyl-3-oxo-1H-benzo[8,8a][1]benzopyrano[2,3-e]isoindole (50b)

Step-1: Synthesis of (6aR,7S,9aS,11R,12S,13aS)-12-acetoxy-5-benzyloxy-2-(t-butoxycarbonyl)-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole (48b)

To a solution of Compound (48a) (51 mg, 0.086 mmol) in 5.0 ml of dichloromethane were added 32 mg (0.26 mmol) of dimethylaminopyridine and 9.2 μl (0.13 mmol) of acetyl chloride under ice-cooling, and the mixture stirred for 30 min at the same temperature. After addition of water, the reaction mixture was extracted with ethyl acetate. The extract was washed sequentially with 1N HCl, water, an aqueous saturated hydrogen carbonate solution, and water, dried with anhydrous magnesium sulfate, and concentrated under reduced pressure. The residue was purified by a column chromatography (Merck, Lobar column, size A; toluene:ethyl acetate=2:1) to give 49 mg (90%) of Compound (48b).

$^1$H NMR (CDCl$_3$) δ: 0.92 (3H, s), 1.63 (3H, s), 1.09 (3H, s), 1.13 (3H, d, J=7.4 Hz), 1.59 (9H, s), 2.13 (3H, s), 2.29 (1H, d, J=18 Hz), 3.18 (1H, d, J=18 Hz), 3.66 (1H, br.s), 4.58 (1H, ABq, A part, J=17 Hz), 4.72 (1H, ABq, B part, J=17 Hz), 5.09 (2H, s), 5.72 (1H, dm, J=11.6 Hz), 6.98 (1H, s), 7.34–7.46 (5H, m) ppm Step-2: Synthesis of (6aR,7S,9aS,11R,12S,13aS)-12-acetoxy-5-benzyloxy-2,3,6,6a,7,8,9,9a,10,11,12,13-dodecahydro-11-hydroxy-6a,7,10,10-tetramethyl-3-oxo-1H-benzo[8,8a][1]benzopyrano[2,3-e]isoindole (49b)

Compound (48b) (275 mg, 0.41 mmol) was subjected to a reaction similar to that in Step-2 of Example 54, and the crude product was purified by a column chromatography (Merck, Lobar column, size A; toluene: ethyl acetate =1: 2). Compound (49b) (57 mg, 26%) was obtained from the nonpolar fractions.

$^1$H NMR (CDCl$_3$) δ: 0.93 (3H, s), 1.06 (3H, s), 1.08 (3H, s), 1.13 (3H, d, J=7.4 Hz), 2.14 (3H, s), 2.30 (1H, d, J=18 Hz), 3.18 (1H, d, J=18 Hz), 3.64 (1H, br.s), 4.33 (1H, ABq, A part, J=16.8 Hz), 4.41 (1H, ABq, B part, J=16.8 Hz), 5.11 (2H, s), 5.76 (1H, dm, J=11.0 Hz), 6.40 (1H, br.s), 7.00 (1H, s), 7.34–7.46 (5H, m) ppm IR ν$_{max}$ (CHCl$_3$) 3456, 1730, 1691, 1627, 1603, 1368, 1245, 1174, 1116, 1094, 1045, 1028, 982 cm$^{-1}$ From the polar fractions of the above chromatography, (6aR,7S,9aS,11R,12S,13aS)-11-acetoxy-5-benzyloxy-2,3,6,6a,7,8,9,9a,10,11,12,13-dodecahydro-12-hydroxy-6a,7,10,10-tetramethyl-3-oxo-1H-benzo[8,8a][1]benzopyrano[2,3-e]isoindole (49f), an isomer in which acetyl group has been rearranged, was obtained (101 mg, 46%).

$^1$H NMR (CDCl$_3$) δ: 0.91 (3H, s), 0.95 (3H, s), 1.13 (3H, s), 1.16 (3H, d, J=7.4 Hz), 2.16 (3H, s), 2.31 (1H, d, J=18 Hz), 3.18 (1H, d, J=18 Hz), 4.23 (1H, ABq, A part, J=17 Hz), 4.33 (1H, ABq, B part, J=17 Hz), 4.67 (1H, m), 5.00 (1H, d, J=3.2 Hz), 5.11 (2H, s), 6.56 (1H, br.s), 7.00 (1H, s), 7.34–7.48 (5H, m) ppm IR ν$_{max}$ (CHCl$_3$) 3446, 1726, 1692, 1626, 1603, 1369, 1250, 1173, 1116, 1093, 981 cm$^{-1}$ Step-3: Synthesis of (50b)

Compound (49b) (70 mg, 0.13 mmol) was catalytically reduced as in Step-3 of Example 54. The product was crystallized from diethyl ether-pentane to give 56 mg (96%) of Compound (50b).

EIMS: m/z 443 [M]+
Other physical properties are shown in Table 9.

Example 56

Synthesis of (6aR,7S,9aS,11R,12S,13aS)-12-benzoyloxy-2,3,6,6a,7,8,9,9a,10,11,12,13-dodecahydro-5,11-dihydroxy-6a,7,10,10-tetramethyl-3-oxo-1H-benzo[8,8a][1]benzopyrano[2,3-e]isoindole (50c)

Step-1: Synthesis of (6aR,7S,9aS,11R,12S,13aS)-12-benzoyloxy-5-benzyloxy-2-(t-butoxycarbonyl)-2,3,6,6a,7,8,9,9a,10,11,12,13-dodecahydro-11-hydroxy-6a,7,10,10-tetramethyl-3-oxo-1H-benzo [8,8a] [1] benzopyrano[2,3-e]isoindole (48c)

A crude product was obtained from Compound (48a) (25 mg, 0.042 mmol) substantially according to the procedure of Step-1 in Example 55 except that benzoyl chloride was used. This material was purified by a preparative thin layer chromatography (Merck, Kieselgel 60 F253, 0.5 mm; n-hexane:ethyl acetate=2:1) to give 29 mg (99%) of Compound (48c).

$^1$H NMR (CDCl$_3$) δ: 0.94 (3H, s), 1.10 (3H, s), 1.16 (3H, s), 1.16 (3H, d, J=7.5 Hz), 1.61 (9H, s), 2.31 (1H, d, J=18 Hz), 3.20 (1H, d, J=18 Hz), 3.82 (1H, d, J=2.7 Hz), 4.64 (1H, ABq, A part, J=17.1 Hz), 4.78 (1H, ABq, B part, J=17.1 Hz), 5.10 (2H, s), 6.00 (1H, m), 7.00 (1H, s), 7.30–7.64 (8H, m), 8.05–8.14 (2H, m) ppm Step-2: Synthesis of (6aR,7S,9aS,11R,12S,13aS)-12-benzoyloxy-5-benzyloxy-2,3,6,6a,7,8,9,9a,10,11,12,13-dodecahydro-11-hydroxy-6a,7,10,10-tetramethyl-3-oxo-1H-benzo[8,8a][1]benzopyrano [2,3-e] isoindole (49c)

Compound (48c) (28 mg, 0.04 mmol) was subjected to a reaction similar to that of Step-2 in Example 54, and the crude product was purified by a preparative thin layer chromatography (Merck, Kieselgel 60 F254, 0.5 mm; chloroform:methanol=30:1) to give 15 mg (63%) of Compound (49c).

$^1$H NMR (CDCl$_3$) δ: 0.96 (3H, s), 1.09 (3H, s), 1.14 (3H, s), 1.17 (3H, d, J=7.4 Hz), 2.32 (1H, d, J=18 Hz), 3.21 (1H, d, J=18 Hz), 3.79 (1H, br.s), 4.38 (1H, ABq, A part, J=16.8 Hz), 4.46 (1H, ABq, B part, J=16.8 Hz), 5.12 (2H, s), 6.03 (1H, m), 6.34 (1H, s), 7.01 (1H, s), 7.30–7.65 (8H, m), 8.05–8.14 (2H, m) ppm Step-3: Synthesis of (50c)

Compound (49c) (15 mg, 0.025 mmol) was catalytically reduced as in Step-3 of Example 54, and the crude product was purified by a preparative thin layer chromatography (Merck, Kieselgel 60 F254, 0.5 mm; chloroform:methanol= 15:1) to give 9 mg (71%) of Compound (50c).

EIMS: m/z 505 [M]+
Other physical properties are shown in Table 9.

Example 57

Synthesis of (6aR,7S,9aS,11R,12S,13aS)-2,3,6,6a,7,8,9,9a,10,11,12,13-dodecahydro-5,11-dihydroxy-6a,7,10,10-tetramethyl-12-methanesulfonyloxy-3-oxo-1H-benzo[8,8a][1]benzopyrano[2,3-e]isoindole (50d)

Step-1: Synthesis of (6aR,7S,9aS,11R,12S,13aS)-5-benzyloxy-2-(t-butoxycarbonyl)-2,3,6,6a,7,8,9,9a,10,11,12, 13-dodecahydro-11-hydroxy-6a,7,10,10-tetramethyl-12-methanesulfonyloxy-3-oxo-1H-benzo[8,8a] [1]-benzopyrano[2,3-e]isoindole (48d)

A crude product was obtained from Compound (48a) substantially according to the procedure of Step-1 in Example 55 except that methanesulfonyl chloride was used. This material was purified by a column chromatography (Merck, Lobar column, size A; toluene:ethyl acetate=4:1) to give 55 mg (89%) of Compound (48d).

$^1$H NMR (CDCl$_3$) δ: 0.94 (3H, s), 1.08 (3H, s), 1.10 (3H, s), 1.14 (3H, d, J=7.4 Hz), 1.59 (9H, s), 2.30 (1H, d, J=18 Hz), 3.12 (3H, s), 3.18 (1H, d, J=18 Hz), 3.85 (1H, br.s), 4.57 (1H, ABq, A part, J=16.8 Hz), 4.70 (1H, ABq, B part, J=16.8 Hz), 5.09 (2H, s), 5.57 (1H, dm, J=10.6 Hz), 7.00 (1H, s), 7.34–7.46 (5H, m) ppm Step-2: Synthesis of (6aR,7S,9aS,11R,12S,13aS)-5-benzyloxy-2,3,6,6a,7,8,9,9a,10,11,12,13-dodecahydro-11-hydroxy-6a,7,10,10-tetramethyl-12-methanesulfonyloxy-3-oxo-1H-benzo[8,8a][1]benzopyrano[2,3-e]isoindole (49d)

Compound (48d) (55 mg, 0.082 mmol) was subjected to a reaction similar to that of Step-2 in Example 54, and the crude product was purified by a column chromatography (Merck, Lobar column, size A; ethyl acetate) to give 43 mg (93%) of Compound (49d).

$^1$H NMR (CDCl$_3$) δ: 0.95 (3H, s), 1.08 (6H, s), 1.14 (3H, d, J=7.4 Hz), 2.32 (1H, d, J=18 Hz), 3.13 (3H, s), 3.18 (1H, d, J=18 Hz), 3.84 (1H, br.s), 4.32 (1H, ABq, A part, J=16.8 Hz), 4.39 (1H, ABq, B part, J=16.8 Hz), 5.11 (2H, s), 5.60 (1H, dm, J=10 Hz), 6.56 (1H, br.s), 7.01 (1H, s), 7.34–7.48 (5H, m) ppm IR ν$_{max}$ (CHCl$_3$) 3446, 1693, 1628, 1602, 1117, 1094, 984, 934, 915 cm$^{-1}$ Step-3: Synthesis of (50d)

Compound (49d) (42 mg, 0.074 mmol) was catalytically reduced as in Step-3 of Example 54, and the crude product was purified by a preparative thin layer chromatography (Merck, Kieselgel 60 F254, 0.5 mm; chloroform:methanol=20:1) to give 30 mg (86%) of Compound (50d).

Melting point: 153°–156° C.
EIMS: m/z 383 [M-MsOH]$^+$
Other physical properties are shown in Table 9.

Example 58

Synthesis of (6aR,7S,9aS,11R,12S,13aS)-2,3,6,6a,7,8,9,9a,10,11,12,13-dodecahydro-5,11-dihydroxy-6a,7,10,10-tetramethyl-12-phenylsulfonyloxy-3-oxo-1H-benzo[8,8a][1]benzopyrano[2,3-e]isoindole (50e)

Step-1: Synthesis of (6aR,7S,9aS,11R,12S,13aS)-5-benzyloxy-2-(t-butoxycarbonyl)-2,3,6,6a,7,8,9,9a,10,11,12,13-dodecahydro-11-hydroxy-6a,7,10,10-tetramethyl-12-phenylsulfonyloxy-3-oxo-1H-benzo[8,8a][1]-benzopyrano[2,3-e]isoindole (48e)

A crude product was obtained from Compound (48a) (20 mg, 0.034 mmol) substantially according to the procedure of Step-1 in Example 55 except that benzenesulfonyl chloride was used. This material was purified by a preparative thin layer chromatography (Merck, Kieselgel 60 F254, 0.5 mm; n-hexane:ethyl acetate=2:1) to give 20 mg (81%) of Compound (48e).

$^1$H NMR (CDCl$_3$) δ: 0.77 (3H, s), 0.92 (3H, s), 1.01 (3H, s), 1.07 (3H, d, J=7.5 Hz), 1.65 (9H, s), 2.24 (1H, d, J=18 Hz), 3.11 (1H, d, J=18 Hz), 3.56 (1H, br.s), 4.49 (1H, ABq, A part, J=16.8 Hz), 4.58 (1H, ABq, B part, J=16.8 Hz), 5.08 (2H, s), 5.25 (1H, m), 6.96 (1H, s), 7.30–7.46 (5H, m), 7.64–7.76 (3H, m), 8.00–8.08 (2H, m) ppm Step-2: Synthesis of (6aR,7S,9aS,11R,12S,13aS)-5-benzyloxy-2,3,6,6a,7,8,9,9a,10,11,12,13-dodecahydro-11-hydroxy-6a,7,10,10-tetramethyl-12-phenylsulfonyloxy-3-oxo-1H-benzo[8,8a][1]benzopyrano[2,3-e]isoindole (49e)

Compound (48e) (20 mg, 0.027 mmol) was subjected to a reaction similar to that of Step-2 in Example 54, and the crude product was purified by a preparative thin layer chromatography (Merck, Kieselgel 60 F254, 0.5 mm; chloroform:methanol=30:1) to give 16 mg (92%) of Compound (49e).

$^1$H NMR (CDCl$_3$) δ: 0.77 (3H, s), 0.97 (3H, s), 1.02 (3H, s), 1.05 (3H, d, J=7.5 Hz), 2.26 (1H, d, J=18 Hz), 3.12 (1H, d, J=18 Hz), 3.63 (1H,. br.s), 4.29 (2H, s), 5.10 (2H, s), 5.38 (1H, m), 6.72 (1H, s), 7.00 (1H, s), 7.30–7.48 (5H, m), 7.57–7.75 (3H, m), 7.98–8.05 (2H, m) ppm Step-3: Synthesis of (50e)

Compound (49e) (16 mg, 0.025 mmol) was catalytically reduced as in Step-3 of Example 54, and the crude product was purified by a preparative thin layer chromatography (Merck, Kieselgel 60 F254, 0.5 mm; chloroform:methanol=15:1) to give 13 mg (95%) of Compound (50e).

Melting point: 142°–144° C. (diethyl ether-pentane)
LSIMS: m/z 542 [M+H]$^+$
Other physical properties are shown in Table 9.

Example 59

Synthesis of (6aR,7S,9aS,11R,12S,13aS)-12-[4-(3-ethoxycarbonyl-1-oxo-2-propenyl)amino]phenylsulfonyloxy-2,3,6,6a,7,8,9,9a,10,11,12,13-dodecahydro-5,11-dihydroxy-6a,7,10,10-tetramethyl-3-oxo-1H-benzo[8,8a][1]benzopyrano[2,3-e]isoindole (50f)

Step-1: Synthesis of (6aR,7S,9aS,11R,12S,13aS)-5-benzyloxy-2-(t-butoxycarbonyl)-2,3,6, 6a,7,8,9,9a,10,11,12,13-dodecahydro-11-hydroxy-6a,7,10,10-tetramethyl-12-(4-nitrophenylsulfonyl)oxy-3-oxo-1H-benzo[8,8a][1]-benzopyrano[2,3-e]isoindole (48f)

To a solution of Compound (48a) (200 mg, 0.34 mmol) in 15 ml of dichloromethane were added 83 mg (0.68 mmol) of dimethylaminopyridine and 112 mg (0.51 mmol) of p-nitrobenzenesulfonyl chloride under ice-cooling, and the mixture stirred for 6 hours at the same temperature. After addition of water, the reaction mixture was extracted with ethyl acetate. The extract was washed sequentially with 1N HCl, water, an aqueous saturated sodium hydrogen carbonate solution, and water, dried over anhydrous sodium sulfate, and concentrated under reduced pressure. The residue was purified by a column chromatography (Merck, Lobar column, size B; toluene:ethyl acetate=4:1) to give 184 mg (70%) of Compound (48f).

$^1$H NMR (CDCl$_3$) δ: 0.83 (3H, s), 0.94 (3H, s), 1.03 (3H, s), 1.08 (3H, d, J=7.5 Hz), 1.66 (9H, s), 2.26 (1H, d, J=18.0 Hz), 2.58 (1H, t, J=12.0 Hz), 3.12 (1H, d, J=18.0 Hz), 3.63 (1H, d, J=2.4 Hz), 4.47 (1H, ABq, A part, J=16.5 Hz), 4.53 (1H, ABq, B part, J=16.5 Hz), 5.08 (2H, s), 5.36 (1H, dm, J=12.0 Hz), 6.96 (1H, s), 7.34–7.46 (5H, m), 8.23 (2H, d, J=9.0 Hz), 8.57 (2H, d, J=9.0 Hz) ppm Step-2: Synthesis of (6aR,7S,9aS,11R,12S,13aS)-5-benzyloxy-2,3,6,6a,7,8,9,9a,10,11,12,13-dodecahydro-11-hydroxy-6a,7,10,10-tetramethyl-12-(4-nitrophenylsulfonyl)oxy-3-oxo-1H-benzo[8,8a][1]benzopyrano[2,3-e]isoindole (48f)

Compound (48f) (180 mg, 0.23 mmol) was subjected to a reaction similar to that of Step-2 in Example 54, ant the crude product was crystallized from ethyl acetate to give 148 mg (93%) of Compound (49f).

$^1$H NMR (CDCl$_3$) δ: 0.84 (3H, s), 1.05 (6H, s), 1.07 (3H, d, J=7.5 Hz), 2.29 (1H, d, J=18.0 Hz), 2.54 (1H, t, J=12.0 Hz), 3.14 (1H, d, J=18.0 Hz), 3.74 (1H, br.s), 4.33 (2H, s), 5.11 (2H, s), 5.62 (1H, dm, J=12.0 Hz), 6.22 (1H, s), 7.02 (1H, s), 7.34–7.48 (5H, m), 8.19 (2H, d, J=9.0 Hz), 8.45 (2H, d, J=9.0 Hz) ppm Step-3: Synthesis of (50f)

i) The above Compound (49f) (127 mg, 0.19 mmol) was dissolved in 12 ml of THF-methanol (1:1), and catalytically reduced for 3 hours by the addition of 40 mg of 10% palladium-carbon. After the palladium-carbon was removed by filtration, the filtrate was concentrated under reduced pressure to give 104 mg of the amino compound. This material was used in the next reaction without further purification.

ii) To a solution of the amino compound in 8 ml of ethyl acetate was added a sodium carbonate aqueous solution (prepared from 27 mg (0.20 mmol) of sodium carbonate and 8.0 ml of water), followed by addition of 31 μl (0.23 mmol) of ethyl 3-chlorocarbonylacrylate with vigorous stirring under ice-cooling. The reaction was stirred for 30 min while allowing to warm to room temperature, and extracted with ethyl acetate. The extract was washed with water, dried over anhydrous sodium sulfate, and concentrated under reduced pressure. The residue was purified by a silica gel column chromatography (silica gel 3.5 g; ethyl acetate) to give 102 mg (80%) of Compound (50f). Physical properties of Compound (50f) are shown in Table 9.

TABLE 9

| Ex. No. | Comp. | $^1$H-NMR δ (DMSO-d$_6$) ppm | IR ν max (Nujol) cm$^{-1}$ |
|---|---|---|---|
| 54 | 50a | 0.86 (3H, s), 0.94 (6H, s), 1.08 (3H, d, J = 7.5 Hz), 2.09 (1H, d, J = 18.0Hz), 3.05 (1H, d, J = 18.0Hz), 3.28 (1H, br.s), 4.03 (1H, ABq, A part, J = 16.8 Hz), 4.16 (1H, ABq, B part, J = 16.8 Hz), 4.28 (1H, m), 6.61 (1H, s), 8.28 (1H, s) | 3326, 1687, 1628, 1610, 1075, 1052, 1035, 983 |
| 55 | 50b | 0.85 (3H, s), 0.94 (3H, s), 0.99 (3H, s), 1.08(3H, d, J = 7.2 Hz), 2.03 (3H, s), 2.12 (1H, d, J = 17.7 Hz), 3.07 (1H, d, J = 17.7 Hz), 3.47 (1H, m), 4.04 (1H, ABq, A part, J = 17.1 Hz), 4.13 (1H, ABq, B part, J = 17.1 Hz), 5.54 (1H, m), 6.63 (1H, s), 8.27 (1H, s) | 3359, 1716, 1681, 1628, 1610, 1259, 1077, 987 |
| 56 | 50c | 0.95 (3H, s), 1.05 (3H, s), 1.09 (3H, s), 1.15 (3H, d, J = 7.2 Hz), 2.28 (1H, d, J = 18.0Hz), 3.23 (1H, d, J = 18.0Hz), 3.79 (1H, br.s), 4.34 (1H, ABq, A part, J = 16.8 Hz), 4.42 (1H, ABq, B part, J = 16.8 Hz), 6.01 (1H, m), 6.61 (1H, m), 7.20 (1H, s), 7.43–7.64 (3H, m), 8.05–8.15 (2H, m) | 3346, 1684, 1628, 1609, 1278, 1114, 1074, 989 |
| 57 | 50d | 0.87 (3H, s), 0.96 (3H, s), 0.99 (3H, s), 1.08 (3H, d, J = 7.5 Hz), 2.13 (1H, d, J = 18.0Hz), 3.07 (1H, d, J = 18.0Hz), 3.21 (3H, s), 3.57 (1H, m), 4.06 (1H, ABq, A part, J = 16.8 Hz), 4.14 (1H, ABq, B part, J = 16.8 Hz), 5.37 (1H, m), 6.64 (1H, s), 8.30 (1H, s) | 3384, 1676, 1629, 1610, 1170, 1077, 989, 940, 919 |
| 58 | 50e | 0.76 (3H, s), 0.93 (3H, s), 1.00 (3H, s), 1.04 (3H, d, J = 7.8 Hz), 2.22 (1H, d, J = 18.0Hz), 3.14 (1H, d, J = 18.0Hz), 3.64 (1H, br.s), 4.24 (1H, ABq, A part, J = 16.8 Hz), 4.27 (1H, ABq, B part, J = 16.8 Hz), 5.37 (1H, m), 6.81 (1H, s), 7.18 (1H, s), 7.56–7.74 (3H, m), 7.97–8.06 (2H, m) | 3383, 1683, 1628, 1610, 1188, 1175, 1076, 987, 940, 918 |
| 59 | 50f | 0.64 (3H, s), 0.82 (3H, s), 0.88 (3H, s), 0.99 (3H, d, J = 7.2 Hz), 1.26 (3H, d, J = 7.5 Hz), 2.00 (1H, d, J = 18.0Hz), 2.35 (1H, t, J = 12.0 Hz), 3.00 (1H, d, J = 18.0Hz), 3.31 (1H, br.s), 4.00 (1H, ABq, A part, J = 16.5 Hz), 4.08 (1H, ABq, B part, J = 16.5 Hz), 4.21 (2H, q, J = 7.5 Hz) 5.14 (1H, dm, J = 12.0 Hz), 6.62 (2H, s), 6.74 (2H, d, J = 15.5 Hz), 7.18 (2H, d, J = 15.5 Hz), 7.96 (4H, s), 8.26 (1H, s), 9.75 (1H, s) | 3327, 1685, 1593, 1536, 1497, 1191, 1171, 1076, 987 |

Reactions in Examples 60–65 are illustrated by the following reaction scheme.

Process 6

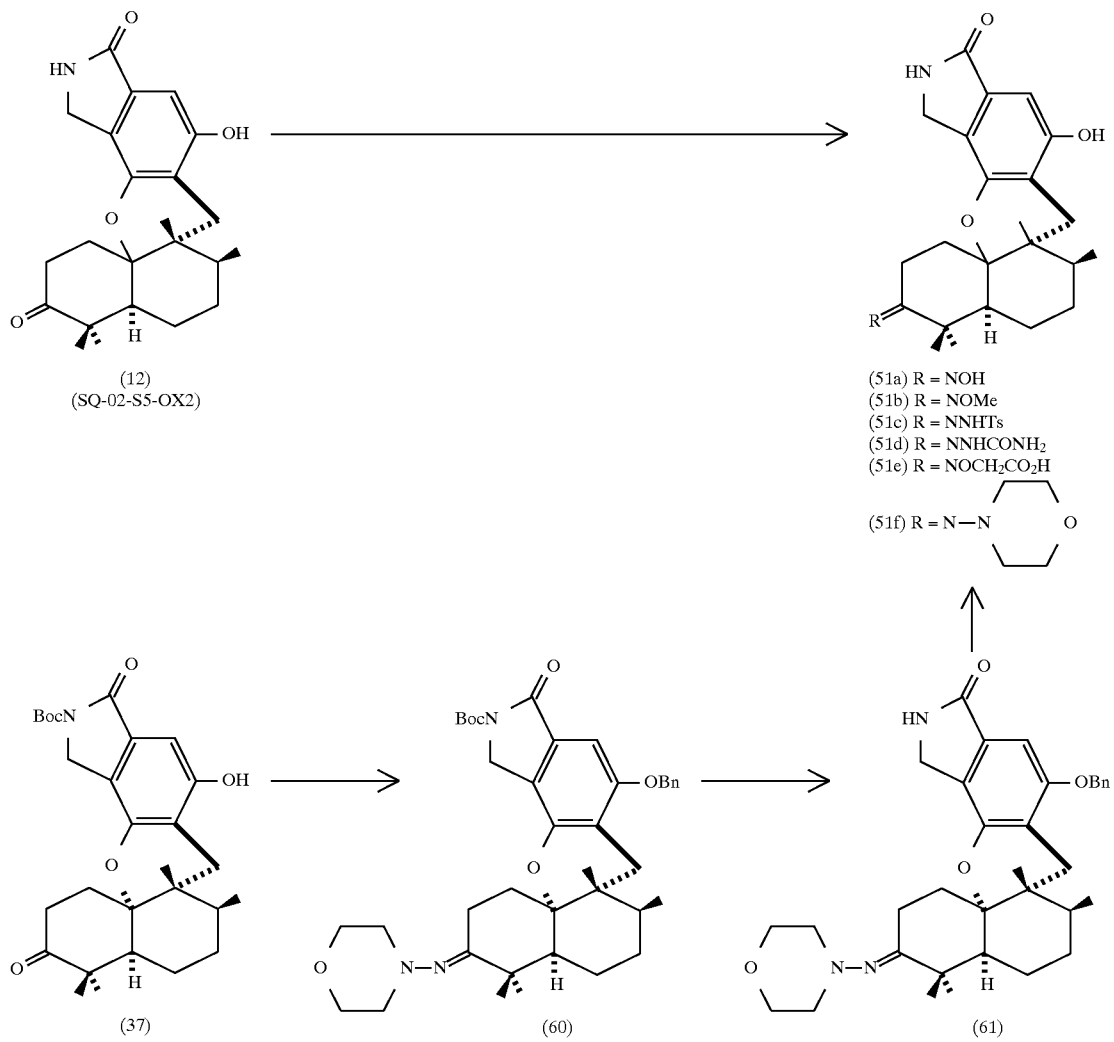

Example 60

Synthesis of (6aR,7S,9aS,13aS)-2,3,6,6a,7,8,9,9a,
10,11,12,13-dodecahydro-5-hydroxy-11-
hydroxyimino-6a,7,10,10-tetramethyl-3-oxo-1H-
benzo[8,8a][1]benzopyrano[2,3-e]isoindole (51a)

To a solution of Compound (12) (Step-2 of Example 55) (30 mg, 0.078 mmol) in 3.0 ml of ethanol were added 0.3 ml (3.70 mmol) of pyridine and 9 mg (0.13 mmol) of hydroxylamine hydrochloride, and the mixture stirred for 3 hours at 80° C. After addition of water, the reaction mixture was extracted with ethyl acetate. The extract was washed sequentially with 1N HCl, water, an aqueous saturated sodium hydrogen carbonate solution and water, and dried over anhydrous magnesium sulfate. The solvent was evaporated under reduced pressure. The crystalline residue was recrystallized from diethyl ether-pentane to give 26 mg (83%) of Compound (51a).

EIMS: m/z 398 [M]+

Other physical properties are shown in Table 10.

Example 61

Synthesis of (6aR,7S,9aS,13aS)-2,3,6,6a,7,8,9,9a,
10,11,12,13-dodecahydro-5-hydroxy-11-
methoxyimino-6a,7,10,10-tetramethyl-3-oxo-1H-
benzo[8,8a][1]benzopyrano[2,3-e]isoindole (51b)

The crude product was obtained from Compound (12) (50 mg, 0.13 mmol) substantially according to the procedure of Example 60 except that O-methylhydroxylamine hydrochloride was used. The product was purified by a preparative thin layer chromatography (Merck, Kieselgel 60 F254, 0.5 mm; chloroform:methanol=10:1) and by crystallization from diethyl ether-pentane to give 39 mg (73%) for Compound (51b).

EIMS: m/z 412 [M]+

Other physical properties are shown in Table 10.

Example 62

Synthesis of (6aR,7S,9aS,13aS)-2,3,6,6a,7,8,9,9a,
10,11,12,13-dodecahydro-5-hydroxy-6a,7,10,10-
tetramethyl-3-oxo-11-(2-p-tolyl-1,1-diazanediyl)-
1H-benzo[8,8a][1]benzopyrano[2,3-e]
isoindole (51c)

Under nitrogen, 60 mg (0.32 mmol) of p-toluenesulfonehydrazide was added to a solution of Compound (12) (30 mg, 0.078 mmol) in 3.0 ml of dry ethanol, and the mixture stirred for 6 hours at 80° C. After addition of water, the reaction mixture was extracted with ethyl acetate. The extract was washed sequentially with 1N HCl, water, an aqueous saturated sodium hydrogen carbonate solution and water, dried over anhydrous magnesium sulfate, and concentrated under reduced pressure. The residue was purified by a preparative thin layer chromatography (Merck, Kieselgel 60 F254, 0.5 mm; chloroform:methanol= 10:1) to give 23 mg (80%) of Compound (51c).

LSIMS: m/z 552 [M+H]$^+$

Other physical properties are shown in Table 10.

Example 63

Synthesis of (6aR,7S,9aS,13aS)-2,3,6,6a,7,8,9,9a, 10,11,12,13-dodecahydro-5-hydroxy-6a,7,10,10-tetramethyl-3-oxo-11-ureidoimino-1H-benzo[8,8a][1]benzopyrano[2,3-e]isoindole (51d)

Under nitrogen, 0.40 ml (4.95 mmol) of pyridine and 22 mg (0.20 mmol) of semicarbazide hydrochloride were added to a solution of Compound (12) (50 mg, 0.13 mmol) in 4.0 ml of dry ethanol, and the mixture stirred for 16 hours at room temperature. After addition of water, the reaction mixture was extracted with ethyl acetate. The exact was washed with water, dried over anhydrous magnesium sulfate, and concentrated under reduced pressure. The residue was purified by a preparative thin layer chromatography (Merck, Kieselgel 60 F254, 0.5 mm; chloroform:methanol= 10:1) and by crystallization from diethyl ether-pentane to give 31 mg (54%) of Compound (51d).

LSIMS: m/z 441 [M+H]$^+$

Other physical properties are shown in Table 10.

Example 64

Synthesis of (6aR,7S,9aS,13aS)-11-carboxymethoxyimino-2,3,6,6a,7,8,9,9a,10,11,12,13-dodecahydro-5-hydroxy-6a,7,10,10-tetramethyl-3-oxo-1H-benzo[8,8a][1]benzopyrano[2,3-e]isoindole (51e)

To a solution of Compound (12) (50 mg, 0.13 mmol) in 5.0 ml of ethanol were added 0.2 ml (2.7 mmol) of pyridine and 30 mg (0.27 mmol) of carboxymethoxylamine hemihydrochloride, and the mixture stirred for 36 hours at room temperature. After addition of water, the reaction mixture was acidified with 1N HCl followed by extraction with ethyl acetate. The extract was washed with water and saturated brine, dried over anhydrous magnesium sulfate, and concentrated under reduced pressure. The residue was crystallized from diethyl ether-pentane to give 47 mg (79%) of Compound (51e).

LSIMS: m/z 457 [M+H]$^+$

Other physical properties are shown in Table 10.

Example 65

Synthesis of (6aR,7S,9aS,13aS)-2,3,6,6a,7,8,9,9a, 10,11,12,13-dodecahydro-5-hydroxy-6a,7,10,10-tetramethyl-11-(1-oxa-4-azacyclohex-4-yl)imino-3-oxo-1H-benzo[8,8a][1]benzopyrano[2,3-e]isoindole (51f)

Step-1: Synthesis of (6aR,7S,9aS,13aS)-5-benzyloxy-2-(t-butoxycarbonyl)-2,3,6,6a,7,8,9,9a,10,11,12,13-dodecahydro-6a,7,10,10-tetramethyl-11-(1-oxa-4-azacyclohex-4-yl)imino-3-oxo-1H-benzo[8,8a][1]benzopyrano[2,3-e]isoindole (60)

To a solution of Compound (37) (573 mg, 1.00 mmol) in 60 ml of ethanol were added 306 mg (3.00 mmol) of N-aminomorpholine and 328 µl (3.51 mmol) of trifluoroacetic acid. The reaction was allowed to proceed for 72 hours. The reaction mixture was then concentrated under reduced pressure. The residue was purified by a silica gel column chromatography (silica gel 100 g; n-hexane:ethyl acetate=7:3) to give 265 mg (40%) of Compound (60).

$^1$H NMR (CDCl$_3$) δ: 0.90 (3H, s), 1.04 (3H, s), 1.09 (3H, d, J=8.0 Hz), 1.24 (3H, s), 1.60 (9H, s), 2.30 (1H, d, J=18 Hz), 2.55 (1H, m), 3.16 (1H, d, J=18 Hz), 3.22 (1H, m), 3.84 (4H, m), 4.64 (2H, q) 5.11 (2H, s), 7.00 (1H, s), 7.30–7.50 (5H, m) ppm Step-2: Synthesis of (6aR,7S,9aS,13aS)-5-benzyloxy-2,3,6, 6a,7,8,9,9a,10,11,12,13-dodecahydro-6a,7,10,10-tetramethyl-11-(1-oxa-4-azacyclohex-4-yl)imino-3-oxo-1H-benzo[8,8a][1]benzopyrano[2,3-e]isoindole (61)

To the above Compound (60) (265 mg, 0.40 mmol) was added 2.0 ml of 4N HCl/dioxane solution, and the mixture stirred for one hour at room temperature. The reaction mixture was made basic with 7% aqueous sodium hydrogen carbonate solution, and extracted with ethyl acetate. The extract was concentrated under reduced pressure. The residue was purified by a silica gel column chromatography (silica gel 10 g; ethyl acetate:methanol=97:3) to give 224 mg (100%) of Compound (61).

$^1$H NMR (CDCl$_3$) δ: 0.91 (3H, s), 1.03 (3H, s), 1.09 (3H, d, J=8 Hz), 1.24 (3H, s), 2.31 (1H, d, J=18 Hz), 2.55 (1H, m), 3.16 (1H, d, J=18 Hz), 3.23 (1H, m), 3.83 (4H, m), 4.32 (2H, s), 5.12 (2H, s), 6.08 (1H, s), 7.02 (1H, s), 7.30–7.50 (5H, m) ppm Step-3: Synthesis of (51f)

To a solution of Compound (61) (224 mg, 0.40 mmol) in 50 ml of methanol containing 1% water was added 180 mg of 10% palladium-carbon, followed by catalytic reduction. After the palladium-carbon was removed by filtration, the filtrate was concentrated under reduced pressure. The residue was purified by a silica gel column chromatography (silica gel 10 g; ethyl acetate:methanol=99:1) and further crystallization from diethyl ether-n-hexane to give 152 mg (79%) of Compound (51f).

Melting point: 202°–205° C.

Elemental analysis for $C_{27}H_{37}N_3O_4.1/6C_6H_{12}.1/2$ $H_2O$ Calcd.: C, 68.49%; H, 8.28%; N, 8.56% Found: C, 68.32%; H, 8.37%; N, 8.34%

Other physical properties are shown in Table 10.

TABLE 10

| Ex. No. | Comp. | $^1$H-NMR δ (DMSO-d$_6$) ppm | IR ν max (Nujol) cm$^{-1}$ |
|---|---|---|---|
| 60 | 51a | 0.84 (3H, s), 0.98 (3H, s), 1.04 (3H, d, J = 7.8 Hz), 1.18 (3H, s), 2.14 (1H, d, J = 18.0Hz), 3.05 (1H, d, J = 18.0Hz), 4.11 (1H, ABq, A part, J = 17.1 Hz), 4.20 (1H, ABq, B part, J = 17.1 Hz), 6.65 (1H, s), 8.32 (1H, s), | 3448, 3348, 1698, 1669, 1635, 1617, 1070, 939, 917 |
| 61 | 51b | 0.83 (3H, s), 0.97 (3H, s), 1.04 (3H, d, J = 7.8 Hz), 1.18 (3H, s), 2.14 (1H, d, J = 18.3Hz), 3.05 (1H, d, J = 18.3Hz), 3.75 (3H, s), 4.11 (1H, ABq, A part, J = 16.8 Hz), 4.19 (1H, ABq, B part, J =16.8 Hz), 6.65 (1H, s), 8.31 (1H, s) | 3288, 1694, 1664, 1631, 1500, 1071, 1050 |
| 62 | 51c | 0.80 (3H, s), 0.81 (3H, s), 0.96 (3H, d, J = 7.5 Hz), 1.08 (3H, s), 2.10 (1H, d, J = 18.0Hz), 2.37 (3H, s), 2.98 (1H, d, J = 18.0Hz), 4.05 (1H, ABq, A part, J = 17.1 Hz), 4.16 (1H, ABq, B part, J =17.1 Hz), 6.32 (1H, s), 7.37 (2H, d, J = 8.1 | 3361, 3214, 1681, 1627, 1610, 1165, 1071 |

TABLE 10-continued

| Ex. No. | Comp. | $^1$H-NMR δ (DMSO-$d_6$) ppm | IR ν max (Nujol) cm$^{-1}$ |
|---|---|---|---|
| | | Hz), 7.72 (2H, d, J = 8.1 Hz), 8.30 (1H, s) | |
| 63 | 51d | 0.84 (3H, s), 1.00 (3H, s), 1.04 (3H, d, J = 7.5 Hz), 1.17 (3H, s), 2.14 (1H, d, J = 18.0Hz), 3.04 (1H, d, J =18.0Hz), 4.10 (1H, ABq, A part, J =17.1 Hz), 4.19 (1H, ABq, B part, J = 17.1 Hz), 6.13 (2H, br.s), 6.65 (1H, s), 8.31 (1H, s) | 3464, 3268, 1677, 1628, 1576, 1074 |
| 64 | 51e | 0.84 (3H, s), 0.94 (3H, s), 1.06 (3H, d, J = 7.5 Hz), 1.21 (3H, s), 2.14 (1H, d, J = 18.0Hz), 3.05 (1H, d, J = 18.0Hz), 4.12 (1H, ABq, A part, J =17.1 Hz), 4.21 (1H, ABq, B part, J = 17.1 Hz), 4.94 (2H, s), 6.66 (1H, s), 8.32 (1H, s), 9.78 (1H, br.s) | 3338, 2924, 2855, 1694, 1629, 1613, 1466, 1366, 1092, 1071 |
| 65 | 51f | 0.92 (3H, s), 1.04 (3H, s), 1.11 (3H, d, J = 8.0 Hz), 1.24 (3H, s), 2.27 (1H, d, J = 18.0Hz), 2.55 (1H, m), 3.20 (1H, d, J = 18.0Hz), 3.24 (1H, m), 3.82 (4H, m), 4.35 (2H, s), 6.18 (1H, s), 6.52 (1H, s), 7.05 (1H, s) (CDCl$_3$) | 3256, 1686, 1626, 1612, 1465, 1365 |

Reactions in Examples 66 and 67 are illustrated by the following reaction scheme.

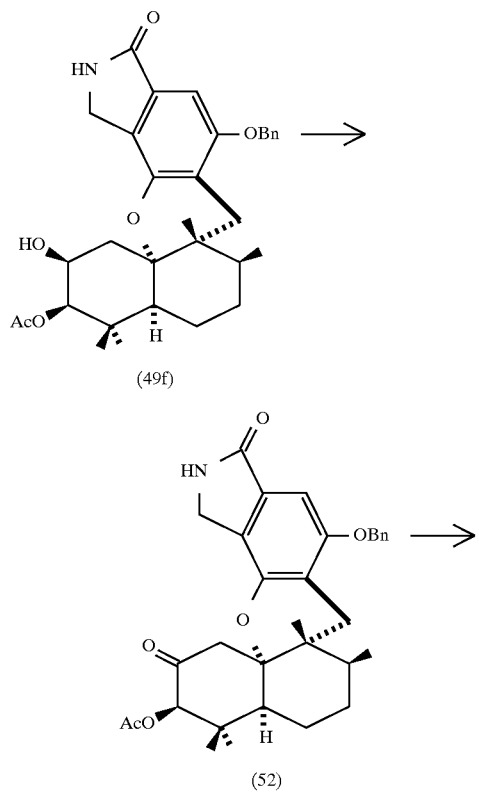

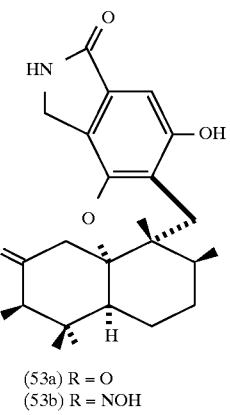

(53a) R = O
(53b) R = NOH

Example 66

Synthesis of (6aR,7S,9aS,11S,13aS11-acetoxy-2,3,6,6a,7,8,9,9a,10,11,12,13-dodecahydro-5-hydroxy-6a,7,10,10-tetramethyl-3,12-dioxo-1H-benzo[8,8a][1]benzopyrano[2,3-e]isoindole (53a)

Step-1: Synthesis of (6aR,7S,9aS,11S,13aS)-11-acetoxy-5-benzyloxy-2,3,6,6a,7,8,9,9a,10,11,12,13-dodecahydro-6a,7,10,10-tetramethyl-3,12-dioxo-1H-benzo[8,8a][1]benzopyrano[2,3-e]isoindole (52)

To a solution of Compound (49f) (Step-2 in Example 55) (116 mg, 0.22 mmol) in 5.0 ml of acetone was added dropwise 65 μl (0.26 mmol) of the Jones reagent under ice-cooling, and the mixture stirred for 30 min at the same temperature. To the reaction mixture was added 100 μl of isopropanol. The mixture was stirred for 5 min, neutralized with an aqueous saturated sodium hydrogen carbonate solution, and concentrated under reduced pressure to a half volume. After addition of water, the mixture was extracted with ethyl acetate. The extract was washed with water and saturated brine, dried over anhydrous magnesium sulfate, and concentrated under reduced pressure. The residue was purified by a column chromatography (Merck, Lobar column, size A; toluene:ethyl acetate=1:1) to give 101 mg (87%) of Compound (52).

$^1$H NMR (CDCl$_3$) δ: 0.92 (3H, s), 0.98 (3H, s), 0.99 (3H, s), 1.07 (3H, d, J=7.2 Hz), 2.21 (3H, s), 2.36 (1H, d, J=18.0 Hz), 2.74 (1H, d, J=17.7 Hz), 3.01 (1H, d, J=17.7 Hz), 3.11 (1H, d, J=18.0 Hz), 4.39 (2H, s), 5.12 (2H, s), 6.00 (1H, s), 6.17 (1H, s), 7.04 (1H, s), 7.30–7.48 (5H, m) ppm Step-2: Synthesis of (53a)

The above compound (52) (100 mg, 0.19 mmol) was catalytically reduced as in Step-3 of Example 54, and the product was crystallized from diethyl ether-pentane to give 64 mg (77%) of Compound (53a).

EIMS: m/z 441 [M]$^+$

Other physical properties are shown in Table 11.

Example 67

Synthesis of (6aR,7S,9aS,11S,13aS)-11-acetoxy-2,3,6,6a,7,8,9,9a,10,11,12,13-dodecahydro-5-hydroxy-12-hydroxyimino-6a,7,10,10-tetramethyl-3-oxo-1H-benzo[8,8a][1]benzopyrano[2,3-e]isoindole (53b)

To a solution of Compound (53a) (25 mg, 0.057 mmol) in 2.0 ml of dry ethanol were added 0.1 ml (1.24 mmol) of pyridine and 6 mg (0.086 mmol) of hydroxylamine hydrochloride, and the mixture stirred for 12 hours at room temperature. After addition of ice-water, the mixture was extracted with ethyl acetate. The extract was washed sequentially with 1N HCl, water, an aqueous saturated sodium hydrogen carbonate solution and water, and dried over anhydrous magnesium sulfate. The solvent was evaporated under reduced pressure. The residue was purified by a preparative thin layer chromatography (Merck, Kieselgel 60 F254, 0.5 mm; chloroform:methanol=10: 1) to give 21 mg (81%) of Compound (53b).

FAB: m/z 457 [M+H]$^+$

Other physical properties are shown in Table 11.

TABLE 11

| Ex. No. | Comp. | $^1$H-NMR δ (DMSO-d$_6$) ppm | IR ν max (Nujol) cm$^{-1}$ |
|---|---|---|---|
| 66 | 53a | 0.86 (3H, s), 0.91 (3H, s), 0.92 (3H, s), 0.97 (3H, d, J = 7.2 Hz), 2.14 (3H, s), 2.23 (1H, d, J = 18.0Hz), 2.68 (1H, d, J =17.7 Hz), 2.98 (1H, d, J = 18.0Hz), 3.00 (1H, d, J = 17.7 Hz), 4.12 (2H, s), 5.82 (1H, s), 6.68 (1H, s), 8.35 (1H, s) | 3371, 3236, 1741, 1729, 1701, 1631, 1612, 1238, 1079 |
| 67 | 53b | 0.87 (3H, s), 0.88 (3H, s), 0.97 (3H, s), 1.11 (3H, d, J = 7.2 Hz), 2.07 (3H, s), 2.17 (1H, d, J = 17.4Hz), 3.06 (1H, d, J = 17.4Hz), 3.96 (1H, ABq, A part, J = 17.1 Hz), 4.01 (1H, ABq, B part, J = 17.1 Hz), 5.22 (1H, s), 6.62 (1H, s), 8.27 (1H, s) | 3267, 1735, 1675, 1630, 1610, 1244, 1083, 1071, 1034 |

Reactions in Examples 68 and 69 are shown in the following reaction scheme.

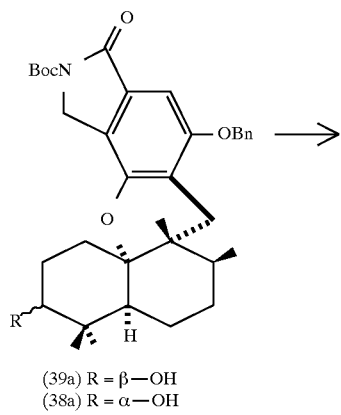

(39a) R = β—OH
(38a) R = α—OH

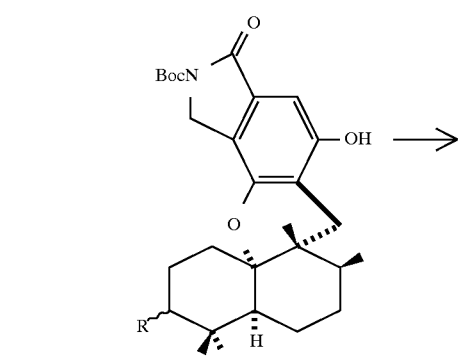

(55a) R = β—OH
(55b) R = α—OH

-continued

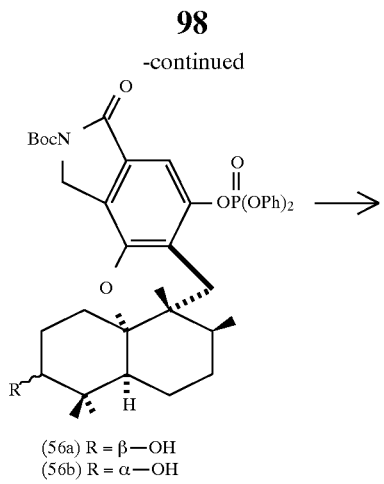

(56a) R = β—OH
(56b) R = α—OH

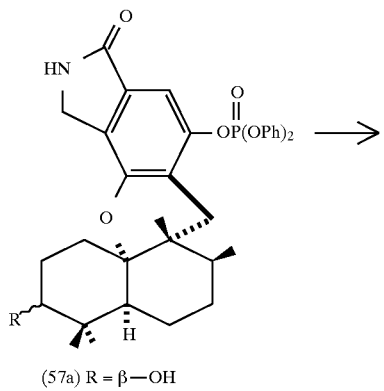

(57a) R = β—OH
(57b) R = α—OH

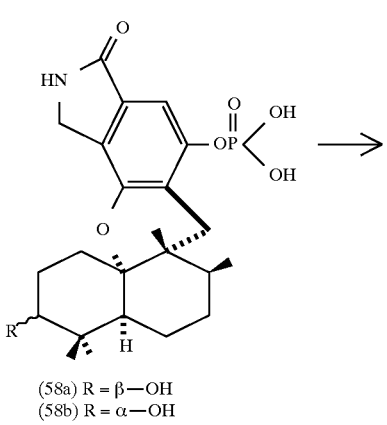

(58a) R = β—OH
(58b) R = α—OH

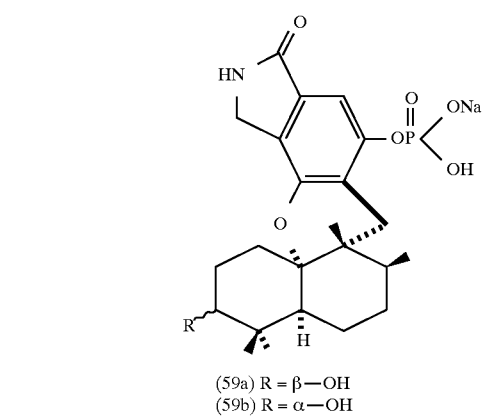

(59a) R = β—OH
(59b) R = α—OH

Example 68

Synthesis of (6aR,7S,9aS,11S,13aS)-2,3,6,6a,7,8,9,9a,10,11,12,13-dodecahydro-11-hydroxy-5-dihydroxyphosphinyloxy-6a,7,10,10-tetramethyl-3-oxo-1H-benzo[8,8a][1]benzopyrano[2,3-e]isoindole monosodium salt (59a)

Step-1: Synthesis of (6aR,7S,9aS,11S,13aS)-2-(t-butoxycarbonyl)-2,3,6,6a,7,8,9,9a,10,11,12,13-dodecahydro-5,11-dihydroxy-6a,7,10,10-tetramethyl-3-oxo-1H-benzo[8,8a][1]benzopyrano[2,3-e]isoindole (55a)

To a solution of Compound (39a) (Step-1 in Example 44) (303 mg, 0.53 mmol) in 10 ml of methanol containing 1% water was added 30 mg of 10% palladium-carbon, followed by catalytic reduction under atomospheric pressure for 2.5 hours. After the catalyst was removed by filtration, the filtrate was concentrated under reduced pressure. The residue was purified by a column chromatography (silica gel 5 g; ethyl acetate) to give 234 mg (91%) of Compound (55a).

Melting point: 165°–169° C. (decomp.)

Elemental analysis for $C_{28}H_{39}NO_6 \cdot 1/4H_2O$ Calcd.: C, 68.61%; H, 8.12%; N, 2.81% Found: C, 68.57%; H, 8.10%; N, 2.81%

IR $\nu_{max}$ (CHCl$_3$): 3690, 3602, 1772, 1728, 1603 cm$^{-1}$

Step-2: Synthesis of (6aR,7S,9aS,11S,13aS)-2-(t-butoxycarbonyl)-2,3,6,6a,7,8,9,9a, 10,11,12,13-dodecahydro-11-hydroxy-6a,7,10,10-tetramethyl-3-oxo-5-diphenoxyphosphinyloxy-1H-benzo[8,8a][1]benzopyrano[2,3-e]isoindole (56a)

Under nitrogen, 40 mg (1.0 mmol) of sodium hydride (ca. 60% in oil) was added to a solution of the above Compound (55a) (234 mg, 0.48 mmol) in 2 ml of dry dimethylformamide, and the mixture stirred for 15 min. To the reaction mixture was added dropwise 120 μl (0.58 mmol) of diphenyl phosphorochloridate, and the mixture stirred for another 1.5 hours at the same temperature. After addition of ice-water under ice-cooling, the reaction mixture was extracted with ethyl acetate. The extract was washed with water and saturated brine, dried over anhydrous magnesium sulfate, and concentrated under reduced pressure. The residue was purified by a column chromatography (silica gel 15 g; n-hexane:ethyl acetate=2:1) to give 277 mg (80%) of Compound (56a) as an oily material.

$^1$H NMR (CDCl$_3$) δ: 0.80 (3H, s), 0.98 (3H, s), 0.99 (3H, s), 1.10 (3H, d, J=7.5 Hz), 1.59 (9H, s), 2.09 (1H, d, J=18 Hz), 3.05 (1H, d, J=18 Hz), 3.56 (1H, br.s), 4.64 (2H, q, J=16.8 Hz), 7.20–7.40 (11H, m) ppm IR $\nu_{max}$ (CHCl$_3$): 3610, 1775, 1735, 1710, 1610, 1590 cm$^{-1}$ Step-3: Synthesis of (6aR,7S,9aS,11S,13aS)-2,3,6,6a,7,8,9,9a,10,11,12,13-dodecahydro-11-hydroxy-6a,7,10,10-tetramethyl-3-oxo-5-diphenoxyphosphinyloxy-1H-benzo[8,8a][1]benzopyrano[2,3-e]isoindole (57a)

To a solution of the above Compound (56a) (256 mg, 0.36 mmol) in 2.5 ml of dry dichloromethane were added 50 μl of anisole and 2.5 ml of trifluoroacetic acid, and the mixture stirred for 10 min at the same temperature, and then for one hour at room temperature. The reaction mixture was concentrated under reduced pressure. The residue was made basic with 7% aqueous sodium hydrogen carbonate solution, and extracted with ethyl acetate. The extract was washed with water, dried over anhydrous magnesium sulfate, and concentrated under reduced pressure. The residue was purified by a column chromatography (silica gel 15 g; ethyl acetate) to give 203 mg (91%) of Compound (57a).

Melting point: 245°–250° C. (decomp.)

Elemental analysis for $C_{35}H_{40}NO_7P \cdot 1/4H_2O$ Calcd.: C, 67.56%; H, 6.56%; N, 2.25%; P, 4.98% Found: C, 67.76%; H, 6.56%; N, 2.38%; P, 4.71%

$^1$H NMR (CDCl$_3$) δ: 0.81 (3H, s), 0.98 (3H, s), 0.99 (3H, s), 1.10 (3H, d, J=7.5 Hz), 2.06 (1H, d, J=18 Hz), 3.05 (1H, d, J=18 Hz), 3.55 (1H, br.s), 4.35 (2H, s), 6.38 (1H, s), 7.20–7.45 (11H, m) ppm IR $\nu_{max}$ (CHCl$_3$): 3422, 3307, 1677, 1603, 1589 cm$^{-1}$ Step-4: Synthesis of (6aR,7S,9aS,11S,13aS)-2,3,6,6a,7,8,9,9a,10,11,12,13-dodecahydro-11-hydroxy-5-dihydroxyphosphinyloxy-6a,7,10,10-tetramethyl-3-oxo-1H-benzo[8,8a][1]benzopyrano[2,3-e]isoindole ditriethylamine salt (58a)

Platinum oxide (80 mg) was reduced in methanol under hydrogen atmosphere for 15 min at room temperature. To the mixture was added the above Compound (57a) (200 mg, 0.32 mmol), followed by catalytic reduction for 14 hours under atomospheric pressure. After the catalyst was removed by filtration, the filtrate was concentrated under reduced pressure. The residue was dissolved in 0.5 ml of 7% aqueous sodium hydrogen carbonate solution and 50 ml of water, and adsorbed onto a column (10×50 cm) charged with diethylaminoethyl cellulose resin (trade name: DE52 HCO$_3^-$). The column was washed with water and eluted with aqueous triethylammonium bicarbonate (a linear gradient of 0 to 0.25M) to give 201 mg (79%) of crude Compound (58a).

$^1$H NMR (CD$_3$OD) δ: 0.92 (3H, s), 0.97 (3H, s), 1.03 (3H, s), 1.20 (3H, d, J=7.0 Hz), 1.20 (18H, t, J=7.0 Hz), 2.46 (1H, d, J=18 Hz), 2.82 (12H, q, J=7.0 Hz), 3.40 (1H, d, J=18 Hz), 3.49 (1H, br.s), 4.29 (2H, s), 6.88 (1H, s), 7.48 (1H, s) ppm Step-5: Synthesis of (59a)

To a solution of Compound (58a) (180 mg, 0.15 mmol) in 0.5 ml of methanol was added 9 ml of 0.05N sodium perchlorate/acetone solution, and the mixture allowed to stand over night. The gray precipitate formed was filtered off, washed with acetone, and dried to give 120 mg (95%) of Compound (59a).

Melting point: 210°–215° C. (decomp.)

Elemental analysis for $C_{23}H_{31}NO_7NaP \cdot 4 H_2O$ Calcd.: C, 49.37%; H, 7.03%; N, 2.50%; Na, 4.94% Found: C, 49.26%; H, 6.94%; N, 2.70%; Na, 4.84%

Other physical properties are shown in Table 12.

Example 69

Synthesis of (6aR,7S,9aS,11R,13aS)-2,3,6,6a,7,8,9,9a,10,11,12,13-dodecahydro-11-hydroxy-5-dihydroxyphosphinyloxy-6a,7,10,10-tetramethyl-3-oxo-1H-benzo[8,8a][1]benzopyrano[2,3-e]isoindole monosodium salt (59b)

Step-1: Synthesis of (6aR,7S,9aS,11R,13aS)-2-(t-butoxycarbonyl)-2,3,6,6a,7,8,9,9a,10,11,12,13-dodecahydro-5,11-dihydroxy-6a,7,10,10-tetramethyl-3-oxo-1H-benzo[8,8a][1]benzopyrano[2,3-e]isoindole (55b)

Compound (38a) (Step-3 in Example 42) (255 mg, 0.436 mmol) was subjected to a reaction similar to that of Step-1 in Example 68 to give 200 mg (94%) of Compound (55b).

$^1$H NMR (CDCl$_3$) δ: 0.87 (3H, s), 0.98 (3H, s), 1.03 (3H, s), 1.12 (3H, d, J=7.5 Hz), 2.27 (1H, d, J=18.9 Hz), 3.13 (1H, d, J=18.9 Hz), 3.72 (1H, br.s), 4.64 (2H, s), 5.80 (1H, s), 6.91 (1H, s) ppm IR $\nu_{max}$ (CHCl$_3$): 3690, 3602, 3380, 1771, 1723, 1624 cm$^{-1}$ Step-2: Synthesis of (6aR,7S,9aS,11R,13aS)-2-(t-butoxycarbonyl)-2,3,6,6a,7,8,9,9a,10,11,12,13-dodecahydro-11-hydroxy-6a,7,10,10-tetramethyl-3-oxo-5-diphenoxyphosphinyloxy-1H-benzo[8,8a][1]benzopyrano[2,3-e]isoindole (56b)

The above Compound (55b) (194 mg, 0.4 mmol) was subjected to a reaction and a column chromatographic purification substantially according to the procedures of Step-2 in Example 68 to give 230 mg (80%) of the target Compound (56b).

$^1$H NMR (CDCl$_3$) δ: 0.77 (3H, s), 0.97 (3H, s), 1.00 (3H, s), 1.07 (3H, d, J=7.5 Hz), 1.60 (9H, s), 2.62 (1H, d, J=18 Hz), 3.01 (1H, d, J=18 Hz), 3.70 (1H, br.s), 4.68 (2H, m), 7.20–7.44 (11H, m) ppm IR ν$_{max}$ (CHCl$_3$): 3611, 3480, 1776, 1735, 1713, 1611, 1591 cm$^{-1}$ Step-3: Synthesis of (6aR,7S,9aS,11R,13aS)-2,3,6,6a,7,8,9, 9a,10,11,12,13-dodecahydro-11-hydroxy-6a,7,10,10-tetramethyl-3-oxo-5-diphenoxyphosphinyloxy-1H-benzo[8, 8a][1]benzopyrano[2,3-e]isoindole (57b)

The above compound (56b) (220 mg, 0.31 mmol) was subjected to a reaction and a column chromatographic purification substantially according to the procedures of Step-3 in Example 68 to give 180 mg (93%) of the target Compound (57b).

Melting point: 220–225 (decomp.) (diethyl ether)

Elemental analysis for C$_{35}$H$_{40}$NO$_7$P.3/4 H$_2$O Calcd.: C, 66.60%; H, 6.63%; N, 2.22%; P, 4.91% Found: C, 66.66%; H, 6.50%; N, 2.64%; P, 4.48%

$^1$H NMR (CDCl$_3$) δ: 0.79 (3H, s), 0.97 (3H, s), 0.99 (3H, s), 1.07 (3H, d, J=7.5 Hz), 2.07 (1H, d, J=18 Hz), 3.01 (1H, d, J=18 Hz), 3.70 (1H, br.s), 4.38 (2H, m), 6.32 (1H, s), 7.20–7.45 (11H, m) ppm IR ν$_{max}$ (Nujol): 3422, 3307, 1677, 1603, 1589 cm$^{-1}$ Step-4: Synthesis of (59b)

The compound (57b) (170 mg, 0.27 mmol) was reacted according to the procedures in Step-4 and Step-5 of Example 68 to give 120 mg (82%) of Compound (59b).

Melting point: 255–260° C. (decomp.)

Other physical properties are shown in Table 12.

Example 70

Synthesis of (6aR,7S,9aS,13aS)-2,3,6,6a,7,8,9,9a, 10,11,12,13-dodecahydro-11-hydroxyimino-5-dihydroxyphosphinyloxy-6a,7,10,10-tetramethyl-3-oxo-1H-benzo[8,8a][1]benzopyrano[2,3-e]isoindole monosodium salt (64)

The reactions in Example 70 are illustrated by the following reaction scheme.

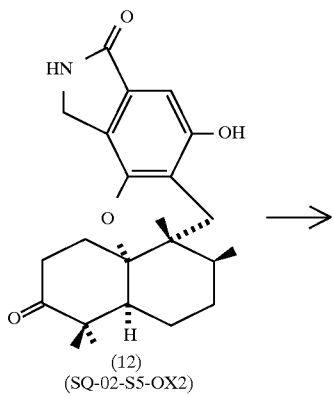

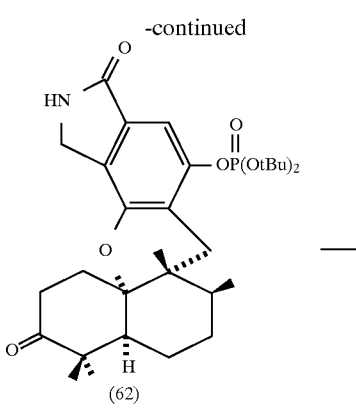

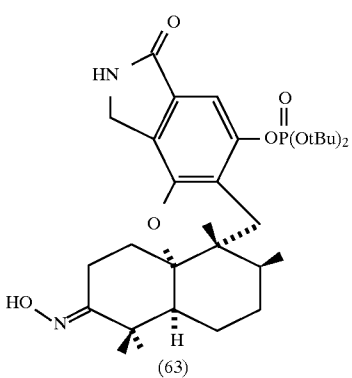

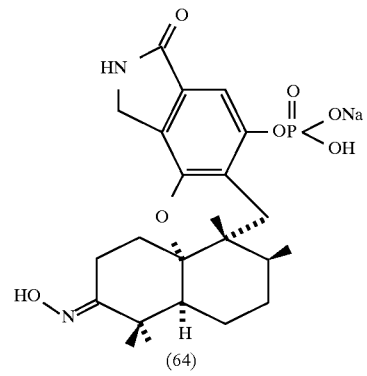

Step-1: Synthesis of (6aR,7S,9aS,13aS)-5-(di-t-butoxyphosphinyloxy)-2,3,6,6a,7,8,9,9a,10,11,12,13-dodecahydro-6a,7,10,10-tetramethyl-3,11-dioxo-1H-benzo[8,8a][1]benzopyrano[2,3-e]isoindole (62)

To a solution of Compound (12) (300 mg, 0.78 mmol) in 8 ml of dry DMF were added 247 mg (3.53 mmol) of tetrazole and 327 μl (1.17 mmol) of di-t-butyldiethylphosphoramidite, and the mixture stirred for one hour. Under ice-cooling, to the reaction mixture was added 358 mg (1.65 mmol) of 80% m-chloroperbenzoic acid dissolved in 3 ml of dichloromethane, followed by stirring for additional one hour at the same temperature. To the reaction mixture was added 3 ml of 10% aqueous sodium hydrogen sulfite solution, followed by extraction with ethyl acetate. The extract was washed with an aqueous saturated sodium hydrogen carbonate, and saturated brine, dried over anhydrous sodium sulfate, and concentrated under reduced pressure. The residue was purified by a silica gel column chromatography (silica gel 25 g; chloroform:methanol=19: 1) to give 435 mg (100%) of Compound (62).

$^1$H NMR (CDCl$_3$) δ: 0.95 (3H, s), 0.99 (3H, s), 1.12 (3H, d, J=7.5 Hz), 1.16 (3H, s), 1.53 (18H, d, J=1.8 Hz), 2.45 (1H, d, J=18.0 Hz), 3.02 (1H, m), 3.28 (1H, d, J=18.0 Hz), 4.33 (1H, ABq, A part, J=17 Hz), 4.38 (1H, ABq, B part, J=17 Hz), 6.65 (1H, s), 7.38 (1H, d, J=1.0 Hz) ppm IR $\nu_{max}$ (CHCl$_3$): 3446, 1698, 1604, 1272, 1038, 1004 cm$^{-1}$ Step-2: Synthesis of (6aR,7S,9aS,13aS)-5-(di-t-butoxyphosphinyloxy)-2,3, 6, 6a,7,8,9,9a,10,11,12,13-dodecahydro-11-hydroxyimino-6a,7,10,10-tetramethyl-3-oxo-1H-benzo[8,8a][1]benzopyrano[2,3-e]isoindole (63)

To a solution of Compound (62) (375 mg, 0.67 mmol) in 10 ml of ethanol was added 1.08 ml (13.4 mmol) of pyridine and 70 mg (1.00 mmol) of hydroxylamine hydrochloride, and the mixture stirred for 7 hours at room temperature. The reaction mixture was concentrated under reduced pressure to a half volume, and ethyl acetate and water were added thereto. After neutralizing with 0.2N HCl, the mixture was extracted with ethyl acetate. The extract was washed with an aqueous saturated sodium hydrogen carbonate solution and saturated brine, dried over anhydrous sodium sulfate, and concentrated under reduced pressure. The residue was purified by a silica gel column chromatography (silica gel 18 g; chloroform:methanol=19: 1) to give 373 mg (97%) of Compound (63).

$^1$H NMR (CDCl$_3$) b: 0.91 (3H, s), 1.08 (3H, s), 1.10 (3H, d, J=7.5 Hz), 1.28 (3H, s), 1.53 (18H, d, J=2.0 Hz), 2.40 (1H, d, J=18.0 Hz), 3.29 (1H, d, J=18.0 Hz), 4.35 (1H, ABq, A part, J=17 Hz), 4.39 (1H, ABq, B part, J=17 Hz), 6.89 (1H, s), 7.38 (1H, d, J=1.2 Hz) ppm IR $\nu_{max}$ (CHCl$_3$): 3446, 3270, 1697, 1605, 1273, 1038, 1004 cm$^{-1}$ Step-3: Synthesis of (64)

To a solution of the above Compound (63) (375 mg, 0.65 mmol) in 4.0 ml of dichloromethane were added 213 μl (1.96 mmol) of anisole and 400 μl (5.23 mmol) of trifluoroacetic acid, and the mixture stirred for 1.5 hours at room temperature. The reaction mixture was concentrated under reduced pressure to dryness. The residue was dissolved in 6.0 ml of 5% aqueous sodium hydrogen carbonate solution. The materials soluble in diethyl ether were extracted, and discarded. The aqueous layer was adsorbed onto a column (40 ml volume) charged with Diaion HP-20. The column was washed with water and eluted with water-methanol (4:1–2:1 mixture) to give 301 mg (92%) of Compound (64). Physical properties of Compound (64) are shown in Table 12.

TABLE 12

| Ex. No. | Comp. | $^1$H-NMR δ (DMSO-d$_6$) ppm | IR ν max (Nujol) cm$^{-1}$ |
|---|---|---|---|
| 68 | 59a | 0.91 (3H, s), 0.96 (3H, s), 1.02 (3H, s), 1.17 (3H, d, J = 7.5 Hz), 1.25–2.55 (11H, m), 2.46 (1H, d, J = 18 Hz), 3.99 (1H, d, J = 18 Hz), 3.48 (1H, br.s), 4.29 (2H, s), 7.48 (1H, s) | 3384, 1679 1626, 1601 |
| 69 | 59b | 0.89 (3H, s), 0.94 (3H, s), 1.01 (3H, s), 1.15 (3H, d, J = 7.5 Hz), 1.30–2.30 (11H, m), 2.43 (1H, d, J = 18 Hz), 3.35 (1H, d, J = 18 Hz), 3.68 (1H, br.s), 4.33 (2H, s), 7.48 (1H, s) | 3358, 1676, 1627, 1600 |
| 70 | 64 | 0.91 (3H, s), 1.01 (3H, s), 1.12 (3H, d, J = 7.5 Hz), 1.26 (3H, s), 2.54 (1H, d, J = 18 Hz), 3.26 (1H, m), 3.31 (1H, d, J = 18 Hz), 4.29 (2H, s), 7.67 (1H, s) | 3234, 1677, 1629, 1599, 1115, 1087, 983, 947 783 |

Reactions in Examples 71 and 72 are illustrated by the following reaction scheme.

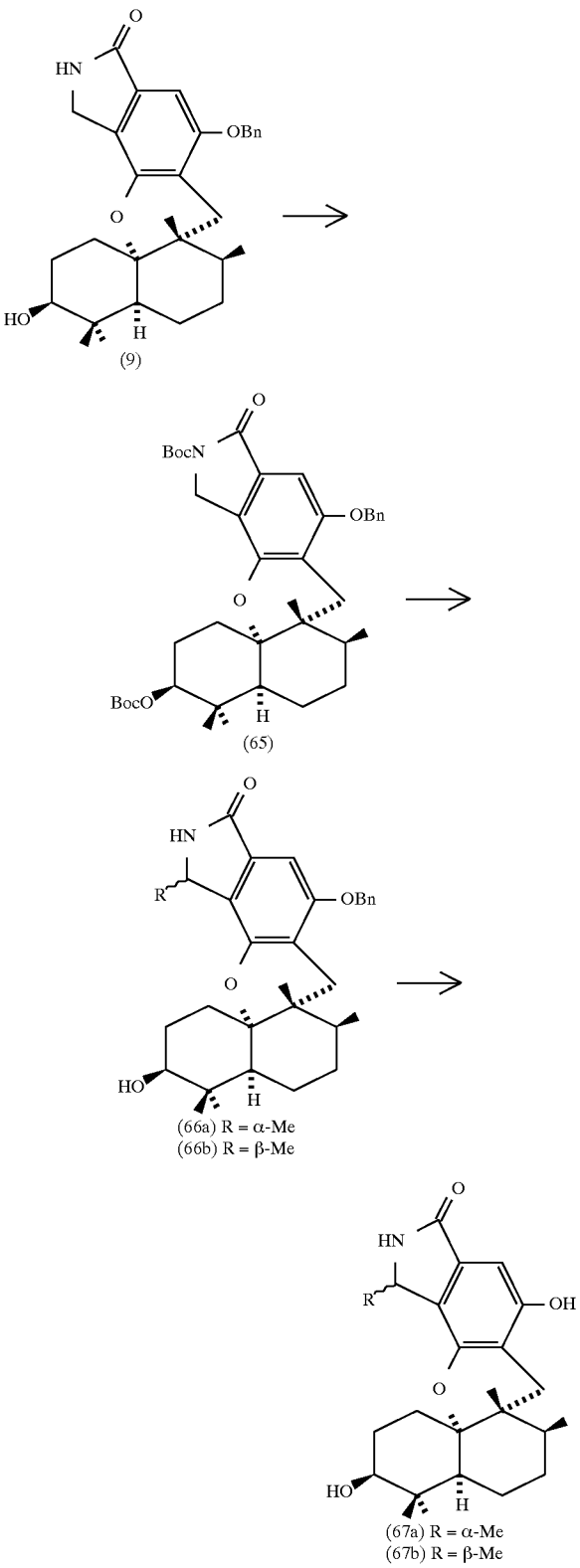

Example 71

Synthesis of (1S, 6aR, 7S, 9aS, 11S, 13aS)-2, 3, 6, 6a, 7, 8, 9, 9a, 10, 11, 12, 13-dodecahydro-5, 11-dihydroxy-1, 6a, 7, 10, 10-pentamethyl-3-oxo-1H- benzo[8,8a][1]benzopyrano [2,3-e]isoindole (67a)

Step-1: Synthesis of (6aR, 7S, 9aS, 11S, 13aS)-5-benzyloxy-2-(t-butoxycarbonyl)-11-(t- butoxycarbonyl)oxy-2, 3, 6, 6a, 7, 8, 9, 9a, 10, 11, 12, 13-dodecahydro-6a, 7, 10, 10-tetramethyl-3-oxo-1H-benzo[8,8a][1]benzopyrano[2,3-e]isoindole (65)

To Compound (9) (Example 10) (1.00 g, 2.10 mmol) suspended in 50 ml of dry THF was added 200 mg (5.0 mmol) of sodium hydride (ca. 60% in oil), and the mixture stirred for 30 min at room temperature. After addition of 1.0 g (4.58 mmol) of di-t-butyl dicarbonate and 50 mg (0.41 mmol) of 4-dimethylaminopyridine, the mixture was stirred for 3 hours at the same temperature. After addition of ice-water, the reaction mixture was extracted with ethyl acetate. The extract was washed with saturated brine, and dried over anhydrous magnesium sulfate. The solvent was evaporated under reduced pressure. The residue was purified by a silica gel column chromatography (silica gel 100 g; n-hexane: ethyl acetate=5:1). Compound (65) was obtained from the nonpolar fractions of the above column chromatography (440 mg, 31%). $^1$H NMR (CDCl$_3$) δ: 0.90 (3H, s), 0.97 (3H, s), 1.12 (3H, s), 1.14 (3H, d, J=7.5 Hz), 1.56 (9H, s), 1.60 (3H, s), 2.29 (1H, d, J=18 Hz), 2.51 (1H, m), 3.18 (1H, d, J=18 Hz), 4.61 (2H, q) 4.72 (1H, s), 5.10 (2H, s), 6.98 (1H, s), 7.27–7.45 (5H, m) ppm From the polar fractions, 740 mg (61%) of Compound (39a) was obtained.

Step-2: Synthesis of (1S, 6aR, 7S, 9aS, 11S, 13aS)-5-benzyloxy-2, 3, 6, 6a, 7, 8, 9, 9a, 10, 11, 12, 13-dodecahydro-11-hydroxy-1, 6a, 7, 10, 10-pentamethyl-3-oxo-1H- benzo[8,8a][1]benzopyrano[2,3-e]isoindole (66a)

i) Under nitrogen, to Compound (65) (495 mg, 0.73 mmol) in 5 ml of dry THF was added dropwise 0.88 ml (0.88 mmol) of 1N sodium bis(trimehylsilyl)amide/THF solution over 10 min at −78° C. After stirring for 20 min at the same temperature, 60 μl (0.96 mmol) of methyl iodide was added. The mixture was stirred for one hour at the same temperature, and then for additional one hour at room temperature. The reaction mixture was cooled to −78° C. and an aqueous saturated ammonium chloride solution was added thereto, followed by extraction with ethyl acetate. The extract was washed with saturated brine, dried over anhydrous magnesium sulfate, and concentrated under reduced pressure. The residue was purified by a silica gel column chromatography (silica gel 150 g; n-hexane:ethyl acetate= 5:1) to give 306 mg (61%) of a mixture of 1-methyl compounds.

ii) To the above mixture (236 mg) dissolved in 2 ml of dichloromethane were added 0.2 ml of anisole and 2.5 ml of trifluoroacetic acid under ice-cooling, and the mixture stirred for one hour. The reaction mixture was evaporated under reduced pressure, and the remaining residue was made basic with an aqueous saturated sodium hydrogen carbonate solution, and extracted with ethyl acetate. The extract was concentrated under reduced pressure. The residue was purified by a silica gel column chromatography (silica gel 20 g; n-hexane: ethyl acetate=1:2). Compound (66a) (28 mg, 16%) was obtained from the nonpolar fractions of the column chromatography. $^1$H NMR (CDCl$_3$) δ: 0.92 (3H, s), 0.93 (3H, s), 1.14 (3H, d, J=7.5 Hz), 1.15 (3H, s), 1.50 (3H, d, J=5.5 Hz), 2.31 (1H, d, J=18 Hz), 2.55 (1H, m), 3.20 (1H, d, J=18 Hz), 4.62 (1H, m), 4.97 (1H, s), 5.10 (2H, s), 6.13 (1H, s), 6.97 (1H, s), 7.43 (5H, m) ppm From the polar fractions, an isomer, (1R, 6aR, 7S, 9aS, 11S, 13aS)-5-benzyloxy-2, 3, 6, 6a, 7, 8, 9, 9a, 10, 11, 12, 13-dodecahydro-11-hydroxy-1,6a,7,10, 10-pentamethyl-3-oxo-1H-benzo[8,8a][1]benzopyrano[2,3-e]isoindole (66b) was obtained (118 mg, 69%). $^1$H NMR (CDCl$_3$) δ: 0.92 (3H, s), 0.97 (3H, s), 1.03 (3H, s), 1.14 (3H, d, J=7.5 Hz), 1.51 (3H, d, J=5.5 Hz), 2.27 (1H, d, J=18 Hz), 2.49 (1H, m), 3.19 (1H, d, J=18 Hz), 3.58 (1H, s), 4.64 (1H, q, J=5.5 Hz), 5.10 (2H, s), 6.12 (1H, s), 6.95 (1H, s), 7.3–7.5 (5H, m) ppm Step-3: Synthesis of (67a)

To Compound (66a) (28 mg, 0.06 mmol) dissolved in 15 ml of methanol containing 10% water was added 20 mg of 10% palladium-carbon, followed by catalytic reduction for 2.5 hours. After the palladium-carbon was removed by filtration, the filtrate was concentrated under reduced pressure. The residue was purified by a silica gel column chromatography (silica gel 5 g; ethyl acetate: methanol= 19:1) and by crystallization from diethyl ether-n-hexane to give 17 mg (74%) of Compound (67a). Melting point: 280°–285° C. (decomp.) Elemental analysis for $C_{24}H_{33}NO_4 \cdot 5/2$ $H_2O$ Calcd.: C, 64.84%; H, 8.62%; N, 3.15% Found: C, 64.53%; H, 8.94%; N, 3.28%

Other physical properties are shown in Table 13.

Example 72

Synthesis of (1R, 6aR, 7S, 9aS, 11S, 13aS)-2, 3, 6, 6a, 7, 8, 9, 9a, 10, 11, 12, 13-dodecahydro-5, 11-dihydroxy-1, 6a, 7, 10, 10-pentamethyl-3-oxo-1H- benzo[8,8a][1]benzopyrano[2,3-e]isoindole (67b)

Compound (66b) (110 mg, 0.23 mmol) was catalytically reduced as in Step-3 of Example 71, and the crude product was purified by a preparative thin layer chromatography (Merck, Kieselgel 60 F254, 0.5 mm; ethyl acetate) and further by crystallization from n-hexane-ethyl acetate to give 77 mg (86%) of Compound (67b). Melting point: >300° C. Elemental analysis for $C_{24}H_{33}NO_4 \cdot 1/10$ $C_4H_8O_2 \cdot 1/10$ $H_2O$ Calcd.: C, 71.56%; H, 8.85%; N, 3.45% Found: C, 71.76%; H, 8.76%; N, 3.56%

Other physical properties are shown in Table 13.

Example 73

Synthesis of (6aR, 7S, 9aS, 11R, 13aS)-2, 3, 6, 6a, 7, 8, 9, 9a, 10, 11, 12, 13- dodecahydro-5, 11-dihydroxy-6a, 7, 10, 10-tetramethyl-13-dioxo-1H- benzo[8,8a][1]benzopyrano[2,3-e]isoindole (70)

Reactions in Example 73 are illustrated by the following reaction scheme.

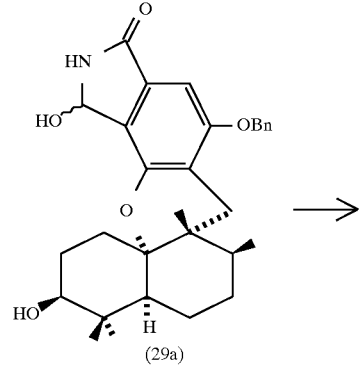

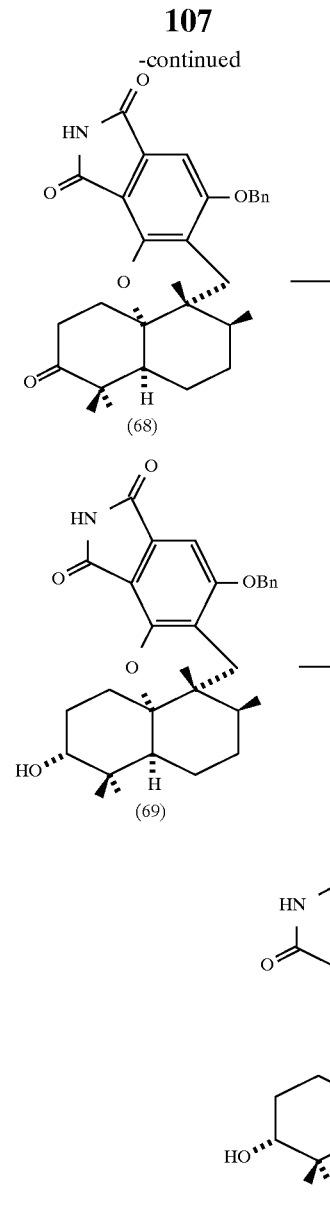

borohydride under ice-cooling, and the mixture stirred for 2 hours. After addition of an aqueous saturated ammonium chloride solution, the reaction mixture was extracted with ethyl acetate. The extract was washed with saturated brine, dried over anhydrous magnesium sulfate, and concentrated under reduced pressure. The residue was purified by a silica gel column chromatography (silica gel 20 g; n-hexane: ethyl acetate=1:1). Compound (69) was obtained from the non-polar fractions of the column chromatography (100 mg, 60%). $^1$H NMR (CDCl$_3$) δ: 0.91 (3H, s), 0.98 (3H, s), 1.04 (3H, s), 1.12 (3H, d, J=8.0 Hz), 2.25 (1H, d, J=18 Hz), 2.35 (1H, m), 3.10 (1H, d, J=18 Hz), 3.65 (1H, m), 5.18 (2H, s), 6.98 (1H, s), 7.3–7.5 (5H, m), ppm From the polar fractions, Compound (31a) was obtained (42 mg, 25%).

Step-3: Synthesis of (70)

Compound (69) (110 mg, 0.22 mmol) was catalytically reduced as in Step-3 of Example 71, and the crude product was purified by a silica gel column chromatography (silica gel 5 g; ethyl acetate) and by crystallization from n-hexane-ethyl acetate to give 82 mg (91%) of Compound (70). Elemental analysis for $C_{23}H_{29}NO_5 \cdot 1/10\ C_4H_8O_2 \cdot H_2O$ Calcd.: C, 65.92%; H, 7.52%; N, 3.29% Found: C, 66.05%; H, 7.59%; N, 3.46%

Other physical properties are shown in Table 13.

TABLE 13

| Ex. No. | Comp. | $^1$H-NMR δ (DMSO-d$_6$) ppm | IR ν max (Nujol) cm$^{-1}$ |
| --- | --- | --- | --- |
| 71 | 67a | 0.85 (3H, s), 0.86 (3H, s), 1.10 (3H, s), 1.16 (3H, d, J = 7.5 Hz) 1.34 (3H, d, J = 8.0 Hz), 2.13 (1H, d, J = 18 Hz) 3.10 (1H, d, J = 18 Hz) 4.43 (1H, q, J = 4 Hz) 4.94 (1H, s), 6.59 (1H, s), 8.39 (1H, s) 9.73 (1H, s) | 3394, 3233, 3068, 1781, 1739, 1688, 1654, 1627, 1498, 1466 |
| 72 | 67b | 0.83 (3H, s), 0.89 (3H, s), 0.94 (3H, s), 1.09 (3H, d, J = 6.0 Hz) 1.33 (3H, d, J = 8 Hz), 2.08 (1H, d, J = 18 Hz), 3.05 (1H, d, J = 18 Hz), 4.31 (1H, q, J = 8 Hz), 4.45 (1H, d, J = 4 Hz), 8.34 (1H, s) 9.65 (1H, s) | 3527, 3396, 3358, 3235, 1687, 1625, 1499, 1465 |
| 73 | 70 | 0.81 (3H, s), 0.83 (3H, s), 0.89 (3H, s), 1.08 (3H, d, J = 8 Hz) 1.19 (3H, d, J = 8 Hz), 2.13 (1H, d, J = 18 Hz), 3.00 (1H, d, J = 18 Hz), 3.52 (1H, m), 6.70 (1H, s) | 3500, 3460, 3208, 1761, 1703, 1655, 1621, 1604, 1498, 1456 |

Step-1: Synthesis of (6aR, 7S, 9aS, 13aS)-5-benzyloxy-2, 3, 6, 6a, 7, 8, 9, 9a, 10,11, 12, 13- dodecahydro-6a, 7, 10, 10-tetramethyl-1, 3, 11-trioxo-1H-benzo[8,8a][1]benzopyrano[2,3- e]isoindole (68)

The reaction in Step-1 of Example 27 was allowed to proceed for longer time (8 hours). The crude product obtained from Compound (29a) (1.488 g, 3.03 mmol) was purified by a column chromatography (Merck, Lobar column, size B; n-hexane: ethyl acetate=2:3). Compound (68) was obtained from the nonpolar fractions of the column chromatography (160 mg, 11%). $^1$H NMR (CDCl$_3$) δ: 0.970 (3H, s), 0.98 (3H, s), 1.11 (3H, d, J=8 Hz), 1.36 (3H, s), 2.33 (1H, d, J=18 Hz), 3.12 (1H, d, J=18 Hz), 3.61 (1H, m), 5.20 (2H, s), 7.03 (1H, s), 7.2–7.5 (5H, m) ppm From the polar fractions, Compound (31a) was obtained (1.288g, 85%).

Step-2: Synthesis of (6aR, 7S, 9aS, 11R, 13aS)-5-benzyloxy-2, 3, 6, 6a, 7, 8, 9, 9a,10, 11, 12, 13-dodecahydro-11-hydroxy-6a, 7, 10-tetramethyl-13-dioxo-1H- benzo[8,8a][1]benzopyrano[2,3-e]isoindole (69)

To Compound (68) (160 mg, 0.33 mmol) suspended in 3 ml of methanol was added 4 mg (0.11 mmol) of sodium Example 74

Synthesis of (6aR, 7S, 9aS, 11S, 13aS)-1, 3, 6, 6a, 7, 8, 9, 9a, 10, 11, 12, 13- dodecahydro-5, 11-dihydroxy-6a, 7, 10, 10-tetramethyl- 3-oxo-1H- benzo[8,8a][1]benzopyrano[2,3-e]isobenzofuran (72)

Reactions in Example 74 are illustrated by the following reaction scheme.

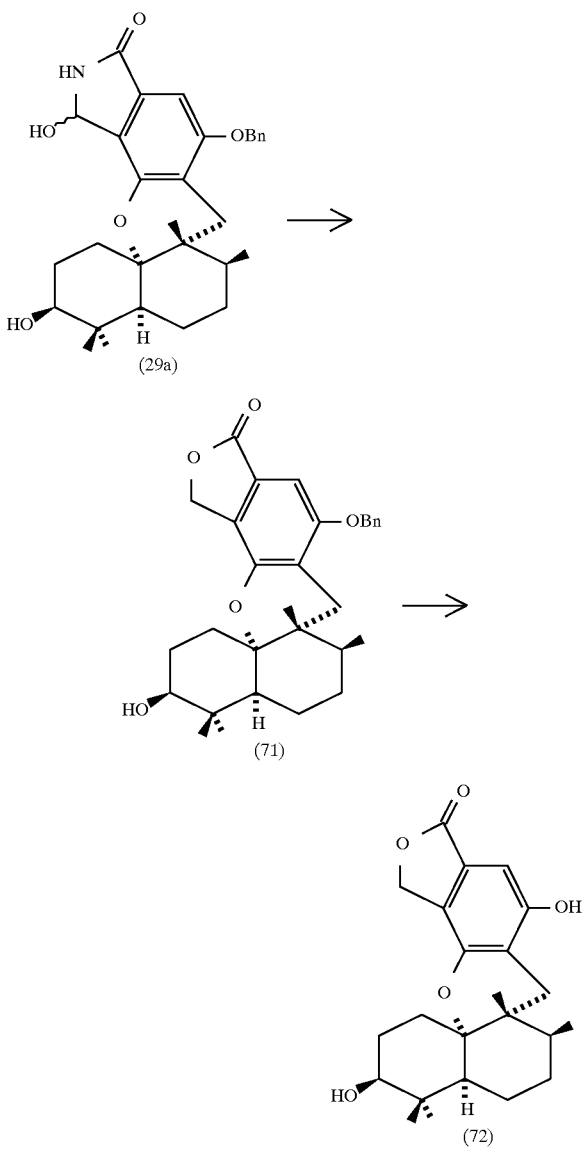

Step-1: Synthesis of (6aR, 7S, 9aS, 11S, 13aS)-5-benzyloxy-1, 3, 6, 6a, 7, 8, 9, 9a,10, 11, 12, 13-dodecahydro-11-hydroxy-6a, 7, 10, 10-tetramethyl- 3-oxo-1H- benzo[8,8a][1]benzopyrano[2,3-e]isobenzofuran (71)

To a solution of Compound (29a) (121 mg, 0.25 mmol) in 2.5 ml of dioxane containing 20% water was added 35 mg (0.92 mmol) of sodium borohydride, and the mixture stirred for 20 hours. After the reaction mixture was diluted with 2 ml of dioxane, 1.8 ml of 1N HCl was added thereto. The mixture was stirred for 40 min. After addition of water, the reaction mixture was extracted with ethyl acetate. The extract was washed sequentially with water, an aqueous saturated sodium hydrogen carbonate solution, and saturated brine, dried over anhydrous magnesium sulfate, and concentrated under reduced pressure. The residue was purified by a column chromatography (Merck, Lobar column, size A; hexane:ethyl acetate=3:1) to give 102 mg (87%) of Compound (71). $^1$H NMR (CDCl$_3$) δ: 0.92 (3H, s), 0.99 (3H, s), 1.00 (3H, s), 1.14 (3H, d, J=7.5 Hz), 2.29 (1H, d, J=18.3Hz), 3.19 (1H, d, J=18.3Hz), 3.56 (1H, br.s), 5.11 (2H, s), 5.18 (1H, d, J=15.0 Hz), 5.23 (1H, d, J=15.0 Hz), 6.96 (1H, s), 7.32–7.48 (5H, m) ppm IR ν$_{max}$ (CHCl$_3$): 3614, 3478, 3002, 1753, 1623, 1113, 1097, 1084, 1026, 969 cm$^{-1}$ Step-2: Synthesis of (72)

The above Compound (71) (100 mg, 0.21 mmol) was catalytically reduced as in Step-3 of Example 54, and the product was crystallized from diethyl ether to give 60 mg (75%) of Compound (72). Melting point: 270°–278° C. (decomp.) $^1$H NMR (DMSO-d$_6$) δ: 0.85 (3H, s), 0.89 (3H, s), 0.91 (3H, s),, 1.09 (3H, d, J=7.8 Hz), 2.13 (1H, d, J=18.3Hz), 3.09 (1H, d, J=18.3Hz), 4.45 (1H, br.s), 5.08 (1H, d, J=15.0 Hz), 5.25 (1H, d, J=15.0 Hz), 6.71 (1H, s) ppm IR ν$_{max}$ (Nujol): 3566, 3490, 3208, 1736, 1707, 1625, 1611, 1074, 1018, 972 cm$^{-1}$ Example 75–1184

In a manner similar to those described in the above Examples, the following Compounds described in (1)–(1110) were synthesized.

(1) (6a R, 7S, 9a S, 12 R*, 13a S)-2, 3, 6, 6a, 7, 8, 9, 9a, 10, 11, 12, 13-dodecahydro-5- dihydroxyphosphinyloxy-12-methanesulfonylamino-6a,7,10,10-tetramethyl-1,3,11-trioxo- 1H-benzo[8,8a][1]benzopyrano[2,3-e]isoindole (2) (1R*, 6a R, 7S, 9a S, 12 S*, 13a S)-i1-cyanoimino-2, 3, 6, 6a, 7, 8, 9, 9a,10, 11, 12, 13- dodecahydro-5-hydroxy-1-methyl-6a,7,10,10-tetramethyl-3-oxo-12-phenylsulfinyl-1H- benzo[8,8a][1]benzopyrano[2,3-e]isoindole (3) (6a R, 7S, 9a S, 12 R*, 13a S)-12-acetoxy-2, 3, 6, 6a, 7, 8, 9, 9a,10,11,12,13- dodecahydro-5-dihydroxyphosphinyloxy-6a,7, 10, 10-tetramethyl-3, 11 -dioxo- 1H- benzo[8,8a][1]benzopyrano[2,3-e]isoindole (4) (1R*, 6a R, 7S, 9a S, 12 S*, 13a S)-1-acetoxy-11-cyanoimino- 2,3,6,6a,7,8,9,9a,10,11,12,13-dodecahydro-5-hydroxy-6a,7,10,10-tetramethyl-3-oxo-12-phenylsulfonyloxy-1H-benzo[8,8a][1]benzopyrano[2,3-e]isoindole (5) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylamino-3-oxo-11-ureidoimino-1H-benzo[8,8a][1]benzopyrano[2,3-e]isoindole (6) (1R*, 6a R, 7S, 9a S, 12 S*, 13a S)-2, 3, 6, 6a, 7, 8, 9, 9a, 10, 11, 12, 13-dodecahydro- 5-hydroxy-11-hydroxyimino-12-methoxy-1-methyl-6a,7,10,10-tetramethyl-3-oxo-1H- benzo[8,8a][1]benzopyrano[2,3-e]isoindole (7) (1R*, 6a R, 7S, 9a S, 12 S*, 13a S)-1-acetoxy-11-hydrazono-2, 3, 6, 6a,7, 8, 9, 9a, 10, 11, 12, 13-dodecahydro-5-hydroxy-12-methanesulfonyloxy-6a,7,10,10-tetramethyl-3-oxo- 1H-benzo[8,8a][1]benzopyrano[2,3-e]isoindole (8) (6a R, 7S, 9a S, 12 R*, 13a S)-2, 3, 6, 6a, 7, 8, 9, 9a, 10, 11, 12, 13-dodecahydro-5- hydroxy-12-methanesulfonylamino-11-methoxyimino-6a,7,10,10-tetramethyl-3-oxo-1H- benzo[8,8a][1]benzopyrano[2,3-e]isoindole (9) (1R*, 6a R, 7S, 9a S, 12 S*, 13a S)-12-carbamoyloxy-2, 3, 6, 6a, 7, 8, 9, 9a, 10, 11, 12, 13-dodecahydro-1,5-dihydroxy-11-methoxyimino-6a,7,10,10-tetramethyl-3-oxo-1H- benzo[8,8a][1]benzopyrano[2,3-e]isoindole

(10) (6a R, 7S, 9a S, 12 R*, 13a S)-12-chloro-2, 3, 6, 6a, 7, 8, 9, 9a,10,11,12,13- dodecahydro-5-hydroxy-6a,7,10,10-tetramethyl-1,3,11-trioxo-1H- benzo[8,8a][1]benzopyrano[2,3-e]isoindole

(11) (6a R, 7S, 9a S, 12 R*, 13a S)-2, 3, 6, 6a, 7, 8, 9, 9a,. 10, 11, 12, 13-dodecahydro-5- hydroxy-12-mercapto-6a,7,10,10-tetramethyl-3,11-dioxo-1H- benzo[8,8a][1]benzopyrano[2,3-e]isoindole

(12) (1R*, 6a R, 7S, 9a S, 12 S*, 13a S)-1-acetoxy-2, 3, 6, 6a, 7, 8, 9, 9a,10,11,12,13- dodecahydro-5-hydroxy-1

1-methoxyimino-6a,7,10,10-tetramethyl-12-methylthio-3-oxo- 1H-benzo[8,8a][1]benzopyrano[2,3-e]isoindole

(13) (6a R, 7S, 9a S, 12 R*, 13a S)-12-ethoxy-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole

(14) (6a R, 7S, 9a S, 12 R*, 13a S)-12-carbamoyloxy-2, 3, 6, 6a, 7, 8, 9, 9a,10,11,12,13- dodecahydro-5-hydroxy-6a,7,10,10-tetramethyl-11-(1-oxa-4-azacyclohex-4-yl)imino-3-oxo- 1H-benzo[8,8a][1]benzopyrano[2,3-e]isoindole

(15) (1R*, 6a R, 7S, 9a S, 12 S*, 13a S)-1-acetoxy-12-ethoxy-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole

(16) (1R*, 6a R, 7S, 9a S, 12 S*, 13a S)-2, 3, 6, 6a, 7, 8, 9, 9a, 10, 11, 12, 13-dodecahydro- 1,5-dihydroxy-11-hydroxyimino-6a,7,10,10-tetramethyl-3-oxo-12-phenoxy-1H- benzo[8,8a][1]benzopyrano[2,3-e]isoindole

(17) (6a R, 7S, 9a S, 12 R*, 13a S)-12-carboxymethyloxy-2, 3, 6, 6a, 7, 8, 9, 9a, 10, 11, 12, 13-dodecahydro-5-hydroxy-6a,7,10,10-tetramethyl-11-(1-oxa-4-azacyclohex-4-yl)imino-3- oxo-1H-benzo[8,8a][1]benzopyrano[2,3-e]isoindole

(18) (1R*, 6a R, 7S, 9a S, 12 S*, 13a S)-1-acetoxy-12-carbamoyloxy-2, 3, 6, 6a, 7, 8, 9, 9a, 10, 11, 12, 13-dodecahydro-5-hydroxy-6a,7,10,10-tetramethyl-11-(1-oxa-4-azacyclohex-4- yl)imino-3-oxo-1H-benzo[8,8a][1]benzopyrano[2,3-e]isoindole

(19) (1R*, 6a R, 7S, 9a S, 12 S*, 13a S)-1-acetoxy-11-cyanoimino-2, 3, 6, 6a, 7, 8, 9, 9a, 10, 11, 12, 13-dodecahydro-5-hydroxy-12-(2-hydroxy)ethoxy-6a,7,10,10-tetramethyl-3- oxo-1H-benzo[8,8a][1]benzopyrano[2,3-e]isoindole

(20) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-methanesulfonylamino-6a,7,10,10-tetramethyl-3-oxo-11- ureidoimino-1H-benzo[8,8a][1]benzopyrano[2,3-e]isoindole

(21) (6a R, 7S, 9a S, 12 R*, 13a S)-1 1-hydrazono-2, 3, 6, 6a, 7, 8, 9, 9a, 10, 11, 12, 13- dodecahydro-5-hydroxy-12-(2-hydroxy)ethoxy-6a,7,10,10-tetramethyl-3-oxo-1H-benzo[8,8a][1]benzopyrano[2,3-e]isoindole

(22) (1R*, 6a R, 7S, 9a S, 12 S*, 13a S)-2, 3, 6, 6a, 7, 8, 9, 9a, 10, 11, 12, 13-dodecahydro- 1,5-dihydroxy-11-methoxyimino-6a,7,10,10-tetramethyl-3-oxo-12-phenylsulfonyl-1H- benzo[8,8a][1]benzopyrano[2,3-e]isoindole

(23) (1R*, 6a R, 7S, 9a S, 12 S*, 13a S)-1-acetoxy-11-hydrazono-2, 3, 6, 6a,7, 8, 9, 9a, 10, 11, 12, 13-dodecahydro-5-hydroxy-6a,7,10,10-tetramethyl-3-oxo-12-(3- pyridyl)carbonyloxy-1H-benzo[8,8a][1]benzopyrano[2,3-e]isoindole

(24) (1R*, 6a R, 7S, 9a S, 12 S*, 13a S)-12-acetoxy-2, 3, 6, 6a, 7, 8, 9, 9a,10, 11, 12, 13- dodecahydro-1,5-dihydroxy-6a,7,10,10-tetramethyl-11-(1-oxa-4-azacyclohex-4-yl)imino-3- oxo-1H-benzo[8,8a][1]benzopyrano[2,3-e]isoindole

(25) (1R*, 6a R, 7S, 9a S, 12 S*, 13a S)-2, 3, 6, 6a, 7, 8, 9, 9a, 10, 11, 12, 13-dodecahydro- 5,12-dihydroxy-1-methyl-6a,7,10,10-tetramethyl-3-oxo-11-ureidoimino-1H- benzo[8,8a][1]benzopyrano[2,3-e]isoindole

(26) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-1,3,11-trioxo-12-phenylsulfonyl-1H- benzo[8,8a][1]benzopyrano[2,3-e]isoindole

(27) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-3-oxo-12-phenylthio-1H- benzo[8,8a][1]benzopyrano[2,3-e]isoindole

(28) (6a R, 7S, 9a S, 12 R*, 13a S)-12-ethoxy-2, 3, 6, 6a, 7, 8, 9, 9a,10,11,12,13- dodecahydro-5-hydroxy-11-methoxyimino-6a,7,10,10-tetramethyl-3-oxo-1H- benzo[8,8a][1]benzopyrano[2,3-e]isoindole

(29) (1R*, 6a R, 7S, 9a S, 12 S*, 13a S)-11-cyanoimino-12-glycylamino-2,3, 6, 6a, 7, 8, 9, 9a, 10, 11, 12, 13-dodecahydro-5-hydroxy-1-methyl-6a,7, 10,10-tetramethyl-3-oxo-1H- benzo[8,8a][1]benzopyrano[2,3-e]isoindole

(30) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10, 10-tetramethyl-3-oxo-12-(3-pyridyl)carbonyloxy-1H- benzo[8,8a][1]benzopyrano[2, 3-e]isoindole

(31) (1R*, 6a R, 7S, 9a S, 12 S*, 13a S)-1-acetoxy-12-amino-2, 3, 6, 6a,7,8, 9, 9a, 10, 11, 12, 13-dodecahydro-5-hydroxy-6a,7, 10,10-tetramethyl-1 1-(1-oxa-4-azacyclohex-4- yl)imino-3-oxo-1H-benzo[8,8a][1]benzopyrano[2,3-e]isoindole

(32) (6a R, 7S, 9a S, 12 R*, 13a S)-12-bromo-2, 3, 6, 6a, 7, 8, 9, 9a, 10, 11, 12, 13- dodecahydro-5-hydroxy-6a,7,10, 10-tetramethyl-3-oxo-1 1-ureidoimino-1H- benzo[8,8a][1]benzopyrano[2,3-e]isoindole

(33) (1R*, 6a R, 7S, 9a S, 12 S*, 13a S)-1-acetoxy-12-chloro-11-hydrazono-2, 3, 6, 6a, 7, 8, 9, 9a, 10, 11, 12,13-dodecahydro-5-hydroxy-6a,7,10,10-tetramethyl-3-oxo-1H- benzo[8,8a][1]benzopyrano[2,3-e]isoindole

(34) (6a R, 7S, 9a S, 12 R*, 13a S)-12-glycylamino-2, 3, 6, 6a, 7, 8, 9, 9a, 10, 11, 12, 13- dodecahydro-5-hydroxy-6a,7,10,10-tetramethyl-3-oxo-1 1-ureidoimino-1H- benzo[8,8a][1]benzopyrano[2,3-e]isoindole

(35) (1R*, 6a R, 7S, 9a S, 12 S*, 13a S)-12-carboxymethyloxy-11-cyanoimino-2, 3, 6, 6a, 7, 8, 9, 9a, 10, 11, 12, 13-dodecahydro-5-hydroxy--methyl-6a,7,10, 10-tetramethyl-3-oxo-1H- benzo[8,8a][1]benzopyrano[2, 3-e]isoindole

(36) (6a R, 7S, 9a S, 12 R*, 13a S)-2, 3, 6, 6a, 7, 8, 9, 9a, 10, 11, 12, 13-dodecahydro-5- hydroxy-12-methoxy-6a, 7,10,10-tetramethyl-3,11-dioxo-1H- benzo[8,8a][1]benzopyrano[2,3-e]isoindole

(37) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-hydroxyimino-6a,7,10,10-tetramethyl-3-oxo-12-phenylsulfonyl- 1H-benzo[8,8a][1]benzopyrano[2,3-e]isoindole

(38) (6a R, 7S, 9a S, 12 R*, 13a S)-11-hydrazono-2,3, 6, 6a, 7, 8, 9, 9a, 1-0, 11, 12, 13- dodecahydro-5-hydroxy-12-mercapto-6a,7,10,10-tetramethyl-13-dioxo-1H- benzo[8, 8a][1]benzopyrano[2,3-e]isoindole

(39) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-(2-hydroxy)ethoxy-11-hydroxyimino-6a,7,10,10-tetramethyl-3- oxo-1H-benzo[8,8a][1]benzopyrano[2,3-e]isoindole

(40) (6a R, 7S, 9a S, 12 R*, 13a S)-12-carbamoyloxy-2, 3, 6, 6a, 7, 8, 9, 9a, 10, 11, 12, 13- dodecahydro-5-hydroxy-6a,7,10,10-tetramethyl-3-oxo-11-ureidoimino-1H- benzo[8,8a][1]benzopyrano[2,3-e]isoindole

(41) (1R*, 6a R, 7S, 9a S, 12 S*, 13a S)-12-benzoylamino-2, 3, 6, 6a, 7, 8, 9, 9a, 10, 11, 12, 13-dodecahydro-5-hydroxy-11-hydroxyimino-1-methyl-6a,7,10,10-tetramethyl-3-oxo-1H- benzo[8,8a][1]benzopyrano[2,3-e]isoindole

(42) (6a R, 7S, 9a S, 12 R*, 13a S)-12-ethoxy-11-hydrazono-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole

(43) (1R*, 6a R, 7S, 9a S, 12 S*, 13a S)-2, 3, 6, 6a, 7, 8, 9, 9a, 10, 11, 12, 13-dodecahydro- 5-hydroxy-1-methyl-6a, 7,10,10-tetramethyl-3-oxo-12-phenoxy-11-ureidoimino-1H- benzo[8,8a][1]benzopyrano[2,3-e]isoindole

(44) (1R*, 6a R, 7S, 9a S, 12 S*, 13a S)-2, 3, 6, 6a, 7, 8, 9, 9a, 10, 11, 12, 13-dodecahydro- 5-hydroxy-12-methanesulfonylamino-11-methoxyimino-1-methyl-6a,7,10,10-tetramethyl-3- oxo-1H-benzo[8,8a][1]benzopyrano[2,3-e]isoindole

(45) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-12-methylthio-3-oxo-1H- benzo[8,8a][1]benzopyrano[2,3-e]isoindole

(46) (1R*, 6a R, 7S, 9a S, 12 S*, 13a S)-12-glycylamino-2, 3, 6, 6a, 7, 8, 9, 9a, 10, 11, 12, 13-dodecahydro-1,5-dihydroxy-6a,7,10,10-tetramethyl-3,11-dioxo-1H- benzo[8,8a][1]benzopyrano[2,3-e]isoindole

(47) (1R*, 6a R, 7S, 9a S, 12 S*, 13a S)-12-acetylamino-11-hydrazono-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole

(48) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-hydroxyimino-6a,7,10,10-tetramethyl-3-oxo-12-phenylsulfinyl- 1H-benzo[8,8a][1]benzopyrano[2,3-e]isoindole

(49) (1R*, 6a R, 7S, 9a S, 12 S*, 13a S)-12-carbamoyloxy-11-cyanoimino-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole

(50) (1R*, 6a R, 7S, 9a S, 12 S*, 13a S)-2, 3, 6, 6a, 7, 8, 9, 9a, 10, 11, 12, 13-dodecahydro- 5-hydroxy-11-hydroxyimino-1-methyl-6a,7,10,10-tetramethyl-3-oxo-12-phenylthio-1H- benzo[8,8a][1]benzopyrano[2,3-e]isoindole

(51) (6a R, 7S, 9a S, 12 R*, 13a S)-12-carboxymethyloxy-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole

(52) (6a R, 7S, 9a S, 12 R*, 13a S)-12-chloro-2, 3, 6, 6a, 7, 8, 9, 9a, 10, 11, 12, 13- dodecahydro-5-hydroxy-11-hydroxyimino-6a,7,10,10-tetramethyl-3-oxo-1H- benzo[8,8a][1]benzopyrano[2,3-e]isoindole

(53) (1R*, 6a R, 7S, 9a S, 12 S*, 13a S)-2, 3, 6, 6a, 7, 8, 9, 9a, 10, 11, 12, 13-dodecahydro- 5-hydroxy-11-hydroxyimino-12-methanesulfonylamino-1-methyl-6a,7,10,10-tetramethyl-3- oxo-1H-benzo[8,8a][1]benzopyrano[2,3-e]isoindole

(54) (1R*, 6a R, 7S, 9a S, 12 S*, 13a S)-12-amino-2, 3, 6, 6a, 7, 8, 9, 9a, 10, 11, 12, 13- dodecahydro-1,5-dihydroxy-6a,7,10,10-tetramethyl-3-oxo-11-ureidoimino-1H- benzo[8,8a][1]benzopyrano[2,3-e]isoindole

(55) (1R*, 6a R, 7S, 9a S, 12 S*, 13a S)-12-carboxymethyloxy-2, 3, 6, 6a, 7, 8, 9, 9a, 10, 11, 12, 13-dodecahydro-1,5-dihydroxy-11-hydroxyimino-6a,7,10,10-tetramethyl-3-oxo-1H- benzo[8,8a][1]benzopyrano[2,3-e]isoindole

(56) (1R*, 6a R, 7S, 9a S, 12 S*, 13a S)-12-acetylamino-2, 3, 6, 6a, 7, 8, 9, 9a, 10, 11, 12, 13-dodecahydro-1,5-dihydroxy-6a,7,10,10-tetramethyl-3-oxo-11-ureidoimino-1H- benzo[8,8a][1]benzopyrano[2,3-e]isoindole

(57) (6a R, 7S, 9a S, 12 R*, 13a S)-2, 3, 6, 6a, 7, 8, 9, 9a, 10, 11, 12, 13-dodecahydro-5- hydroxy-12-methanesulfonylamino-6a,7,10,10-tetramethyl-3,11-dioxo-1H- benzo[8,8a][1]benzopyrano[2,3-e]isoindole

(58) (1R*, 6a R, 7S, 9a S, 12 S*, 13a S)-12-benzoyloxy-11-cyanoimino-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole

(59) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylamino-1,3,11-trioxo-1H- benzo[8,8a][1]benzopyrano[2,3-e]isoindole

(60) (6a R, 7S, 9a S, 12 R*, 13a S)-2, 3, 6, 6a, 7, 8, 9, 9a, 10, 11, 12, 13-dodecahydro-5- dihydroxyphosphinyloxy-12-methoxy-6a,7,10,10-tetramethyl-3,11-dioxo-1H- benzo[8,8a][1]benzopyrano[2,3-e]isoindole

(61) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-12-methylthio-11-(1-oxa-4-azacyclohex-4- yl)imino-3-oxo-1H-benzo[8,8a][1]benzopyrano[2,3-e]isoindole

(62) (6a R, 7S, 9a S, 12 R*, 13a S)-12-benzyloxycarbonylamino-2, 3, 6, 6a, 7, 8, 9, 9a, 10, 11, 12, 13-dodecahydro-5-hydroxy-11-methoxyimino-6a,7,10,10-tetramethyl-13-dioxo-1H- benzo[8,8a][1]benzopyrano[2,3-e]isoindole

(63) (1R*, 6a R, 7S, 9a S, 12 S*, 13a S)-12-azido-2, 3, 6, 6a, 7, 8, 9, 9a, 10, 11, 12, 13- dodecahydro-1,5-dihydroxy-6a,7,10,10-tetramethyl-11-(1-oxa-4-azacyclohex-4-yl)imino-3- oxo-1H-benzo[8,8a][1]benzopyrano[2,3-e]isoindole

(64) (6a R, 7S, 9a S, 12 R*, 13a S)-12-acetoxy-2, 3, 6, 6a, 7, 8, 9, 9a, 10, 11, 12, 13- dodecahydro-5-hydroxy-6a,7,10,10-tetramethyl-13-dioxo-11-ureidoimino-1H- benzo[8,8a][1]benzopyrano[2,3-e]isoindole

(65) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-1,3,11-trioxo-12-phenylthio-1H- benzo[8,8a][1]benzopyrano[2,3-e]isoindole

(66) (1R*, 6a R, 7S, 9a S, 12 S*, 13a S)-2, 3, 6, 6a, 7, 8, 9, 9a, 10, 11, 12, 13-dodecahydro- 5-hydroxy-1-methyl-6a,7,10,10-tetramethyl-11-(1-oxa-4-azacyclohex-4-yl)imino-3-oxo-12- phenoxy-1H-benzo[8,8a][1]benzopyrano[2,3-e]isoindole

(67) (1R*, 6a R, 7S, 9a S, 12 S*, 13a S)-12-acetylamino-11-cyanoimino-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole

(68) (6a R, 7S, 9a S, 12 R*, 13a S)-2, 3, 6, 6a, 7, 8, 9, 9a, 10, 11, 12, 13-dodecahydro-5- hydroxy-12-mercapto-6a,7,10,10-tetramethyl-13-dioxo-11-ureidoimino-1H- benzo[8,8a][1]benzopyrano[2,3-e]isoindole

(69) (1R*, 6a R, 7S, 9a S, 12 S*, 13a S)-1-acetoxy-11-hydrazono-2, 3, 6,-6a, 7, 8, 9, 9a, 10, 11, 12, 13-dodecahydro-5-hydroxy-6a,7,10,10-tetramethyl-3-oxo-12-phenylsulfonylamino- 1H-benzo[8,8a][1]benzopyrano[2,3-e]isoindole

(70) (1R*, 6a R, 7S, 9a S, 12 S*, 13a S)-2, 3, 6, 6a, 7, 8, 9, 9a, 10, 11, 12, 13-dodecahydro- 5-hydroxy-12-methanesulfonylamino-1-methyl-6a,7,10,10-tetramethyl-3-oxo-11- ureidoimino-1H-benzo[8,8a][1]benzopyrano[2,3-e]isoindole

(71) (1R*, 6a R, 7S, 9a S, 12 S*, 13a S)-11-ureidoimino-2, 3, 6, 6a, 7, 8, 9, 9a, 10, 11, 12, 13-dodecahydro-1,5,12-trihydroxy-6a,7,10,10-tetramethyl-3-oxo-1H- benzo[8,8a][1]benzopyrano[2,3-e]isoindole

(72) (1R*, 6a R, 7S, 9a S, 12 S*, 13a S)-12-benzoyloxy-2, 3, 6, 6a, 7, 8, 9, 9a, 10, 11, 12, 13-dodecahydro-1,5-dihydroxy-11-hydroxyimino-6a,7,10,10-tetramethyl-3-oxo-1H- benzo[8,8a][1]benzopyrano[2,3-e]isoindole

(73) (1R*, 6a R, 7S, 9a S, 12 S*, 13a S)-2, 3, 6, 6a, 7, 8, 9, 9a, 10, 11, 12, 13-dodecahydro- 5-hydroxy-12-methanesulfonylamino-1-methyl-6a,7,10,10-tetramethyl-3,11-dioxo-1H- benzo[8,8a][1]benzopyrano[2,3-e]isoindole

(74) (1R*, 6a R, 7S, 9a S, 12 S*, 13a S)-1-acetoxy-12-acetylamino-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole

(75) (1R*, 6a R, 7S, 9a S, 12 S*, 13a S)-1-acetoxy-11-hydrazono-2, 3, 6, 6a, 7, 8, 9, 9a, 10, 11, 12, 13-dodecahydro-5-hydroxy-6a,7,10,10-tetramethyl-3-oxo-12-phenylsulfonyloxy- 1H-benzo[8,8a][1]benzopyrano[2,3-e]isoindole

(76) (1R*, 6a R, 7S, 9a S, 12 S*, 13a S)-2, 3, 6, 6a, 7, 8, 9, 9a, 10, 11, 12, 13-dodecahydro- 5-hydroxy-11-hydroxyimino-1-methyl-6a,7,10,10-tetramethyl-3-oxo-12-phenylsulfonyl-1H- benzo[8,8a][1]benzopyrano[2,3-e]isoindole

(77) (1R*, 6a R, 7S, 9a S, 12 S*, 13a S)-12-amino-11-cyanoimino-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole

(78) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-3-oxo- 12-phenylsulfonyloxy-1H-benzo[8,8a][1]benzopyrano[2,3-e]isoindole

(79) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-13-dioxo-12-phenylsulfonylamino-1H- benzo[8,8a][1]benzopyrano[2,3-e]isoindole

(80) (6a R, 7S, 9a S, 12 R*, 13a S)-2, 3, 6, 6a, 7, 8, 9, 9a, 10, 11, 12, 13-dodecahydro-5- hydroxy-12-(2-hydroxy)ethoxy-11-methoxyimino-6a,7,10,10-tetramethyl-3-oxo-1H- benzo[8,8a][1]benzopyrano[2,3-e]isoindole

(81) (6a R, 7S, 9a S, 12 R*, 13a S)-12-carbamoyloxy-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole

(82) (6a R, 7S, 9a S, 12 R*, 13a S)-11-(1-oxa-4-azacyclohex-4-yl)imino-2, 3, 6, 6a, 7, 8, 9, 9a, 10, 11, 12, 13-dodecahydro-5,12-dihydroxy-6a,7,10,10-tetramethyl-3-oxo-1H- benzo[8,8a][1]benzopyrano[2,3-e]isoindole

(83) (1R*, 6a R, 7S, 9a S, 12 S*, 13a S)-11-cyanoimino-2, 3, 6, 6a, 7, 8, 9, 9a, 10, 11, 12, 13-dodecahydro-5-hydroxy-1-methyl-6a,7,10,10-tetramethyl-12-methylsulfinyl-3-oxo-1H- benzo[8,8a][1]benzopyrano[2,3-e]isoindole

(84) (1R*, 6a R, 7S, 9a S, 12 S*, 13a S)-1-acetoxy-12-azido-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole

(85) (1R*, 6a R, 7S, 9a S, 12 S*, 13a S)-12-benzoyloxy-2, 3, 6, 6a, 7, 8, 9, 9a, 10, 11, 12, 13-dodecahydro-1,5-dihydroxy-6a,7,10,10-tetramethyl-3-oxo-11-ureidoimino-1H- benzo[8,8a][1]benzopyrano[2,3-e]isoindole

(86) (6a R. 7S, 9a S, 12 R*, 13a S)-12-azido-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole

(87) (6a R, 7S, 9a S, 12 R*, 13a S)-11-cyanoimino-2, 3, 6, 6a, 7, 8, 9, 9a, 10, 11, 12, 13- dodecahydro-5-hydroxy-12-mercapto-6a,7,10,10-tetramethyl-3-oxo-1H- benzo[8,8a][1]benzopyrano[2,3-e]isoindole

(88) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-3-oxo-12-phenylsulfonylamino-11-ureidoimino-1H- benzo[8,8a][1]benzopyrano[2,3-e]isoindole

(89) (1R*, 6a R, 7S, 9a S, 12 S*, 13a S)-1-acetoxy-12-benzoyloxy-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole

(90) (1R*, 6a R, 7S, 9a S, 12 S*, 13a S)-12-acetylamino-11-hydrazono-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole

(91) (6a R, 7S, 9a S, 12 R*, 13a S)-12-acetylamino-2, 3, 6, 6a, 7, 8, 9, 9a, 10, 11, 12, 13- dodecahydro-5-hydroxy-11-hydroxyimino-6a,7,10,10-tetramethyl-3-oxo-1H- benzo[8,8a][1]benzopyrano[2,3-e]isoindole

(92) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-3,11-dioxo-12-phenylsulfinyl-1H- benzo[8,8a][1]benzopyrano[2,3-e]isoindole

(93) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-11-(1-oxa-4-azacyclohex-4-yl)imino-3-oxo-12-(3- pyridyl)carbonyloxy-1H-benzo[8,8a][1]benzopyrano[2,3-e]isoindole

(94) (6a R, 7S, 9a S, 12 R*, 13a S)-12-benzyloxy-2, 3, 6, 6a, 7, 8, 9, 9a, 10, 11, 12, 13- dodecahydro-5-hydroxy-6a,7,10,10-tetramethyl-1,3,11-trioxo-1H- benzo[8,8a][1]benzopyrano[2,3-e]isoindole

(95) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-methanesulfonyloxy-6a,7,10,10-tetramethyl-3,11-dioxo-1H- benzo[8,8a][1]benzopyrano[2,3-e]isoindole

(96) (6a R, 7S, 9a S, 12 R*, 13a S)-12-bromo-2, 3, 6, 6a, 7, 8, 9, 9a, 10, 11, 12, 13- dodecahydro-5-hydroxy-11-methoxyimino-6a,7,10,10-tetramethyl-13-dioxo-1H- benzo[8,8a][1]benzopyrano[2,3-e]isoindole

(97) (1R*, 6a R, 7S, 9a S, 12 S*, 13a S)-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-12-phenoxy-1H- benzo[8,8a][1]benzopyrano[2,3-e]isoindole

(98) (6a R, 7S, 9a S, 12 R*, 13a S)-12-amino-2, 3, 6, 6a, 7, 8, 9, 9a, 10, 11, 12, 13- dodecahydro-5-hydroxy-6a,7, 10,10-tetramethyl-3-oxo-11-ureidoimino-1H- benzo[8,8a][1]benzopyrano[2,3-e]isoindole

(99) (6a R, 7S, 9a S, 12 R*, 13a S)-12-carboxymethyloxy-2, 3, 6, 6a, 7, 8, 9, 9a, 10, 11, 12, 13-dodecahydro-5-hydroxy-6a,7,10,10-tetramethyl-3-oxo-11-ureidoimino-1H- benzo[8,8a][1]benzopyrano[2,3-e]isoindole (100) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-1,3,11-trioxo-12-(3-pyridyl)carbonyloxy- 1H-benzo[8,8a][1]benzopyrano[2,3-e]isoindole (101) (1R*, 6a R, 7S, 9a S, 12 S*, 13a S)-12-carbamoyloxy-2, 3, 6, 6a, 7, 8, 9, 9a, 10, 11, 12, 13-dodecahydro-1,5-dihydroxy-6a,7,10,10-tetramethyl-11-(1-oxa-4-azacyclohex-4- yl)imino-3-oxo-1H-benzo[8,8a][1]benzopyrano[2,3-e]isoindole (102) (6a R, 7S, 9a S, 12 R*, 13a S)-12-carboxymethyloxy-2, 3, 6, 6a, 7, 8, 9, 9a, 10, 11, 12, 13-dodecahydro-5-hydroxy-6a,7,10,10-tetramethyl-13-dioxo-11-ureidoimino-1H- benzo[8,8a][1]benzopyrano[2,3-e]isoindole (103) (1R*, 6a R, 7S, 9a S, 12 S*, 13a S)-1-acetoxy-12-carboxymethyloxy-11-cyanoimino- 2, 3, 6, 6a, 7, 8, 9, 9a, (104) (1R*, 6a R, 7S, 9a S, 12 S*, 13a S)-2, 3, 6, 6a, 7, 8, 9, 9a, 10, 11, 12, 13- dodecahydro-5-hydroxy-12-methoxy-1-methyl-6a,7,10,10-tetramethyl-3-oxo-11-ureidoimino-1H-benzo[8,8a][1]benzopyrano[2,3-e]isoindole (105) (1R*, 6a R, 7S, 9a S, 12 S*, 13a S)-12-benzoyloxy-2, 3, 6, 6a, 7, 8, 9, 9a, 10, 11, 12, 13-dodecahydro-5-hydroxy-1-methyl-6a,7, 10,10-tetramethyl-3-oxo-11-ureidoimino-1H- benzo[8,8a][1]benzopyrano[2,3-e]isoindole (106) (6a R, 7S, 9a S, 12 R*, 13a S)-2, 3, 6, 6a, 7, 8, 9, 9a, 10, 11, 12, 13-dodecahydro-5- hydroxy-11-hydroxyimino-12-mercapto-6a,7,10,10-tetramethyl-13-dioxo-1H- benzo[8,8a][1]benzopyrano[2,3-e]isoindole (107) (1R*, 6a R, 7S, 9a S, 12 S*, 13a S)-12-bromo-2, 3, 6, 6a, 7, 8, 9, 9a, 10, 11, 12, 13- dodecahydro-1,5-dihydroxy-11-methoxyimino-6a,7,10,10-tetramethyl-3-oxo-1H- benzo[8,8a][1]benzopyrano[2,3-e]isoindole (108) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-hydroxyimino-12-methoxy-6a,7,10,10-tetramethyl-3-oxo-1H- benzo[8,8a][1]benzopyrano[2,3-e]isoindole (109) (1R*, 6a R, 7S, 9a S, 12 S*, 13a S)-1-acetoxy-12-glycylamino-2, 3, 6, 6a, 7, 8, 9, 9a, 10, 11, 12, 13-dodecahydro-5-hydroxy-6a,7,10,10-tetramethyl-3-oxo-11-ureidoimino-1H- benzo[8,8a][1]benzopyrano[2,3-e]isoindole (110) (1R*, 6a R, 7S, 9a S, 12 S*, 13a S)-2, 3, 6, 6a, 7, 8, 9, 9a, 10, 11, 12, 13- dodecahydro-1,5-dihydroxy-12-(2-hydroxy)ethoxy-6a,7,10,10-tetramethyl-3-oxo-11-ureidoimino-1H-benzo[8,8a][1]benzopyrano[2,3-e]isoindole (111) (1R*, 6a R, 7S, 9a S, 12 S*, 13a S)-12-carboxymethyloxy-11-hydrazono-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (112) (1R*, 6a R, 7S, 9a S, 12 S*, 13a S)-1-acetoxy-12-amino-2, 3, 6, 6a, 7, 8, 9, 9a, 10, 11, 12, 13-dodecahydro-5-hydroxy-11-methoxyimino-6a,7,10,10-tetramethyl-3-oxo-1H- benzo[8,8a][1]benzopyrano[2,3-e]isoindole (113) (1R*, 6a R, 7S, 9a S, 12 S*, 13a S)-12-chloro-11-cyanoimino-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (114) (1R*, 6a R, 7S, 9a S, 12 S*, 13a S)-1-acetoxy-12-chloro-2, 3, 6, 6a, 7, 8, 9, 9a, 10, 11, 12, 13-dodecahydro-5-hydroxy-6a,7,10,10-tetramethyl-3-oxo-11-ureidoimino-1H- benzo[8,8a][1]benzopyrano[2,3-e]isoindole (115) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-12-methylamino-13-dioxo-1H-benzo[8,8a][1]benzopyrano[2,3-e]isoindole (116) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-3-oxo-12-(3-pyridyl)carbonyloxy-11- ureidoimino-1H-benzo[8,8a][1]benzopyrano[2,3-e]isoindole (117) (6a R, 7S, 9a S, 12 R*, 13a S)-12-carboxymethyloxy-2, 3, 6, 6a, 7, 8, 9, 9a, 10, 11, 12, 13-dodecahydro-5-dihydroxyphosphinyloxy-6a,7,10,10-tetramethyl-3,11-dioxo-1H- benzo[8,8a][1]benzopyrano[2,3-e]isoindole (118) (6a R, 7S, 9a S, 12 R*, 13a S)-11-cyanoimino-2, 3, 6, 6a, 7, 8, 9, 9a, 10, 11, 12, 13- dodecahydro-5-hydroxy-12-methoxy-6a,7,10,10-tetramethyl-3-oxo-1H- benzo[8,8a][1]benzopyrano[2,3-e]isoindole (119) (1R*, 6a R, 7S, 9a S, 12 S*, 13a S)-2, 3, 6, 6a, 7, 8, 9, 9a, 10, 11, 12, 13- dodecahydro-5-hydroxy-11-methoxyimino-1-methyl-6a,7,10,10-tetramethyl-12-methylamino-3-oxo-1H-benzo[8,8a][1]benzopyrano[2,3-e]isoindole (120) (1R*, 6a R, 7S, 9a S, 12 S*, 13a S)-1-acetoxy-11-hydrazono-2, 3, 6, 6a, 7, 8, 9, 9a, 10, 11, 12, 13-dodecahydro-5-hydroxy-12-methanesulfonylamino-6a,7,10,10-tetramethyl-3- oxo-1H-benzo[8,8a][1]benzopyrano[2,3-e]isoindole (121) (6a R, 7S, 9a S, 12 R*, 13a S)-2, 3, 6, 6a, 7, 8, 9, 9a, 10, 11, 12, 13-dodecahydro-5- hydroxy-12-methoxy-11-methoxyimino-6a,7,10,10-tetramethyl-13-dioxo-1H-benzo[8,8a][1]benzopyrano[2,3-e]isoindole (122) (1R*, 6a R, 7S, 9a S, 12 S*, 13a S)-2, 3, 6, 6a, 7, 8, 9, 9a, 10, 11, 12, 13- dodecahydro-5-hydroxy-12-(2-hydroxy)ethoxy-11-methoxyimino-1-methyl-6a,7,10,10-tetramethyl-3-oxo-1H-benzo[8,8a][1]benzopyrano[2,3-e]isoindole (123) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylthio-11-(1-oxa-4-azacyclohex-4-yl)imino-3-oxo- 1H-benzo[8,8a][1]benzopyrano[2,3-e]isoindole (124) (6a R, 7S, 9a S, 12 R*, 13a S)-12-acetylamino-2, 3, 6, 6a, 7, 8, 9, 9a, 10, 11, 12, 13- dodecahydro-5-hydroxy-11-hydroxyimino-6a,7,10,10-tetramethyl-13-dioxo-1H-benzo[8,8a][1]benzopyrano[2,3-e]isoindole (125) (1R*, 6a R, 7S, 9a S, 12 S*, 13a S)-1-acetoxy-12-bromo-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (126) (1R*, 6a R, 7S, 9a S, 12 S*, 13a S)-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-12-phenylsulfonyloxy- 1H-benzo[8,8a][1]benzopyrano[2,3-e]isoindole (127) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-13-dioxo-12-(3-pyridyl)carbonyloxy-1H- benzo[8,8a][1]benzopyrano[2,3-e]isoindole (128) (6a R, 7S, 9a S, 12 R*, 13a S)-2, 3, 6, 6a, 7, 8, 9, 9a, 10, 11, 12, 13-dodecahydro-5- hydroxy-12-methanesulfonylamino-6a,7,10,10-tetramethyl-3-oxo-11-ureidoimino-1H- benzo[8,8a][1]benzopyrano[2,3-e]isoindole (129) (1R*, 6a R, 7S, 9a S, 12 S*, 13a S)-12-chloro-2, 3, 6, 6a, 7, 8, 9, 9a, 10, 11, 12, 13- dodecahydro-1,5-dihydroxy-11-methoxyimino-6a,7,10,10-tetramethyl-3-oxo-1H- benzo[8,8a][1]benzopyrano[2,3-e]isoindole (130) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-12-methylthio-3-oxo-1H- benzo[8,8a][1]benzopyrano[2,3-e]isoindole (131) (6a R, 7S, 9a S, 12 R*, 13a S)-12-azido-11-hydrazono-2, 3, 6, 6a, 7; 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (132) (1R*, 6a R, 7S, 9a S, 12 S*, 13a S)-12-benzoyloxy-2, 3, 6, 6a, 7, 8, 9, 9a, 10, 11 12, 13-dodecahydro-1,5-dihydroxy-6a,7,10,10-tetramethyl-3,11-dioxo-1H- benzo[8,8a][1]benzopyrano[2,3-e]isoindole (133) (1R*, 6a R, 7S, 9a S, 12 S*, 13a S)-1-acetoxy-2, 3, 6, 6a, 7, 8, 9, 9a,10, 11, 12, 13- dodecahydro-5-hydroxy-6a, 7,10,10-tetramethyl-3,11-dioxo-12-phenylsulfonyloxy-1H- benzo[8,8a][1]benzopyrano[2,3-e]isoindole (134) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7, 10,10-tetramethyl-13-dioxo-12-phenylsulfonyl-1H- benzo[8,8a][1]benzopyrano[2,3-e]isoindole (135) (1R*, 6a R, 7S, 9a S, 12 S*, 13a S)-12-glycylamino-2, 3, 6, 6a, 7, 8, 9, 9a, 10, 11, 12, 13-dodecahydro-5-hydroxy-11-hydroxyimino-1-methyl-6a,7,10,10-tetramethyl-3-oxo-1H- benzo[8,8a][1]benzopyrano[2,3-e]isoindole (136) (1R*, 6a R, 7S, 9a S, 12 S*, 13a S)-12-amino-11-hydrazono-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (137) (1R*, 6a R, 7S, 9a S, 12 S*, 13a S)-12-carbamoyloxy-2, 3, 6, 6a, 7, 8, 9, 9a, 10, 11, 12, 13-dodecahydro-5-hydroxy-11-methoxyimino-1-methyl-6a,7,10,10-tetramethyl-3-oxo- 1H-benzo[8,8a][1]benzopyrano[2,3-e]isoindole (138) (6a R, 7S, 9a S, 12 R*, 13a S)-12-ethoxy-2, 3, 6, 6a, 7, 8, 9, 9a, 10, 11, 12, 13- dodecahydro-5-hydroxy-6a,7,10,10-tetramethyl-3-oxo-11-ureidoimino-1H- benzo[8,8a][1]benzopyrano[2,3-e]isoindole (139) (6a R, 7S, 9a S, 12 R*, 13a S)-12-carbamoyloxy-2, 3, 6, 6a, 7, 8, 9, 9a, 10, 11, 12, 13-dodecahydro-5-dihydroxyphosphinyloxy-6a,7,10,10-tetramethyl-1,3,11-trioxo-1H- benzo[8,8a][1]benzopyrano[2,3-e]isoindole (140) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-11-(1-oxa-4-azacyclohex-4-yl)imino-3-oxo-12-phenylsulfinyl-1H-benzo[8,8a][1]benzopyrano[2,3-e]isoindole (141) (1R*, 6a R, 7S, 9a S, 12 S*, 13a S)-12-benzyloxy-2, 3, 6, 6a, 7, 8, 9, 9a, 10, 11, 12, 13-dodecahydro-1,5-dihydroxy-11-methoxyimino-6a,7,10,10-tetramethyl-3-oxo-1H- benzo[8,8a][1]benzopyrano[2,3-e]isoindole (142) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-12-methylsulfinyl-3-oxo-1H- benzo[8,8a][1]benzopyrano[2,3-e]isoindole (143) (1R*, 6a R, 7S, 9a S, 12 S*, 13a S)-11-cyanoimino-2, 3, 6, 6a, 7, 8, 9, 9a, 10, 11, 12, 13-dodecahydro-5-hydroxy-12-methanesulfonylamino-1-methyl-6a,7,10,10-tetramethyl-3- oxo-1H-benzo[8,8a][1]benzopyrano[2,3-e]isoindole (144) (1R*, 6a R, 7S, 9a S, 12 S*, 13a S)-2, 3, 6, 6a, 7, 8, 9, 9a, 10, 11, 12, 13- dodecahydro-1,5-dihydroxy-11-methoxyimino-6a,7,10,10-tetramethyl-12-methylsulfinyl-3- oxo-1H-benzo[8,8a][1]benzopyrano[2,3-e]isoindole (145) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-12-methylamino-3-oxo-11-ureidoimino- 1H-benzo[8,8a][1]benzopyrano[2,3-e]isoindole (146) (6a R, 7S, 9a S, 12 R*, 13a S)-12-benzyloxycarbonylamino-2, 3, 6, 6a, 7, 8, 9, 9a, 10, 11, 12, 13-dodecahydro-5-hydroxy-6a,7,10,10-tetramethyl-11-(1-oxa-4-azacyclohex-4- yl)imino-3-oxo-1H-benzo[8,8a][1]benzopyrano[2,3-e]isoindole (147) (6a R, 7S, 9a S, 12 R*, 13a S)-11-hydrazono-2, 3, 6, 6a, 7, 8, 9, 9a, 10, 11, 12, 13- dodecahydro-5-hydroxy-12-mercapto-6a,7,10,10-tetramethyl-3-oxo-1H- benzo[8,8a][1]benzopyrano[2,3-e]isoindole (148) (6a R, 7S, 9a S, 12 R*, 13a S)-2, 3, 6, 6a, 7, 8, 9, 9a, 10, 11, 12, 13-dodecahydro-5- hydroxy-12-methoxy-11-methoxyimino-6a,7,10,10-tetramethyl-3-oxo-1H- benzo[8,8a][1]benzopyrano[2,3-e]isoindole (149) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-1,3,11-trioxo-12-phenylthio-1H- benzo[8,8a][1]benzopyrano[2,3-e]isoindole (150) (1R*, 6a R, 7S, 9a S, 12 S*, 13a S)-2, 3, 6, 6a, 7, 8, 9, 9a, 10, 11, 12, 13- dodecahydro-5-hydroxy-11-hydroxyimino-1-methyl-6a,7,10,10-tetramethyl-3-oxo-12-(3- pyridyl)carbonyloxy-1H-benzo[8,8a][1]benzopyrano[2,3-e]isoindole (151) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-12-methylamino-13-dioxo-1H- benzo[8,8a][1]benzopyrano[2,3-e]isoindole (152) (6a R, 7S, 9a S, 12 R*, 13a S)-12-benzoyloxy-2, 3, 6, 6a, 7, 8, 9, 9a, 10, 11, 12, 13- dodecahydro-5-hydroxy-11-hydroxyimino-6a,7,10,10-tetramethyl-3-oxo-1H-benzo[8,8a][1]benzopyrano[2,3-e]isoindole (153) (6a R, 7S, 9a S, 12 R*, 13a S)-12-carbamoyloxy-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (154) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-13-dioxo-12-phenylsulfonylamino-11-ureidoimino-1H- benzo[8,8a][1]benzopyrano[2,3-e]isoindole (155) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-methoxyimino-6a,7,10,10-tetramethyl-3-oxo-12-(3- pyridyl)carbonyloxy-1H-benzo[8,8a][1]benzopyrano[2,3-e]isoindole (156) (6a R, 7S, 9a S, 12 R*, 13a S)-11-hydrazono-2, 3, 6, 6a, 7, 8, 9, 9a, 10, 11, 12, 13- dodecahydro-5,12-dihydroxy-6a,7,10,10-tetramethyl-13-dioxo-1H- benzo[8,8a][1]benzopyrano[2,3-e]isoindole (157) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-3-oxo-12-phenylthio-11-ureidoimino- 1H-benzo[8,8a][1]benzopyrano[2,3-e]isoindole (158) (6a R, 7S, 9a S, 12 R*, 13a S)-12-benzoylamino-2, 3, 6, 6a, 7, 8, 9, 9a, 10, 11, 12, 13- dodecahydro-5-hydroxy-6a,7,10,10-tetramethyl-3-oxo-11-ureidoimino-1H- benzo[8,8a][1]benzopyrano[2,3-e]isoindole (159) (6a R, 7S, 9a S, 12 R*, 13a S)-12-benzyloxy-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-3-oxo- 1H-benzo[8,8a][1]benzopyrano[2,3-e]isoindole (160) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylsulfinyl-1,3,11-trioxo-1H- benzo[8,8a][1]benzopyrano[2,3-e]isoindole (161) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-12-methylsulfinyl-13-dioxo-1H- benzo[8,8a][1]benzopyrano[2,3-e]isoindole (162) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylsulfinyl-3,11-dioxo-1H- benzo[8,8a][1]benzopyrano[2,3-e]isoindole (163) (6a R, 7S, 9a S, 12 R*, 13a S)-2, 3, 6, 6a, 7, 8, 9, 9a, 10, 11, 12, 13-dodecahydro-5- hydroxy-11-

(164) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-3-oxo-12-phenylsulfonylamino-11- ureidoimino-1H-benzo[8,8a][1]benzopyrano[2,3-e]isoindole (165) (1R*, 6a R, 7S, 9a S, 12 S*, 13a S)-12-benzyloxycarbonylamino-2, 3, 6, 6a, 7, 8, 9, 9a, 10, 11, 12, 13-dodecahydro-1,5-dihydroxy-11-methoxyimino-6a, 7,10,10-tetramethyl-3- oxo-1H-benzo[8,8a][1]benzopyrano[2,3-e]isoindole (166) (1R*, 6a R, 7S, 9a S, 12 S*, 13a S)-1-acetoxy-12-carbamoyloxy-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (167) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-12-methylsulfinyl-3-oxo-1H-benzo[8,8a][1]benzopyrano[2,3-e]isoindole (168) (1R*, 6a R, 7S, 9a S, 12 S*, 13a S)-12-ethoxy-11-hydrazono-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (169) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-3,11-dioxo-12-(3-pyridyl)carbonyloxy-1H-benzo[8,8a][1]benzopyrano[2,3-e]isoindole (170) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-1 1-(1-oxa-4-azacyclohex-4-yl)imino-3-oxo- 12-phenylsulfonylamino-1H-benzo[8,8a][1]benzopyrano[2,3-e]isoindole (171) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-1 1-(1-oxa-4-azacyclohex-4-yl)imino-3-oxo-12-phenylsulfonyloxy-1H-benzo[8,8a][1]benzopyrano[2,3-e]isoindole (172) (6a R, 7S, 9a S, 12 R*, 13a S)-12-azido-2, 3, 6, 6a, 7, 8, 9, 9a, 10, 11, 12, 13- dodecahydro-5-dihydroxyphosphinyloxy-6a,7,10,10-tetramethyl-3,11-dioxo-1H- -benzo[8,8a][1]benzopyrano[2,3-e]isoindole (173) (1R*, 6a R, 7S, 9a S, 12 S*, 13a S)-1-acetoxy-12-acetylamino-2, 3, 6, 6a, 7, 8, 9, 9a, 10, 11, 12, 13-dodecahydro-5-hydroxy-11-hydroxyimino-6a,7,10, 10-tetramethyl-3-oxo-1H- benzo[8,8a][1]benzopyrano[2,3-e]isoindole (174) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7, 10,10-tetramethyl-3, 11-dioxo-12-phenoxy-1H-benzo[8,8a][1]benzopyrano[2,3-e]isoindole (175) (6a R, 7S, 9a S, 12 R*, 13a S)-2, 3, 6, 6a, 7, 8, 9, 9a, 10, 11, 12, 13-dodecahydro-5- hydroxy-12-methanesulfonyloxy-11-methoxyimino-6a,7,10,10-tetramethyl-3-oxo-1H- benzo[8,8a][1]benzopyrano[2,3-e]isoindole (176) (6a R, 7S, 9a S, 12 R*, 13a S)-11-hydrazono-2, 3, 6, 6a, 7, 8, 9, 9a, 10, 11, 12, 13- dodecahydro-5-hydroxy-12-(2-hydroxy)ethoxy-6a,7,10,10-tetramethyl-13-dioxo-1H- benzo[8,8a][1]benzopyrano[2,3-e]isoindole (177) (1R*, 6a R, 7S, 9a S, 12 S*, 13a S)-1-acetoxy-12-benzoylamino-2, 3, 6, 6a, 7, 8, 9, 9a, 10, 11, 12, 13-dodecahydro-5-hydroxy-6a,7,10,10-tetramethyl-11-(1-oxa-4-azacyclohex-4- yl)imino-3-oxo-1H-benzo[8,8a][1]benzopyrano[2,3-e]isoindole (178) (6a R, 7S, 9a S, 12 R*, 13a S)-12-ethoxy-2, 3, 6, 6a, 7, 8, 9, 9a, 10, 11, 12, 13- dodecahydro-5-dihydroxyphosphinyloxy-6a,7,10,10-tetramethyl-1,3,1 1-trioxo-1H- benzo[8,8a][1]benzopyrano[2,3-e]isoindole (179) (6a R, 7S, 9a S, 12 R*, 13a S)-12-amino-11-hydrazono-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (180) (1R*, 6a R, 7S, 9a S, 12 S*, 13a S)-12-chloro-2, 3, 6, 6a, 7, 8, 9, 9a, 10, 11, 12, 13- dodecahydro-1,5-dihydroxy-11-hydroxyimino-6a,7,10,10-tetramethyl-3-oxo-1H- benzo[8,8a][1]benzopyrano[2,3-e]isoindole (181) (6a R, 7S, 9a S, 12 R*, 13a S)-12-acetylamino-2, 3, 6, 6a, 7, 8, 9, 9a, 10, 11, 12, 13- dodecahydro-5-dihydroxyphosphinyloxy-6a,7,10,10-tetramethyl-3,11-dioxo-1H- benzo[8,8a][1]benzopyrano[2,3-e]isoindole (182) (1R*, 6a R, 7S, 9a S, 12 S*, 13a S)-11-cyanoimino-2, 3, 6, 6a, 7, 8, 9, 9a, 10, 11, 12, 13-dodecahydro-5,12-dihydroxy-1-methyl-6a,7,10,10-tetramethyl-3-oxo-1H-benzo[8,8a][1]benzopyrano[2,3-e]isoindole (183) (1R*, 6a R, 7S, 9a S, 12 S*, 13a S)-12-benzoylamino-2, 3, 6, 6a, 7, 8, 9, 9a, 10, 11, 12, 13-dodecahydro-5-hydroxy-11-methoxyimino-1-methyl-6a,7,10,10-tetramethyl-3-oxo- 1H-benzo[8,8a][1]benzopyrano[2,3-e]isoindole (184) (1R*, 6a R, 7S, 9a S, 12 S*, 13a S)-12-benzoyloxy-2, 3, 6, 6a, 7, 8, 9, 9a, 10, 11, 12, 13-dodecahydro-5-hydroxy-1-methyl-6a,7,10,10-tetramethyl-11-(1-oxa-4-azacyclohex-4- yl)imino-3-oxo-1H-benzo[8,8a][1]benzopyrano[2,3-e]isoindole (185) (1R*, 6a R, 7S, 9a S, 12 S*, 13a S)-12-benzoylamino-2, 3, 6, 6a, 7, 8, 9, 9a, 10, 11, 12, 13-dodecahydro-5-hydroxy-1-methyl-6a,7,10,10-tetramethyl-11-(1-oxa-4-azacyclohex- 4-yl)imino-3-oxo-1H-benzo[8,8a][1]benzopyrano[2,3-e]isoindole (186) (6a R, 7S, 9a S, 12 R*, 13a S)-2, 3, 6, 6a, 7, 8, 9, 9a, 10, 11, 12, 13-dodecahydro-5- dihydroxyphosphinyloxy-12-methanesulfonyloxy-6a,7,10,10-tetramethyl-1,3,11-trioxo-1H- benzo[8,8a][1]benzopyrano[2,3-e]isoindole (187) (6a R, 7S, 9a S, 12 R*, 13a S)-12-carbamoyloxy-2, 3, 6, 6a, 7, 8, 9, 9a, 10, 11, 12, 13-dodecahydro-5-hydroxy-6a,7,10,10-tetramethyl-1,3,11-trioxo-1H- benzo[8,8a][1]benzopyrano[2,3-e]isoindole (188) (1R*, 6a R, 7S, 9a S, 12 S*, 13a S)-2, 3, 6, 6a, 7, 8, 9, 9a, 10, 11, 12, 13- dodecahydro-5-hydroxy-11-hydroxyimino-1-methyl-6a,7,10,10-tetramethyl-12-methylamino-3-oxo-1H-benzo[8,8a][1]benzopyrano[2,3-e]isoindole (189) (1R*, 6a R, 7S, 9a S, 12 S*, 13a S)-12-carboxymethyloxy-2, 3, 6, 6a, 7, 8, 9, 9a, 10, 11, 12, 13-dodecahydro-5-hydroxy-1-methyl-6a,7,10,10-tetramethyl-3,11-dioxo-1H- benzo[8,8a][1]benzopyrano[2,3-e]isoindole (190) (1R*, 6a R, 7S, 9a S, 12 S*, 13a S)-12-azido-2, 3, 6, 6a, 7, 8, 9, 9a, 10, 11, 12, 13- dodecahydro-1,5-dihydroxy-6a,7,10,10-tetramethyl-3-oxo-11- ureidoimino-1H- benzo[8,8a][1]benzopyrano[2,3-e]isoindole (191) (6a R, 7S, 9a S, 12 R*, 13a S)-12-amino-2, 3, 6, 6a, 7, 8, 9, 9a, 10, 11, 12, 13- dodecahydro-5-hydroxy-6a,7, 10,10-tetramethyl-1,3,11-trioxo-1H- benzo[8,8a][1]benzopyrano[2,3-e]isoindole (192) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7, 10,10-tetramethyl-3-oxo-12-phenylsulfonyl-11- ureidoimino-1H-benzo[8,8a][1]benzopyrano[2,3-e]isoindole (193) (6a R, 7S, 9a S, 12 R*, 13a S)-12-acetylamino-2, 3, 6, 6a, 7, 8, 9, 9a, 10, 11, 12, 13- dodecahydro-5-hydroxy- 6a,7,10,10-tetramethyl-3,11-dioxo-1H- benzo[8,8a][1]benzopyrano[2,3-e]isoindole (194) (1R*, 6a R, 7S, 9a S, 12 S*, 13a S)-2, 3, 6, 6a, 7, 8, 9, 9a, 10, 11, 12, 13- dodecahydro-1,5-dihydroxy-12-methoxy-6a,7,10,10-tetramethyl-1 1-(1-oxa-4-azacyclohex- 4-yl)imino-3-oxo-1H-benzo[8,8a][1]benzopyrano[2,3-e]isoindole (195) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-3-oxo-12-phenylsulfonyl-11-ureidoimino-1H-benzo[8,8a][1]benzopyrano[2,3-e]isoindole (196) (6a R, 7S, 9a S, 12 R*, 13a S)-12-carboxymethyloxy-2, 3, 6, 6a, 7, 8, 9, 9a, 10, 11, 12, 13-dodecahydro-5-hydroxy-11-hydroxyimino-6a,7,10,10-tetramethyl-13-dioxo-1H- benzo[8,8a][1]benzopyrano[2,3-e]isoindole (197) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-11-(1-oxa-4-azacyclohex-4-yl)imino-13-dioxo-12- phenylthio-1H-benzo[8,8a][1]benzopyrano[2,3-e]isoindole (198) (6a R, 7S, 9a S, 12 R*, 13a S)-12-carbamoyloxy-11-hydrazono-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (199) (1R*, 6a R, 7S, 9a S, 12 S*, 13a S)-2, 3, 6, 6a, 7, 8, 9, 9a, 10, 11, 12, 13- dodecahydro-5-hydroxy-12-methanesulfonyloxy-1 1-methoxyimino-1-methyl-6a,7,10,10- tetramethyl-3-oxo-1H-benzo[8,8a][1]benzopyrano[2,3-e]isoindole (200) (6a R, 7S, 9a S, 12 R*, 13a S)-12-carbamoyloxy-2, 3, 6, 6a, 7, 8, 9, 9a, 10, 11, 12, 13-dodecahydro-5-hydroxy-6a,7,10,10-tetramethyl-13-dioxo-11-ureidoimino-1H-benzo[8,8a][1]benzopyrano[2,3-e]isoindole (201) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-3-oxo-12-phenylsulfinyl-11-ureidoimino- 1H-benzo[8,8a][1]benzopyrano[2,3-e]isoindole (202) (6a R, 7S, 9a S, 12 R*, 13a S)-12-benzyloxy-2, 3, 6, 6a, 7, 8, 9, 9a, 10, 11, 12, 13- dodecahydro-5-hydroxy-11-methoxyimino-6a,7,10,10-tetramethyl-13-dioxo-1H-benzo[8,8a][1]benzopyrano[2,3-e]isoindole (203) (1R*, 6a R, 7S, 9a S, 12 S*, 13a S)-2, 3, 6, 6a, 7, 8, 9, 9a, 10, 11, 12, 13- dodecahydro-5-hydroxy-12-methanesulfonyloxy-1-methyl-6a,7,10,10-tetramethyl-11-(1- oxa-4-azacyclohex-4-yl)imino-3-oxo-1H-benzo[8,8a][1]benzopyrano[2,3-e]isoindole (204) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-hydroxyimino-6a,7,10,10-tetramethyl-3-oxo-12-phenoxy-1H- benzo[8,8a][1]benzopyrano[2,3-e]isoindole (205) (1R*, 6a R, 7S, 9a S, 12 S*, 13a S)-1-acetoxy-12-azido-2, 3, 6, 6a, 7, 8, 9, 9a, 10, 11, 12, 13-dodecahydro-5-hydroxy-11-methoxyimino-6a,7,10,10-tetramethyl-3-oxo-1H- benzo[8,8a][1]benzopyrano[2,3-e]isoindole (206) (6a R, 7S, 9a S, 12 R*, 13a S)-11-hydrazono-2, 3, 6, 6a, 7, 8, 9, 9a, 10, 11, 12, 13- dodecahydro-5-hydroxy-12-methanesulfonyloxy-6a,7,10,10-tetramethyl-3-oxo-1H- benzo[8,8a][1]benzopyrano[2,3-e]isoindole (207) (1R*, 6a R, 7S, 9a S, 12 S*, 13a S)-12-ethoxy-2, 3, 6, 6a, 7, 8, 9, 9a, 10, 11, 12, 13- dodecahydro-1,5-dihydroxy-6a,7,10,10-tetramethyl-3-oxo-11-ureidoimino-1H- benzo[8,8a][1]benzopyrano[2,3-e]isoindole (208) (6a R, 7S, 9a S, 12 R*, 13a S)-2, 3, 6, 6a, 7, 8, 9, 9a, 10, 11, 12, 13-dodecahydro-5- dihydroxyphosphinyloxy-12-methoxy-6a,7,10,10-tetramethyl-1,3,11-trioxo-1H- benzo[8,8a][1]benzopyrano[2,3-e]isoindole (209) (1R*, 6a R, 7S, 9a S, 12 S*, 13a S)-1-acetoxy-12-carboxymethyloxy-2, 3, 6, 6a, 7, 8, 9, 9a, 10, 11, 12, 13-dodecahydro-5-hydroxy-11-hydroxyimino-6a,7,10,10-tetramethyl-3- oxo-1H-benzo[8,8a][1]benzopyrano[2,3-e]isoindole (210) (6a R, 7S, 9a S, 12 R*, 13a S)-12-benzoyloxy-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-3-oxo- 1H-benzo[8,8a][1]benzopyrano[2,3-e]isoindole (211) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-12-methylamino-11-(1-oxa-4-azacyclohex- 4-yl)imino-3-oxo-1H-benzo[8,8a][1]benzopyrano[2,3-e]isoindole (212) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-methanesulfonylamino-11-methoxyimino-6a,7,10,10- tetramethyl-3-oxo-1H-benzo[8,8a][1]benzopyrano[2,3-e]isoindole (213) (6a R, 7S, 9a S, 12 R*, 13a S)-2, 3, 6, 6a, 7, 8, 9, 9a, 10, 11, 12, 13-dodecahydro-5- hydroxy-12-mercapto-6a,7,10,10-tetramethyl-11-(1-oxa-4-azacyclohex-4-yl)imino-3-oxo- 1H-benzo[8,8a][1]benzopyrano[2,3-e]isoindole (214) (6a R, 7S, 9a S, 12 R*, 13a S)-12-benzoyloxy-2, 3, 6, 6a, 7, 8, 9, 9a, 10, 11, 12, 13- dodecahydro-5-hydroxy-11-methoxyimino-6a,7,10,10-tetramethyl-3-oxo-1H-benzo[8,8a][1]benzopyrano[2,3-e]isoindole (215) (1R*, 6a R, 7S, 9a S, 12 S*, 13a S)-2, 3, 6, 6a, 7, 8, 9, 9a, 10, 11, 12, 13- dodecahydro-1,5-dihydroxy-11-hydroxyimino-12-methoxy-6a,7,10,10-tetramethyl-3-oxo- 1H-benzo[8,8a][1]benzopyrano[2,3-e]isoindole (216) (1R*, 6a R, 7S, 9a S, 12 S*, 13a S)-12-glycylamino-2, 3, 6, 6a, 7, 8, 9, 9a, 10, 11, 12, 13-dodecahydro-1,5-dihydroxy-11-methoxyimino-6a,7,10,10-tetramethyl-3-oxo-1H- benzo[8,8a][1]benzopyrano[2,3-e]isoindole (217) (1R*, 6a R, 7S, 9a S, 12 S*, 13a S)-12-carboxymethyloxy-2, 3, 6, 6a, 7, 8, 9, 9a, 10, 11, 12, 13-dodecahydro-5-hydroxy-1-methyl-6a,7,10,10-tetramethyl-3-oxo-11-ureidoimino- 1H-benzo[8,8a][1]benzopyrano[2,3-e]isoindole (218) (6a R, 7S, 9a S, 12 R*, 13a S)-2, 3, 6, 6a, 7, 8, 9, 9a, 10, 11, 12, 13-dodecahydro-12- (2-hydroxy)ethoxy5-dihydroxyphosphinyloxy-6a,7,10,10-tetramethyl-3,11-dioxo-1H- benzo[8,8a][1]benzopyrano[2,3-e]isoindole (219) (6a R, 7S, 9a S, 12 R*, 13a S)-12-carbamoyloxy-11-cyanoimino-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (220) (6a R, 7S, 9a S, 12 R*, 13a S)-12-acetoxy-2, 3, 6, 6a, 7, 8, 9, 9a, 10, 11, 12, 13- dodecahydro-5-hydroxy-11-methoxyimino-6a,7,10,10-tetramethyl-13-dioxo-1H- benzo[8,8a][1]benzopyrano[2,3-e]isoindole (221) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-12-methylthio-3,11-dioxo-1H- benzo[8,8a][1]benzopyrano[2,3-e]isoindole (222) (1R*, 6a R, 7S, 9a S, 12 S*, 13a S)-12-acetylamino-2, 3, 6, 6a, 7, 8, 9, 9a, 10, 11, 12, 13-dodecahydro-5-hydroxy-11-hydroxyimino-1-methyl-6a,7,10,10-tetramethyl-3-oxo-1H- benzo[8,8a][1]benzopyrano[2,3-e]isoindole (223) (1R*, 6a R, 7S, 9a S, 12 S*, 13a S)-2, 3, 6, 6a, 7, 8, 9, 9a, 10, 11, 12, 13- dodecahydro-5-hydroxy-1-methyl- (223) 6a,7,10,10-tetramethyl-12-methylamino-11-(1-oxa-4-azacyclohex-4-yl)imino-3-oxo-1H-benzo[8,8a][1]benzopyrano[2,3-e]isoindole
(224) (1R*, 6a R, 7S, 9a S, 12 S*, 13a S)-12-amino-2, 3, 6, 6a, 7, 8, 9, 9a, 10, 11, 12, 13- dodecahydro-5-hydroxy-1-methyl-6a,7,10,10-tetramethyl-3-oxo-11-ureidoimino-1H- benzo[8,8a][1]benzopyrano[2,3-e]isoindole
(225) (1R*, 6a R, 7S, 9a S, 12 S*, 13a S)-12-acetoxy-2, 3, 6, 6a, 7, 8, 9, 9a, 10, 11, 12, 13- dodecahydro-1,5-dihydroxy-6a,7,10,10-tetramethyl-3,11-dioxo-1H- benzo[8,8a][1]benzopyrano[2,3-e]isoindole
(226) (1R*, 6a R, 7S, 9a S, 12 S*, 13a S)-12-azido-11-cyanoimino-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole
(227) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-12-methylthio-3,11-dioxo-1H- benzo[8,8a][1]benzopyrano[2,3-e]isoindole
(228) (6a R, 7S, 9a S, 12 R*, 13a S)-12-acetoxy-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-3-oxo- 1H-benzo[8,8a][1]benzopyrano[2,3-e]isoindole
(229) (1R*, 6a R, 7S, 9a S, 12 S*, 13a S)-11-cyanoimino-2, 3, 6, 6a, 7, 8, 9, 9a, 10, 11, 12, 13-dodecahydro-1,5-dihydroxy-6a,7,10,10-tetramethyl-3-oxo-12-phenylsulfonyl-1H- benzo[8,8a][1]benzopyrano[2,3-e]isoindole
(230) (6a R, 7S, 9a S, 12 R*, 13a S)-2, 3, 6, 6a, 7, 8, 9, 9a, 10, 11, 12, 13-dodecahydro-12- hydroxy-5-dihydroxyphosphinyloxy-6a,7,10,10-tetramethyl-3,11-dioxo-1H- benzo[8,8a][1]benzopyrano[2,3-e]isoindole
(231) (6a R, 7S, 9a S, 12 R*, 13a S)-12-bromo-2, 3, 6, 6a, 7, 8, 9, 9a, 10, 11, 12, 13- dodecahydro-5-hydroxy-11-methoxyimino-6a,7,10,10-tetramethyl-3-oxo-1H- benzo[8,8a][1]benzopyrano[2,3-e]isoindole
(232) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-3,11-dioxo-12-phenoxy-1H-benzo[8,8a][1]benzopyrano[2,3-e]isoindole
(233) (1R*, 6a R, 7S, 9a S, 12 S*, 13a S)-12-chloro-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole
(234) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-3-oxo-12-phenylsulfonylamino-1H- benzo[8,8a][1]benzopyrano[2,3-e]isoindole
(235) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-13-dioxo-12-phenylsulfonyloxy-1H- benzo[8,8a][1]benzopyrano[2,3-e]isoindole
(236) (6a R, 7S, 9a S, 12 R*, 13a S)-2, 3, 6, 6a, 7, 8, 9, 9a, 10, 11, 12, 13-dodecahydro-5- hydroxy-12-(2-hydroxy)ethoxy-6a,7,10,10-tetramethyl-3-oxo-11-ureidoimino-1H- benzo[8,8a][1]benzopyrano[2,3-e]isoindole
(237) (6a R, 7S, 9a S, 12 R*, 13a S)-12-glycylamino-2, 3, 6, 6a, 7, 8, 9, 9a, 10, 11, 12, 13- dodecahydro-5-hydroxy-6a,7,10,10-tetramethyl-1,3,11-trioxo-1H- benzo[8,8a][1]benzopyrano[2,3-e]isoindole
(238) (6a R, 7S, 9a S, 12 R*, 13a S)-2, 3, 6, 6a, 7, 8, 9, 9a, 10, 11, 12, 13-dodecahydro-5- hydroxy-11-hydroxyimino-12-methoxy-6a,7,10,10-tetramethyl-3-oxo-1H- benzo[8,8a][1]benzopyrano[2,3-e]isoindole
(239) (6a R, 7S, 9a S, 12 R*, 13a S)-11-cyanoimino-2, 3, 6, 6a, 7, 8, 9, 9a, 10, 11, 12, 13- dodecahydro-5,12-dihydroxy-6a,7,10,10-tetramethyl-13-dioxo-1H- benzo[8,8a][1]benzopyrano[2,3-e]isoindole
(240) (6a R, 7S, 9a S, 12 R*, 13a S)-12-benzoyloxy-2, 3, 6, 6a, 7, 8, 9, 9a, 10, 11, 12, 13- dodecahydro-5-hydroxy-6a,7,10,10-tetramethyl-3-oxo-11-ureidoimino-1H- benzo[8,8a][1]benzopyrano[2,3-e]isoindole
(241) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-12-methylamino-3,11-dioxo-1H-benzo[8,8a][1]benzopyrano[2,3-e]isoindole
(242) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-3,11 -dioxo-12-phenylsulfonyl-1H-benzo[8,8a][1]benzopyrano[2,3-e]isoindole
(243) (1R*, 6a R, 7S, 9a S, 12 S*, 13a S)-2, 3, 6, 6a, 7, 8, 9, 9a, 10, 11, 12, 13- dodecahydro-1,5-dihydroxy-12-methoxy-6a,7,10,10-tetramethyl-3,11-dioxo-1H- benzo[8,8a][1]benzopyrano[2,3-e]isoindole
(244) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-11-(1-oxa-4-azacyclohex-4-yl)imino-13-dioxo-12- phenylsulfonyl-1H-benzo[8,8a][1]benzopyrano[2,3-e]isoindole
(245) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-1,3,11-trioxo-12-(3-pyridyl)carbonyloxy-1H- benzo[8,8a][1]benzopyrano[2,3-e]isoindole
(246) (1R*, 6a R, 7S, 9a S, 12 S*, 13a S)-12-azido-2, 3, 6, 6a, 7, 8, 9, 9a, 10, 11, 12, 13- dodecahydro-5-hydroxy-1-methyl-6a,7,10,10-tetramethyl-3-oxo-11-ureidoimino-1H- benzo[8,8a][1]benzopyrano[2,3-e]isoindole
(247) (6a R, 7S, 9a S, 12 R*, 13a S)-12-acetylamino-2, 3, 6, 6a, 7, 8, 9, 9a, 10, 11, 12, 13- dodecahydro-5-hydroxy-6a,7,10,10-tetramethyl-13-dioxo-11-ureidoimino-1H-benzo[8,8a][1]benzopyrano[2,3-e]isoindole
(248) (6a R, 7S, 9a S, 12 R*, 13a S)-12-bromo-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-13- dioxo-1H-benzo[8,8a][1]benzopyrano[2,3-e]isoindole
(249) (1R*, 6a R, 7S, 9a S, 12 S*, 13a S)-2, 3, 6, 6a, 7, 8, 9, 9a, 10, 11, 12, 13- dodecahydro-1,5-dihydroxy-11-hydroxyimino-6a,7,10,10-tetramethyl-3-oxo-12-phenylsulfonyloxy-1H-benzo[8,8a][1]benzopyrano[2,3-e]isoindole
(250) (1R*, 6a R, 7S, 9a S, 12 S*, 13a S)-12-carboxymethyloxy-2, 3, 6, 6a, 7, 8, 9, 9a, 10, 11, 12, 13-dodecahydro-5-hydroxy-11-methoxyimino-1-methyl-6a,7,10,10-tetramethyl-3- oxo-1H-benzo[8,8a][1]benzopyrano[2,3-e]isoindole
(251) (1R*, 6a R, 7S, 9a S, 12 S*, 13a S)-1-acetoxy-12-bromo-2, 3, 6, 6a, 7, 8, 9, 9a, 10, 11, 12, 13-dodecahydro-5-hydroxy-6a,7,10,10-tetramethyl-3-oxo-11-ureidoimino-1H- benzo[8,8a][1]benzopyrano[2,3-e]isoindole
(252) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-mercapto-11-methoxyimino-6a,7,10,10-tetramethyl-3-oxo-1H- benzo[8,8a][1]benzopyrano[2,3-e]isoindole
(253) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylsulfinyl-13-dioxo-11-ureidoimino-1H- benzo[8,8a][1]benzopyrano[2,3-e]isoindole
(254) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-3-oxo-12-phenylsulfonylamino-1H- benzo[8,8a][1]benzopyrano[2,3-e]isoindole (255) (6a R, 7S, 9a S, 12 R*, 13a S)-12-chloro-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (256) (6a R, 7S, 9a S, 12 R*, 13a S)-12-ethoxy-2, 3, 6, 6a, 7, 8, 9, 9a, 10, 11, 12, 13- dodecahydro-5-hydroxy-11-hydroxyimino-6a,7,10,10-tetramethyl-3-oxo-1H- benzo[8,8a][1]benzopyrano[2,3-e]isoindole (257) (1R*, 6a R, 7S, 9a S, 12 S*, 13a S)-1-acetoxy-11-cyanoimino-2, 3, 6, 6a, 7, 8, 9, 9a, 10, 11, 12, 13-dodecahydro-5-hydroxy-12-methanesulfonyloxy-6a,7,10,10-tetramethyl-3- oxo-1H-benzo[8,8a][1]benzopyrano[2,3-e]isoindole (258) (1R*, 6a R, 7S, 9a S, 12 S*, 13a S)-2, 3, 6, 6a, 7, 8, 9, 9a, 10, 11, 12, 13- dodecahydro-1,5-dihydroxy-12-mercapto-11-methoxyimino-6a,7,10,10-tetramethyl-3-oxo- 1H-benzo[8,8a][1]benzopyrano[2,3-e]isoindole (259) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-13-dioxo-12-phenylsulfinyl-1H- benzo[8,8a][1]benzopyrano[2,3-e]isoindole (260) (6a R, 7S, 9a S, 12 R*, 13a S)-12-amino-2, 3, 6, 6a, 7, 8, 9, 9a, 10, 11, 12, 13- dodecahydro-5-hydroxy-11-hydroxyimino-6a,7,10,10-tetramethyl-3-oxo-1H- benzo[8,8a][1]benzopyrano[2,3-e]isoindole (261) (1R*, 6a R, 7S, 9a S, 12 S*, 13a S)-12-azido-2, 3, 6, 6a, 7, 8, 9, 9a, 10, 11, 12, 13- dodecahydro-5-hydroxy-1-methyl-6a,7,10,10-tetramethyl-11-(1-oxa-4-azacyclohex-4- yl)imino-3-oxo-1H-benzo[8,8a][1]benzopyrano[2,3-e]isoindole (262) (6a R, 7S, 9a S, 12 R*, 13a S)-12-benzoyloxy-2, 3, 6, 6a, 7, 8, 9, 9a, 10, 11, 12, 13- dodecahydro-5-dihydroxyphosphinyloxy-6a,7,10,10-tetramethyl-1,3,11-trioxo-1H- benzo[8,8a][1]benzopyrano[2,3-e]isoindole (263) (6a R, 7S, 9a S, 12 R*, 13a S)-11-cyanoimino-2, 3, 6, 6a, 7, 8, 9, 9a, 10, 11, 12, 13- dodecahydro-5-hydroxy-12-mercapto-6a,7,10,10-tetramethyl-13-dioxo-1H- benzo[8,8a][1]benzopyrano[2,3-e]isoindole (264) (1R*, 6a R, 7S, 9a S, 12 S*, 13a S)-12-acetylamino-2, 3, 6, 6a, 7, 8, 9, 9a, 10, 11, 12, 13-dodecahydro-5-hydroxy-11-methoxyimino-1-methyl-6a,7,10,10-tetramethyl-3-oxo-1H- benzo[8,8a][1]benzopyrano[2,3-e]isoindole (265) (6a R, 7S, 9a S, 12 R*, 13a S)-12-benzyloxy-2, 3, 6, 6a, 7, 8, 9, 9a, 10, 11, 12, 13- dodecahydro-5-hydroxy-11-methoxyimino-6a,7,10,10-tetramethyl-3-oxo-1H- benzo[8,8a][1]benzopyrano[2,3-e]isoindole (266) (1R*, 6a R, 7S, 9a S, 12 S*, 13a S)-11-cyanoimino-2, 3, 6, 6a, 7, 8, 9, 9a, 10, 11, 12, 13-dodecahydro-1,5-dihydroxy-6a,7,10,10-tetramethyl-3-oxo-12-(3-pyridyl)carbonyloxy- 1H-benzo[8,8a][1]benzopyrano[2,3-e]isoindole (267) (6a R, 7S, 9a S, 12 R*, 13a S)-2, 3, 6, 6a, 7, 8, 9, 9a, 10, 11, 12, 13-dodecahydro-5- hydroxy-12-methanesulfonylamino-6a,7,10,10-tetramethyl-13-dioxo-11-ureidoimino-1H- benzo[8,8a][1]benzopyrano[2,3-e]isoindole (268) (1R*, 6a R, 7S, 9a S, 12 S*, 13a S)-2, 3, 6, 6a, 7, 8, 9, 9a, 10, 11, 12, 13- dodecahydro-1,5-dihydroxy-11-hydroxyimino-12-methanesulfonylamino-6a,7,10,10-tetramethyl-3-oxo-1H-benzo[8,8a][1]benzopyrano[2,3-e]isoindole (269) (1R*, 6a R, 7S, 9a S, 12 S*, 13a S)-2, 3, 6, 6a, 7, 8, 9, 9a, 10, 11, 12, 13- dodecahydro-1,5-dihydroxy-11-hydroxyimino-12-mercapto-6a,7,10,10-tetramethyl-3-oxo- 1H-benzo[8,8a][1]benzopyrano[2,3-e]isoindole (270) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-13-dioxo-12-phenylsulfonyl-1H- benzo[8,8a][1]benzopyrano[2,3-e]isoindole (271) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylamino-11-(1-oxa-4-azacyclohex-4-yl)imino-3- oxo-1H-benzo[8,8a][1]benzopyrano[2,3-e]isoindole (272) (1R*, 6a R, 7S, 9a S, 12 S*, 13a S)-12-benzyloxycarbonylamino-2, 3, 6, 6a, 7, 8, 9, 9a, 10, 11, 12, 13-dodecahydro-5-hydroxy-1-methyl-6a,7,10,10-tetramethyl-3-oxo-11- ureidoimino-1H-benzo [8,8a][1]benzopyrano [2,3-e]isoindole (273) (1R*, 6a R, 7S, 9a S, 12 S*, 13a S)-1-acetoxy-11-hydrazono-2, 3, 6, 6a, 7, 8, 9, 9a, 10, 11, 12, 13-dodecahydro-5-hydroxy-6a,7,10,10-tetramethyl-3-oxo-12-phenoxy-1H- benzo[8,8a][1]benzopyrano[2,3-e]isoindole (274) (6a R, 7S, 9a S, 12 R*, 13a S)-12-acetoxy-2, 3, 6, 6a, 7, 8, 9, 9a, 10, 11, 12, 13- dodecahydro-5-hydroxy-6a,7,10,10-tetramethyl-1,3,11-trioxo-1H- benzo[8,8a][1]benzopyrano[2,3-e]isoindole (275) (1R*, 6a R, 7S, 9a S, 12 S*, 13a S)-1-acetoxy-12-chloro-2, 3, 6, 6a, 7, 8, 9, 9a, 10, 11, 12, 13-dodecahydro-5-hydroxy-11-hydroxyimino-6a,7,10,10-tetramethyl-3-oxo-1H- benzo[8,8a][1]benzopyrano[2,3-e]isoindole (276) (6a R, 7S, 9a S, 12 R*, 13a S)-12-azido-2, 3, 6, 6a, 7, 8, 9, 9a, 10, 11, 12, 13- dodecahydro-5-hydroxy-6a,7,10,10-tetramethyl-13-dioxo-11-ureidoimino-1H- benzo[8,8a][1]benzopyrano[2,3-e]isoindole (277) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-12-methylthio-3,11-dioxo-1H- benzo[8,8a][1]benzopyrano[2,3-e]isoindole (278) (6a R, 7S, 9a S, 12 R*, 13a S)-2, 3, 6, 6a, 7, 8, 9, 9a, 10, 11, 12, 13-dodecahydro-5- hydroxy-12-(2-hydroxy)ethoxy-6a,7,10,10-tetramethyl-1,3,11-trioxo-1H- benzo[8,8a][1]benzopyrano[2,3-e]isoindole (279) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-13-dioxo-12-phenylsulfonyloxy-1H- benzo[8,8a][1]benzopyrano[2,3-e]isoindole (280) (1R*, 6a R, 7S, 9a S, 12 S*, 13a S)-12-benzyloxy-11-hydrazono-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (281) (1R*, 6a R, 7S, 9a S, 12 S*, 13a S)-1-acetoxy-12-benzoyloxy-2, 3, 6, 6a, 7, 8, 9, 9a, 10, 11, 12, 1³-dodecahydro-5-hydroxy-6a,7,10,10-tetramethyl-11-(1-oxa-4-azacyclohex-4- yl)imino-3-oxo-1H-benzo[8,8a][1]benzopyrano[2,3-e]isoindole (282) (6a R, 7S, 9a S, 12 R*, 13a S)-12-glycylamino-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-13- dioxo-1H-benzo[8,8a][1]benzopyrano[2,3-e]isoindole (283) (1R*, 6a R, 7S, 9a S, 12 S*, 13a S)-11-cyanoimino-12-ethoxy-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (284) (1R*, 6a R, 7S, 9a S, 12 S*, 13a S)-12-amino-2, 3, 6, 6a, 7, 8, 9, 9a, 10, 11, 12, 13- dodecahydro-5-hydroxy-11-hydroxyimino-1-methyl-6a,7,10,10-tetramethyl-3-oxo-1H- benzo[8,8a][1]benzopyrano[2,3-e]isoindole (285) (6a R, 7S, 9a S, 12 R*, 13a S)-2, 3, 6, 6a, 7, 8, 9, 9a, 10, 11, 12, 13-dodecahydro-5- hydroxy-6a,7,10,10- tetramethyl-3-oxo-12-phenylsulfonyloxy-11-ureidoimino-1H- benzo[8,8a][1]benzopyrano[2,3-e]isoindole (286) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-3-oxo- 12-(3-pyridyl)carbonyloxy-1H-benzo[8,8a][1]benzopyrano[2,3-e]isoindole (287) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-12-methylamino-11-(1-oxa-4-azacyclohex-4-yl)imino-3-oxo-1H-benzo[8,8a][1]benzopyrano[2,3-e]isoindole (288) (1R*, 6a R, 7S, 9a S, 12 S*, 13a S)-12-ethoxy-2, 3, 6, 6a, 7, 8, 9, 9a, 10, 11, 12, 13- dodecahydro-1,5-dihydroxy-11-hydroxyimino-6a,7,10,10-tetramethyl-3-oxo-1H- benzo[8,8a][1]benzopyrano[2,3-e]isoindole (289) (1R*, 6a R, 7S, 9a S, 12 S*, 13a S)-11-hydrazono-2, 3, 6, 6a, 7, 8, 9, 9a, 10, 11, 12, 13-dodecahydro-5-hydroxy-12-methanesulfonyloxy-1-methyl-6a,7,10,10-tetramethyl-3- oxo-1H-benzo[8,8a][1]benzopyrano[2,3-e]isoindole (290) (6a R, 7S, 9a S, 12 R*, 13a S)-12-ethoxy-2, 3, 6, 6a, 7, 8, 9, 9a, 10, 11, 12, 13- dodecahydro-5-hydroxy-11-hydroxyimino-6a,7,10,10-tetramethyl-13-dioxo-1H-benzo[8,8a][1]benzopyrano[2,3-e]isoindole (291) (1R*, 6a R, 7S, 9a S, 12 S*, 13a S)-11-hydrazono-2, 3, 6, 6a, 7, 8, 9, 9a, 10, 11, 12, 13-dodecahydro-1,5-dihydroxy-12-(2-hydroxy)ethoxy-6a,7,10,10-tetramethyl-3-oxo-1H- benzo[8,8a][1]benzopyrano[2,3-e]isoindole (292) (1R*, 6a R, 7S, 9a S, 12 S*, 13a S)-2, 3, 6, 6a, 7, 8, 9, 9a, 10, 11, 12, 13- dodecahydro-5-hydroxy-11-hydroxyimino-12-mercapto-1-methyl-6a,7,10,10-tetramethyl-3- oxo-1H-benzo[8,8a][1]benzopyrano[2,3-e]isoindole (293) (1R*, 6a R, 7S, 9a S, 12 S*, 13a S)-2, 3, 6, 6a, 7, 8, 9, 9a, 10, 11, 12, 13- dodecahydro-5-hydroxy-12-(2-hydroxy)ethoxy-11-hydroxyimino-1-methyl-6a,7,10,10-tetramethyl-3-oxo-1H-benzo[8,8a][1]benzopyrano[2,3-e]isoindole (294) (1R*, 6a R, 7S, 9a S, 12 S*, 13a S)-2, 3, 6, 6a, 7, 8, 9, 9a, 10, 11, 12, 13- dodecahydro-5-hydroxy-12-methoxy-1-methyl-6a,7,10,10-tetramethyl-11-(1-oxa-4-azacyclohex-4-yl)imino-3-oxo-1H-benzo[8,8a][1]benzopyrano[2,3-e]isoindole (295) (1R*, 6a R, 7S, 9a S, 12 S*, 13a S)-11-cyanoimino-2, 3, 6, 6a, 7, 8, 9, 9a, 10, 11, 12, 13-dodecahydro-5-hydroxy-12-mercapto-1-methyl-6a,7,10,10-tetramethyl-3-oxo-1H- benzo[8,8a][1]benzopyrano[2,3-e]isoindole (296) (6a R, 7S, 9a S, 12 R*, 13a S)-12-acetoxy-2, 3, 6, 6a, 7, 8, 9, 9a, 10, 11, 12, 13- dodecahydro-5-hydroxy-11-hydroxyimino-6a,7,10,10-tetramethyl-3-oxo-1H- benzo[8,8a][1]benzopyrano[2,3-e]isoindole (297) (6a R, 7S, 9a S, 12 R*, 13a S)-2, 3, 6, 6a, 7, 8, 9, 9a, 10, 11, 12, 13-dodecahydro-5- hydroxy-11-hydroxyimino-12-methanesulfonyloxy-6a,7,10,10-tetramethyl-13-dioxo-1H- benzo[8,8a][1]benzopyrano[2,3-e]isoindole (298) (1R*, 6a R, 7S, 9a S, 12 S*, 13a S)-11-hydrazono-2, 3, 6, 6a, 7, 8, 9, 9a, 10, 11, 12, 13-dodecahydro-1,5-dihydroxy-12-methanesulfonylamino-6a,7,10,10-tetramethyl-3-oxo- 1H-benzo[8,8a][1]benzopyrano[2,3-e]isoindole (299) (1R*, 6a R, 7S, 9a S, 12 S*, 13a S)-12-benzyloxycarbonylamino-2, 3, 6, 6a, 7, 8, 9, 9a, 10, 11, 12, 13-dodecahydro-5-hydroxy-1-methyl-6a,7,10,10-tetramethyl-11-(1-oxa-4- azacyclohex-4-yl)imino-3-oxo-1H-benzo[8,8a][1]benzopyrano[2,3-e]isoindole (300) (1R*, 6a R, 7S, 9a S, 12 S*, 13a S)-1-acetoxy-12-chloro-2, 3, 6, 6a, 7, 8, 9, 9a, 10, 11, 12, 13-dodecahydro-5-hydroxy-11-methoxyimino-6a,7,10,10-tetramethyl-3-oxo-1H- benzo[8,8a][1]benzopyrano[2,3-e]isoindole (301) (1R*, 6a R, 7S, 9a S, 12 S*, 13a S)-12-ethoxy-2, 3, 6, 6a, 7, 8, 9, 9a, 10, 11, 12, 13- dodecahydro-1,5-dihydroxy-6a,7,10,10-tetramethyl-11-(1-oxa-4-azacyclohex-4-yl)imino-3- oxo-1H-benzo[8,8a][1]benzopyrano[2,3-e]isoindole (302) (1R*, 6a R, 7S, 9a S, 12 S*, 13a S)-1-acetoxy-12-chloro-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (303) (6a R, 7S, 9a S, 12 R*, 13a S)-5,12-dihydroxy-2, 3, 6, 6a, 7, 8, 9, 9a, 10, 11, 12, 13- dodecahydro-6a,7,10,10-tetramethyl-1,3,11-trioxo-1H-benzo[8,8a][1]benzopyrano[2,3- e]isoindole (304) (6a R, 7S, 9a S, 12 R*, 13a S)-2, 3, 6, 6a, 7, 8, 9, 9a, 10, 11, 12, 13-dodecahydro-12- hydroxy-5-dihydroxyphosphinyloxy-6a,7,10,10-tetramethyl-1,3,11-trioxo-1H- benzo[8,8a][1]benzopyrano[2,3-e]isoindole (305) (6a R, 7S, 9a S, 12 R*, 13a S)-11-hydrazono-2, 3, 6, 6a, 7, 8, 9, 9a, 10, 11, 12, 13- dodecahydro-5-hydroxy-12-methoxy-6a,7,10,10-tetramethyl-3-oxo-1H- benzo[8,8a][1]benzopyrano[2,3-e]isoindole (306) (1R*, 6a R, 7S, 9a S, 12 S*, 13a S)-2, 3, 6, 6a, 7, 8, 9, 9a, 10, 11, 12, 13- dodecahydro-5-hydroxy-12-(2-hydroxy)ethoxy-1-methyl-6a,7,10,10-tetramethyl-11-(1-oxa- 4-azacyclohex-4-yl)imino-3-oxo-1H-benzo[8,8a][1]benzopyrano[2,3-e]isoindole (307) (6a R, 7S, 9a S, 12 R*, 13a S)-12-chloro-11-hydrazono-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (308) (6a R, 7S, 9a S, 12 R*, 13a S)-12-benzoyloxy-2, 3, 6, 6a, 7, 8, 9, 9a, 10, 11, 12, 13- dodecahydro-5-dihydroxyphosphinyloxy-6a,7,10,10-tetramethyl-3,11-dioxo-1H- benzo[8,8a][1]benzopyrano[2,3-e]isoindole (309) (1R*, 6a R, 7S, 9a S, 12 S*, 13a S)-2, 3, 6, 6a, 7, 8, 9, 9a, 10, 11, 12, 13- dodecahydro-5-hydroxy-12-(2-hydroxy)ethoxy-1-methyl-6a,7,10,10-tetramethyl-3-oxo-11- ureidoimino-1H-benzo[8,8a][1]benzopyrano[2,3-e]isoindole (310) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-11-(1-oxa-4-azacyclohex-4-yl)imino-3- oxo-12-phenylsulfonylamino-1H-benzo[8,8a][1]benzopyrano[2,3-e]isoindole (311) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-3-oxo- 12-phenylthio-1H-benzo[8,8a][1]benzopyrano[2,3-e]isoindole (312) (1R*, 6a R, 7S, 9a S, 12 S*, 13a S)-12-azido-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (313) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-3,11-dioxo-12-phenylsulfonyloxy-1H-benzo[8,8a][1]benzopyrano[2,3-e]isoindole (314) (1R*, 6a R, 7S, 9a S, 12 S*, 13a S)-12-carboxymethyloxy-11-cyanoimino-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (315) (1R*, 6a R, 7S, 9a S, 12 S*, 13a S)-2, 3, 6, 6a, 7, 8, 9, 9a, 10, 11, 12, 13- dodecahydro-5-hydroxy-12-methoxy-1-methyl-6a,7,10,10-tetramethyl-3,11-dioxo-1H- benzo[8,8a][1]benzopyrano[2,3-e]isoindole (316) (6a R, 7S, 9a S, 12 R*, 13a S)-12-benzoyloxy-11-cyanoimino-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (317) (1R*, 6a R, 7,8, 9a S, 12 S*, 13a S)-12-bromo-2, 3, 6, 6a, 7, 8, 9, 9a, 10, 11, 12, 13- dodecahydro-5-hydroxy-1-methyl-6a,7,10,10-tetramethyl-3-oxo-11-ureidoimino-1H- benzo[8,8a][1]benzopyrano[2,3-e]isoindole (318) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-3,11-dioxo-12-(3-pyridyl)carbonyloxy- 1H-benzo[8,8a][1]benzopyrano[2,3-e]isoindole (319) (1R*, 6a R, 7S, 9a S, 12 S*, 13a S)-2, 3, 6, 6a, 7, 8, 9, 9a, 10, 11, 12, 13- dodecahydro-1,5-dihydroxy-12-methanesulfonyloxy-11-methoxyimino-6a,7,10,10-tetramethyl-3-oxo-1H-benzo[8,8a][1]benzopyrano[2,3-e]isoindole (320) (1R*, 6a R, 7S, 9a S, 12 S*, 13a S)-2, 3, 6, 6a, 7, 8, 9, 9a, 10, 11, 12, 13- dodecahydro-5-hydroxy-11-methoxyimino-1-methyl-6a,7,10,10-tetramethyl-3-oxo-12-(3- pyridyl)carbonyloxy-1H-benzo[8,8a][1]benzopyrano[2,3-e]isoindole (321) (6a R, 7S, 9a S, 12 R*, 13a S)-2, 3, 6, 6a, 7, 8, 9, 9a, 10, 11, 12, 13-dodecahydro-5- hydroxy-12-methanesulfonylamino-11-methoxyimino-6a,7,10,10-tetramethyl-13-dioxo-1H- benzo [8,8a][1]benzopyrano[2,3-e]isoindole (322) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-12-methylamino-3,11-dioxo-1H-benzo[8,8a][1]benzopyrano[2,3-e]isoindole (323) (6a R, 7S, 9a S, 12 R*, 13a S)-2, 3, 6, 6a, 7, 8, 9, 9a, 10, 11, 12, 13-dodecahydro-5- hydroxy-12-mercapto-6a,7,10,10-tetramethyl-1,3,11-trioxo-1H- benzo[8,8a][1]benzopyrano[2,3-e]isoindole (324) (1R*, 6a R, 7S, 9a S, 12 S*, 13a S)-1-acetoxy-12-carboxymethyloxy-11-hydrazono-2, 3, 6, 6a, 7, 8, 9, 9a, 10, 11, 12, 13-dodecahydro-5-hydroxy-6a,7,10,10-tetramethyl-3-oxo- 1H-benzo[8,8a][1]benzopyrano[2,3-e]isoindole (325) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-3,11-dioxo-12-phenylsulfonylamino-1H-benzo[8,8a][1]benzopyrano[2,3-e]isoindole (326) (1R*, 6a R, 7S, 9a S, 12 S*, 13a S)-2, 3, 6, 6a, 7, 8, 9, 9a, 10, 11, 12, 13- dodecahydro-5-hydroxy-11-methoxyimino-1-methyl-6a,7,10,10-tetramethyl-3-oxo-12- phenylthio-1H-benzo[8,8a][1]benzopyrano[2,3-e]isoindole (327) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-12-methylthio-3-oxo-1H- benzo[8,8a][1]benzopyrano[2,3-e]isoindole (328) (1R*, 6a R, 7S, 9a S, 12 S*, 13a S)-12-benzyloxy-2, 3, 6, 6a, 7, 8, 9, 9a, 10, 11, 12, 13-dodecahydro-5-hydroxy-1-methyl-6a,7,10,10-tetramethyl-3-oxo-11-ureidoimino-1H- benzo[8,8a][1]benzopyrano[2,3-e]isoindole (329) (1R*, 6a R, 7S, 9a S, 12 S*, 13a S)-1-acetoxy-12-carbamoyloxy-2, 3, 6, 6a, 7, 8, 9, 9a, 10, 11, 12, 13-dodecahydro-5-hydroxy-11-methoxyimino-6a,7,10,10-tetramethyl-3-oxo- 1H-benzo[8,8a][1]benzopyrano[2,3-e]isoindole (330) (1R*, 6a R, 7S, 9a S, 12 S*, 13a S)-2, 3, 6, 6a, 7, 8, 9, 9a, 10, 11, 12, 13- dodecahydro-1,5-dihydroxy-12-(2-hydroxy)ethoxy-11-hydroxyimino-6a,7,10,10-tetramethyl-3-oxo-1H-benzo[8,8a][1]benzopyrano[2,3-e]isoindole (331) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-3,11-dioxo-12-phenylsulfonyloxy-1H-benzo[8,8a][1]benzopyrano[2,3-e]isoindole (332) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylamino-3,11-dioxo-1H- benzo[8,8a][1]benzopyrano[2,3-e]isoindole (333) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-12-methylsulfinyl-13-dioxo-1H- benzo[8,8a][1]benzopyrano[2,3-e]isoindole (334) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-11-(1-oxa-4-azacyclohex-4-yl)imino-3-oxo-12- phenylsulfonylamino-1H-benzo[8,8a][1]benzopyrano[2,3-e]isoindole (335) (6a R, 7S, 9a S, 12 R*, 13a S)-12-benzyloxy-11-hydrazono-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (336) (1R*, 6a R, 7S, 9a S, 12 S*, 13a S)-12-benzoylamino-11-hydrazono-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (337) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-11-(1-oxa-4-azacyclohex-4-yl)imino-3-oxo-12- phenylsulfonyl-1H-benzo[8,8a][1]benzopyrano[2,3-e]isoindole (338) (1R*, 6a R, 7S, 9a S, 12 S*, 13a S)-1-acetoxy-11-cyanoimino-2, 3, 6, 6a, 7, 8, 9, 9a, 10, 11, 12, 13-dodecahydro-5-hydroxy-6a,7,10,10-tetramethyl-3-oxo-12-phenylsulfinyl-1H- benzo[8,8a][1]benzopyrano[2,3-e]isoindole (339) (1R*, 6a R, 7S, 9a S, 12 S*, 13a S)-11-hydrazono-2, 3, 6, 6a, 7, 8, 9, 9a, 10, 11, 12, 13-dodecahydro-1,5-dihydroxy-6a,7,10,10-tetramethyl-12-methylthio-3-oxo-1H- benzo[8,8a][1]benzopyrano[2,3-e]isoindole (340) (1R*, 6a R, 7S, 9a S, 12 S*, 13a S)-1-acetoxy-12-glycylamino-2, 3, 6, 6a, 7, 8, 9, 9a, 10, 11, 12, 13-dodecahydro-5-hydroxy-11-hydroxyimino-6a,7,10,10-tetramethyl-3-oxo-1H- benzo[8,8a][1]benzopyrano[2,3-e]isoindole (341) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-12-methylamino-3,11-dioxo-1H-benzo[8,8a][1]benzopyrano[2,3-e]isoindole (342) (6a R, 7S, 9a S, 12 R*, 13a S)-12-benzyloxy-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (343) (1R*, 6a R, 7S, 9a S, 12 S*, 13a S)-2, 3, 6, 6a, 7, 8, 9, 9a, 10, 11, 12, 13- dodecahydro-5-hydroxy-12-mercapto-11-methoxyimino-1-methyl-6a,7,10,10-tetramethyl-3- oxo-1H-benzo[8,8a][1]benzopyrano[2,3-e]isoindole (344) (1R*, 6a R, 7S, 9a S, 12 S*, 13a S)-12-carboxymethyloxy-2, 3, 6, 6a, 7, 8, 9, 9a, 10, 11, 12, 13-dodecahydro-1,5-dihydroxy-11-methoxyimino-6a,7,10,10-tetramethyl-3-oxo-1H- benzo[8,8a][1]benzopyrano[2,3-e]isoindole (345) (6a R, 7S, 9a S, 12 R*, 13a S)-11-hydroxyimino-2, 3, 6, 6a, 7, 8, 9, 9a, 10, 11, 12, 13- dodecahydro-5,12-dihydroxy-6a,7,10,10-tetramethyl-13-dioxo-1H- benzo[8,8a][1]benzopyrano[2,3-e]isoindole (346) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-3-oxo-12-phenylsulfonyl-1H- benzo[8,8a][1]benzopyrano[2,3-e]isoindole (347) (6a R, 7S, 9a S, 12 R*, 13a S)-2, 3, 6, 6a, 7, 8, 9, 9a, 10, 11, 12, 13-dodecahydro-5- hydroxy-12-methanesulfonyloxy-6a,7,10,10-tetramethyl-3-oxo-11-ureidoimino-1H- benzo[8,8a][1]benzopyrano[2,3-e]isoindole (348) (1R*, 6a R, 7S, 9a S, 12 R*, 13a S)-12-benzoylamino-2, 3, 6, 6a, 7, 8, 9, 9a, 10, 11, 12, 13-dodecahydro-1,5-dihydroxy-6a,7,10,10-tetramethyl-3,11-dioxo-1H- benzo[8,8a][1]benzopyrano[2,3-e]isoindole (349) (6a R, 7S, 9a S, 12 R*, 13a S)-12-carbamoyloxy-2, 3, 6, 6a, 7, 8, 9, 9a, 10, 11, 12, 13-dodecahydro-5-hydroxy-11-methoxyimino-6a,7,10,10-tetramethyl-3-oxo-1H-benzo[8,8a][1]benzopyrano[2,3-e]isoindole (350) (6a R, 7S, 9a S, 12 R*, 13a S)-2, 3, 6, 6a, 7, 8, 9, 9a, 10, 11, 12, 13-dodecahydro-5- hydroxy-12-mercapto-6a,7,10,10-tetramethyl-3-oxo-11-ureidoimino-1H- benzo[8,8a][1]benzopyrano[2,3-e]isoindole (351) (6a R, 7S, 9a S, 12 R*, 13a S)-12-acetoxy-11-hydrazono-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (352) (1R*, 6a R, 7S, 9a S, 12 S*, 13a S)-12-azido-2, 3, 6, 6a, 7, 8, 9, 9a, 10, 11, 12, 13- dodecahydro-1,5-dihydroxy-11-methoxyimino-6a,7,10,10-tetramethyl-3-oxo-1H- benzo[8,8a][1]benzopyrano[2,3-e]isoindole (353) (6a R, 7S, 9a S, 12 R*, 13a S)-12-bromo-2, 3, 6, 6a, 7, 8, 9, 9a, 10, 11, 12, 13- dodecahydro-5-hydroxy-6a,7,10,10-tetramethyl-3,11-dioxo-1H- benzo [8,8a][1]benzopyrano [2,3-e]isoindole (354) (1R*, 6a R, 7S, 9a S, 12 S*, 13a S)-1-acetoxy-11-cyanoimino-2, 3, 6, 6a, 7, 8, 9, 9a, 10, 11, 12, 13-dodecahydro-5-hydroxy-12-methoxy-6a,7,10,10-tetramethyl-3-oxo-1H- benzo[8,8a][1]benzopyrano[2,3-e]isoindole (355) (1R*, 6a R. 7S, 9a S, 12 S*, 13a S)-2, 3, 6, 6a, 7, 8, 9, 9a, 10, 11, 12, 13- dodecahydro-1,5-dihydroxy-11-methoxyimino-6a,7,10,10-tetramethyl-3-oxo-12-phenylsulfonylamino-1H-benzo[8,8a][1]benzopyrano[2,3-e]isoindole (356) (1R*, 6a R, 7S, 9a S, 12 S*, 13a S)-12-bromo-11-cyanoimino-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (357) (6a R, 7S, 9a S, 12 R*, 13a S)-12-benzyloxycarbonylamino-2, 3, 6, 6a, 7, 8, 9, 9a, 10, 11, 12, 13-dodecahydro-5-hydroxy-11-hydroxyimino-6a,7,10,10-tetramethyl-13-dioxo-1H- benzo[8,8a][1]benzopyrano[2,3-e]isoindole (358) (1R*, 6a R, 7S, 9a S, 12 S*, 13a S)-1,12-diacetoxy-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (359) (1R*, 6a R, 7S, 9a S, 12 S*, 13a S)-12-acetoxy-2, 3, 6, 6a, 7, 8, 9, 9a, 10, 11, 12, 13- dodecahydro-1,5-dihydroxy-11-methoxyimino-6a,7,10,10-tetramethyl-3-oxo-1H- benzo[8,8a][1]benzopyrano[2,3-e]isoindole (360) (1R*, 6a R, 7S, 9a S, 12 S*, 13a S)-2, 3, 6, 6a, 7, 8, 9, 9a, 10, 11, 12, 13- dodecahydro-1,5-dihydroxy-11-hydroxyimino-6a,7,10,10-tetramethyl-3-oxo-12-(3-pyridyl)carbonyloxy-1H-benzo[8,8a][1]benzopyrano[2,3-e]isoindole (361) (1R*, 6a R, 7S, 9a S, 12 S*, 13a S)-2, 3, 6, 6a, 7, 8, 9, 9a, 10, 11, 12, 13- dodecahydro-1,5-dihydroxy-11-hydroxyimino-6a,7,10,10-tetramethyl-3-oxo-12-phenylsulfonylamino-1H-benzo[8,8a][1]benzopyrano[2,3-e]isoindole (362) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-11-(1-oxa-4-azacyclohex-4-yl)imino-13-dioxo-12-(3- pyridyl)carbonyloxy-1H-benzo[8,8a][1]benzopyrano[2,3-e]isoindole (363) (1R*, 6a R, 7S, 9a S, 12 S*, 13a S)-12-acetoxy-11-hydrazono-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (364) (1R*, 6a R, 7S, 9a S, 12 S*, 13a S)-11-hydrazono-2, 3, 6, 6a, 7, 8, 9, 9a, 10, 11, 12, 13-dodecahydro-5-hydroxy-12-(2-hydroxy)ethoxy-1-methyl-6a,7,10,10-tetramethyl-3-oxo- 1H-benzo[8,8a][1]benzopyrano[2,3-e]isoindole (365) (6a R, 7S, 9a S, 12 R*, 13a S)-2, 3, 6, 6a, 7, 8, 9, 9a, 10, 11, 12, 13-dodecahydro-5- hydroxy-12-methanesulfonylamino-6a,7,10,10-tetramethyl-11-(1-oxa-4-azacyclohex-4- yl)imino-3-oxo-1H-benzo[8,8a][1]benzopyrano[2,3-e]isoindole (366) (1R*, 6a R, 7S, 9a S, 12 S*, 13a S)-12-benzoylamino-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (367) (1R*, 6a R, 7S, 9a S, 12 S*, 13a S)-11-cyanoimino-2, 3, 6, 6a, 7, 8, 9, 9a, 10, 11, 12, 13-dodecahydro-5-hydroxy-12-(2-hydroxy)ethoxy-1-methyl-6a,7,10,10-tetramethyl-3-oxo- 1H-benzo[8,8a][1]benzopyrano[2,3-e]isoindole (368) (6a R, 7S, 9a S, 12 R*, 13a S)-12-benzyloxycarbonylamino-2, 3, 6, 6a, 7, 8, 9, 9a, 10, 11, 12, 13-dodecahydro-5-hydroxy-11-hydroxyimino-6a,7,10,10-tetramethyl-3-oxo-1H- benzo[8,8a][1]benzopyrano[2,3-e]isoindole (369) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-13-dioxo-12-phenylsulfonyl-11-ureidoimino-1H- benzo[8,8a][1]benzopyrano[2,3-e]isoindole (370) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-12-methylamino-13-dioxo-1H- benzo[8,8a][1]benzopyrano[2,3-e]isoindole (371) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-3-oxo-12-phenylthio-1H- benzo[8,8a][1]benzopyrano [2,3-e]isoindole (372) (1R*, 6a R, 7S, 9a S, 12 S*, 13a S)-12-benzoylamino-2, 3, 6, 6a, 7, 8, 9, 9a, 10, 11, 12, 13-dodecahydro-1,5-dihydroxy-6a,7,10,10-tetramethyl-3-oxo-11-ureidoimino-1H- benzo[8,8a][1]benzopyrano [2,3-e]isoindole (373) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-12-methylsulfinyl-3,11-dioxo-1H- benzo[8,8a][1]benzopyrano[2,3-e]isoindole (374) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-mercapto-6a,7,10,10-tetramethyl-3-oxo-11-ureidoimino-1H- benzo[8,8a][1]benzopyrano[2,3-e]isoindole (375) (1R*, 6a R, 7S, 9a S, 12 S*, 13a S)-2, 3, 6, 6a, 7, 8, 9, 9a, 10, 11, 12, 13- dodecahydro-5-hydroxy-11-hydroxyimino-1-methyl-6a,7,10,10-tetramethyl-3-oxo-12- phenylsulfonyloxy-1H-benzo[8,8a][1]benzopyrano[2,3-e]isoindole (376) (6a R, 7S, 9a S, 12 R*, 13a S)-1 1-hydrazono-2, 3, 6, 6a, 7, 8, 9, 9a, 10, 11, 12, 13- dodecahydro-5-hydroxy-6a,7,10,10-tetramethyl-12-methylamino-3-oxo-1H-benzo[8,8a][1]benzopyrano[2,3-e]isoindole (377) (1R*, 6a R, 7S, 9a S, 12 S*, 13a S)-1-acetoxy-12-benzoylamino-2, 3, 6, 6a, 7, 8, 9, 9a, 10, 11, 12, 13-dodecahydro-5-hydroxy-11-hydroxyimino-6a,7,10, 10-tetramethyl-3-oxo-1H- benzo[8,8a][1]benzopyrano[2,3-e]isoindole (378) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-13-dioxo-12-phenylsulfonylamino-1H- benzo[8,8a][1]benzopyrano[2,3-e]isoindole (379) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-13-dioxo-12-phenoxy-1H- benzo[8,8a][1]benzopyrano[2,3-e]isoindole (380) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-11-(1-oxa-4-azacyclohex-4-yl)imino-3-oxo-12- phenylsulfonyloxy-1H-benzo[8,8a][1]benzopyrano[2,3-e]isoindole (381) (1R*, 6a R, 7S, 9a S, 12 S*, 13a S)-2, 3, 6, 6a, 7, 8, 9, 9a, 10, 11, 12, 13- dodecahydro-1,5-dihydroxy-12-(2-hydroxy)ethoxy-11-methoxyimino-6a,7,10,10-tetramethyl-3-oxo-1H-benzo[8,8a][1]benzopyrano[2,3-e]isoindole (382) (1R*, 6a R, 7S, 9a S, 12 S*, 13a S)-12-benzoyloxy-2, 3, 6, 6a, 7, 8, 9, 9a, 10, 11, 12, 13-dodecahydro-5-hydroxy-11-hydroxyimino-1-methyl-6a,7,10,10-tetramethyl-3-oxo-1H- benzo[8,8a][1]benzopyrano[2,3-e]isoindole (383) (1R*, 6a R, 7S, 9a S, 12 S*, 13a S)-12-chloro-2, 3, 6, 6a, 7, 8, 9, 9a, 10, 11, 12, 13- dodecahydro-1,5-dihydroxy-6a,7,10,10-tetramethyl-3,11-dioxo-1H- benzo[8,8a][1]benzopyrano[2,3-e]isoindole (384) (1R*, 6a R, 7S, 9a S, 12 S*, 13a S)-12-azido-11-hydrazono-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (385) (6a R, 7S, 9a S, 12 R*, 13a S)-12-benzoylamino-11-hydrazono-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (386) (1R*, 6a R, 7S, 9a S, 12 S*, 13a S)-1-acetoxy-11-hydrazono-2, 3, 6, 6a, 7, 8, 9, 9a, 10, 11, 12, 13-dodecahydro-5-hydroxy-6a,7,10,10-tetramethyl-3-oxo-12-phenylthio-1H- benzo[8,8a][1]benzopyrano[2,3-e]isoindole (387) (1R*, 6a R, 7S, 9a S, 12 S*, 13a S)-11-hydrazono-2, 3, 6, 6a, 7, 8, 9, 9a, 10, 11, 12, 13-dodecahydro-5-hydroxy-1-methyl-6a,7,10,10-tetramethyl-3-oxo-12-phenylthio-1H- benzo[8,8a][1]benzopyrano[2,3-e]isoindole (388) (1R*, 6a R, 7S, 9a S, 12 S*, 13a S)-12-acetylamino-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (389) (6a R, 7S, 9a S, 12 R*, 13a S)-12-carbamoyloxy-2, 3, 6, 6a, 7, 8, 9, 9a, 10, 11, 12, 13-dodecahydro-5-hydroxy-6a,7,10,10-tetramethyl-11-(1-oxa-4-azacyclohex-4-yl)imino-13- dioxo-1H-benzo[8,8a][1]benzopyrano[2,3-e]isoindole (390) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylthio-11-(1-oxa-4-azacyclohex-4-yl)imino-13- dioxo-1H-benzo[8,8a][1]benzopyrano[2,3-e]isoindole (391) (1R*, 6a R, 7S, 9a S, 12 S*, 13a S)-12-carbamoyloxy-11-hydrazono-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (392) (1R*, 6a R, 7S, 9a S, 12 S*, 13a S)-12-benzyloxycarbonylamino-2, 3, 6, 6a, 7, 8, 9, 9a, 10, 11, 12,13-dodecahydro-1,5-dihydroxy-11-hydroxyimino-6a, 7,10,10-tetramethyl-3- oxo-1H-benzo[8,8a][1]benzopyrano[2,3-e]isoindole (393) (6a R, 7S, 9a S, 12 R*, 13a S)-12-glycylamino-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-3-oxo- 1H-benzo[8,8a][1]benzopyrano[2,3-e]isoindole (394) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-12-methylsulfinyl-3,11-dioxo-1H- benzo[8,8a][1]benzopyrano[2,3-e]isoindole (395) (1R*, 6a R, 7S, 9a S, 12 S*, 13a S)-2, 3, 6, 6a, 7, 8, 9, 9a, 10, 11, 12, 13- dodecahydro-5-hydroxy-11-hydroxyimino-1-methyl-6a,7,10,10-tetramethyl-3-oxo-12- phenylsulfinyl-1H-benzo[8,8a][1]benzopyrano[2,3-e]isoindole (396) (6a R, 7S, 9a S, 12 R*, 13a S)-12-glycylamino-2, 3, 6, 6a, 7, 8, 9, 9a, 10, 11, 12, 13- dodecahydro-5-hydroxy-6a,7,10,10-tetramethyl-3,11-dioxo-1H- benzo[8,8a][1]benzopyrano[2,3-e]isoindole (397) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-11-(1-oxa-4-azacyclohex-4-yl)imino-3- oxo-12-phenoxy-1H-benzo[8,8a][1]benzopyrano[2,3-e]isoindole (398) (1R*, 6a R, 7S, 9a S, 12 S*, 13a S)-2, 3, 6, 6a, 7, 8, 9, 9a, 10, 11, 12, 13- dodecahydro-5-hydroxy-11-methoxyimino-1-methyl-6a,7,10,10-tetramethyl-3-oxo-12- phenylsulfinyl-1H-benzo[8,8a][1]benzopyrano[2,3-e]isoindole (399) (1R*, 6a R, 7S, 9a S, 12 S*, 13a S)-12-amino-11-hydrazono-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (400) (1R*, 6a R, 7S, 9a S, 12 S*, 13a S)-1,12-diacetoxy-2, 3, 6, 6a, 7, 8, 9, 9a, 10, 11, 12, 13-dodecahydro-5-hydroxy-11-methoxyimino-6a,7,10,10-tetramethyl-3-oxo-1H- benzo[8,8a][1]benzopyrano[2,3-e]isoindole (401) (6a R, 7S, 9a S, 12 R*, 13a S)-12-benzyloxy-2, 3, 6, 6a, 7, 8, 9, 9a, 10, 11, 12, 13- dodecahydro-5-hydroxy-11-hydroxyimino-6a,7,10,10-tetramethyl-3-oxo-1H-benzo[8,8a][1]benzopyrano[2,3-e]isoindole (402) (1R*, 6a R, 7S, 9a S, 12 S*, 13a S)-11-cyanoimino-2, 3, 6, 6a, 7, 8, 9, 9a, 10, 11, 12, 13-dodecahydro-1,5-dihydroxy-12-methanesulfonylamino-6a,7,10,10-tetramethyl-3-oxo- 1H-benzo[8,8a][1]benzopyrano[2,3-e]isoindole (403) (1R*, 6a R, 7S, 9a S, 12 S*, 13a S)-12-benzyloxycarbonylamino-11-cyanoimino-2,3, 6, 6a, 7, 8, 9, 9a, 10, 11, 12, 13-dodecahydro-1,5-dihydroxy-6a,7,10,10-tetramethyl-3-oxo- 1H-benzo[8,8a][1]benzopyrano[2,3-e]isoindole (404) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-3,11-dioxo-12-phenylthio-1H-benzo[8,8a][1]benzopyrano[2,3-e]isoindole (405) (1R*, 6a R, 7S, 9a S, 12 S*, 13a S)-12-acetylamino-2, 3, 6, 6a, 7, 8, 9, 9a, 10, 11, 12, 13-dodecahydro-5-hydroxy-1-methyl-6a,7,10,10-tetramethyl-3,11-dioxo-1H- benzo[8,8a][1]benzopyrano[2,3-e]isoindole (406) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-3-oxo-12-phenoxy-1H- benzo[8,8a][1]benzopyrano[2,3-e]isoindole (407) (1R*, 6a R, 7S, 9a S, 12 S*, 13a S)-1-acetoxy-12-azido-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (408) (1R*, 6a R, 7S, 9a S, 12 S*, 13a S)-2, 3, 6, 6a, 7, 8, 9, 9a, 10, 11, 12, 13- dodecahydro-5-hydroxy-12-mercapto-1-methyl-6a,7,10,10-tetramethyl-11-(1-oxa-4-azacyclohex-4-yl)imino-3-oxo-1H-benzo[8,8a][1]benzopyrano[2,3-e]isoindole (409) (1R*, 6a R, 7S, 9a S, 12 S*, 13a S)-12-acetoxy-2, 3, 6, 6a, 7, 8, 9, 9a, 10, 11, 12, 13- dodecahydro-5-hydroxy-1-methyl-6a,7,10,10-tetramethyl-3,11-dioxo-1H- benzo[8,8a][1]benzopyrano[2,3-e]isoindole (410) (1R*, 6a R, 7S, 9a S, 12 S*, 13a S)-11-cyanoimino-2, 3, 6, 6a, 7, 8, 9, 9a, 10, 11, 12, 13-dodecahydro-1,5-dihydroxy-6a,7,10,10-tetramethyl-3-oxo-12-phenylsulfonylamino-1H- benzo[8,8a][1]benzopyrano[2,3-e]isoindole (411) (6a R, 7S, 9a S, 12 R*, 13a S)-12-benzyloxy-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (412) (1R*, 6a R, 7S, 9a S, 12 S*, 13a S)-12-carboxymethyloxy-2, 3, 6, 6a, 7, 8, 9, 9a, 10, 11, 12, 13-dodecahydro-1,5-dihydroxy-6a,7,10,10-tetramethyl-3-oxo-11-ureidoimino-1H- benzo[8,8a][1]benzopyrano[2,3-e]isoindole (413) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-methanesulfonyloxy-6a,7,10,10-tetramethyl-3-oxo-11- ureidoimino-1H-benzo[8,8a][1]benzopyrano[2,3-e]isoindole (414) (1R*, 6a R, 7S, 9a S, 12 S*, 13a S)-12-carbamoyloxy-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (415) (1R*, 6a R, 7S, 9a S, 12 S*, 13a S)-12-ethoxy-11-hydrazono-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (416) (1R*, 6a R, 7S, 9a S, 12 S*, 13a S)-2, 3, 6, 6a, 7, 8, 9, 9a, 10, 11, 12, 13- dodecahydro-1,5-dihydroxy-12-(2-hydroxy)ethoxy-6a,7,10,10-tetramethyl-11-(1-oxa-4-azacyclohex-4-yl)imino-3-oxo-1H-benzo[8,8a][1]benzopyrano[2,3-e]isoindole (417) (6a R, 7S, 9a S, 12 R*, 13a S)-12-carboxymethyloxy-11-hydrazono-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (418) (6a R, 7S, 9a S, 12 R*, 13a S)-12-benzyloxy-2, 3, 6, 6a, 7, 8, 9, 9a, 10, 11, 12, 13- dodecahydro-5-dihydroxyphosphinyloxy-6a,7,10,10-tetramethyl-3,11-dioxo-1H- benzo[8,8a][1]benzopyrano[2,3-e]isoindole (419) (1R*, 6a R, 7S, 9a S, 12 S*, 13a S)-12-benzoylamino-2, 3, 6, 6a, 7, 8, 9, 9a, 10, 11, 12, 13-dodecahydro-5-hydroxy-1-methyl-6a,7,10,10-tetramethyl-3,11-dioxo-1H- benzo[8,8a][1]benzopyrano[2,3-e]isoindole (420) (6a R, 7S, 9a S, 12 R*, 13a S)-12-benzyloxycarbonylamino-2, 3, 6, 6a, 7, 8, 9, 9a, 10, 11, 12, 13-dodecahydro-5-dihydroxyphosphinyloxy-6a,7,10, 10-tetramethyl-3,11-dioxo-1H- benzo[8,8a][1]benzopyrano[2,3-e]isoindole (421) (1R*, 6a R, 7S, 9a S, 12 S*, 13a S)-1-acetoxy-12-benzyloxy-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (422) (6a R, 7S, 9a S, 12 R*, 13a S)-12-benzyloxy-2, 3, 6, 6a, 7, 8, 9, 9a, 10, 11, 12, 13- dodecahydro-5-dihydroxyphosphinyloxy-6a,7,10,10-tetramethyl-1,3,11-trioxo-1H- benzo[8,8a][1]benzopyrano[2,3-e]isoindole (423) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-(2-hydroxy)ethoxy-6a,7,10,10-tetramethyl-3,11-dioxo-1H- benzo[8,8a][1]benzopyrano[2,3-e]isoindole (424) (1R*, 6a R, 7S, 9a S, 12 S*, 13a S)-1,12-diacetoxy-2, 3, 6, 6a, 7, 8, 9, 9a, 10, 11, 12, 13-dodecahydro-5-hydroxy-6a,7,10,10-tetramethyl-11-(1-oxa-4-azacyclohex-4-yl)imino-3- oxo-1H-benzo[8,8a][1]benzopyrano[2,3-e]isoindole (425) (1R*, 6a R, 7S, 9a S, 12 S*, 13a S)-12-benzyloxy-2, 3, 6, 6a, 7, 8, 9, 9a, 10, 11, 12, 13-dodecahydro-1,5-dihydroxy-6a,7,10,10-tetramethyl-3-oxo-11-ureidoimino-1H- benzo[8,8a][1]benzopyrano[2,3-e]isoindole (426) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-12-methylsulfinyl-11-(1-oxa-4-azacyclohex-4-yl)imino-3-oxo-1H-benzo[8,8a][1]benzopyrano[2,3-e]isoindole (427) (1R*, 6a R, 7S, 9a S, 12 S*, 13a S)-1-acetoxy-12-benzyloxy-2, 3, 6, 6a, 7, 8, 9, 9a, 10, 11, 12, 13-dodecahydro-5-hydroxy-11-hydroxyimino-6a,7,10, 10-tetramethyl-3-oxo-1H- benzo[8,8a][1]benzopyrano[2,3-e]isoindole (428) (1R*, 6a R, 7S, 9a S, 12 S*, 13a S)-2, 3, 6, 6a, 7, 8, 9, 9a, 10, 11, 12, 13- dodecahydro-1,5-dihydroxy-11-methoxyimino-6a,7,10,10-tetramethyl-3-oxo-12-phenoxy- 1H-benzo[8,8a][1]benzopyrano[2,3-e]isoindole (429) (1R*, 6a R, 7S, 9a S, 12 S*, 13a S)-2, 3, 6, 6a, 7, 8, 9, 9a, 10, 11, 12, 13- dodecahydro-1,5-dihydroxy-12-methanesulfonyloxy-6a,7,10,10-tetramethyl-11-(1-oxa-4-azacyclohex-4-yl)imino-3-oxo-1H-benzo[8,8a][1]benzopyrano[2,3-e]isoindole (430) (1R*, 6a R, 7S, 9a S, 12 S*, 13a S)-11-cyanoimino-12-ethoxy-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (431) (1R*, 6a R, 7S, 9a S, 12 S*, 13a S)-12-ethoxy-2, 3, 6, 6a, 7, 8, 9, 9a, 10, 11, 12, 13- dodecahydro-5-hydroxy-11-methoxyimino-1-methyl-6a,7,10,10-tetramethyl-3-oxo-1H- benzo[8,8a][1]benzopyrano[2,3-e]isoindole (432) (6a R, 7S, 9a S, 12 R*, 13a S)-12-acetoxy-2, 3, 6, 6a, 7, 8, 9, 9a, 10, 11, 12, 13- dodecahydro-5-hydroxy-11-hydroxyimino-6a,7,10,10-tetramethyl-13-dioxo-1H- benzo[8,8a][1]benzopyrano[2,3-e]isoindole (433) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-3-oxo-12-phenylsulfonyl-11-ureidoimino-1H- benzo[8,8a][1]benzopyrano[2,3-e]isoindole (434) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylamino-11-(1-oxa-4-azacyclohex-4-yl)imino-13- dioxo-1H-benzo[8,8a][1]benzopyrano[2,3-e]isoindole (435) (1R*, 6a R, 7S, 9a S, 12 S*, 13a S)-2, 3, 6, 6a, 7, 8, 9, 9a, 10, 11, 12, 13- dodecahydro-5-hydroxy-12-methoxy-11-methoxyimino-1-methyl-6a,7,10,10-tetramethyl-3- oxo-1H-benzo[8,8a][1]benzopyrano[2,3-e]isoindole (436) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-3-oxo-12-phenylthio-1H- benzo[8,8a][1]benzopyrano[2,3-e]isoindole (437) (1R*, 6a R, 7S, 9a S, 12 S*, 13a S)-11-hydrazono-2, 3, 6, 6a, 7, 8, 9, 9a, 10, 11, 12, 13-dodecahydro-1,5-dihydroxy-6a,7,10,10-tetramethyl-3-oxo-12-phenylthio-1H- benzo[8,8a][1]benzopyrano[2,3-e]isoindole (438) (6a R, 7S, 9a S, 12 R*, 13a S)-12-azido-2, 3, 6, 6a, 7, 8, 9, 9a, 10, 11, 12, 13- dodecahydro-5-hydroxy-11-methoxyimino-6a,7,10,10-tetramethyl-13-dioxo-1H-benzo[8,8a][1]benzopyrano[2,3-e]isoindole (439) (1R*, 6a R, 7S, 9a S, 12 S*, 13a S)-2, 3, 6, 6a, 7, 8, 9, 9a, 10, 11, 12, 13- dodecahydro-5-hydroxy-11-hydroxyimino-1-methyl-6a,7,10,10-tetramethyl-3-oxo-12- phenoxy-1H-benzo[8,8a][1]benzopyrano[2,3-e]isoindole (440) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-mercapto-6a,7,10,10-tetramethyl-3,11-dioxo-1H-benzo[8,8a][1]benzopyrano[2,3-e]isoindole (441) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-methoxy-11-methoxyimino-6a,7,10,10-tetramethyl-3-oxo-1H- benzo[8,8a][1]benzopyrano[2,3-e]isoindole (442) (6a R, 7S, 9a S, 12 R*, 13a S)-12-amino-2, 3, 6, 6a, 7, 8, 9, 9a, 10, 11, 12, 13- dodecahydro-5-hydroxy-11-hydroxyimino-6a,7,10,10-tetramethyl-13-dioxo-1H-benzo[8,8a][1]benzopyrano[2,3-e]isoindole (443) (1R*, 6a R, 7S, 9a S, 12 S*, 13a S)-12-carboxymethyloxy-2, 3, 6, 6a, 7, 8, 9, 9a, 10, 11, 12, 13-dodecahydro-5-hydroxy-1-methyl-6a,7,10,10-tetramethyl-1 1-(1-oxa-4- azacyclohex-4-yl)imino-3-oxo-1H-benzo[8,8a][1]benzopyrano[2,3-e]isoindole (444) (1R*, 6a R, 7S, 9a S, 12 S*, 13a S)-12-amino-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (445) (1R*, 6a R, 7S, 9a S, 12 S*, 13a S)-1-acetoxy-11-cyanoimino-2, 3, 6, 6a, 7, 8, 9, 9a, 10, 11, 12, 13-dodecahydro-5,12-dihydroxy-6a,7,10,10-tetramethyl-3-oxo-1H- benzo[8,8a][1]benzopyrano[2,3-e]isoindole (446) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-13-dioxo-12-phenylsulfonyloxy-1H- benzo[8,8a][1]benzopyrano[2,3-e]isoindole (447) (1R*, 6a R, 7S, 9a S, 12 S*, 13a S)-12-benzyloxycarbonylamino-2, 3, 6, 6a, 7, 8, 9, 9a, 10, 11, 12, 13-dodecahydro-5-hydroxy-11-methoxyimino-1-methyl-6a,7,10,10- tetramethyl-3-oxo-1H-benzo[8,8a][1]benzopyrano[2,3-e]isoindole (448) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-12-methylthio-1,3,11-trioxo-1H-benzo[8,8a][1]benzopyrano[2,3-e]isoindole (449) (1R*, 6a R, 7S, 9a S, 12 S*, 13a S)-12-benzyloxycarbonylamino-2, 3, 6, 6a, 7, 8, 9, 9a, 10, 11, 12, 13-dodecahydro-5-hydroxy-11-hydroxyimino-1-methyl-6a,7,10,10- tetramethyl-3-oxo-1H-benzo[8,8a][1]benzopyrano[2,3-e]isoindole (450) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-11-(1-oxa-4-azacyclohex-4-yl)imino-3-oxo-12-phenylsulfonylamino-1H-benzo[8,8a][1]benzopyrano[2,3-e]isoindole (451) (6a R, 7S, 9a S, 12 R*, 13a S)-12-carbamoyloxy-2, 3, 6, 6a, 7, 8, 9, 9a, 10, 11, 12, 13-dodecahydro-5-hydroxy-11-hydroxyimino-6a,7,10,10-tetramethyl-3-oxo-1H-benzo[8,8a][1]benzopyrano[2,3-e]isoindole (452) (6a R, 7S, 9a S, 12 R*, 13a S)-12-benzoylamino-2, 3, 6, 6a, 7, 8, 9, 9a, 10, 11, 12, 13- dodecahydro-5-hydroxy-11-methoxyimino-6a,7,10,10-tetramethyl-13-dioxo-1H-benzo[8,8a][1]benzopyrano[2,3-e]isoindole (453) (1R*, 6a R, 7S, 9a S, 12 S*, 13a S)-12-acetoxy-2, 3, 6, 6a, 7, 8, 9, 9a, 10, 11, 12, 13- dodecahydro-5-hydroxy-11-methoxyimino-1-methyl-6a,7,10,10-tetramethyl-3-oxo-1H- benzo[8,8a][1]benzopyrano[2,3-e]isoindole (454) (1R*, 6a R, 7S, 9a S, 12 S*, 13a S)-1-acetoxy-12-amino-2, 3, 6, 6a, 7, 8, 9, 9a, 10, 11, 12, 13-dodecahydro-5-hydroxy-6a,7,10,10-tetramethyl-3-oxo-11-ureidoimino-1H- benzo[8,8a][1]benzopyrano[2,3-e]isoindole (455) (1R*, 6a R, 7S, 9a S, 12 S*, 13a S)-2, 3, 6, 6a, 7, 8, 9, 9a, 10, 11, 12, 13- dodecahydro-1,5-dihydroxy-11-hydroxyimino-12-methanesulfonyloxy-6a,7,10,10- tetramethyl-3-oxo-1H-benzo[8,8a][1]benzopyrano[2,3-e]isoindole (456) (6a R, 7S, 9a S, 12 R*, 13a S)-12-azido-2, 3, 6, 6a, 7, 8, 9, 9a, 10, 11, 12, 13- dodecahydro-5-hydroxy-11-methoxyimino-6a,7,10,10-tetramethyl-3-oxo-1H- benzo[8,8a][1]benzopyrano[2,3-e]isoindole (457) (1R*, 6a R, 7S, 9a S, 12 S*, 13a S)-1-acetoxy-12-benzyloxy-2, 3, 6, 6a, 7, 8, 9, 9a, 10, 11, 12, 13-dodecahydro-5-hydroxy-11-methoxyimino-6a,7,10,10-tetramethyl-3-oxo-1H- benzo[8,8a][1]benzopyrano[2,3-e]isoindole (458) (1R*, 6a R, 7S, 9a S, 12 S*, 13a S)-11-cyanoimino-2, 3, 6, 6a, 7, 8, 9, 9a, 10, 11, 12, 13-dodecahydro-5-hydroxy-12-methoxy-1-methyl-6a,7,10,10-tetramethyl-3-oxo-1H- benzo[8,8a][1]benzopyrano [2,3-e]isoindole (459) (6a R, 7S, 9a S, 12 R*, 13a S)-12-amino-2, 3, 6, 6a, 7, 8, 9, 9a, 10, 11, 12, 13- dodecahydro-5-dihydroxyphosphinyloxy-6a,7,10,10-tetramethyl-3,11-dioxo-1H- benzo[8,8a][1]benzopyrano[2,3-e]isoindole (460) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-3-oxo-12-phenylsulfonyloxy-1H- benzo[8,8a][1]benzopyrano[2,3-e]isoindole (461) (1R*, 6a R, 7S, 9a S, 12 S*, 13a S)-2, 3, 6, 6a, 7, 8, 9, 9a, 10, 11, 12, 13- dodecahydro-1,5-dihydroxy-11-hydroxyimino-6a,7,10,10-tetramethyl-12-methylsulfinyl-3- oxo-1H-benzo[8,8a][1]benzopyrano[2,3-e]isoindole (462) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-13-dioxo-12-phenylthio-1H- benzo[8,8a][1]benzopyrano[2,3-e]isoindole (463) (6a R, 7S, 9a S, 12 R*, 13a S)-2, 3, 6, 6a, 7, 8, 9, 9a, 10, 11, 12, 13-dodecahydro-5- hydroxy-11-hydroxyimino-12-methoxy-6a,7,10,10-tetramethyl-13-dioxo-1H- benzo[8,8a][1]benzopyrano[2,3-e]isoindole (464) (1R*, 6a R, 7S, 9a S, 12 S*, 13a S)-12-glycylamino-11-hydrazono-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (465) (6a R, 7S, 9a S, 12 R*, 13a S)-12-benzoylamino-2, 3, 6, 6a, 7, 8, 9, 9a, 10, 11, 12, 13- dodecahydro-5-dihydroxyphosphinyloxy-6a,7,10,10-tetramethyl-3,11-dioxo-1H- benzo[8,8a][1]benzopyrano[2,3-e]isoindole (466) (6a R, 7S, 9a S, 12 R*, 13a S)-12-bromo-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (467) (6a R, 7S, 9a S, 12 R*, 13a S)-12-benzoylamino-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (468) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-hydroxyimino-12-methanesulfonyloxy-6a,7,10,10-tetramethyl- 3-oxo-1H-benzo[8,8a][1]benzopyrano[2,3-e]isoindole (469) (1R*, 6a R, 7S, 9a S, 12 S*, 13a S)-12-carboxymethyloxy-2, 3, 6, 6a, 7, 8, 9, 9a, 10, 11, 12, 13-dodecahydro-5-hydroxy-11-hydroxyimino-1-methyl-6a,7,10,10-tetramethyl-3- oxo-1H-benzo[8,8a][1]benzopyrano[2,3-e]isoindole (470) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-13-dioxo-12-phenylsulfonyloxy-11-ureidoimino-1H- benzo[8,8a][1]benzopyrano[2,3-e]isoindole (471) (1R*, 6a R, 7S, 9a S, 12 S*, 13a S)-12-benzoylamino-2, 3, 6, 6a, 7, 8, 9, 9a, 10, 11, 12, 13-dodecahydro-1,5-dihydroxy-6a,7,10,10-tetramethyl-11-(1-oxa-4-azacyclohex-4- yl)imino-3-oxo-1H-benzo[8,8a][1]benzopyrano[2,3-e]isoindole (472) (1R*, 6a R, 7S, 9a S, 12 S*, 13a S)-12-benzyloxy-11-cyanoimino-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (473) (6a R, 7S, 9a S, 12 R*, 13a S)-12-benzoylamino-11-cyanoimino-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (474) (1R*, 6a R, 7S, 9a S, 12 S*, 13a S)-1-acetoxy-12-ethoxy-2,3,6,6a,7,8,9,9a,10,11,12, 13-dodecahydro-5-hydroxy-11-methoxyimino-6a,7,10,10-tetramethyl-3-oxo-1H- benzo[8,8a][1]benzopyrano[2,3-e]isoindole (475) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-3-oxo-12-phenylsulfonyl-11-ureidoimino- 1H-benzo[8,8a][1]benzopyrano[2,3-e]isoindole (476) (6a R, 7S, 9a S, 12 R*, 13a S)-12-benzyloxycarbonylamino-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (477) (6a R, 7S, 9a S, 12 R*, 13a S)-2, 3, 6, 6a, 7, 8, 9, 9a, 10, 11, 12, 13-dodecahydro-5- hydroxy-12-(2-hydroxy)ethoxy-11-hydroxyimino-6a,7,10,10-tetramethyl-13-dioxo-1H- benzo[8,8a][1]benzopyrano[2,3-e]isoindole (478) (1R*, 6a R, 7S, 9a S, 12 S*, 13a S)-11-hydrazono-2, 3, 6, 6a, 7, 8, 9, 9a, 10, 11, 12, 13-dodecahydro-1,5-dihydroxy-6a,7,10,10-tetramethyl-3-oxo-12-phenylsulfonylamino-1H- benzo[8,8a][1]benzopyrano[2, 3-e]isoindole (479) (6a R, 7S, 9a S, 12 R*, 13a S)-12-benzyloxy-11-cyanoimino-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (480) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-11-(1-oxa-4-azacyclohex-4-yl)imino-3- oxo-12-phenylsulfonyloxy-1H-benzo[8,8a][1]benzopyrano[2,3-e]isoindole (481) (6a R, 7S, 9a S, 12 R*, 13a S)-12-amino-2, 3, 6, 6a, 7, 8, 9, 9a, 10, 11, 12, 13- dodecahydro-5-hydroxy-11-methoxyimino-6a,7,10,10-tetramethyl-13-dioxo-1H- benzo[8,8a][1]benzopyrano[2,3-e]isoindole (482) (1R*, 6a R, 7S, 9a S, 12 S*, 13a S)-2, 3, 6, 6a, 7, 8, 9, 9a, 10, 11, 12, 13- dodecahydro-5-hydroxy-11-methoxyimino-1-methyl-6a,7,10,10-tetramethyl-12-methylsulfinyl-3-oxo-1H-benzo[8,8a][1]benzopyrano[2, 3-e]isoindole (483) (1R*, 6a R, 7S, 9a S, 12 S*, 13a S)-2, 3, 6, 6a, 7, 8, 9, 9a, 10, 11, 12, 13- dodecahydro-1,5-dihydroxy-12-mercapto-6a,7,10,10-tetramethyl-11-(1-oxa-4-azacyclohex- 4-yl)imino-3-oxo-1H-benzo[8,8a][1]benzopyrano[2,3-e]isoindole (484) (6a R, 7S, 9a S, 12 R*, 13a S)-12-chloro-11-cyanoimino-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (485) (1R*, 6a R, 7S, 9a S, 12 S*, 13a S)-11-cyanoimino-2, 3, 6, 6a, 7, 8, 9, 9a, 10, 11, 12, 13-dodecahydro-1,5-dihydroxy-6a,7,10,10-tetramethyl-12-methylthio-3-oxo-1H- benzo[8,8a][1]benzopyrano[2,3-e]isoindole (486) (1R*, 6a R, 7S, 9a S, 12 S*, 13a S)-2, 3, 6, 6a, 7, 8, 9, 9a, 10, 11, 12, 13- dodecahydro-5-hydroxy-11-methoxyimino-1-methyl-6a,7,10,10-tetramethyl-3-oxo-12- phenylsulfonyloxy-1H-benzo[8,8a][1]benzopyrano[2,3-e]isoindole (487) (6a R, 7S, 9a S, 12 R*, 13a S)-12-bromo-2, 3, 6, 6a, 7, 8, 9, 9a, 10, 11, 12, 13- dodecahydro-5-hydroxy-11-hydroxyimino-6a,7,10,10-tetramethyl-13-dioxo-1H- benzo[8,8a][1]benzopyrano[2,3-e]isoindole (488) (1R*, 6a R, 7S, 9a S, 12 S*, 13a S)-12-acetylamino-2, 3, 6, 6a, 7, 8, 9, 9a, 10, 11, 12, 13-dodecahydro-1,5-dihydroxy-11-methoxyimino-6a,7,10,10-tetramethyl-3-oxo-1H- benzo[8,8a][1]benzopyrano[2,3-e]isoindole (489) (1R*, 6a R, 7S, 9a S, 12 S*, 13a S)-12-acetylamino-2, 3, 6, 6a, 7, 8, 9, 9a, 10, 11, 12, 13-dodecahydro-1,5-dihydroxy-6a,7,10,10-tetramethyl-3,11-dioxo-1H- benzo[8,8a][1]benzopyrano[2,3-e]isoindole (490) (1R*, 6a R, 7S, 9a S, 12 S*, 13a S)-12-acetoxy-2, 3, 6, 6a, 7, 8, 9, 9a, 10, 11, 12, 13- dodecahydro-1,5-dihydroxy-11-hydroxyimino-6a,7,10,10-tetramethyl-3-oxo-1H- benzo[8,8a][1]benzopyrano[2,3-e]isoindole (491) (1R*, 6a R, 7S, 9a S, 12 S*, 13a S)-1-acetoxy-12-benzyloxycarbonylamino-2, 3, 6, 6a, 7, 8, 9, 9a, 10, 11, 12, 13-dodecahydro-5-hydroxy-6a,7,10,10-tetramethyl-3-oxo-11- ureidoimino-1H-benzo[8,8a][1]benzopyrano[2,3-e]isoindole (492) (1R*, 6a R, 7S, 9a S, 12 S*, 13a S)-12-benzoylamino-2, 3, 6, 6a, 7, 8, 9, 9a, 10, 11, 12, 13-dodecahydro-5-hydroxy-1-methyl-6a,7,10,10-tetramethyl-3-oxo-11-ureidoimino-1H- benzo[8,8a][1]benzopyrano[2,3-e]isoindole (493) (1R*, 6a R, 7S, 9a S, 12 S*, 13a S)-2, 3, 6, 6a, 7, 8, 9, 9a, 10, 11, 12, 13- dodecahydro-5-hydroxy-12-mercapto-1-methyl-6a,7,10,10-tetramethyl-3,11-dioxo-1H- benzo[8,8a][1]benzopyrano[2,3-e]isoindole (494) (1R*, 6a R, 7S, 9a S, 12 S*, 13a S)-2, 3, 6, 6a, 7, 8, 9, 9a, 10, 11, 12, 13- dodecahydro-1,5-dihydroxy-11-hydroxyimino-6a,7,10,10-tetramethyl-3-oxo-12-phenylsulfinyl-1H-benzo[8,8a][1]benzopyrano[2,3-e]isoindole (495) (6a R, 7S, 9a S, 12 R*, 13a S)-11-methoxyimino-2, 3, 6, 6a, 7, 8, 9, 9a, 10, 11, 12, 13-dodecahydro-5,12-dihydroxy-6a,7,10,10-tetramethyl-13-dioxo-1H- benzo[8,8a][1]benzopyrano[2,3-e]isoindole (496) (6a R, 7S, 9a S, 12 R*, 13a S)-12-carboxymethyloxy-2, 3, 6, 6a, 7, 8, 9, 9a, 10, 11, 12, 13-dodecahydro-5-hydroxy-11-methoxyimino-6a,7,10,10-tetramethyl-3-oxo-1H- benzo[8,8a][1]benzopyrano[2,3-e]isoindole (497) (1R*, 6a R, 7S, 9a S, 12 S*, 13a S)-1-acetoxy-12-carboxymethyloxy-2, 3, 6, 6a, 7, 8, 9, 9a, 10, 11, 12, 13-dodecahydro-5-hydroxy-11-methoxyimino-6a,7,10,10-tetramethyl-3- oxo-1H-benzo[8,8a][1]benzopyrano[2,3-e]isoindole (498) (6a R, 7S, 9a S, 12 R*, 13a S)-2, 3, 6, 6a, 7, 8, 9, 9a, 10, 11, 12, 13-dodecahydro-5- hydroxy-12-methanesulfonylamino-6a,7,10,10-tetramethyl-1,3,11-trioxo-1H- benzo[8,8a][1]benzopyrano[2,3-e]isoindole (499) (1R*, 6a R, 7S, 9a S, 12 S*, 13a S)-12-azido-2, 3, 6, 6a, 7, 8, 9, 9a, 10, 11, 12, 13- dodecahydro-5-hydroxy-1-methyl-6a,7,10,10-tetramethyl-3,11-dioxo-1H- benzo[8,8a][1]benzopyrano[2,3-e]isoindole (500) (6a R, 7S, 9a S, 12 R*, 13a S)-12-carboxymethyloxy-2, 3, 6, 6a, 7, 8, 9, 9a, 10, 11, 12, 13-dodecahydro-5-hydroxy-11-hydroxyimino-6a,7,10,10-tetramethyl-3-oxo-1H- benzo[8,8a][1]benzopyrano[2,3-e]isoindole (501) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-13-dioxo-12-(3-pyridyl)carbonyloxy-1H- benzo[8,8a][1]benzopyrano[2,3-e]isoindole (502) (1R*, 6a R, 7S, 9a S, 12 S*, 13a S)-1-acetoxy-12-glycylamino-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (503) (1R*, 6a R, 7S, 9a S, 12 S*, 13a S)-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-12-(3-pyridyl)carbonyloxy-1H-benzo[8,8a][1]benzopyrano[2,3-e]isoindole (504) (1R*, 6a R, 7S, 9a S, 12 S*, 13a S)-12-azido-11-hydrazono-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (505) (1R*, 6a R, 7S, 9a S, 12 S*, 13a S)-12-benzoyloxy-11-hydrazono-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (506) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-3,11-dioxo-12-phenylsulfonyloxy-1H- benzo[8,8a][1]benzopyrano[2,3-e]isoindole (507) (1R*, 6a R, 7S, 9a S, 12 S*, 13a S)-1-acetoxy-2, 3, 6, 6a, 7, 8, 9, 9a, 10, 11, 12, 13- dodecahydro-5,12-dihydroxy-11-hydroxyimino-6a,7,10,10-tetramethyl-3-oxo-1H- benzo [8,8a][1]benzopyrano [2,3-e]isoindole (508) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-3,11-dioxo-12-(3-pyridyl)carbonyloxy- 1H-benzo[8,8a][1]benzopyrano[2,3-e]isoindole (509) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-13-dioxo-12-phenylthio-1H-benzo[8,8a][1]benzopyrano[2,3-e]isoindole (510) (1R*, 6a R, 7S, 9a S, 12 S*, 13a S)-12-benzyloxycarbonylamino-2, 3, 6, 6a, 7, 8, 9, 9a, 10, 11, 12, 13-dodecahydro-1,5-dihydroxy-6a,7,10,10-tetramethyl-3,11-dioxo-1H- benzo[8,8a][1]benzopyrano[2,3-e]isoindole (511) (1R*, 6a R, 7S, 9a S, 12 S*, 13a S)-11-cyanoimino-2, 3, 6, 6a, 7, 8, 9, 9a, 10, 11, 12, 13-dodecahydro-1,5-dihydroxy-6a,7,10,10-tetramethyl-3-oxo-12-phenylsulfonyloxy-1H- benzo[8,8a][1]benzopyrano[2,3-e]isoindole (512) (1R*, 6a R, 7S, 9a S, 12 S*, 13a S)-12-amino-2, 3, 6, 6a, 7, 8, 9, 9a, 10, 11, 12, 13- dodecahydro-5-hydroxy-11-methoxyimino-1-methyl-6a,7,10,10-tetramethyl-3-oxo-1H- benzo[8,8a][1]benzopyrano[2,3-e]isoindole (513) (1R*, 6a R, 7S, 9a S, 12 S*, 13a S)-12-carboxymethyloxy-2, 3, 6, 6a, 7, 8, 9, 9a, 10, 11, 12, 13-dodecahydro-1,5-dihydroxy-6a,7,10,10-tetramethyl-11-(1-oxa-4-azacyclohex-4- yl)imino-3-oxo-1H-benzo[8,8a][1]benzopyrano[2,3-e]isoindole (514) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-3,11-dioxo-12-phenylsulfinyl-1H-benzo[8,8a][1]benzopyrano[2,3-e]isoindole (515) (1R*, 6a R, 7S, 9a S, 12 S*, 13a S)-11-cyanoimino-2, 3, 6, 6a, 7, 8, 9, 9a, 10, 11, 12, 13-dodecahydro-1,5-dihydroxy-6a,7,10,10-tetramethyl-3-oxo-12-phenoxy-1H- benzo[8,8a][1]benzopyrano[2,3-e]isoindole (516) (1R*, 6a R, 7S, 9a S, 12 S*, 13a S)-12-benzoylamino-11-hydrazono-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (517) (6a R, 7S, 9a S, 12 R*, 13a S)-12-carboxymethyloxy-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (518) (6a R, 7S, 9a S, 12 R*, 13a S)-12-benzoylamino-2, 3, 6, 6a, 7, 8, 9, 9a, 10, 11, 12, 13- dodecahydro-5-hydroxy-6a,7,10,10-tetramethyl-1,3,11-trioxo-1H- benzo[8,8a][1]benzopyrano[2,3-e]isoindole (519) (1R*, 6a R, 7S, 9a S, 12 S*, 13a S)-1-acetoxy-11-hydrazono-2, 3, 6, 6a, 7, 8, 9, 9a, 10, 11, 12, 13-dodecahydro-5-hydroxy-6a,7,10,10-tetramethyl-3-oxo-12-phenylsulfinyl-1H- benzo[8,8a][1]benzopyrano[2,3-e]isoindole (520) (1R*, 6a R, 7S, 9a S, 12 S*, 13a S)-1-acetoxy-11-cyanoimino-2, 3, 6, 6a, 7, 8, 9, 9a, 10, 11, 12, 13-dodecahydro-5-hydroxy-6a,7,10,10-tetramethyl-12-methylsulfinyl-3-oxo-1H- benzo[8,8a][1]benzopyrano[2,3-e]isoindole (521) (1R*, 6a R, 7S, 9a S, 12 S*, 13a S)-12-glycylamino-2, 3, 6, 6a, 7, 8, 9, 9a, 10, 11, 12, 13-dodecahydro-5-hydroxy-1-methyl-6a,7,10,10-tetramethyl-3-oxo-11-ureidoimino-1H- benzo[8,8a][1]benzopyrano[2,3-e]isoindole (522) (6a R, 7S, 9a S, 12 R*, 13a S)-12-glycylamino-2, 3, 6, 6a, 7, 8, 9, 9a, 10, 11, 12, 13- dodecahydro-5-hydroxy-11-hydroxyimino-6a,7,10,10-tetramethyl-3-oxo-1H- benzo[8,8a][1]benzopyrano[2,3-e]isoindole (523) (6a R, 7S, 9a S, 12 R*, 13a S)-11-cyanoimino-2, 3, 6, 6a, 7, 8, 9, 9a, 10, 11, 12, 13- dodecahydro-5-hydroxy-12-methanesulfonyloxy-6a,7,10,10-tetramethyl-3-oxo-1H- benzo[8,8a][1]benzopyrano[2,3-e]isoindole (524) (6a R, 7S, 9a S, 12 R*, 13a S)-12-benzyloxycarbonylamino-2, 3, 6, 6a, 7, 8, 9, 9a, 10, 11, 12, 13-dodecahydro-5-hydroxy-6a,7,10,10-tetramethyl-3, 11-dioxo-1H- benzo[8,8a][1]benzopyrano[2,3-e]isoindole (525) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-methoxyimino-6a,7,10,10-tetramethyl-3-oxo-12-phenylthio-1H- benzo[8,8a][1]benzopyrano[2,3-e]isoindole (526) (6a R, 7S, 9a S, 12 R*, 13a S)-12-ethoxy-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-13- dioxo-1H-benzo[8,8a][1]benzopyrano[2,3-e]isoindole (527) (1R*, 6a R, 7S, 9a S, 12 S*, 13a S)-11-hydrazono-2, 3, 6, 6a, 7, 8, 9, 9a, 10, 11, 12, 13-dodecahydro-1,5,12-trihydroxy-6a,7,10,10-tetramethyl-3-oxo-1H- benzo[8,8a][1]benzopyrano[2,3-e]isoindole (528) (1R*, 6a R, 7S, 9a S, 12 S*, 13a S)-12-carbamoyloxy-2, 3, 6, 6a, 7, 8, 9, 9a, 10, 11, 12, 13-dodecahydro-5-hydroxy-1-methyl-6a,7,10,10-tetramethyl-11-(1-oxa-4-azacyclohex- 4-yl)imino-3-oxo-1H-benzo[8,8a][1]benzopyrano[2,3-e]isoindole (529) (6a R, 7S, 9a S, 12 R*, 13a S)-2, 3, 6, 6a, 7, 8, 9, 9a, 10, 11, 12, 13-dodecahydro-5- hydroxy-12-mercapto-11-methoxyimino-6a,7,10,10-tetramethyl-13-dioxo-1H-benzo[8,8a][1]benzopyrano[2,3-e]isoindole (530) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-3-oxo-12-phenylsulfinyl-1H- benzo[8,8a][1]benzopyrano[2,3-e]isoindole (531) (1R*, 6a R, 7S, 9a S, 12 S*, 13a S)-1-acetoxy-11-cyanoimino-2, 3, 6, 6a, 7, 8, 9, 9a, 10, 11, 12, 13-dodecahydro-5-hydroxy-6a,7,10,10-tetramethyl-3-oxo-12-phenylthio-1H- benzo[8,8a][1]benzopyrano[2,3-e]isoindole (532) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-3-oxo-12-phenylsulfonyl-1H- benzo[8,8a][1]benzopyrano[2,3-e]isoindole (533) (6a R, 7S, 9a S, 12 R*, 13a S)-12-chloro-2, 3, 6, 6a, 7, 8, 9, 9a, 10, 11, 12, 13- dodecahydro-5-hydroxy-11-methoxyimino-6a,7,10,10-tetramethyl-3-oxo-1H- benzo[8,8a][1]benzopyrano[2,3-e]isoindole (534) (1R*, 6a R, 7S, 9a S, 12 S*, 13a S)-11-hydrazono-2, 3, 6, 6a, 7, 8, 9, 9a, 10, 11, 12, 13-dodecahydro-1,5-dihydroxy-6a,7,10,10-tetramethyl-3-oxo-12-phenoxy-1H- benzo[8,8a][1]benzopyrano[2,3-e]isoindole (535) (1R*, 6a R, 7S, 9a S, 12 S*, 13a S)-2, 3, 6, 6a, 7, 8, 9, 9a, 10, 11, 12, 13- dodecahydro-5-hydroxy-12-methanesulfonyloxy-1-methyl-6a,7,10,10-tetramethyl-3-oxo- 11-ureidoimino-1H-benzo[8,8a][1]benzopyrano[2,3-e]isoindole (536) (1R*, 6a R, 7S, 9a S, 12 S*, 13a S)-12-benzyloxycarbonylamino-11-hydrazono-2, 3, 6, 6a, 7, 8, 9, 9a, 10, 11, 12, 13-dodecahydro-5-hydroxy-1-methyl-6a,7,10,10-tetramethyl-3- oxo-1H-benzo[8,8a][1]benzopyrano[2,3-e]isoindole (537) (1R*, 6a R, 7S, 9a S, 12 S*, 13a S)-12-chloro-2, 3, 6, 6a, 7, 8, 9, 9a, 10, 11, 12, 13- dodecahydro-1,5-dihydroxy-6a,7,10,10-tetramethyl-11-(1-oxa-4-azacyclohex-4-yl)imino-3- oxo-1H-benzo[8,8a][1]benzopyrano[2,3-e]isoindole (538) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-3,11-dioxo-12-phenylsulfonylamino-1H- benzo[8,8a][1]benzopyrano[2,3-e]isoindole (539) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-3-oxo-12-phenoxy-11-ureidoimino-1H- benzo[8,8a][1]benzopyrano[2,3-e]isoindole (540) (6a R, 7S, 9a S, 12 R*, 13a S)-12-carboxymethyloxy-11-cyanoimino-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (541) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-12-methylsulfinyl-3,11-dioxo-1H-benzo[8,8a][1]benzopyrano[2,3-e]isoindole (542) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylthio-13-dioxo-11-ureidoimino-1H- benzo[8,8a][1]benzopyrano[2,3-e]isoindole (543) (6a R, 7S, 9a S, 12 R*, 13a S)-12-acetylamino-2, 3, 6, 6a, 7, 8, 9, 9a, 10, 11, 12, 13- dodecahydro-5-hydroxy-6a,7,10,10-tetramethyl-3-oxo-11-ureidoimino-1H- benzo[8,8a][1]benzopyrano[2,3-e]isoindole (544) (1R*, 6a R, 7S, 9a S, 12 S*, 13a S)-12-bromo-11-hydrazono-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (545) (1R*, 6a R, 7S, 9a S, 12 S*, 13a S)-11-cyanoimino-2, 3, 6, 6a, 7, 8, 9, 9a, 10, 11, 12, 13-dodecahydro-1,5-dihydroxy-6a,7,10,10-tetramethyl-3-oxo-12-phenylsulfinyl-1H- benzo[8,8a][1]benzopyrano[2,3-e]isoindole (546) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-12-methylamino-3-oxo-1H- benzo[8,8a][1]benzopyrano[2,3-e]isoindole (547) (1R*, 6a R, 7S, 9a S, 12 S*, 13a S)-12-benzoyloxy-2, 3, 6, 6a, 7, 8, 9, 9a, 10, 11, 12, 13-dodecahydro-5-hydroxy-1-methyl-6a,7,10,10-tetramethyl-3,11-dioxo-1H- benzo[8,8a][1]benzopyrano[2,3-e]isoindole (548) (6a R, 7S, 9a S, 12 R*, 13a S)-11-cyanoimino-2, 3, 6, 6a, 7, 8, 9, 9a, 10, 11, 12, 13- dodecahydro-5-hydroxy-12-(2-hydroxy)ethoxy-6a,7,10,10-tetramethyl-13-dioxo-1H- benzo[8,8a][1]benzopyrano[2,3-e]isoindole (549) (6a R, 7S, 9a S, 12 R*, 13a S)-12-amino-2, 3, 6, 6a, 7, 8, 9, 9a, 10, 11, 12, 13- dodecahydro-5-hydroxy-6a,7,10,10-tetramethyl-3,11-dioxo-1H- benzo[8,8a][1]benzopyrano[2,3-e]isoindole (550) (1R*, 6a R, 7S, 9a S, 12 S*, 13a S)-12-azido-2, 3, 6, 6a, 7, 8, 9, 9a, 10, 11, 12, 13- dodecahydro-5-hydroxy-11-hydroxyimino-1-methyl-6a,7,10,10-tetramethyl-3-oxo-1H- benzo[8,8a][1]benzopyrano[2,3-e]isoindole (551) (1R*, 6a R, 7S, 9a S, 12 S*, 13a S)-2, 3, 6, 6a, 7, 8, 9, 9a, 10, 11, 12, 13- dodecahydro-1,5-dihydroxy-11-hydroxyimino-6a,7,10,10-tetramethyl-3-oxo-12-phenylsulfonyl-1H-benzo[8,8a][1]benzopyrano[2,3-e]isoindole (552) (6a R, 7S, 9a S, 12 R*, 13a S)-12-benzoylamino-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-3-oxo- 1H-benzo[8,8a][1]benzopyrano[2,3-e]isoindole (553) (6a R, 7S, 9a S, 12 R*, 13a S)-12-carboxymethyloxy-2, 3, 6, 6a, 7, 8, 9, 9a, 10, 11, 12, 13-dodecahydro-5- hydroxy-6a,7,10,10-tetramethyl-11-(1-oxa-4-azacyclohex-4-yl)imino-13- dioxo-1H-benzo[8,8a][1]benzopyrano[2,3-e]isoindole
(554) (1R*, 6a R, 7S, 9a S, 12 S*, 13a S)-11-hydroxyimino-2, 3, 6, 6a, 7, 8, 9, 9a, 10, 11, 12, 13-dodecahydro-1,5,12-trihydroxy-6a,7,10,10-tetramethyl-3-oxo-1H- benzo[8,8a][1]benzopyrano[2,3-e]isoindole
(555) (1R*, 6a R, 7S, 9a S, 12 S*, 13a S)-1,12-diacetoxy-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole
(556) (1R*, 6a R, 7S, 9a S, 12 S*, 13a S)-12-acetylamino-2, 3, 6, 6a, 7, 8, 9, 9a, 10, 11, 12, 13-dodecahydro-5-hydroxy-1-methyl-6a,7,10,10-tetramethyl-3-oxo-11-ureidoimino-1H- benzo[8,8a][1]benzopyrano[2,3-e]isoindole
(557) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-11-(1-oxa-4-azacyclohex-4-yl)imino-13-dioxo-12- phenylsulfonyloxy-1H-benzo[8,8a][1]benzopyrano[2,3-e]isoindole
(558) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-12-methylamino-3-oxo-11-ureidoimino-1H-benzo[8,8a][1]benzopyrano[2,3-e]isoindole
(559) (1R*, 6a R, 7S, 9a S, 12 S*, 13a S)-1-acetoxy-12-bromo-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole
(560) (6a R, 7S, 9a S, 12 R*, 13a S)-12-bromo-2, 3, 6, 6a, 7, 8, 9, 9a, 10, 11, 12, 13- dodecahydro-5-hydroxy-6a,7,10,10-tetramethyl-13-dioxo-11-ureidoimino-1H- benzo[8,8a][1]benzopyrano[2,3-e]isoindole
(561) (1R*, 6a R, 7S, 9a S, 12 S*, 13a S)-12-benzoyloxy-2, 3, 6, 6a, 7, 8, 9, 9a, 10, 11, 12, 13-dodecahydro-1,5-dihydroxy-11-methoxyimino-6a,7,10,10-tetramethyl-3-oxo-1H- benzo[8,8a][1]benzopyrano[2,3-e]isoindole
(562) (1R*, 6a R, 7S, 9a S, 12 S*, 13a S)-12-ethoxy-2, 3, 6, 6a, 7, 8, 9, 9a, 10, 11, 12, 13- dodecahydro-5-hydroxy-1-methyl-6a,7,10,10-tetramethyl-3-oxo-11-ureidoimino-1H- benzo[8,8a][1]benzopyrano[2,3-e]isoindole
(563) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-3-oxo-12-phenylthio-11-ureidoimino-1H- benzo[8,8a][1]benzopyrano[2,3-e]isoindole
(564) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-(2-hydroxy)ethoxy-6a,7,10,10-tetramethyl-11-(1-oxa-4- azacyclohex-4-yl)imino-3-oxo-1H-benzo[8,8a][1]benzopyrano[2,3-e]isoindole
(565) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-13-dioxo-12-phenylthio-11-ureidoimino-1H-benzo[8,8a][1]benzopyrano[2,3-e]isoindole
(566) (6a R, 7S, 9a S, 12 R*, 13a S)-12-benzoyloxy-2, 3, 6, 6a, 7, 8, 9, 9a, 10, 11, 12, 13- dodecahydro-5-hydroxy-6a,7,10,10-tetramethyl-3,11-dioxo-1H- benzo[8,8a][1]benzopyrano[2,3-e]isoindole
(567) (1R*, 6a R, 7S, 9a S, 12 S*, 13a S)-12-azido-2, 3, 6, 6a, 7, 8, 9, 9a, 10, 11, 12, 13- dodecahydro-1,5-dihydroxy-11-hydroxyimino-6a,7,10,10-tetramethyl-3-oxo-1H- benzo[8,8a][1]benzopyrano[2,3-e]isoindole
(568) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-12-methylamino-3-oxo-1H- benzo[8,8a][1]benzopyrano[2,3-e]isoindole
(569) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-methoxyimino-6a,7,10,10-tetramethyl-3-oxo-12-phenoxy-1H- benzo[8,8a][1]benzopyrano[2,3-e]isoindole
(570) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-3,11-dioxo-12-phenylthio-1H-benzo[8,8a][1]benzopyrano[2,3-e]isoindole
(571) (1R*, 6a R, 7S, 9a S, 12 S*, 13a S)-1-acetoxy-12-benzoyloxy-2, 3, 6, 6a, 7, 8, 9, 9a, 10, 11, 12, 13-dodecahydro-5-hydroxy-6a,7,10,10-tetramethyl-3-oxo-11-ureidoimino-1H- benzo[8,8a][1]benzopyrano[2,3-e]isoindole
(572) (1R*, 6a R, 7S, 9a S, 12 S*, 13a S)-2, 3, 6, 6a, 7, 8, 9, 9a, 10, 11, 12, 13- dodecahydro-1,5-dihydroxy-11-hydroxyimino-6a,7,10,10-tetramethyl-3-oxo-12-phenylthio- 1H-benzo[8,8a][1]benzopyrano[2,3-e]isoindole
(573) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-3-oxo-12-(3-pyridyl)carbonyloxy- 11-ureidoimino-1H-benzo[8,8a][1]benzopyrano[2,3-e]isoindole
(574) (1R*, 6a R, 7S, 9a S, 12 S*, 13a S)-11-cyanoimino-2, 3, 6, 6a, 7, 8, 9, 9a, 10, 11, 12, 13-dodecahydro-1,5-dihydroxy-12-mercapto-6a,7,10,10-tetramethyl-3-oxo-1H- benzo[8,8a][1]benzopyrano[2,3-e]isoindole
(575) (1R*, 6a R, 7S, 9a S, 12 S*, 13a S)-1-acetoxy-12-benzyloxy-2, 3, 6, 6a, 7, 8, 9, 9a, 10, 11, 12, 13-dodecahydro-5-hydroxy-6a,7,10,10-tetramethyl-11-(1-oxa-4-azacyclohex-4- yl)imino-3-oxo-1H-benzo[8,8a][1]benzopyrano[2,3-e]isoindole
(576) (6a R, 7S, 9a S, 12 R*, 13a S)-12-amino-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-3-oxo- 1H-benzo[8,8a][1]benzopyrano[2,3-e]isoindole
(577) (1R*, 6a R, 7S, 9a S, 12 S*, 13a S)-11-cyanoimino-12-glycylamino-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole
(578) (1R*, 6a R, 7S, 9a S, 12 S*, 13a S)-1-acetoxy-12-carbamoyloxy-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole
(579) (6a R, 7S, 9a S, 12 R*, 13a S)-12-acetoxy-2, 3, 6, 6a, 7, 8, 9, 9a, 10, 11, 12, 13- dodecahydro-5-hydroxy-6a,7,10,10-tetramethyl-3-oxo-11-ureidoimino-1H- benzo[8,8a][1]benzopyrano[2,3-e]isoindole
(580) (1R*, 6a R, 7S, 9a S, 12 S*, 13a S)-2, 3, 6, 6a, 7, 8, 9, 9a, 10, 11, 12, 13- dodecahydro-5-hydroxy-11-hydroxyimino-12-methanesulfonyloxy-1-methyl-6a,7,10, 10- tetramethyl-3-oxo-1H-benzo[8,8a][1]benzopyrano[2,3-e]isoindole
(581) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-3-oxo- 12-phenoxy-1H-benzo[8,8a][1]benzopyrano[2,3-e]isoindole
(582) (1R*, 6a R, 7S, 9a S, 12 S*, 13a S)-1-acetoxy-12-chloro-2, 3, 6, 6a, 7, 8, 9, 9a, 10, 11, 12, 13-dodecahydro-5-hydroxy-6a,7,10,10-tetramethyl-11-(1-oxa-4-azacyclohex-4- yl)imino-3-oxo-1H-benzo[8,8a][1]benzopyrano[2,3-e]isoindole
(583) (1R*, 6a R, 7S, 9a S, 12 S*, 13a S)-12-benzoyloxy-11-hydrazono-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (584) (1R*, 6a R, 7S, 9a S, 12 S*, 13a S)-2, 3, 6, 6a, 7, 8, 9, 9a, 10, 11, 12, 13- dodecahydro-1,5-dihydroxy-12-methoxy-6a,7,10,10-tetramethyl-3-oxo-11-ureidoimino-1H- benzo[8,8a][1]benzopyrano[2,3-e]isoindole (585) (6a R, 7S, 9a S, 12 R*, 13a S)-2, 3, 6, 6a, 7, 8, 9, 9a, 10, 11, 12, 13-dodecahydro-5- hydroxy-12-(2-hydroxy)ethoxy-6a,7,10,10-tetramethyl-3,11-dioxo-1H- benzo[8,8a][1]benzopyrano[2,3-e]isoindole (586) (1R*, 6a R, 7S, 9a S, 12 S*, 13a S)-12-benzyloxy-2, 3, 6, 6a, 7, 8, 9, 9a, 10, 11, 12, 13-dodecahydro-5-hydroxy-1-methyl-6a,7,10,10-tetramethyl-11-(1-oxa-4-azacyclohex-4- yl)imino-3-oxo-1H-benzo[8,8a][1]benzopyrano[2,3-e]isoindole (587) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-hydroxyimino-6a,7,10,10-tetramethyl-3-oxo-12-phenylthio-1H- benzo[8,8a][1]benzopyrano[2,3-e]isoindole (588) (6a R, 7S, 9a S, 12 R*, 13a S)-11-ureidoimino-2, 3, 6, 6a, 7, 8, 9, 9a, 10, 11, 12, 13- dodecahydro-5,12-dihydroxy-6a,7,10,10-tetramethyl-13-dioxo-1H- benzo[8,8a][1]benzopyrano[2,3-e]isoindole (589) (6a R, 7S, 9a S, 12 R*, 13a S)-12-benzoyloxy-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (590) (1R*, 6a R, 7S, 9a S, 12 S*, 13a S)-12-glycylamino-2, 3, 6, 6a, 7, 8, 9, 9a, 10, 11, 12, 13-dodecahydro-5-hydroxy-11-methoxyimino-1-methyl-6a,7,10,10-tetramethyl-3-oxo-1H- benzo[8,8a][1]benzopyrano[2,3-e]isoindole (591) (1R*, 6a R, 7S, 9a S, 12 S*, 13a S)-2, 3, 6, 6a, 7, 8, 9, 9a, 10, 11, 12, 13- dodecahydro-5-hydroxy-12-methanesulfonylamino-1-methyl-6a,7,10,10-tetramethyl-11-(1- oxa-4-azacyclohex-4-yl)imino-3-oxo-1H-benzo[8,8a][1]benzopyrano[2,3-e]isoindole (592) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-3,11-dioxo-12-phenylthio-1H-benzo[8,8a][1]benzopyrano[2,3-e]isoindole (593) (1R*, 6a R, 7S, 9a S, 12 S*, 13a S)-12-bromo-2, 3, 6, 6a, 7, 8, 9, 9a, 10, 11, 12, 13- dodecahydro-1,5-dihydroxy-11-hydroxyimino-6a,7,10,10-tetramethyl-3-oxo-1H- benzo[8,8a][1]benzopyrano[2,3-e]isoindole (594) (1R*, 6a R, 7S, 9a S, 12 S*, 13a S)-1-acetoxy-12-benzoyloxy-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (595) (6a R, 7S, 9a S, 12 R*, 13a S)-12-acetylamino-2, 3, 6, 6a, 7, 8, 9, 9a, 10, 11, 12, 13- dodecahydro-5-hydroxy-11-methoxyimino-6a,7,10,10-tetramethyl-13-dioxo-1H- benzo[8,8a][1]benzopyrano[2,3-e]isoindole (596) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-12-methylamino-3-oxo-1H-benzo[8,8a][1]benzopyrano[2,3-e]isoindole (597) (1R*, 6a R, 7S, 9a S, 12 S*, 13a S)-2, 3, 6, 6a, 7, 8, 9, 9a, 10, 11, 12, 13- dodecahydro-1,5-dihydroxy-12-mercapto-6a,7,10,10-tetramethyl-3,11-dioxo-1H- benzo[8,8a][1]benzopyrano[2,3-e]isoindole (598) (6a R, 7S, 9a S, 12 R*, 13a S)-2, 3, 6, 6a, 7, 8, 9, 9a, 10, 11, 12, 13-dodecahydro-5- hydroxy-12-methanesulfonyloxy-6a,7,10,10-tetramethyl-3,11-dioxo-1H- benzo[8,8a][1]benzopyrano[2,3-e]isoindole (599) (1R*, 6a R, 7S, 9a S, 12 S*, 13a S)-12-chloro-11-hydrazono-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (600) (1R*, 6a R, 7S, 9a S, 12 S*, 13a S)-1-acetoxy-12-acetylamino-2, 3, 6, 6a, 7, 8, 9, 9a, 10, 11, 12, 13-dodecahydro-5-hydroxy-6a,7,10,10-tetramethyl-11-(1-oxa-4-azacyclohex-4- yl)imino-3-oxo-1H-benzo[8,8a][1]benzopyrano[2,3-e]isoindole (601) (1R*, 6a R, 7S, 9a S, 12 S*, 13a S)-11-hydrazono-2, 3, 6, 6a, 7, 8, 9, 9a, 10, 11, 12, 13-dodecahydro-1,5-dihydroxy-12-mercapto-6a,7,10,10-tetramethyl-3-oxo-1H- benzo[8,8a][1]benzopyrano[2,3-e]isoindole (602) (6a R, 7S, 9a S, 12 R*, 13a S)-12-acetylamino-11-cyanoimino-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (603) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-3-oxo-12-phenylsulfonyloxy-11-ureidoimino-1H-benzo[8,8a][1]benzopyrano[2,3-e]isoindole (604) (6a R, 7S, 9a S, 12 R*, 13a S)-2, 3, 6, 6a, 7, 8, 9, 9a, 10, 11, 12, 13-dodecahydro-5- hydroxy-12-methanesulfonylamino-6a,7,10,10-tetramethyl-11-(1-oxa-4-azacyclohex-4- yl)imino-13-dioxo-1H-benzo[8,8a][1]benzopyrano[2,3-e]isoindole (605) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-12-methylthio-3-oxo-11-ureidoimino-1H-benzo[8,8a][1]benzopyrano[2,3-e]isoindole (606) (1R*, 6a R, 7S, 9a S, 12 S*, 13a S)-12-chloro-2, 3, 6, 6a, 7, 8, 9, 9a, 10, 11, 12, 13- dodecahydro-5-hydroxy-11-methoxyimino-1-methyl-6a,7,10,10-tetramethyl-3-oxo-1H- benzo[8,8a][1]benzopyrano[2,3-e]isoindole (607) (6a R, 7S, 9a S, 12 R*, 13a S)-12-glycylamino-2, 3, 6, 6a, 7, 8, 9, 9a, 10, 11, 12, 13- dodecahydro-5-hydroxy-6a,7,10,10-tetramethyl-13-dioxo-11-ureidoimino-1H-benzo[8,8a][1]benzopyrano[2,3-e]isoindole (608) (1R*, 6a R, 7S, 9a S, 12 S*, 13a S)-1-acetoxy-2, 3, 6, 6a, 7, 8, 9, 9a, 10, 11, 12, 13- dodecahydro-5,12-dihydroxy-6a,7,10,10-tetramethyl-11-(1-oxa-4-azacyclohex-4-yl)imino- 3-oxo-1H-benzo[8,8a][1]benzopyrano[2,3-e]isoindole (609) (1R*, 6a R, 7S, 9a S, 12 S*, 13a S)-2, 3, 6, 6a, 7, 8, 9, 9a, 10, 11, 12, 13- dodecahydro-1,5-dihydroxy-12-methanesulfonylamino-6a,7,10,10-tetramethyl-3-oxo-11-ureidoimino-1H-benzo[8,8a][1]benzopyrano[2,3-e]isoindole (610) (1R*, 6a R, 7S, 9a S, 12 S*, 13a S)-1-acetoxy-11-cyanoimino-2, 3, 6, 6a, 7, 8, 9, 9a, 10, 11, 12, 13-dodecahydro-5-hydroxy-6a,7,10,10-tetramethyl-3-oxo-12-phenoxy-1H- benzo[8,8a][1]benzopyrano[2,3-e]isoindole (611) (1R*, 6a R, 7S, 9a S, 12 S*, 13a S)-1-acetoxy-11-cyanoimino-12-ethoxy-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (612) (6a R, 7S, 9a S, 12 R*, 13a S)-2, 3, 6, 6a, 7, 8, 9, 9a, 10, 11, 12, 13-dodecahydro-5- hydroxy-12-methoxy-6a,7,10,10-tetramethyl-3-oxo-11-ureidoimino-1H- benzo[8,8a][1]benzopyrano[2,3-e]isoindole (613) (1R*, 6a R, 7S, 9a S, 12 S*, 13a S)-1-acetoxy-12-carbamoyloxy-2, 3, 6, 6a, 7, 8, 9, 9a, 10, 11, 12, 13-dodecahydro-5-hydroxy-11-hydroxyimino-6a,7,10,10-tetramethyl-3-oxo- 1H-benzo [8,8a][1]benzopyrano[2,3-e]isoindole (614) (6a R, 7S, 9a S, 12 R*, 13a S)-12-amino-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (615) (1R*, 6a R, 7S, 9a S, 12 S*, 13a S)-1-acetoxy-12-benzoyloxy-2, 3, 6, 6a, 7, 8, 9, 9a, 10, 11, 12, 13-dodecahydro-5-hydroxy-11-hydroxyimino-6a,7,10,10-tetramethyl-3-oxo-1H- benzo[8,8a][1]benzopyrano[2,3-e]isoindole (616) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-3,11-dioxo-12-phenylsulfonylamino-1H-benzo[8,8a][1]benzopyrano[2,3-e]isoindole (617) (6a R, 7S, 9a S, 12 R*, 13a S)-12-benzyloxycarbonylamino-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (618) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-11-(1-oxa-4-azacyclohex-4-yl)imino-13-dioxo-12- phenylsulfinyl-1H-benzo[8,8a][1]benzopyrano[2,3-e]isoindole (619) (1R*, 6a R, 7S, 9a S, 12 S*, 13a S)-2, 3, 6, 6a, 7, 8, 9, 9a, 10, 11, 12, 13- dodecahydro-1,5-dihydroxy-11-methoxyimino-6a,7,10,10-tetramethyl-3-oxo-12-phenylsulfonyloxy-1H-benzo[8,8a][1]benzopyrano[2,3-e]isoindole (620) (1R*, 6a R, 7S, 9a S, 12 S*, 13a S)-2, 3, 6, 6a, 7, 8, 9, 9a, 10, 11, 12, 13- dodecahydro-1,5-dihydroxy-11-hydroxyimino-6a,7,10,10-tetramethyl-12-methylamino-3- oxo-1H-benzo[8,8a][1]benzopyrano[2,3-e]isoindole (621) (6a R, 7S, 9a S, 12 R*, 13a S)-12-carbamoyloxy-11-cyanoimino-2, 3, 6, 6a, 7, 8, 9, 10, 11, 12, 13-dodecahydro-5-hydroxy-6a,7,10,10-tetramethyl-3-oxo-1H- benzo[8,8a][1]benzopyrano[2,3-e]isoindole (622) (1R*, 6a R, 7S, 9a S, 12 S*, 13a S)-1-acetoxy-12-amino-2, 3, 6, 6a, 7, 8, 9, 9a, 10, 11, 12, 13-dodecahydro-5-hydroxy-11-hydroxyimino-6a,7,10,10-tetramethyl-3-oxo-1H- benzo[8,8a][1]benzopyrano[2,3-e]isoindole (623) (6a R, 7S, 9a S, 12 R*, 13a S)-12-benzoyloxy-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (624) (6a R, 7S, 9a S, 12 R*, 13a S)-12-ethoxy-2, 3, 6, 6a, 7, 8, 9, 9a, 10, 11, 12, 13- dodecahydro-5-hydroxy-6a,7,10,10-tetramethyl-3,11-dioxo-1H- benzo[8,8a][1]benzopyrano[2,3-e]isoindole (625) (1R*, 6a R, 7S, 9a S, 12 S*, 13a S)-12-benzoyloxy-2, 3, 6, 6a, 7, 8, 9, 9a, 10, 11, 12, 13-dodecahydro-5-hydroxy-11-methoxyimino-1-methyl-6a,7,10,10-tetramethyl-3-oxo-1H- benzo[8,8a][1]benzopyrano[2,3-e]isoindole (626) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-11-(1-oxa-4-azacyclohex-4-yl)imino-3-oxo-12-(3-pyridyl)carbonyloxy-1H-benzo[8,8a][1]benzopyrano[2,3-e]isoindole (627) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-12-methylsulfinyl-11-(1-oxa-4-azacyclohex-4-yl)imino-3-oxo-1H-benzo[8,8a][1]benzopyrano[2,3-e]isoindole (628) (1R*, 6a R, 7S, 9a S, 12 S*, 13a S)-12-glycylamino-2, 3, 6, 6a, 7, 8, 9, 9a, 10, 11, 12, 13-dodecahydro-1,5-dihydroxy-6a,7,10,10-tetramethyl-3-oxo-11-ureidoimino-1H- benzo[8,8a][1]benzopyrano[2,3-e]isoindole (629) (1R*, 6a R, 7S, 9a S, 12 S*, 13a S)-11-hydrazono-2, 3, 6, 6a, 7, 8, 9, 9a, 10, 11, 12, 13-dodecahydro-1,5-dihydroxy-12-methanesulfonyloxy-6a,7,10,10-tetramethyl-3-oxo-1H- benzo[8,8a][1]benzopyrano[2,3-e]isoindole (630) (1R*, 6a R, 7S, 9a S, 12 S*, 13a S)-1-acetoxy-12-benzyloxycarbonylamino-2, 3, 6, 6a, 7, 8, 9, 9a, 10, 11, 12, 13-dodecahydro-5-hydroxy-6a,7,10,10-tetramethyl-3,11-dioxo- 1H-benzo[8,8a][1]benzopyrano[2,3-e]isoindole (631) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-11-(1-oxa-4-azacyclohex-4-yl)imino-3-oxo-12-phenylthio-1H-benzo[8,8a][1]benzopyrano[2,3-e]isoindole (632) (1R*, 6a R, 7S, 9a S, 12 S*, 13a S)-12-amino-2, 3, 6, 6a, 7, 8, 9, 9a, 10, 11, 12, 13- dodecahydro-5-hydroxy-1-methyl-6a,7,10,10-tetramethyl-3,11-dioxo-1H- benzo[8,8a][1]benzopyrano[2,3-e]isoindole (633) (6a R, 7S, 9a S, 12 R*, 13a S)-12-benzoylamino-2, 3, 6, 6a, 7, 8, 9, 9a, 10, 11, 12, 13- dodecahydro-5-hydroxy-11-hydroxyimino-6a,7,10,10-tetramethyl-3-oxo-1H- benzo[8,8a][1]benzopyrano[2,3-e]isoindole (634) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-13-dioxo-12-phenoxy-1H- benzo[8,8a][1]benzopyrano[2,3-e]isoindole (635) (1R*, 6a R, 7S, 9a S, 12 S*, 13a S)-1,12-diacetoxy-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (636) (6a R, 7S, 9a S, 12 R*, 13a S)-2, 3, 6, 6a, 7, 8, 9, 9a, 10, 11, 12, 13-dodecahydro-5- dihydroxyphosphinyloxy-12-mercapto-6a,7,10,10-tetramethyl-1,3,11-trioxo-1H- benzo[8,8a][1]benzopyrano[2,3-e]isoindole (637) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-12-methylthio-13-dioxo-1H- benzo[8,8a][1]benzopyrano[2,3-e]isoindole (638) (6a R, 7S, 9a S, 12 R*, 13a S)-2, 3, 6, 6a, 7, 8, 9, 9a, 10, 11, 12, 13-dodecahydro-5- hydroxy-12-methoxy-6a,7,10,10-tetramethyl-11-(1-oxa-4-azacyclohex-4-yl)imino-3-oxo- 1H-benzo[8,8a][1]benzopyrano[2,3-e]isoindole (639) (1R*, 6a R, 7S, 9a S, 12 S*, 13a S)-11-hydrazono-2, 3, 6, 6a, 7, 8, 9, 9a, 10, 11, 12, 13-dodecahydro-5,12-dihydroxy-1-methyl-6a,7,10,10-tetramethyl-3-oxo-1H- benzo[8,8a][1]benzopyrano[2,3-e]isoindole (640) (6a R, 7S, 9a S, 12 R*, 13a S)-12-benzoylamino-2, 3, 6, 6a, 7, 8, 9, 9a, 10, 11, 12, 13- dodecahydro-5-hydroxy-11-methoxyimino-6a,7,10,10-tetramethyl-3-oxo-1H- benzo[8,8a][1]benzopyrano[2,3-e]isoindole (641) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-12-methylthio-13-dioxo-1H- benzo[8,8a][1]benzopyrano[2,3-e]isoindole (642) (6a R, 7S, 9a S, 12 R*, 13a S)-2, 3, 6, 6a, 7, 8, 9, 9a, 10, 11, 12, 13-dodecahydro-12- (2-hydroxy)ethoxy-5-dihydroxyphosphinyloxy-6a,7,10,10-tetramethyl-1,3,11-trioxo-1H- benzo[8,8a][1]benzopyrano[2,3-e]isoindole (643) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-12-methylsulfinyl-11-(1-oxa-4-azacyclohex-4-yl)imino-3-oxo-1H-benzo[8,8a][1]benzopyrano[2,3-e]isoindole (644) (1R*, 6a R, 7S, 9a S, 12 S*, 13a S)-1,12-diacetoxy-2, 3, 6, 6a, 7, 8, 9, 9a, 10, 11, 12, 13-dodecahydro-5-hydroxy-6a,7,10,10-tetramethyl-3-oxo-11-ureidoimino-1H- benzo[8,8a][1]benzopyrano[2,3-e]isoindole (645) (6a R, 7S, 9a S, 12 R*, 13a S)-2, 3, 6, 6a, 7, 8, 9, 9a, 10, 11, 12, 13-dodecahydro-5- hydroxy-11- methoxyimino-6a,7,10,10-tetramethyl-13-dioxo-12-phenylsulfonyl-1H- benzo[8,8a][1]benzopyrano[2,3-e]isoindole
(646) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-13-dioxo-12-phenoxy-1H- benzo[8,8a][1]benzopyrano[2,3-e]isoindole
(647) (1R*, 6a R, 7S, 9a S, 12 S*, 13a S)-1-acetoxy-12-benzyloxycarbonylamino-11- cyanoimino-2, 3, 6, 6a, 7, 8, 9, 9a, 10, 11, 12, 13-dodecahydro-5-hydroxy-6a,7,10,10-tetramethyl-3-oxo-1H-benzo[8,8a][1]benzopyrano[2,3-e]isoindole
(648) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-3-oxo-12-phenylsulfonyloxy-1H-benzo[8,8a][1]benzopyrano[2,3-e]isoindole
(649) (1R*, 6a R, 7S, 9a S, 12 S*, 13a S)-2, 3, 6, 6a, 7, 8, 9, 9a, 10, 11, 12, 13- dodecahydro-1,5-dihydroxy-12-(2-hydroxy)ethoxy-6a,7,10,10-tetramethyl-3,11-dioxo-1H-benzo[8,8a][1]benzopyrano[2,3-e]isoindole
(650) (6a R, 7S, 9a S, 12 R*, 13a S)-12-benzyloxycarbonylamino-2, 3, 6, 6a, 7, 8, 9, 9a, 10, 11, 12, 13-dodecahydro-5-hydroxy-6a,7,10,10-tetramethyl-3-oxo-11-ureidoimino-1H- benzo[8,8a][1]benzopyrano[2,3-e]isoindole
(651) (1R*, 6a R, 7S, 9a S, 12 S*, 13a S)-1-acetoxy-12-glycylamino-2, 3, 6, 6a, 7, 8, 9, 9a, 10, 11, 12, 13-dodecahydro-5-hydroxy-11-methoxyimino-6a,7,10,10-tetramethyl-3-oxo-1H- benzo[8,8a][1]benzopyrano[2,3-e]isoindole
(652) (1R*, 6a R, 7S, 9a S, 12 S*, 13a S)-1-acetoxy-12-benzoylamino-2, 3, 6, 6a, 7, 8, 9, 9a, 10, 11, 12, 13-dodecahydro-5-hydroxy-11-methoxyimino-6a,7,10,10-tetramethyl-3-oxo-1H- benzo[8,8a][1]benzopyrano[2,3-e]isoindole
(653) (6a R, 7S, 9a S, 12 R*, 13a S)-12-ethoxy-2, 3, 6, 6a, 7, 8, 9, 9a, 10, 11, 12, 13- dodecahydro-5-hydroxy-6a,7,10,10-tetramethyl-1,3,11-trioxo-1H- benzo[8,8a][1]benzopyrano[2,3-e]isoindole
(654) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylsulfinyl-3-oxo-11-ureidoimino-1H- benzo[8,8a][1]benzopyrano[2,3-e]isoindole
(655) (6a R, 7S, 9a S, 12 R*, 13a S)-12-chloro-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole
(656) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-13-dioxo-12-phenylsulfonylamino-1H- benzo[8,8a][1]benzopyrano[2,3-e]isoindole
(657) (1R*, 6a R, 7S, 9a S, 12 S*, 13a S)-11-hydrazono-2, 3, 6, 6a, 7, 8, 9, 9a, 10, 11, 12, 13-dodecahydro-1,5-dihydroxy-6a,7,10,10-tetramethyl-3-oxo-12-phenylsulfonyl-1H- benzo[8,8a][1]benzopyrano[2,3-e]isoindole
(658) (6a R, 7S, 9a S, 12 R*, 13a S)-2, 3, 6, 6a, 7, 8, 9, 9a, 10, 11, 12, 13-dodecahydro-5- dihydroxyphosphinyloxy-12-methanesulfonylamino-6a,7,10,10-tetramethyl-3,11-dioxo-1H- benzo[8,8a][1]benzopyrano[2,3-e]isoindole
(659) (1R*, 6a R, 7S, 9a S, 12 S*, 13a S)-2, 3, 6, 6a, 7, 8, 9, 9a, 10, 11, 12, 13- dodecahydro-1,5-dihydroxy-11-hydroxyimino-6a,7,10,10-tetramethyl-12-methylthio-3-oxo- 1H-benzo[8,8a][1]benzopyrano[2,3-e]isoindole
(660) (6a R, 7S, 9a S, 12 R*, 13a S)-12-amino-11-cyanoimino-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole
(661) (6a R, 7S, 9a S, 12 R*, 13a S)-12-acetylamino-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole
(662) (6a R, 7S, 9a S, 12 R*, 13a S)-12-benzoyloxy-2, 3, 6, 6a, 7, 8, 9, 9a, 10, 11, 12, 13- dodecahydro-5-hydroxy-11-hydroxyimino-6a,7,10,10-tetramethyl-13-dioxo-1H-benzo[8,8a][1]benzopyrano[2,3-e]isoindole
(663) (6a R, 7S, 9a S, 12 R*, 13a S)-2, 3, 6, 6a, 7, 8, 9, 9a, 10, 11, 12, 13-dodecahydro-5- hydroxy-12-methoxy-6a,7,10,10-tetramethyl-11-(1-oxa-4-azacyclohex-4-yl)imino-13- dioxo-1H-benzo[8,8a][1]benzopyrano[2,3-e]isoindole
(664) (1R*, 6a R, 7S, 9a S, 12 S*, 13a S)-12-carboxymethyloxy-2, 3, 6, 6a, 7, 8, 9, 9a, 10, 11, 12, 13-dodecahydro-1,5-dihydroxy-6a,7,10,10-tetramethyl-3,11-dioxo-1H- benzo[8,8a][1]benzopyrano[2,3-e]isoindole
(665) (1R*, 6a R, 7S, 9a S, 12 S*, 13a S)-1-acetoxy-12-carbamoyloxy-2, 3, 6, 6a, 7, 8, 9, 9a, 10, 11, 12, 13-dodecahydro-5-hydroxy-6a,7,10,10-tetramethyl-3-oxo-11-ureidoimino- 1H-benzo[8,8a][1]benzopyrano[2,3-e]isoindole
(666) (1R*, 6a R, 7S, 9a S, 12 S*, 13a S)-1-acetoxy-12-bromo-2, 3, 6, 6a, 7, 8, 9, 9a, 10, 11, 12, 13-dodecahydro-5-hydroxy-11-hydroxyimino-6a,7,10,10-tetramethyl-3-oxo-1H- benzo[8,8a][1]benzopyrano[2,3-e]isoindole
(667) (1R*, 6a R, 7S, 9a S, 12 S*, 13a S)-2, 3, 6, 6a, 7, 8, 9, 9a, 10, 11, 12, 13- dodecahydro-5-hydroxy-12-mercapto-1-methyl-6a,7,10,10-tetramethyl-3-oxo-11-ureidoimino-1H-benzo[8,8a][1]benzopyrano[2,3-e]isoindole
(668) (6a R, 7S, 9a S, 12 R*, 13a S)-12-carbamoyloxy-2, 3, 6, 6a, 7, 8, 9, 9a, 10, 11, 12, 13-dodecahydro-5-dihydroxyphosphinyloxy-6a,7,10,10-tetramethyl-3,11-dioxo-1H- benzo[8,8a][1]benzopyrano[2,3-e]isoindole
(669) (1R*, 6a R, 7S, 9a S, 12 S*, 13a S)-11-(1-oxa-4-azacyclohex-4-yl)imino-2, 3, 6, 6a, 7, 8, 9, 9a, 10, 11, 12, 13-dodecahydro-1,5,12-trihydroxy-6a,7,10,10-tetramethyl-3-oxo-1H- benzo[8,8a][1]benzopyrano[2,3-e]isoindole
(670) (1R*, 6a R, 7S, 9a S, 12 S*, 13a S)-1,12-diacetoxy-2, 3, 6, 6a, 7, 8, 9, 9a, 10, 11, 12, 13-dodecahydro-5-hydroxy-11-hydroxyimino-6a,7,10,10-tetramethyl-3-oxo-1H- benzo[8,8a][1]benzopyrano[2,3-e]isoindole
(671) (6a R, 7S, 9a S, 12 R*, 13a S)-2, 3, 6, 6a, 7, 8, 9, 9a, 10, 11, 12, 13-dodecahydro-5- hydroxy-12-methanesulfonyloxy-6a,7,10,10-tetramethyl-11-(1-oxa-4-azacyclohex-4- yl)imino-3-oxo-1H-benzo[8,8a][1]benzopyrano[2,3-e]isoindole
(672) (1R*, 6a R, 7S, 9a S, 12 S*, 13a S)-11-hydrazono-2, 3, 6, 6a, 7, 8, 9, 9a, 10, 11, 12, 13-dodecahydro-5-hydroxy-1-methyl-6a,7,10,10-tetramethyl-3-oxo-12-phenylsulfonyloxy- 1H-benzo[8,8a][1]benzopyrano[2,3-e]isoindole
(673) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-methanesulfonyloxy-6a,7,10,10-tetramethyl-11-(1-oxa-4- azacyclohex-4-yl)imino-3-oxo-1H-benzo[8,8a][1]benzopyrano[2,3-e]isoindole
(674) (1R*, 6a R, 7S, 9a S, 12 S*, 13a S)-1-acetoxy-11-hydrazono-2, 3, 6, 6a, 7, 8, 9, 9a, 10, 11, 12, 13-dodecahydro-5-hydroxy-6a,7,10,10-tetramethyl-12-methylsulfinyl-3-oxo-1H- benzo[8,8a][1]benzopyrano[2,3-e]isoindole (675) (1R*, 6a R, 7S, 9a S, 12 S*, 13a S)-2, 3, 6, 6a, 7, 8, 9, 9a, 10, 11, 12, 13- dodecahydro-1,5-dihydroxy-11-methoxyimino-6a,7,10,10-tetramethyl-12-methylamino-3- oxo-1H-benzo[8,8a][1]benzopyrano[2,3-e]isoindole (676) (6a R, 7S, 9a S, 12 R*, 13a S)-11-cyanoimino-2, 3, 6, 6a, 7, 8, 9, 9a, 10, 11, 12, 13- dodecahydro-5-hydroxy-12-methoxy-6a,7,10,10-tetramethyl-13-dioxo-1H- benzo[8,8a][1]benzopyrano[2,3-e]isoindole (677) (6a R, 7S, 9a S, 12 R*, 13a S)-1 1-hydrazono-2, 3, 6, 6a, 7, 8, 9, 9a, 10, 11, 12, 13- dodecahydro-5-hydroxy-12-methanesulfonyloxy-6a,7,10,10-tetramethyl-13-dioxo-1H- benzo[8,8a][1]benzopyrano[2,3-e]isoindole (678) (1R*, 6a R, 7S, 9a S, 12 S*, 13a S)-12-amino-2, 3, 6, 6a, 7, 8, 9, 9a, 10, 11, 12, 13- dodecahydro-1,5-dihydroxy-11-hydroxyimino-6a,7,10,10-tetramethyl-3-oxo-1H- benzo[8,8a][1]benzopyrano[2,3-e]isoindole (679) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-12-methylamino-3-oxo-11-ureidoimino-1H-benzo[8,8a][1]benzopyrano[2,3-e]isoindole (680) (6a R, 7S, 9a S, 12 R*, 13a S)-12-benzoylamino-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (681) (1R*, 6a R, 7S, 9a S, 12 S*, 13a S)-12-ethoxy-2, 3, 6, 6a, 7, 8, 9, 9a, 10, 11, 12, 13- dodecahydro-1,5-dihydroxy-11-methoxyimino-6a,7,10,10-tetramethyl-3-oxo-1H- benzo[8,8a][1]benzopyrano[2,3-e]isoindole (682) (1R*, 6a R, 7S, 9a S, 12 S*, 13a S)-1-acetoxy-12-glycylamino-2, 3, 6, 6a, 7, 8, 9, 9a, 10, 11, 12, 13-dodecahydro-5-hydroxy-6a,7,10,10-tetramethyl-11-(1-oxa-4-azacyclohex-4- yl)imino-3-oxo-1H-benzo[8,8a][1]benzopyrano[2,3-e]isoindole (683) (1R*, 6a R, 7S, 9a S, 12 S*, 13a S)-12-chloro-2, 3, 6, 6a, 7, 8, 9, 9a, 10, 11, 12, 13- dodecahydro-5-hydroxy-1-methyl-6a,7,10,10-tetramethyl-3,11-dioxo-1H- benzo[8,8a][1]benzopyrano[2,3-e]isoindole (684) (6a R, 7S, 9a S, 12 R*, 13a S)-12-azido-11-cyanoimino-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (685) (1R*, 6a R, 7S, 9a S, 12 S*, 13a S)-1-acetoxy-12-acetylamino-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (686) (1R*, 6a R, 7S, 9a S, 12 S*, 13a S)-12-bromo-2, 3, 6, 6a, 7, 8, 9, 9a, 10, 11, 12, 13- dodecahydro-1,5-dihydroxy-6a,7,10,10-tetramethyl-3,11-dioxo-1H- benzo[8,8a][1]benzopyrano[2,3-e]isoindole (687) (1R*, 6a R, 7S, 9a S, 12 S*, 13a S)-12-ethoxy-2, 3, 6, 6a, 7, 8, 9, 9a, 10, 11, 12, 13- dodecahydro-5-hydroxy-1-methyl-6a,7,10,10-tetramethyl-3,11-dioxo-1H- benzo[8,8a][1]benzopyrano[2,3-e]isoindole (688) (6a R, 7S, 9a S, 12 R*, 13a S)-12-amino-2, 3, 6, 6a, 7, 8, 9, 9a, 10, 11, 12, 13- dodecahydro-5-hydroxy-11-methoxyimino-6a,7,10,10-tetramethyl-3-oxo-1H- benzo[8,8a][1]benzopyrano[2,3-e]isoindole (689) (1R*, 6a R, 7S, 9a S, 12 S*, 13a S)-1-acetoxy-2, 3, 6, 6a, 7, 8, 9, 9a, 10, 11, 12, 13- dodecahydro-5,12-dihydroxy-6a,7,10,10-tetramethyl-3-oxo-11-ureidoimino-1H- benzo[8,8a][1]benzopyrano[2,3-e]isoindole (690) (6a R, 7S, 9a S, 12 R*, 13a S)-12-azido-2, 3, 6, 6a, 7, 8, 9, 9a, 10, 11, 12, 13- dodecahydro-5-hydroxy-11-hydroxyimino-6a,7,10,10-tetramethyl-3-oxo-1H- benzo[8,8a][1]benzopyrano[2,3-e]isoindole (691) (6a R, 7S, 9a S, 12 R*, 13a S)-2, 3, 6, 6a, 7, 8, 9, 9a, 10, 11, 12, 13-dodecahydro-5- hydroxy-12-(2-hydroxy)ethoxy-6a,7,10,10-tetramethyl-11-(1-oxa-4-azacyclohex-4- yl)imino-13-dioxo-1H-benzo[8,8a][1]benzopyrano[2,3-e]isoindole (692) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-methoxyimino-6a,7,10,10-tetramethyl-3-oxo-12-phenylsulfinyl- 1H-benzo[8,8a][1]benzopyrano[2,3-e]isoindole (693) (1R*, 6a R, 7S, 9a S, 12 S*, 13a S)-12-glycylamino-2, 3, 6, 6a, 7, 8, 9, 9a, 10, 11, 12, 13-dodecahydro-5-hydroxy-1-methyl-6a,7,10,10-tetramethyl-3,11-dioxo-1H- benzo[8,8a][1]benzopyrano[2,3-e]isoindole (694) (1R*, 6a R, 7S, 9a S, 12 S*, 13a S)-12-benzyloxycarbonylamino-11-hydrazono-2, 3, 6, 6a, 7, 8, 9, 9a, 10, 11, 12, 13-dodecahydro-1,5-dihydroxy-6a,7,10,10-tetramethyl-3-oxo- 1H-benzo[8,8a][1]benzopyrano[2,3-e]isoindole (695) (6a R, 7S, 9a S, 12 R*, 13a S)-12-acetylamino-2, 3, 6, 6a, 7, 8, 9, 9a, 10, 11, 12, 13- dodecahydro-5-hydroxy-11-methoxyimino-6a,7,10,10-tetramethyl-3-oxo-1H- benzo[8,8a][1]benzopyrano[2,3-e]isoindole (696) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-methoxyimino-6a,7,10,10-tetramethyl-12-methylsulfinyl-3-oxo- 1H-benzo[8,8a][1]benzopyrano[2,3-e]isoindole (697) (1R*, 6a R, 7S, 9a S, 12 S*, 13a S)-11-cyanoimino-2, 3, 6, 6a, 7, 8, 9, 9a, 10, 11, 12, 13-dodecahydro-1,5,12-trihydroxy-6a,7,10,10-tetramethyl-3-oxo-1H- benzo[8,8a][1]benzopyrano[2,3-e]isoindole (698) (1R*, 6a R, 7S, 9a S, 12 S*, 13a S)-1-acetoxy-12-bromo-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (699) (1R*, 6a R, 7S, 9a S, 12 S*, 13a S)-11-hydrazono-2, 3, 6, 6a, 7, 8, 9, 9a, 10, 11, 12, 13-dodecahydro-5-hydroxy-12-methoxy-1-methyl-6a,7,10,10-tetramethyl-3-oxo-1H- benzo[8,8a][1]benzopyrano[2,3-e]isoindole (700) (6a R, 7S, 9a S, 12 R*, 13a S)-11-cyanoimino-2, 3, 6, 6a, 7, 8, 9, 9a, 10, 11, 12, 13- dodecahydro-5-hydroxy-12-methanesulfonylamino-6a,7,10,10-tetramethyl-13-dioxo-1H- benzo[8,8a][1]benzopyrano[2,3-e]isoindole (701) (1R*, 6a R, 7S, 9a S, 12 S*, 13a S)-1-acetoxy-12-benzyloxy-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (702) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-3-oxo-12-phenylsulfinyl-11-ureidoimino-1H-benzo[8,8a][1]benzopyrano[2,3-e]isoindole (703) (1R*, 6a R, 7S, 9a S, 12 S*, 13a S)-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-12-phenylsulfonylamino-1H-benzo[8,8a][1]benzopyrano[2,3-e]isoindole (704) (6a R, 7S, 9a S, 12 R*, 13a S)-11-cyanoimino-12-glycylamino-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (705) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-methoxy-6a,7,10,10-tetramethyl-11-(1-oxa-4-azacyclohex-4- yl)imino-3-oxo-1H-benzo[8,8a][1]benzopyrano[2,3-e]isoindole (706) (1R*, 6a R, 7S, 9a S, 12 S*, 13a S)-12-chloro-2, 3, 6, 6a, 7, 8, 9, 9a, 10, 11, 12, 13- dodecahydro-5-hydroxy-11-hydroxyimino-1-methyl-6a,7,10,10-tetramethyl-3-oxo-1H- benzo[8,8a][1]benzopyrano[2,3-e]isoindole (707) (1R*, 6a R, 7S, 9a S, 12 S*, 13a S)-1-acetoxy-11-cyanoimino-2, 3, 6, 6a, 7, 8, 9, 9a, 10, 11, 12, 13-dodecahydro-5-hydroxy-6a,7,10,10-tetramethyl-12-methylthio-3-oxo-1H- benzo[8,8a][1]benzopyrano[2,3-e]isoindole (708) (1R*, 6a R, 7S, 9a S, 12 S*, 13a S)-11-hydrazono-2, 3, 6, 6a, 7, 8, 9, 9a, 10, 11, 12, 13-dodecahydro-5-hydroxy-12-mercapto-1-methyl-6a,7,10,10-tetramethyl-3-oxo-1H- benzo[8,8a][1]benzopyrano[2,3-e]isoindole (709) (6a R, 7S, 9a S, 12 R*, 13a S)-12-chloro-2, 3, 6, 6a, 7, 8, 9, 9a, 10, 11, 12, 13- dodecahydro-5-hydroxy-6a,7,10,10-tetramethyl-13-dioxo-11-ureidoimino-1H- benzo[8,8a][1]benzopyrano[2,3-e]isoindole (710) (1R*, 6a R, 7S, 9a S, 12 S*, 13a S)-11-hydrazono-2, 3, 6, 6a, 7, 8, 9, 9a, 10, 11, 12, 13-dodecahydro-5-hydroxy-1-methyl-6a,7,10,10-tetramethyl-3-oxo-12-phenoxy-1H- benzo[8,8a][1]benzopyrano[2,3-e]isoindole (711) (1R*, 6a R, 7S, 9a S, 12 S*, 13a S)-1-acetoxy-12-benzoylamino-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (712) (1R*, 6a R, 7S, 9a S, 12 S*, 13a S)-12-azido-2, 3, 6, 6a, 7, 8, 9, 9a, 10, 11, 12, 13- dodecahydro-5-hydroxy-11-methoxyimino-1-methyl-6a,7,10,10-tetramethyl-3-oxo-1H- benzo[8,8a][1]benzopyrano[2,3-e]isoindole (713) (1R*, 6a R, 7S, 9a S, 12 S*, 13a S)-2, 3, 6, 6a, 7, 8, 9, 9a, 10, 11, 12, 13- dodecahydro-5-hydroxy-12-(2-hydroxy)ethoxy-1-methyl-6a,7,10,10-tetramethyl-3,11-dioxo-1H-benzo[8,8a][1]benzopyrano[2,3-e]isoindole (714) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-13-dioxo-12-phenylthio-1H- benzo[8,8a][1]benzopyrano[2,3-e]isoindole (715) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-hydroxyimino-12-methanesulfonylamino-6a,7,10,10-tetramethyl-3-oxo-1H-benzo[8,8a][1]benzopyrano[2,3-e]isoindole (716) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-13-dioxo-12-phenylthio-1H-benzo[8,8a][1]benzopyrano[2,3-e]isoindole (717) (1R*, 6a R, 7S, 9a S, 12 S*, 13a S)-2, 3, 6, 6a, 7, 8, 9, 9a, 10, 11, 12, 13- dodecahydro-1,5-dihydroxy-11-methoxyimino-6a,7,10,10-tetramethyl-3-oxo-12-phenylthio- 1H-benzo[8,8a][1]benzopyrano[2,3-e]isoindole (718) (1R*, 6a R, 7S, 9a S, 12 S*, 13a S)-2, 3, 6, 6a, 7, 8, 9, 9a, 10, 11, 12, 13- dodecahydro-5,12-dihydroxy-11-hydroxyimino-1-methyl-6a,7,10,10-tetramethyl-3-oxo-1H- benzo[8,8a][1]benzopyrano[2,3-e]isoindole (719) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-3-oxo-12-phenylsulfonylamino-1H- benzo[8,8a][1]benzopyrano[2,3-e]isoindole (720) (6a R, 7S, 9a S, 12 R*, 13a S)-11-cyanoimino-12-ethoxy-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (721) (6a R, 7S, 9a S, 12 R*, 13a S)-12-benzoyloxy-2, 3, 6, 6a, 7, 8, 9, 9a, 10, 11, 12, 13- dodecahydro-5-hydroxy-6a,7,10,10-tetramethyl-13-dioxo-11-ureidoimino-1H-benzo[8,8a][1]benzopyrano[2,3-e]isoindole (722) (1R*, 6a R, 7S, 9a S, 12 S*, 13a S)-1-acetoxy-12-carboxymethyloxy-2, 3, 6, 6a, 7, 8, 9, 9a, 10, 11, 12, 13-dodecahydro-5-hydroxy-6a,7,10,10-tetramethyl-3-oxo-11-ureidoimino- 1H-benzo[8,8a][1]benzopyrano[2,3-e]isoindole (723) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-3-oxo-12-phenylsulfinyl-11-ureidoimino-1H- benzo[8,8a][1]benzopyrano[2,3-e]isoindole (724) (1R*, 6a R, 7S, 9a S, 12 S*, 13a S)-2, 3, 6, 6a, 7, 8, 9, 9a, 10, 11, 12, 13- dodecahydro-1,5-dihydroxy-12-methoxy-11-methoxyimino-6a,7,10,10-tetramethyl-3-oxo- 1H-benzo[8,8a][1]benzopyrano[2,3-e]isoindole (725) (6a R, 7S, 9a S, 12 R*, 13a S)-12-glycylamino-2, 3, 6, 6a, 7, 8, 9, 9a, 10, 11, 12, 13- dodecahydro-5-dihydroxyphosphinyloxy-6a,7, 10, 10-tetramethyl-1,3,11-trioxo-1H- benzo[8,8a][1]benzopyrano[2,3-e]isoindole (726) (6a R, 7S, 9a S, 12 R*, 13a S)-12-azido-2, 3, 6, 6a, 7, 8, 9, 9a, 10, 11, 12, 13- dodecahydro-5-hydroxy-6a,7,10, 10-tetramethyl-11-(1-oxa-4-azacyclohex-4-yl)imino-13-dioxo-1H-benzo[8,8a][1]benzopyrano[2,3-e]isoindole (727) (1R*, 6a R, 7S, 9a S, 12 S*, 13a S)-1-acetoxy-2, 3, 6, 6a, 7, 8, 9, 9a, 10, 11, 12, 13- dodecahydro-5,12-dihydroxy-11-methoxyimino-6a,7,10,10-tetramethyl-3-oxo-1H- benzo[8,8a][1]benzopyrano[2,3-e]isoindole (728) (6a R, 7S, 9a S, 12 R*, 13a S)-11-hydrazono-2, 3, 6, 6a, 7, 8, 9, 9a, 10, 11, 12, 13- dodecahydro-5-hydroxy-12-methoxy-6a,7,10,10-tetramethyl-13-dioxo-1H- benzo[8,8a][1]benzopyrano[2,3-e]isoindole (729) (1R*, 6a R, 7S, 9a S, 12 S*, 13a S)-1-acetoxy-12-carbamoyloxy-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (730) (1R*, 6a R, 7S, 9a S, 12 S*, 13a S)-12-azido-2, 3, 6, 6a, 7, 8, 9, 9a, 10, 11, 12, 13- dodecahydro-1,5-dihydroxy-6a,7,10,10-tetramethyl-3,11-dioxo-1H- benzo[8,8a][1]benzopyrano[2,3-e]isoindole (731) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-13-dioxo-12-phenylsulfonyloxy-1H- benzo[8,8a][1]benzopyrano[2,3-e]isoindole (732) (1R*, 6a R, 7S, 9a S, 12 S*, 13a S)-2, 3, 6, 6a, 7, 8, 9, 9a, 10, 11, 12, 13- dodecahydro-1,5-dihydroxy-12-methanesulfonylamino-6a,7,10,10-tetramethyl-11-(1-oxa-4- azacyclohex-4-yl)imino-3-oxo-1H-benzo[8,8a][1]benzopyrano[2,3-e]isoindole (733) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-11-(1-oxa-4-azacyclohex-4-yl)imino-3- oxo-12-phenylthio-1H-benzo[8,8a][1]benzopyrano[2,3-e]isoindole (734) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-3-oxo-12-phenylsulfinyl-1H- benzo[8,8a][1]benzopyrano[2,3-e]isoindole (735) (6a R, 7S, 9a S, 12 R*, 13a S)-12-benzoyloxy-2, 3, 6, 6a, 7, 8, 9, 9a, 10, 11, 12, 13- dodecahydro-5-hydroxy-11-methoxyimino-6a,7,10,10-tetramethyl-13-dioxo-1H- benzo[8,8a][1]benzopyrano[2,3-e]isoindole (736) (1R*, 6a R, 7S, 9a S, 12 S*, 13a S)-2, 3, 6, 6a, 7, 8, 9, 9a, 10, 11, 12, 13- dodecahydro-1,5-dihydroxy-12-methanesulfonylamino-11-methoxyimino-6a,7,10,10-tetramethyl-3-oxo-1H-benzo[8,8a][1]benzopyrano[2,3-e]isoindole (737) (6a R, 7S, 9a S, 12 R*, 13a S)-11-cyanoimino-2, 3, 6, 6a, 7, 8, 9, 9a, 10, 11, 12, 13- dodecahydro-5-hydroxy- 12-(2-hydroxy)ethoxy-6a,7,10,10-tetramethyl-3-oxo-1H-benzo[8,8a][1]benzopyrano[2,3-e]isoindole
(738) (6a R, 7S, 9a S, 12 R*, 13a S)-2, 3, 6, 6a, 7, 8, 9, 9a, 10, 11, 12, 13-dodecahydro-5- hydroxy-11-hydroxyimino-12-methanesulfonylamino-6a,7,10,10-tetramethyl-3-oxo-1H- benzo[8,8a][1]benzopyrano[2,3-e]isoindole
(739) (1R*, 6a R, 7S, 9a S, 12 S*, 13a S)-1-acetoxy-11-cyanoimino-2, 3, 6, 6a, 7, 8, 9, 9a, 10, 11, 12, 13-dodecahydro-5-hydroxy-6a,7,10,10-tetramethyl-3-oxo-12- phenylsulfonylamino-1H-benzo[8,8a][1]benzopyrano[2,3-e]isoindole
(740) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-3-oxo-12-phenoxy-1H- benzo[8,8a][1]benzopyrano[2,3-e]isoindole
(741) (1R*, 6a R, 7S, 9a S, 12 S*, 13a S)-1-acetoxy-11-cyanoimino-2, 3, 6, 6a, 7, 8, 9, 9a, 10, 11, 12, 13-dodecahydro-5-hydroxy-6a,7,10,10-tetramethyl-3-oxo-12-(3- pyridyl)carbonyloxy-1H-benzo[8,8a][1]benzopyrano[2,3-e]isoindole
(742) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-1,3,11-trioxo-12-phenylsulfonyloxy-1H-benzo[8,8a][1]benzopyrano[2,3-e]isoindole
(743) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylsulfinyl-11-(1-oxa-4-azacyclohex-4-yl)imino-3- oxo-1H-benzo[8,8a][1]benzopyrano[2,3-e]isoindole
(744) (1R*, 6a R, 7S, 9a S, 12 S*, 13a S)-1-acetoxy-12-azido-2, 3, 6, 6a, 7, 8, 9, 9a, 10, 11, 12, 13-dodecahydro-5-hydroxy-6a,7,10,10-tetramethyl-11-(1-oxa-4-azacyclohex-4- yl)imino-3-oxo-1H-benzo[8,8a][1]benzopyrano[2,3-e]isoindole
(745) (1R*, 6a R, 7S, 9a S, 12 S*, 13a S)-12-benzyloxy-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole
(746) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-3-oxo-12-phenoxy-1H- benzo[8,8a][1]benzopyrano[2,3-e]isoindole
(747) (6a R, 7S, 9a S, 12 R*, 13a S)-12-acetylamino-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole
(748) (6a R, 7S, 9a S, 12 R*, 13a S)-12-benzyloxycarbonylamino-2, 3, 6, 6a, 7, 8, 9, 9a, 10, 11, 12, 13-dodecahydro-5-hydroxy-6a,7,10,10-tetramethyl-11-(1-oxa-4-azacyclohex-4- yl)imino-13-dioxo-1H-benzo[8,8a][1]benzopyrano[2,3-e]isoindole
(749) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-12-methylsulfinyl-3-oxo-11- ureidoimino-1H-benzo[8,8a][1]benzopyrano[2,3-e]isoindole
(750) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-3,11-dioxo-12-phenylsulfinyl-1H- benzo[8,8a][1]benzopyrano[2,3-e]isoindole
(751) (1R*, 6a R, 7S, 9a S, 12 S*, 13a S)-12-chloro-2, 3, 6, 6a, 7, 8, 9, 9a; 10, 11, 12, 13- dodecahydro-5-hydroxy-1-methyl-6a,7,10,10-tetramethyl-3-oxo-11-ureidoimino-1H- benzo[8,8a][1]benzopyrano[2,3-e]isoindole
(752) (6a R, 7S, 9a S, 12 R*, 13a S)-12-benzyloxycarbonylamino-2, 3, 6, 6a, 7, 8, 9, 9a, 10, 11, 12, 13-dodecahydro-5-hydroxy-6a,7,10,10-tetramethyl-1,3,11-trioxo-1H- benzo[8,8a][1]benzopyrano[2,3-e]isoindole
(753) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-12-methylthio-11-(1-oxa-4-azacyclohex-4-yl)imino-3-oxo-1H-benzo[8,8a][1]benzopyrano[2,3-e]isoindole
(754) (1R*, 6a R, 7S, 9a S, 12 S*, 13a S)-1-acetoxy-12-acetylamino-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole
(755) (1R*, 6a R, 7S, 9a S, 12 S*, 13a S)-11-hydrazono-2, 3, 6, 6a, 7, 8, 9, 9a, 10, 11, 12, 13-dodecahydro-5-hydroxy-1-methyl-6a,7,10,10-tetramethyl-3-oxo-12-phenylsulfonyl-1H- benzo[8,8a][1]benzopyrano[2,3-e]isoindole
(756) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-methanesulfonyloxy-11-methoxyimino-6a,7,10,10-tetramethyl- 3-oxo-1H-benzo [8,8a][1]benzopyrano [2,3-e]isoindole
(757) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-1,3,11-trioxo-12-phenylsulfonylamino-1H- benzo[8,8a][1]benzopyrano[2,3-e]isoindole
(758) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-13-dioxo-12-phenylsulfinyl-1H- benzo[8,8a][1]benzopyrano[2,3-e]isoindole
(759) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-3-oxo-12-phenoxy-11-ureidoimino-1H- benzo[8,8a][1]benzopyrano[2,3-e]isoindole
(760) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-(2-hydroxy)ethoxy-6a,7,10,10-tetramethyl-3-oxo-11-ureidoimino-1H-benzo[8,8a][1]benzopyrano[2,3-e]isoindole
(761) (1R*, 6a R, 7S, 9a S, 12 S*, 13a S)-11-cyanoimino-2, 3, 6, 6a, 7, 8, 9, 9a, 10, 11, 12, 13-dodecahydro-1,5-dihydroxy-6a,7,10,10-tetramethyl-12-methylsulfinyl-3-oxo-1H- benzo[8,8a][1]benzopyrano[2,3-e]isoindole
(762) (1R*, 6a R, 7S, 9a S, 12 S*, 13a S)-1-acetoxy-11-cyanoimino-2, 3, 6, 6a, 7, 8, 9, 9a, 10, 11, 12, 13-dodecahydro-5-hydroxy-6a,7,10,10-tetramethyl-3-oxo-12-phenylsulfonyl- 1H-benzo[8,8a][1]benzopyrano[2,3-e]isoindole
(763) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-3-oxo-12-phenylsulfonyloxy-1H-benzo[8,8a][1]benzopyrano[2,3-e]isoindole
(764) (1R*, 6a R, 7S, 9a S, 12 S*, 13a S)-11-hydrazono-2, 3, 6, 6a, 7, 8, 9, 9a, 10, 11, 12, 13-dodecahydro-1,5-dihydroxy-6a,7,10,10-tetramethyl-12-methylamino-3-oxo-1H- benzo[8,8a][1]benzopyrano[2,3-e]isoindole
(765) (1R*, 6a R, 7S, 9a S, 12 S*, 13a S)-12-benzyloxy-2, 3, 6, 6a, 7, 8, 9, 9a, 10, 11, 12, 13-dodecahydro-1,5-dihydroxy-6a,7,10,10-tetramethyl-3,11-dioxo-1H- benzo[8,8a][1]benzopyrano[2,3-e]isoindole
(766) (6a R, 7S, 9a S, 12 R*, 13a S)-2, 3, 6, 6a, 7, 8, 9, 9a, 10, 11, 12, 13-dodecahydro-5- hydroxy-12-methanesulfonyloxy-6a,7,10,10-tetramethyl-13-dioxo-11-ureidoimino-1H- benzo[8,8a][1]benzopyrano[2,3-e]isoindole
(767) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7, 10,10-tetramethyl-12-methylsulfinyl-3,11-dioxo-1H-benzo[8,8a][1]benzopyrano[2,3-e]isoindole (768) (6a R, 7S, 9a S, 12 R*, 13a S)-12-carboxymethyloxy-2, 3, 6, 6a, 7, 8, 9, 9a, 10, 11, 12, 13-dodecahydro-5-hydroxy-6a,7,10,10-tetramethyl-1,3,11-trioxo-1H- benzo[8,8a][1]benzopyrano[2,3-e]isoindole (769) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylthio-3-oxo-11-ureidoimino-1H-benzo[8,8a][1]benzopyrano[2,3-e]isoindole (770) (1R*, 6a R, 7S, 9a S, 12 S*, 13a S)-2, 3, 6, 6a, 7, 8, 9, 9a, 10, 11, 12, 13- dodecahydro-5-hydroxy-11-methoxyimino-1-methyl-6a,7,10,10-tetramethyl-12-methylthio- 3-oxo-1H-benzo[8,8a][1]benzopyrano[2,3-e]isoindole (771) (6a R, 7S, 9a S, 12 R*, 13a S)-12-chloro-2, 3, 6, 6a, 7, 8, 9, 9a, 10, 11, 12, 13- dodecahydro-5-dihydroxyphosphinyloxy-6a,7,10,10-tetramethyl-3,11-dioxo-1H- benzo[8,8a][1]benzopyrano[2,3-e]isoindole (772) (1R*, 6a R, 7S, 9a S, 12 S*, 13a S)-11-cyanoimino-2, 3, 6, 6a, 7, 8, 9, 9a, 10, 11, 12, 13-dodecahydro-1,5-dihydroxy-12-(2-hydroxy)ethoxy-6a,7,10,10-tetramethyl-3-oxo-1H- benzo[8,8a][1]benzopyrano[2,3-e]isoindole (773) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-3-oxo-12-(3-pyridyl)carbonyloxy-1H- benzo[8,8a][1]benzopyrano[2,3-e]isoindole (774) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-methoxy-6a,7,10,10-tetramethyl-3,11-dioxo-1H-benzo[8,8a][1]benzopyrano[2,3-e]isoindole (775) (6a R, 7S, 9a S, 12 R*, 13a S)-2, 3, 6, 6a, 7, 8, 9, 9a, 10, 11, 12, 13-dodecahydro-5- hydroxy-12-(2-hydroxy)ethoxy-11-methoxyimino-6a,7,10,10-tetramethyl-13-dioxo-1H- benzo[8,8a][1]benzopyrano[2,3-e]isoindole (776) (1R*, 6a R, 7S, 9a S, 12 S*, 13a S)-12-ethoxy-2, 3, 6, 6a, 7, 8, 9, 9a, 10, 11, 12, 13- dodecahydro-5-hydroxy-1-methyl-6a,7,10,10-tetramethyl-11-(1-oxa-4-azacyclohex-4- yl)imino-3-oxo-1H-benzo[8,8a][1]benzopyrano[2,3-e]isoindole (777) (1R*, 6a R, 7S, 9a S, 12 S*, 13a S)-12-acetoxy-2, 3, 6, 6a, 7, 8, 9, 9a, 10, 11, 12, 13- dodecahydro-5-hydroxy-1-methyl-6a,7,10,10-tetramethyl-3-oxo-11-ureidoimino-1H- benzo[8,8a][1]benzopyrano[2,3-e]isoindole (778) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylamino-13-dioxo-11-ureidoimino-1H- benzo[8,8a][1]benzopyrano[2,3-e]isoindole (779) (1R*, 6a R, 7S, 9a S, 12 S*, 13a S)-12-glycylamino-2, 3, 6, 6a, 7, 8, 9, 9a, 10, 11, 12, 13-dodecahydro-1,5-dihydroxy-11-hydroxyimino-6a,7,10,10-tetramethyl-3-oxo-1H- benzo[8,8a][1]benzopyrano[2,3-e]isoindole (780) (1R*, 6a R, 7S, 9a S, 12 S*, 13a S)-1-acetoxy-12-glycylamino-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (781) (6a R, 7S, 9a S, 12 R*, 13a S)-12-acetoxy-2, 3, 6, 6a, 7, 8, 9, 9a, 10, 11, 12, 13- dodecahydro-5-dihydroxyphosphinyloxy-6a,7,10,10-tetramethyl-1,3,11-trioxo-1H-benzo[8,8a][1]benzopyrano[2,3-e]isoindole (782) (6a R, 7S, 9a S, 12 R*, 13a S)-12-acetylamino-2, 3, 6, 6a, 7, 8, 9, 9a, 10, 11, 12, 13- dodecahydro-5-hydroxy-6a,7,10,10-tetramethyl-1,3,11-trioxo-1H- benzo[8,8a][1]benzopyrano[2,3-e]isoindole (783) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-3-oxo-12-phenylsulfonylamino-1H- benzo[8,8a][1]benzopyrano[2,3-e]isoindole (784) (6a R, 7S, 9a S, 12 R*, 13a S)-12-amino-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (785) (1R*, 6a R, 7S, 9a S, 12 S*, 13a S)-1-acetoxy-12-chloro-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (786) (6a R, 7S, 9a S, 12 R*, 13a S)-12-benzyloxycarbonylamino-11-cyanoimino-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (787) (1R*, 6a R, 7S, 9a S, 12 S*, 13a S)-2, 3, 6, 6a, 7, 8, 9, 9a, 10, 11, 12, 13- dodecahydro-1,5-dihydroxy-12-mercapto-6a,7,10,10-tetramethyl-3-oxo-11-ureidoimino-1H-benzo[8,8a][1]benzopyrano[2,3-e]isoindole (788) (1R*, 6a R, 7S, 9a S, 12 S*, 13a S)-1,5,12-trihydroxy-2, 3, 6, 6a, 7, 8, 9, 9a, 10, 11, 12, 13-dodecahydro-6a,7,10,10-tetramethyl-3,11-dioxo-1H-benzo[8,8a][1]benzopyrano[2,3- e]isoindole (789) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-methoxyimino-6a,7,10,10-tetramethyl-3-oxo-12-phenylsulfonyl-1H-benzo[8,8a][1]benzopyrano[2,3-e]isoindole (790) (1R*, 6a R, 7S, 9a S, 12 S*, 13a S)-12-bromo-2, 3, 6, 6a, 7, 8, 9, 9a, 10, 11, 12, 13- dodecahydro-1,5-dihydroxy-6a,7, 10,10-tetramethyl-11-(1-oxa-4-azacyclohex-4-yl)imino-3- oxo-1H-benzo[8,8a][1]benzopyrano[2,3-e]isoindole (791) (6a R, 7S, 9a S, 12 R*, 13a S)-2, 3, 6, 6a, 7, 8, 9, 9a, 10, 11, 12, 13-dodecahydro-5- hydroxy-12-mercapto-11-methoxyimino-6a,7,10,10-tetramethyl-3-oxo-1H- benzo[8,8a][1]benzopyrano[2,3-e]isoindole (792) (1R*, 6a R, 7S, 9a S, 12 S*, 13a S)-2, 3, 6, 6a, 7, 8, 9, 9a, 10, 11, 12, 13- dodecahydro-5-hydroxy-11-methoxyimino-1-methyl-6a,7,10,10-tetramethyl-3-oxo-12- phenylsulfonylamino-1H-benzo[8,8a][1]benzopyrano[2,3-e]isoindole (793) (1R*, 6a R, 7S, 9a S, 12 S*, 13a S)-12-acetylamino-2, 3, 6, 6a, 7, 8, 9, 9a, 10, 11, 12, 13-dodecahydro-5-hydroxy-1-methyl-6a,7,10,10-tetramethyl-11-(1-oxa-4-azacyclohex-4- yl)imino-3-oxo-1H-benzo [8,8a][1]benzopyrano [2,3-e]isoindole (794) (1R*, 6a R, 7S, 9a S, 12 S*, 13a S)-12-acetylamino-2, 3, 6, 6a, 7, 8, 9, 9a, 10, 11, 12, 13-dodecahydro-1,5-dihydroxy-11-hydroxyimino-6a,7,10,10-tetramethyl-3-oxo-1H- benzo[8,8a][1]benzopyrano[2,3-e]isoindole (795) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-13-dioxo-12-(3-pyridyl)carbonyloxy-11-ureidoimino-1H- benzo[8,8a][1]benzopyrano[2,3-e]isoindole (796) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylthio-1,3,11-trioxo-1H- benzo[8,8a][1]benzopyrano[2,3-e]isoindole (797) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-3,11-dioxo-12-phenylsulfinyl-1H- benzo[8,8a][1]benzopyrano[2,3-e]isoindole (798) (6a R, 7S, 9a S, 12 R*, 13a S)-1$^2$-glycylamino-11-hydrazono-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (799) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-3-oxo-12-(3-pyridyl)carbonyloxy-1H- benzo[8,8a][1]benzopyrano[2,3-e]isoindole (800) (6a R, 7S, 9a S, 12 R*, 13a S)-12-benzyloxy-2, 3, 6, 6a, 7, 8, 9, 9a, 10, 11, 12, 13- dodecahydro-5-hydroxy-11-hydroxyimino-6a,7,10,10-tetramethyl-13-dioxo-1H-benzo[8,8a][1]benzopyrano[2,3-e]isoindole (801) (1R*, 6a R, 7S, 9a S, 12 S*, 13a S)-1-acetoxy-12-benzyloxycarbonylamino-2, 3, 6, 6a, 7, 8, 9, 9a, 10, 11, 12, 13-dodecahydro-5-hydroxy-11-methoxyimino-6a,7,10,10- tetramethyl-3-oxo-1H-benzo[8,8a][1]benzopyrano[2,3-e]isoindole (802) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylthio-3,11-dioxo-1H- benzo[8,8a][1]benzopyrano[2,3-e]isoindole (803) (6a R, 7S, 9a S, 12 R*, 13a S)-12-carboxymethyloxy-2, 3, 6, 6a, 7, 8, 9, 9a, 10, 11, 12, 13-dodecahydro-5-hydroxy-11-methoxyimino-6a,7,10,10-tetramethyl-13-dioxo-1H- benzo[8,8a][1]benzopyrano[2,3-e]isoindole (804) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-1,3,11-trioxo-12-phenylsulfonyloxy-1H- benzo[8,8a][1]benzopyrano[2,3-e]isoindole (805) (1R*, 6a R, 7S, 9a S, 12 S*, 13a S)-1-acetoxy-11-hydrazono-2, 3, 6, 6a, 7, 8, 9, 9a, 10, 11, 12, 13-dodecahydro-5-hydroxy-6a,7,10,10-tetramethyl-12-methylthio-3-oxo-1H- benzo[8,8a][1]benzopyrano[2,3-e]isoindole (806) (6a R, 7S, 9a S, 12 R*, 13a S)-2, 3, 6, 6a, 7, 8, 9, 9a, 10, 11, 12, 13-dodecahydro-5- hydroxy-12-mercapto-6a,7,10,10-tetramethyl-11-(1-oxa-4-azacyclohex-4-yl)imino-13- dioxo-1H-benzo[8,8a][1]benzopyrano[2,3-e]isoindole (807) (1R*, 6a R, 7S, 9a S, 12 S*, 13a S)-1-acetoxy-12-amino-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (808) (1R*, 6a R, 7S, 9a S, 12 S*, 13a S)-12-amino-2, 3, 6, 6a, 7, 8, 9, 9a, 10, 11, 12, 13- dodecahydro-5-hydroxy-1-methyl-6a,7,10,10-tetramethyl-11-(1-oxa-4-azacyclohex-4- yl)imino-3-oxo-1H-benzo[8,8a][1]benzopyrano[2,3-e]isoindole (809) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-3,11-dioxo-12-phenylsulfonylamino-1H- benzo[8,8a][1]benzopyrano[2,3-e]isoindole (810) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-3,11-dioxo-12-phenylthio-1H- benzo[8,8a][1]benzopyrano[2,3-e]isoindole (811) (1R*, 6a R, 7S, 9a S, 12 S*, 13a S)-11-hydrazono-2, 3, 6, 6a, 7, 8, 9, 9a, 10, 11, 12, 13-dodecahydro-1,5-dihydroxy-6a,7,10,10-tetramethyl-3-oxo-12-(3-pyridyl)carbonyloxy- 1H-benzo[8,8a][1]benzopyrano[2,3-e]isoindole (812) (1R*, 6a R, 7S, 9a S, 12 S*, 13a S)-1-acetoxy-11-hydrazono-2, 3, 6, 6a, 7, 8, 9, 9a, 10, 11, 12, 13-dodecahydro-5-hydroxy-12-methoxy-6a,7,10,10-tetramethyl-3-oxo-1H- benzo[8,8a][1]benzopyrano[2,3-e]isoindole (813) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-hydroxyimino-12-mercapto-6a,7,10,10-tetramethyl-3-oxo-1H- benzo[8,8a][1]benzopyrano[2,3-e]isoindole (814) (1R*, 6a R, 7S, 9a S, 12 S*, 13a S)-11-hydrazono-2, 3, 6, 6a, 7, 8, 9, 9a, 10, 11, 12, 13-dodecahydro-5-hydroxy-1-methyl-6a,7,10,10-tetramethyl-12-methylsulfinyl-3-oxo-1H- benzo[8,8a][1]benzopyrano[2,3-e]isoindole (815) (6a R, 7S, 9a S, 12 R*, 13a S)-2, 3, 6, 6a, 7, 8, 9, 9a, 10, 11, 12, 13-dodecahydro-5- hydroxy-12-(2-hydroxy)ethoxy-11-hydroxyimino-6a,7,10,10-tetramethyl-3-oxo-1H- benzo[8,8a][1]benzopyrano[2,3-e]isoindole (816) (6a R, 7S, 9a S, 12 R*, 13a S)-12-glycylamino-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (817) (6a R, 7S, 9a S. 12 R*, 13a S)-2, 3, 6, 6a, 7, 8, 9, 9a, 10, 11, 12, 13-dodecahydro-5- dihydroxyphosphinyloxy-6a,7,10,10-tetramethyl-3,11-dioxo-12-phenylsulfonyl-1H- benzo[8,8a][1]benzopyrano[2,3-e]isoindole (818) (1R*, 6a R, 7S, 9a S, 12 S*, 13a S)-11-cyanoimino-2, 3, 6, 6a, 7, 8, 9, 9a, 10, 11, 12, 13-dodecahydro-1,5-dihydroxy-6a,7,10,10-tetramethyl-12-methylamino-3-oxo-1H- benzo[8,8a][1]benzopyrano[2,3-e]isoindole (819) (1R*, 6a R, 7S, 9a S, 12 S*, 13a S)-11-hydrazono-2, 3, 6, 6a, 7, 8, 9, 9a, 10, 11, 12, 13-dodecahydro-1,5-dihydroxy-12-methoxy-6a,7,10,10-tetramethyl-3-oxo-1H- benzo[8,8a][1]benzopyrano[2,3-e]isoindole (820) (1R*, 6a R, 7S, 9a S, 12 S*, 13a S)-1-acetoxy-12-ethoxy-2,3,6,6a,7,8,9,9a,10,11,12,13-dodecahydro-5-hydroxy-6a,7,10,10-tetramethyl-3-oxo-11-ureidoimino-1H- benzo[8,8a][1]benzopyrano[2,3-e]isoindole (821) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-3,11-dioxo-12-phenylsulfinyl-1H- benzo[8,8a][1]benzopyrano[2,3-e]isoindole (822) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-hydroxyimino-6a,7,10,10-tetramethyl-3-oxo-12-phenylsulfonyloxy-1H-benzo[8,8a][1]benzopyrano[2,3-e]isoindole (823) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-12-methylsulfinyl-3-oxo-11-ureidoimino-1H-benzo[8,8a][1]benzopyrano[2,3-e]isoindole (824) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-3,11-dioxo-12-phenylsulfonylamino-1H-benzo[8,8a][1]benzopyrano[2,3-e]isoindole (825) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-11-(1-oxa-4-azacyclohex-4-yl)imino-3-oxo-12-phenylthio- 1H-benzo[8,8a][1]benzopyrano[2,3-e]isoindole (826) (6a R, 7S, 9a S, 12 R*, 13a S)-12-acetoxy-2, 3, 6, 6a, 7, 8, 9, 9a, 10, 11, 12, 13- dodecahydro-5-hydroxy-11-methoxyimino-6a,7,10,10-tetramethyl-3-oxo-1H- benzo[8,8a][1]benzopyrano[2,3-e]isoindole (827) (1R*, 6a R, 7S, 9a S, 12 S*, 13a S)-11-cyanoimino-2, 3, 6, 6a, 7, 8, 9, 9a, 10, 11, 12, 13-dodecahydro-5-hydroxy-1-methyl-6a,7,10,10-tetramethyl-12-methylamino-3-oxo-1H- benzo[8,8a][1]benzopyrano[2,3-e]isoindole (828) (6a R, 7S, 9a S, 12 R*, 13a S)-12-acetylamino-2, 3, 6, 6a, 7, 8, 9, 9a, 10, 11, 12, 13- dodecahydro-5-hydroxy- (828 cont.) 6a,7,10,10-tetramethyl-11-(1-oxa-4-azacyclohex-4-yl) imino-3-oxo- 1H-benzo[8,8a][1]benzopyrano[2,3-e] isoindole (829) (6a R, 7S, 9a S, 12 R*, 13a S)-12-carboxymethyloxy-2, 3, 6, 6a, 7, 8, 9, 9a, 10, 11, 12, 13-dodecahydro-5-dihydroxyphosphinyloxy 6a,7,10,10-tetramethyl-1,3,11-trioxo-1H-benzo[8,8a][1]benzopyrano[2,3-e]isoindole (830) (1R*, 6a R, 7S, 9a S, 12 S*, 13a S)-12-acetoxy-11-hydrazono-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (831) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-11-(1-oxa-4-azacyclohex-4-yl) imino-3- oxo-12-phenylsulfinyl-1H-benzo[8,8a][1] benzopyrano[2,3-e]isoindole (832) (1R*, 6a R, 7S, 9a S, 12 S*, 13a S)-1-acetoxy-12-ethoxy-2, 3, 6, 6a, 7, 8, 9, 9a, 10, 11, 12, 13-dodecahydro-5-hydroxy-6a,7,10,10-tetramethyl-11-(1-oxa-4-azacyclohex-4- yl)imino-3-oxo-1H-benzo[8,8a][1] benzopyrano[2,3-e]isoindole (833) (6a R, 7S, 9a S, 12 R*, 13a S)-12-azido-2, 3, 6, 6a, 7, 8, 9, 9a, 10, 11, 12, 13- dodecahydro-5-hydroxy-11-hydroxyimino-6a,7,10,10-tetramethyl-13-dioxo-1H-benzo[8,8a][1]benzopyrano[2,3-e]isoindole (834) (6a R, 7S, 9a S, 12 R*, 13a S)-12-benzyloxy-2, 3, 6, 6a, 7, 8, 9, 9a, 10, 11, 12, 13- dodecahydro-5-hydroxy-6a,7,10,10-tetramethyl-13-dioxo-11-ureidoimino-1H-benzo[8,8a][1]benzopyrano[2,3-e]isoindole (835) (1R*, 6a R, 7S, 9a S, 12 S*, 13a S)-1-acetoxy-12-bromo-2, 3, 6, 6a, 7, 8, 9, 9a, 10, 11, 12, 13-dodecahydro-5-hydroxy-11-methoxyimino-6a,7,10,10-tetramethyl-3-oxo-1H- benzo[8,8a][1]benzopyrano[2,3-e]isoindole (836) (6a R, 7S, 9a S, 12 R*, 13a S)-12-azido-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-3-oxo- 1H-benzo[8,8a][1]benzopyrano[2,3-e]isoindole (837) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-13-dioxo-12-phenylsulfinyl-11-ureidoimino-1H- benzo[8,8a][1]benzopyrano[2,3-e]isoindole (838) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-3,11-dioxo-12-phenylsulfonyloxy-1H- benzo[8,8a][1]benzopyrano[2,3-e]isoindole (839) (6a R, 7S, 9a S, 12 R*, 13a S)-12-benzoylamino-2, 3, 6, 6a, 7, 8, 9, 9a, 10, 11, 12, 13- dodecahydro-5-hydroxy-11-hydroxyimino-6a,7,10,10-tetramethyl-13-dioxo-1H-benzo[8,8a][1]benzopyrano[2,3-e]isoindole (840) (6a R, 7S, 9a S, 12 R*, 13a S)-12-azido-2, 3, 6, 6a, 7, 8, 9, 9a, 10, 11, 12, 13- dodecahydro-5-dihydroxyphosphinyloxy-6a,7,10,10-tetramethyl-1,3,11-trioxo-1H- benzo[8,8a][1]benzopyrano[2,3-e]isoindole (841) (1R*, 6a R, 7S, 9a S, 12 S*, 13a S)-12-ethoxy-2, 3, 6, 6a, 7, 8, 9, 9a, 10, 11, 12, 13- dodecahydro-5-hydroxy-11-hydroxyimino-1-methyl-6a,7,10,10-tetramethyl-3-oxo-1H- benzo[8,8a][1]benzopyrano [2,3-e]isoindole (842) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-13-dioxo-12-phenylsulfinyl-1H-benzo[8,8a][1]benzopyrano[2,3-e]isoindole (843) (6a R, 7S, 9a S, 12 R*, 13a S)-12-bromo-2, 3, 6, 6a, 7, 8, 9, 9a, 10, 11, 12, 13- dodecahydro-5-dihydroxyphosphinyloxy-6a,7,10,10-tetramethyl-1,3,11-trioxo-1H- benzo[8,8a][1]benzopyrano[2,3-e]isoindole (844) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-1,3,11-trioxo-12-phenylsulfinyl-1H- benzo[8,8a][1]benzopyrano[2,3-e]isoindole (845) (6a R, 7S, 9a S, 12 R*, 13a S)-12-bromo-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-3-oxo- 1H-benzo[8,8a][1]benzopyrano[2,3-e]isoindole (846) (1R*, 6a R, 7S, 9a S, 12 S*, 13a S)-12-acetoxy-2, 3, 6, 6a, 7, 8, 9, 9a, 10, 11, 12, 13- dodecahydro-1,5-dihydroxy-6a,7,10,10-tetramethyl-3-oxo-11-ureidoimino-1H- benzo[8,8a][1]benzopyrano[2,3-e]isoindole (847) (1R*, 6a R, 7S, 9a S, 12 S*, 13a S)-2, 3, 6, 6a, 7, 8, 9, 9a, 10, 11, 12, 13- dodecahydro-5-hydroxy-11-methoxyimino-1-methyl-6a,7,10,10-tetramethyl-3-oxo-12- phenoxy-1H-benzo[8,8a][1]benzopyrano[2,3-e]isoindole (848) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-12-methylamino-3,11-dioxo-1H-benzo[8,8a][1]benzopyrano[2,3-e]isoindole (849) (1R*, 6a R, 7S, 9a S, 12 S*, 13a S)-2, 3, 6, 6a, 7, 8, 9, 9a, 10, 11, 12, 13- dodecahydro-5,12-dihydroxy-11-methoxyimino-1-methyl-6a,7,10,10-tetramethyl-3-oxo- 1H-benzo[8,8a][1]benzopyrano[2,3-e]isoindole (850) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-3-oxo-12-phenylthio-1H- benzo[8,8a][1]benzopyrano[2,3-e]isoindole (851) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-hydroxyimino-6a,7,10,10-tetramethyl-12-methylamino-3-oxo- 1H-benzo [8,8a][1]benzopyrano [2,3-e]isoindole (852) (6a R, 7S, 9a S, 12 R*, 13a S)-12-chloro-2, 3, 6, 6a, 7, 8, 9, 9a, 10, 11, 12, 13- dodecahydro-5-dihydroxyphosphinyloxy-6a,7,10,10-tetramethyl-1,3,11-trioxo-1H- benzo[8,8a][1]benzopyrano[2,3-e]isoindole (853) (1R*, 6a R, 7S, 9a S, 12 S*, 13a S)-11-hydrazono-2, 3, 6, 6a, 7, 8, 9, 9a,10, 11, 12, 13-dodecahydro-5-hydroxy-1-methyl-6a,7,10,10-tetramethyl-3-oxo-12-phenylsulfinyl-1H- benzo[8,8a][1]benzopyrano[2,3-e]isoindole (854) (1R*, 6a R, 7S, 9a S, 12 S*, 13a S)-12-benzyloxy-11-hydrazono-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (855) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-methanesulfonylamino-6a,7,10,10-tetramethyl-11-(1-oxa-4- azacyclohex-4-yl)imino-3-oxo-1H-benzo[8,8a][1]benzopyrano[2,3-e]isoindole (856) (6a R, 7S, 9a S, 12 R*, 13a S)-12-benzyloxy-2, 3, 6, 6a, 7, 8, 9, 9a, 10, 11, 12, 13- dodecahydro-5-hydroxy-6a,7,10,10-tetramethyl-3-oxo-11-ureidoimino-1H- benzo[8,8a][1]benzopyrano[2,3-e]isoindole (857) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-3,11-dioxo-12-phenylsulfonyl-1H-benzo[8,8a][1]benzopyrano[2,3-e]isoindole (858) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-1,3,11-trioxo-12-phenoxy-1H- benzo[8,8a][1]benzopyrano[2,3-e]isoindole (859) (1R*, 6a R, 7S, 9a S, 12 S*, 13a S)-1-acetoxy-11-cyanoimino-12-glycylamino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (860) (6a R, 7S, 9a S, 12 R*, 13a S)-12-chloro-2, 3, 6, 6a, 7, 8, 9, 9a, 10, 11, 12, 13- dodecahydro-5-hydroxy-11-hydroxyimino-6a,7,10,10-tetramethyl-13-dioxo-1H- benzo[8,8a][1]benzopyrano[2,3-e]isoindole (861) (1R*, 6a R, 7S, 9a S, 12 S*, 13a S)-12-chloro-2, 3, 6, 6a, 7, 8, 9, 9a, 10, 11, 12, 13- dodecahydro-5-hydroxy-1-methyl-6a,7,10,10-tetramethyl-11-(1-oxa-4-azacyclohex-4- yl)imino-3-oxo-1H-benzo[8,8a][1]benzopyrano[2,3-e]isoindole (862) (1R*, 6a R, 7S, 9a S, 12 S*, 13a S)-2, 3, 6, 6a, 7, 8, 9, 9a, 10, 11, 12, 13-dodecahydro-5-hydroxy-1-methyl-6a,7,10,10-tetramethyl-11-(1-oxa-4-azacyclohex-4- yl)imino-3-oxo-12-phenylsulfonyl-1H-benzo[8,8a][1]benzopyrano[2,3-e]isoindole (863) (6a R, 7S, 9a S, 12 R*, 13a S)-11-ureidoimino-2, 3, 6, 6a, 7, 8, 9, 9a, 10, 11, 12, 13- dodecahydro-5,12-dihydroxy-6a,7,10,10-tetramethyl-3-oxo-1H- benzo[8,8a][1]benzopyrano[2,3-e]isoindole (864) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-1,3,11-trioxo-12-phenylsulfonylamino-1H-benzo[8,8a][1]benzopyrano[2,3-e]isoindole (865) (6a R, 7S, 9a S, 12 R*, 13a S)-12-acetylamino-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-13- dioxo-1H-benzo[8,8a][1]benzopyrano[2,3-e]isoindole (866) (6a R, 7S, 9a S, 12 R*, 13a S)-11-cyanoimino-2, 3, 6, 6a, 7, 8, 9, 9a, 10, 11, 12, 13- dodecahydro-5-hydroxy-12-methanesulfonylamino-6a,7,10,10-tetramethyl-3-oxo-1H- benzo[8,8a][1]benzopyrano[2,3-e]isoindole (867) (6a R, 7S, 9a S, 12 R*, 13a S)-11-hydrazono-2, 3, 6, 6a, 7, 8, 9, 9a, 10, 11, 12, 13- dodecahydro-5-hydroxy-12-methanesulfonylamino-6a,7,10,10-tetramethyl-13-dioxo-1H- benzo[8,8a][1]benzopyrano[2,3-e]isoindole (868) (6a R, 7S, 9a S, 12 R*, 13a S)-12-amino-2, 3, 6, 6a, 7, 8, 9, 9a, 10, 11, 12, 13- dodecahydro-5-hydroxy-6a,7,10,10-tetramethyl-13-dioxo-11-ureidoimino-1H- benzo[8,8a][1]benzopyrano[2,3-e]isoindole (869) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-1,3,11-trioxo-12-phenoxy-1H- benzo[8,8a][1]benzopyrano[2,3-e]isoindole (870) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-3-oxo-12-phenylsulfonylamino-11-ureidoimino-1H-benzo[8,8a][1]benzopyrano[2,3-e]isoindole (871) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-3-oxo-12-phenylsulfonyloxy-11-ureidoimino-1H-benzo[8,8a][1]benzopyrano[2,3-e]isoindole (872) (1R*, 6a R, 7S, 9a S, 12 S*, 13a S)-1-acetoxy-11-hydrazono-2, 3, 6, 6a, 7, 8, 9, 9a, 10, 11, 12, 13-dodecahydro-5,12-dihydroxy-6a,7,10,10-tetramethyl-3-oxo-1H- benzo[8,8a][1]benzopyrano[2,3-e]isoindole (873) (1R*, 6a R, 7S, 9a S, 12 S*, 13a S)-11-hydrazono-2, 3, 6, 6a, 7, 8, 9, 9a, 10, 11, 12, 13-dodecahydro-5-hydroxy-1-methyl-6a,7,10,10-tetramethyl-3-oxo-12-phenylsulfonylamino-1H-benzo[8,8a][1]benzopyrano[2,3-e]isoindole (874) (6a R, 7S, 9a S, 12 R*, 13a S)-12-ethoxy-2, 3, 6, 6a, 7, 8, 9, 9a, 10, 11, 12, 13- dodecahydro-5-dihydroxyphosphinyloxy-6a,7,10,10-tetramethyl-3,11-dioxo-1H- benzo[8,8a][1]benzopyrano[2,3-e]isoindole (875) (6a R, 7S, 9a S, 12 R*, 13a S)-12-amino-2, 3, 6, 6a, 7, 8, 9, 9a, 10, 11, 12, 13- dodecahydro-5-dihydroxyphosphinyloxy-6a,7,10,10-tetramethyl-1,3,11-trioxo-1H- benzo[8,8a][1]benzopyrano[2,3-e]isoindole (876) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-3,11-dioxo-12-phenoxy-1H- benzo[8,8a][1]benzopyrano[2,3-e]isoindole (877) (6a R, 7S, 9a S, 12 R*, 13a S)-12-bromo-11-cyanoimino-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (878) (1R*, 6a R, 7S, 9a S, 12 S*, 13a S)-1-acetoxy-11-cyanoimino-2, 3, 6, 6a, 7, 8, 9, 9a, 10, 11, 12, 13-dodecahydro-5-hydroxy-12-methanesulfonylamino-6a,7,10,10-tetramethyl-3- oxo-1H-benzo[8,8a][1]benzopyrano[2,3-e]isoindole (879) (6a R, 7S, 9a S, 12 R*, 13a S)-12-bromo-11-hydrazono-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (880) (6a R, 7S, 9a S, 12 R*, 13a S)-2,3,6,6a, 7, 8, 9, 9a, 10, 11, 12, 13-dodecahydro-5- hydroxy-6a,7,10,10-tetramethyl-3,11-dioxo-12-phenylsulfonyl-1H- benzo[8,8a][1]benzopyrano[2,3-e]isoindole (881) (6a R, 7S, 9a S, 12 R*, 13a S)-12-amino-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-13- dioxo-1H-benzo[8,8a][1]benzopyrano[2,3-e]isoindole (882) (1R*, 6a R, 7S, 9a S, 12 S*, 13a S)-12-acetoxy-2, 3, 6, 6a, 7, 8, 9, 9a, 10, 11, 12, 13- dodecahydro-5-hydroxy-1-methyl-6a,7,10,10-tetramethyl-11-(1-oxa-4-azacyclohex-4- yl)imino-3-oxo-1H-benzo[8,8a][1]benzopyrano[2,3-e]isoindole (883) (1R*, 6a R, 7S, 9a S, 12 S*, 13a S)-12-bromo-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (884) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-hydroxyimino-6a,7,10,10-tetramethyl-3-oxo-12-phenylsulfonylamino-1H-benzo[8,8a][1]benzopyrano[2,3-e]isoindole (885) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-11-(1-oxa-4-azacyclohex-4-yl)imino-13-dioxo-12- phenoxy-1H-benzo[8,8a][1]benzopyrano[2,3-e]isoindole (886) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-13-dioxo-12-phenylsulfonylamino-1H- benzo[8,8a][1]benzopyrano[2,3-e]isoindole (887) (1R*, 6a R, 7S, 9a S, 12 S*, 13a S)-1-acetoxy-12-ethoxy-2, 3, 6, 6a, 7, 8, 9, 9a, 10, 11, 12, 13-dodecahydro-5-hydroxy-11-hydroxyimino-6a,7,10,10-tetramethyl-3-oxo-1H- benzo[8,8a][1]benzopyrano[2,3-e]isoindole (888) (6a R, 7S, 9a S, 12 R*, 13a S)-2, 3, 6, 6a, 7, 8, 9, 9a, 10, 11, 12, 13-dodecahydro-5- hydroxy-12-(2-hydroxy)ethoxy-6a,7,10,10-tetramethyl-13-dioxo-11-ureidoimino-1H- benzo[8,8a][1]benzopyrano[2,3-e]isoindole (889) (1R*, 6a R, 7S, 9a S, 12 S*, 13a S)-1-acetoxy-12-azido-2, 3, 6, 6a, 7, 8, 9, 9a, 10, 11, 12, 13-dodecahydro-5-hydroxy-11-hydroxyimino-6a,7,10,10-tetramethyl-3-oxo-1H- benzo[8,8a][1]benzopyrano[2,3-e]isoindole (890) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-3-oxo-12-phenoxy-11-ureidoimino-1H- benzo[8,8a][1]benzopyrano[2,3-e]isoindole (891) (6a R, 7S, 9a S, 12 R*, 13a S)-12-chloro-2, 3, 6, 6a, 7, 8, 9, 9a, 10, 11, 12, 13- dodecahydro-5-hydroxy-6a,7,10,10-tetramethyl-3,11-dioxo-1H- benzo[8,8a][1]benzopyrano[2,3-e]isoindole (892) (6a R, 7S, 9a S, 12 R*, 13a S)-11-(1-oxa-4-azacyclohex-4-yl)imino-2, 3, 6, 6a, 7, 8, 9, 9a, 10, 11, 12, 13-dodecahydro-5,12-dihydroxy-6a,7,10,10-tetramethyl-13-dioxo-1H- benzo[8,8a][1]benzopyrano[2,3-e]isoindole (893) (1R*, 6a R, 7S, 9a S, 12 S*, 13a S)-2, 3, 6, 6a, 7, 8, 9, 9a, 10, 11, 12, 13- dodecahydro-5-hydroxy-11-hydroxyimino-1-methyl-6a,7,10,10-tetramethyl-12-methylsulfinyl-3-oxo-1H-benzo[8,8a][1]benzopyrano[2,3-e]isoindole (894) (1R*, 6a R, 7S, 9a S, 12 S*, 13a S)-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-12-phenylthio-1H- benzo[8,8a][1]benzopyrano[2,3-e]isoindole (895) (1R*, 6a R, 7S, 9a S, 12 S*, 13a S)-11-hydrazono-2, 3, 6, 6a, 7, 8, 9, 9a, 10, 11, 12, 13-dodecahydro-5-hydroxy-12-methanesulfonylamino-1-methyl-6a,7,10,10-tetramethyl-3- oxo-1H-benzo[8,8a][1]benzopyrano[2,3-e]isoindole (896) (6a R, 7S, 9a S, 12 R*, 13a S)-12-acetoxy-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (897) (1R*, 6a R, 7S, 9a S, 12 S*, 13a S)-1-acetoxy-12-carboxymethyloxy-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (898) (1R*, 6a R, 7S, 9a S, 12 S*, 13a S)-2, 3, 6, 6a, 7, 8, 9, 9a, 10, 11, 12, 13- dodecahydro-5-hydroxy-11-hydroxyimino-1-methyl-6a,7,10,10-tetramethyl-12-methylthio- 3-oxo-1H-benzo[8,8a][1]benzopyrano[2,3-e]isoindole (899) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-3-oxo- 12-phenylsulfonyl-1H-benzo[8,8a][1]benzopyrano[2,3-e]isoindole (900) (6a R, 7S, 9a S, 12 R*, 13a S)-1 1-methoxyimino-2, 3, 6, 6a, 7, 8, 9, 9a, 10, 11, 12, 13-dodecahydro-5,12-dihydroxy-6a,7,10,10-tetramethyl-3-oxo-1H- benzo[8,8a][1]benzopyrano[2,3-e]isoindole (901) (6a R, 7S, 9a S, 12 R*, 13a S)-12-benzyloxy-2, 3, 6, 6a, 7, 8, 9, 9a, 10, 11, 12, 13- dodecahydro-5-hydroxy-6a,7,10,10-tetramethyl-3,11-dioxo-1H- benzo[8,8a][1]benzopyrano[2,3-e]isoindole (902) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-(2-hydroxy)ethoxy-11-methoxyimino-6a,7,10,10-tetramethyl-3- oxo-1H-benzo[8,8a][1]benzopyrano[2,3-e]isoindole (903) (6a R, 7S, 9a S, 12 R*, 13a S)-12-benzyloxy-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-13- dioxo-1H-benzo[8,8a][1]benzopyrano[2,3-e]isoindole (904) (1R*, 6a R, 7S, 9a S, 12 S*, 13a S)-1-acetoxy-12-benzoyloxy-2, 3, 6, 6a, 7, 8, 9, 9a, 10, 11, 12, 13-dodecahydro-5-hydroxy-11-methoxyimino-6a,7,10, 10-tetramethyl-3-oxo-1H- benzo[8,8a][1]benzopyrano[2, 3-e]isoindole (905) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-3-oxo-12-phenylsulfinyl-1H- benzo[8,8a][1]benzopyrano[2,3-e]isoindole (906) (1R*, 6a R, 7S, 9a S, 12 S*, 13a S)-1-acetoxy-12-benzyloxy-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (907) (6a R, 7S, 9a S, 12 R*, 13a S)-2, 3, 6, 6a, 7, 8, 9, 9a, 10, 11, 12, 13-dodecahydro-5- dihydroxyphosphinyloxy-12-methanesulfonyloxy-6a,7,10,10-tetramethyl-3,11-dioxo-1H- benzo[8,8a][1]benzopyrano[2,3-e]isoindole (908) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-11-(1-oxa-4-azacyclohex-4-yl)imino-13-dioxo-12- phenylsulfonylamino-1H-benzo[8,8a][1]benzopyrano[2,3-e]isoindole (909) (1R*, 6a R, 7S, 9a S, 12 S*, 13a S)-12-benzyloxy-2, 3, 6, 6a, 7, 8, 9, 9a, 10, 11, 12, 13-dodecahydro-1,5-dihydroxy-6a,7,10,10-tetramethyl-11-(1-oxa-4-azacyclohex-4- yl)imino-3-oxo-1H-benzo[8,8a][1]benzopyrano[2,3-e]isoindole (910) (1R*, 6a R, 7S, 9a S, 12 S*, 13a S)-12-carbamoyloxy-2, 3, 6, 6a, 7, 8, 9, 9a, 10, 11, 12, 13-dodecahydro-5-hydroxy-1-methyl-6a,7,10,10-tetramethyl-3-oxo-11-ureidoimino-1H- benzo[8,8a][1]benzopyrano[2,3-e]isoindole (911) (6a R, 7S, 9a S, 12 R*, 13a S)-12-benzyloxycarbonylamino-2, 3, 6, 6a, 7, 8, 9, 9a, 10, 11, 12, 13-dodecahydro-5-hydroxy-6a,7,10,10-tetramethyl-13-dioxo-11-ureidoimino-1H- benzo[8,8a][1]benzopyrano[2,3-e]isoindole (912) (1R*, 6a R, 7S, 9a S, 12 S*, 13a S)-12-carbamoyloxy-11-hydrazono-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (913) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-3-oxo-12-(3-pyridyl)carbonyloxy-11- ureidoimino-1H-benzo[8,8a][1]benzopyrano[2,3-e]isoindole (914) (6a R, 7S, 9a S, 12 R*, 13a S)-12-bromo-2, 3, 6, 6a, 7, 8, 9, 9a, 10, 11, 12, 13- dodecahydro-5-dihydroxyphosphinyloxy-6a,7,10,10-tetramethyl-3,11-dioxo-1H- benzo[8,8a][1]benzopyrano[2,3-e]isoindole (915) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-11-(1-oxa-4-azacyclohex-4-yl)imino-3- oxo-12-phenylsulfonyl-1H-benzo[8,8a][1]benzopyrano[2,3-e]isoindole (916) (6a R, 7S, 9a S, 12 R*, 13a S)-11-cyanoimino-12-glycylamino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (917) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-methanesulfonylamino-6a,7,10,10-tetramethyl-3,11-dioxo-1H- benzo[8,8a][1]benzopyrano[2,3-e]isoindole (918) (6a R, 7S, 9a S, 12 R*, 13a S)-2, 3, 6, 6a, 7, 8, 9, 9a, 10, 11, 12, 13-dodecahydro-5- hydroxy-12-methanesulfonyloxy-11-methoxyimino-6a,7,10,10-tetramethyl-13-dioxo-1H- benzo[8,8a][1]benzopyrano[2, 3-e]isoindole (919) (6a R, 7S, 9a S, 12 R*, 13a S)-12-benzyloxycarbonylamino-2, 3, 6, 6a, 7, 8, 9, 9a, 10, 11, 12, 13-dodecahydro-5-dihydroxyphosphinyloxy-6a,7,10,10-tetramethyl-1,3,11-trioxo- 1H-benzo[8,8a][1]benzopyrano[2,3-e]isoindole (920) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-3-oxo-12-phenylthio-11-ureidoimino-11H-benzo[8,8a][1]benzopyrano[2,3-e]isoindole (921) (1R*, 6a R, 7S, 9a S, 12 S*, 13a S)-11-hydrazono-2, 3, 6, 6a, 7, 8, 9, 9a, 10, 11, 12, 13-dodecahydro-5-hydroxy-1-methyl-6a,7,10,10-tetramethyl-3-oxo-12-(3-pyridyl)carbonyloxy-1H-benzo[8,8a][1]benzopyrano[2,3-e]isoindole (922) (1R*, 6a R, 7S, 9a S, 12 S*, 13a S)-2, 3, 6, 6a, 7, 8, 9, 9a, 10, 11, 12, 13- dodecahydro-1,5-dihydroxy-11-methoxyimino-6a,7,10,10-tetramethyl-3-oxo-12-phenylsulfinyl-1H-benzo[8,8a][1]benzopyrano[2,3-e]isoindole (923) (1R*, 6a R, 7S, 9a S, 12 S*, 13a S)-12-carbamoyloxy-2, 3, 6, 6a, 7, 8, 9, 9a, 10, 11, 12, 13-dodecahydro-1,5-dihydroxy-11-hydroxyimino-6a,7,10,10-tetramethyl-3-oxo-1H- benzo[8,8a][1]benzopyrano[2,3-e]isoindole (924) (6a R, 7S, 9a S, 12 R*, 13a S)-1 1-cyanoimino-2, 3, 6, 6a, 7, 8, 9, 9a, 10, 11, 12, 13- dodecahydro-5-hydroxy-6a,7,10,10-tetramethyl-12-methylsulfinyl-13-dioxo-1H-benzo[8,8a][1]benzopyrano[2,3-e]isoindole (925) (1R*, 6a R, 7S, 9a S, 12 S*, 13a S)-1-acetoxy-12-benzyloxycarbonylamino-2, 3, 6, 6a, 7, 8, 9, 9a, 10, 11, 12, 13-dodecahydro-5-hydroxy-11-hydroxyimino-6a,7,10,10- tetramethyl-3-oxo-1H-benzo[8,8a][1]benzopyrano[2,3-e]isoindole (926) (1R*, 6a R, 7S, 9a S, 12 S*, 13a S)-11-hydrazono-2, 3, 6, 6a, 7, 8, 9, 9a, 10, 11, 12, 13-dodecahydro-5-hydroxy-1-methyl-6a,7,10,10-tetramethyl-12-methylthio-3-oxo-1H- benzo[8,8a][1]benzopyrano[2,3-e]isoindole (927) (1R*, 6a R, 7S, 9a S, 12 S*, 13a S)-11-cyanoimino-2, 3, 6, 6a, 7, 8, 9, 9a, 10, 11, 12, 13-dodecahydro-1,5-dihydroxy-12-methoxy-6a,7,10,10-tetramethyl-3-oxo-1H- benzo[8,8a][1]benzopyrano[2,3-e]isoindole (928) (1R*, 6a R, 7S, 9a S, 12 S*, 13a S)-12-benzyloxy-2, 3, 6, 6a, 7, 8, 9, 9a, 10, 11, 12, 13-dodecahydro-1,5-dihydroxy-11-hydroxyimino-6a,7,10,10-tetramethyl-3-oxo-1H- benzo[8,8a][1]benzopyrano[2,3-e]isoindole (929) (6a R, 7S, 9a S, 12 R*, 13a S)-12-acetoxy-11-cyanoimino-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (930) (1R*, 6a R, 7S, 9a S, 12 S*, 13a S)-12-carbamoyloxy-2, 3, 6, 6a, 7, 8, 9, 9a, 10, 11, 12, 13-dodecahydro-1,5-dihydroxy-6a,7,10,10-tetramethyl-3-oxo-11-ureidoimino-1H- benzo[8,8a][1]benzopyrano[2,3-e]isoindole (931) (6a R, 7S, 9a S, 12 R*, 13a S)-2, 3, 6, 6a, 7, 8, 9, 9a, 10, 11, 12, 13-dodecahydro-5- hydroxy-11-hydroxyimino-12-mercapto-6a,7,10,10-tetramethyl-3-oxo-1H- benzo[8,8a][1]benzopyrano[2,3-e]isoindole (932) (1R*, 6a R, 7S, 9a S, 12 S*, 13a S)-12-carbamoyloxy-2, 3, 6, 6a, 7, 8, 9, 9a, 10, 11, 12, 13-dodecahydro-1,5-dihydroxy-6a,7,10,10-tetramethyl-3,11-dioxo-1H- benzo[8,8a][1]benzopyrano[2,3-e]isoindole (933) (1R*, 6a R, 7S, 9a S, 12 S*, 13a S)-1-acetoxy-2, 3, 6, 6a, 7, 8, 9, 10, 11, 12, 13- dodecahydro-5-hydroxy-6a,7,10,10-tetramethyl-11-(1-oxa-4-azacyclohex-4-yl)imino-3-oxo- 12-phenylsulfinyl-1H-benzo[8,8a][1]benzopyrano[2,3-e]isoindole (934) (1R*, 6a R, 7S, 9a S, 12 S*, 13a S)-2, 3, 6, 6a, 7, 8, 9, 9a, 10, 11, 12, 13- dodecahydro-5-hydroxy-12-methanesulfonyloxy-1-methyl-6a,7,10,10-tetramethyl-3,11- dioxo-1H-benzo[8,8a][1]benzopyrano[2,3-e]isoindole (935) (1R*, 6a R, 7S, 9a S, 12 S*, 13a S)-1-acetoxy-12-benzyloxy-2, 3, 6, 6a, 7, 8, 9, 9a, 10, 11, 12, 13-dodecahydro-5-hydroxy-6a,7,10,10-tetramethyl-3-oxo-11-ureidoimino-1H- benzo[8,8a][1]benzopyrano[2,3-e]isoindole (936) (1R*, 6a R, 7S, 9a S, 12 S*, 13a S)-12-bromo-2, 3, 6, 6a, 7, 8, 9, 9a, 10, 11, 12, 13- dodecahydro-5-hydroxy-1-methyl-6a,7,10,10-tetramethyl-3,11-dioxo-1H- benzo[8,8a][1]benzopyrano[2,3-e]isoindole (937) (6a R, 7S, 9a S, 12 R*, 13a S)-12-benzoyloxy-2, 3, 6, 6a, 7, 8, 9, 9a, 10, 11, 12, 13- dodecahydro-5-hydroxy-6a,7,10,10-tetramethyl-1,3,11-trioxo-1H- benzo[8,8a][1]benzopyrano[2,3-e]isoindole (938) (1R*, 6a R, 7S, 9a S, 12 S*, 13a S)-12-glycylamino-2, 3, 6, 6a, 7, 8, 9, 9a, 10, 11, 12, 13-dodecahydro-5-hydroxy-1-methyl-6a,7,10,10-tetramethyl- 11-(1-oxa-4-azacyclohex-4- yl)imino-3-oxo-1H-benzo[8,8a][1]benzopyrano[2,3-e]isoindole (939) (1R*, 6a R, 7S, 9a S, 12 S*, 13a S)-12-benzyloxy-2, 3, 6, 6a, 7, 8, 9, 9a, 10, 11, 12, 13-dodecahydro-5-hydroxy-1-methyl-6a,7,10,10-tetramethyl-3,11-dioxo-1H- benzo[8,8a][1]benzopyrano[2,3-e]isoindole (940) (6a R, 7S, 9a S, 12 R*, 13a S)-12-chloro-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-13- dioxo-1H-benzo[8,8a][1]benzopyrano[2,3-e]isoindole (941) (6a R, 7S, 9a S, 12 R*, 13a S)-12-azido-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (942) (1R*, 6a R, 7S, 9a S, 12 S*, 13a S)-12-benzoylamino-11-cyanoimino-2, 3, 6, 6a, 7, 8, 9, 9a, 10, 11, 12, 13-dodecahydro-1,5-dihydroxy-6a,7,10,10-tetramethyl-3-oxo-1H- benzo [8,8a][1]benzopyrano [2,3-e]isoindole (943) (1R*, 6a R, 7S, 9a S, 12 S*, 13a S)-2, 3, 6, 6a, 7, 8, 9, 9a, 10, 11, 12, 13- dodecahydro-5-hydroxy-11-methoxyimino-1-methyl-6a,7,10,10-tetramethyl-3-oxo-12- phenylsulfonyl-1H-benzo[8,8a][1]benzopyrano[2,3-e]isoindole (944) (6a R, 7S, 9a S, 12 R*, 13a S)-12-azido-2, 3, 6, 6a, 7, 8, 9, 9a, 10, 11, 12, 13- dodecahydro-5-hydroxy-6a,7,10,10-tetramethyl-3-oxo-11-ureidoimino-1H- benzo[8,8a][1]benzopyrano[2,3-e]isoindole (945) (6a R, 7S, 9a S, 12 R*, 13a S)-12-benzoyloxy-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-13- dioxo-1H-benzo[8,8a][1]benzopyrano[2,3-e]isoindole (946) (1R*, 6a R, 7S, 9a S, 12 S*, 13a S)-1-acetoxy-12-ethoxy-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (947) (6a R, 7S, 9a S, 12 R*, 13a S)-1 1-hydrazono-2, 3, 6, 6a, 7, 8, 9, 9a, 10, 11, 12, 13-dodecahydro-5-hydroxy-6a,7,10,10-tetramethyl-3-oxo-12-phenylsulfonyl-1H-benzo[8,8a][1]benzopyrano[2,3-e]isoindole (948) (1R*, 6a R, 7S, 9a S, 12 S*, 13a S)-12-carbamoyloxy-2, 3, 6, 6a, 7, 8, 9, 9a, 10, 11, 12, 13-dodecahydro-5-hydroxy-11-hydroxyimino-1-methyl-6a,7,10,10-tetramethyl-3-oxo- 1H-benzo[8,8a][1]benzopyrano[2,3-e]isoindole (949) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-3-oxo-12-(3-pyridyl)carbonyloxy-11-ureidoimino-1H- benzo[8,8a][1]benzopyrano[2,3-e]isoindole (950) (6a R, 7S, 9a S, 12 R*, 13a S)-12-acetoxy-2, 3, 6, 6a, 7, 8, 9, 9a, 10, 11, 12, 13- dodecahydro-5-hydroxy-6a,7,10,10-tetramethyl-3,11-dioxo-1H- benzo[8,8a][1]benzopyrano[2,3-e]isoindole (951) (1R*, 6a R, 7S, 9a S, 12 S*, 13a S)-12-benzyloxy-2, 3, 6, 6a, 7, 8, 9, 9a, 10, 11, 12, 13-dodecahydro-5-hydroxy-11-methoxyimino-11-methyl-6a,7,10,10-tetramethyl-3-oxo-1H- benzo[8,8a][1]benzopyrano[2,3-e]isoindole (952) (1R*, 6a R, 7S, 9a S, 12 S*, 13a S)-2, 3, 6, 6a, 7, 8, 9, 9a, 10, 11, 12, 13- dodecahydro-5-hydroxy-11-hydroxyimino-1-methyl-6a,7,10,10-tetramethyl-3-oxo-12- phenylsulfonylamino-1H-benzo[8,8a][1]benzopyrano[2,3-e]isoindole (953) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-12-methylsulfinyl-3-oxo-1H- benzo[8,8a][1]benzopyrano[2,3-e]isoindole (954) (1R*, 6a R, 7S, 9a S, 12 S*, 13a S)-1-acetoxy-12-carboxymethyloxy-2, 3, 6, 6a, 7, 8, 9, 9a, 10, 11, 12, 13-dodecahydro-5-hydroxy-6a,7,10,10-tetramethyl-11-(1-oxa-4- azacyclohex-4-yl)imino-3-oxo-1H-benzo[8,8a][1]benzopyrano[2,3-e]isoindole (955) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-11-(1-oxa-4-azacyclohex-4-yl)imino-3-oxo-12- phenylsulfinyl-1H-benzo[8,8a][1]benzopyrano[2,3-e]isoindole (956) (6a R, 7S, 9a S, 12 R*, 13a S)-5,12-dihydroxy-2, 3, 6, 6a, 7, 8, 9, 9a, 10, 11, 12, 13- dodecahydro-6a,7,10,10-tetramethyl-3,11-dioxo-1H-benzo[8,8a][1]benzopyrano[2,3- e]isoindole (957) (1R*, 6a R, 7S, 9a S, 12 S*, 13a S)-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-12-phenylsulfonyl-1H- benzo[8,8a][1]benzopyrano[2,3-e]isoindole (958) (1R*, 6a R, 7S, 9a S, 12 S*, 13a S)-11-cyanoimino-2, 3, 6, 6a, 7, 8, 9, 9a, 10, 11, 12, 13-dodecahydro-5-hydroxy- 12-methanesulfonyloxy- 1-methyl-6a,7,10,10-tetramethyl-3- oxo-1H-benzo[8,8a][1]benzopyrano[2,3-e]isoindole (959) (1R*, 6a R, 7S, 9a S, 12 S*, 13a S)-1-acetoxy-12-amino-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (960) (1R*, 6a R, 7S, 9a S, 12 S*, 13a S)-12-benzyloxy-2, 3, 6, 6a, 7, 8, 9, 9a, 10, 11, 12, 13-dodecahydro-5-hydroxy-11-hydroxyimino-1-methyl-6a,7,10,10-tetramethyl-3-oxo-1H- benzo[8,8a][1]benzopyrano[2,3-e]isoindole (961) (1R*, 6a R, 7S, 9a S, 12 S*, 13a S)-11-hydrazono-2, 3, 6, 6a, 7, 8, 9, 9a, 10, 11, 12, 13-dodecahydro-1,5-dihydroxy-6a,7,10,10-tetramethyl-3-oxo-12-phenylsulfinyl-1H- benzo[8,8a][1]benzopyrano[2,3-e]isoindole (962) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-3,11-dioxo-12-phenylsulfonyl-1H- benzo[8,8a][1]benzopyrano[2,3-e]isoindole (963) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7, 10,10-tetramethyl-3-oxo-12-phenylsulfinyl-11-ureidoimino-1H-benzo[8,8a][1]benzopyrano[2,3-e]isoindole (964) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-11-(-oxa-4-azacyclohex-4-yl)imino-3-oxo-12-phenoxy- 1H-benzo[8,8a][1]benzopyrano[2,3-e]isoindole (965) (6a R, 7S, 9a S, 12 R*, 13a S)-12-carbamoyloxy-2, 3, 6, 6a, 7, 8, 9, 9a, 10, 11, 12, 13-dodecahydro-5-hydroxy-11-methoxyimino-6a,7,10,10-tetramethyl-13-dioxo-1H-benzo[8,8a][1]benzopyrano[2,3-e]isoindole (966) (6a R, 7S, 9a S, 12 R*, 13a S)-11-hydrazono-2, 3, 6, 6a, 7, 8, 9, 9a, 10, 11, 12, 13- dodecahydro-5-hydroxy-12-methanesulfonylamino-6a,7,10,10-tetramethyl-3-oxo-1H- benzo[8,8a][1]benzopyrano[2,3-e]isoindole (967) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-12-methylthio-3-oxo-11-ureidoimino-1H-benzo[8,8a][1]benzopyrano[2,3-e]isoindole (968) (1R*, 6a R, 7S, 9a S, 12 S*, 13a S)-1-acetoxy-12-benzoylamino-2, 3, 6, 6a, 7, 8, 9, 9a, 10, 11, 12, 13-dodecahydro-5-hydroxy-6a,7,10,10-tetramethyl-3-oxo-11-ureidoimino-1H- benzo[8,8a][1]benzopyrano[2,3-e]isoindole (969) (6a R, 7S, 9a S, 12 R*, 13a S)-2, 3, 6, 6a, 7, 8, 9, 9a, 10, 11, 12, 13-dodecahydro-5- hydroxy-12-methanesulfonyloxy-6a,7,10,10-tetramethyl-1,3,11-trioxo-1H- benzo[8,8a][1]benzopyrano[2,3-e]isoindole (970) (6a R, 7S, 9a S, 12 R*, 13a S)-12-acetylamino-11-hydrazono-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (971) (1R*, 6a R, 7S, 9a S, 12 S*, 13a S)-2, 3, 6, 6a, 7, 8, 9, 9a, 10, 11, 12, 13- dodecahydro-5,12-dihydroxy-1-methyl-6a,7,10,10-tetramethyl-3,11-dioxo-1H- benzo[8,8a][1]benzopyrano[2,3-e]isoindole (972) (6a R, 7S, 9a S, 12 R*, 13a S)-12-glycylamino-2, 3, 6, 6a, 7, 8, 9, 9a, 10, 11, 12, 13- dodecahydro-5-dihydroxyphosphinyloxy-6a,7,10,10-tetramethyl-3,11-dioxo-1H- benzo[8,8a][1]benzopyrano[2,3-e]isoindole (973) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-13-dioxo-12-(3-pyridyl)carbonyloxy- 1H-benzo[8,8a][1]benzopyrano[2,3-e]isoindole (974) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-3,11-dioxo-12-phenoxy-1H-benzo[8,8a][1]benzopyrano[2,3-e]isoindole (975) (1R*, 6a R, 7S, 9a S, 12 S*, 13a S)-1-acetoxy-12-amino-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (976) (1R*, 6a R, 7S, 9a S, 12 S*, 13a S)-2, 3, 6, 6a, 7, 8, 9, 9a, 10, 11, 12, 13- dodecahydro-1,5-dihydroxy-12-methanesulfonylamino-6a,7,10,10-tetramethyl-3,11-dioxo- 1H-benzo[8,8a][1]benzopyrano[2,3-e]isoindole (977) (6a R, 7S, 9a S, 12 R*, 13a S)-2, 3, 6, 6a, 7, 8, 9, 9a, 10, 11, 12, 13-dodecahydro-5- hydroxy-12-methoxy-6a,7,10,10-tetramethyl-13-dioxo-11-ureidoimino-1H- benzo[8,8a][1]benzopyrano[2,3-e]isoindole (978) (1R*, 6a R, 7S, 9a S, 12 S*, 13a S)-11-hydrazono-2, 3, 6, 6a, 7, 8, 9, 9a, 10, 11, 12, 13-dodecahydro-1,5-dihydroxy-6a,7,10,10-tetramethyl-3-oxo-12-phenylsulfonyloxy-1H- benzo[8,8a][1]benzopyrano[2,3-e]isoindole (979) (1R*, 6a R, 7S, 9a S, 12 S*, 13a S)-11-hydrazono-2, 3, 6, 6a, 7, 8, 9, 9a, 10, 11, 12, 13-dodecahydro-5-hydroxy-1-methyl-6a,7,10,10-tetramethyl-12-methylamino-3-oxo-1H- benzo[8,8a][1]benzopyrano[2,3-e]isoindole (980) (1R*, 6a R, 7S, 9a S, 12 S*, 13a S)-1-acetoxy-11-hydrazono-2, 3, 6, 6a, 7, 8, 9, 9a, 10, 11, 12, 13-dodecahydro-5-hydroxy-12-mercapto-6a,7,10,10-tetramethyl-3-oxo-1H- benzo[8,8a][1]benzopyrano[2,3-e]isoindole (981) (1R*, 6a R, 7S, 9a S, 12 S*, 13a S)-11-methoxyimino-2, 3, 6, 6a, 7, 8, 9, 9a, 10, 11, 12, 13-dodecahydro-1,5,12-trihydroxy-6a,7,10,10-tetramethyl-3-oxo-1H- benzo[8,8a][1]benzopyrano[2,3-e]isoindole (982) (1R*, 6a R, 7S, 9a S, 12 S*, 13a S)-2, 3, 6, 6a, 7, 8, 9, 9a, 10, 11, 12, 13- dodecahydro-1,5-dihydroxy-12-methanesulfonyloxy-6a,7,10,10-tetramethyl-3,11-dioxo-1H- benzo[8,8a][1]benzopyrano[2,3-e]isoindole (983) (6a R, 7S, 9a S, 12 R*, 13a S)-12-benzoylamino-2, 3, 6, 6a, 7, 8, 9, 9a, 10, 11, 12, 13- dodecahydro-5-dihydroxyphosphinyloxy-6a,7,10,10-tetramethyl-1,3,11-trioxo-1H- benzo[8,8a][1]benzopyrano[2,3-e]isoindole (984) (6a R, 7S, 9a S, 12 R*, 13a S)-12-acetoxy-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-13- dioxo-1H-benzo[8,8a][1]benzopyrano[2,3-e]isoindole (985) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-3,11-dioxo-12-(3-pyridyl)carbonyloxy-1H- benzo[8,8a][1]benzopyrano[2,3-e]isoindole (986) (1R*, 6a R, 7S, 9a S, 12 S*, 13a S)-2, 3, 6, 6a, 7, 8, 9, 9a, 10, 11, 12, 13- dodecahydro-1,5-dihydroxy-12-methanesulfonyloxy-6a,7,10,10-tetramethyl-3-oxo-11-ureidoimino-1H-benzo[8,8a][1]benzopyrano[2,3-e]isoindole (987) (6a R, 7S, 9a S, 12 R*, 13a S)-12-benzoylamino-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-13- dioxo-1H-benzo[8,8a][1]benzopyrano[2,3-e]isoindole (988) (6a R, 7S, 9a S, 12 R*, 13a S)-12-glycylamino-2, 3, 6, 6a, 7, 8, 9, 9a, 10, 11, 12, 13- dodecahydro-5-hydroxy-11-methoxyimino-6a,7,10,10-tetramethyl-3-oxo-1H-benzo[8,8a][1]benzopyrano[2,3-e]isoindole (989) (1R*, 6a R, 7S, 9a S, 12 S*, 13a S)-1-acetoxy-12-benzyloxycarbonylamino-11- hydrazono-2, 3, 6, 6a, 7, 8, 9, 9a, 10, 11, 12, 13-dodecahydro-5-hydroxy-6a,7,10,10-tetramethyl-3-oxo-1H-benzo[8,8a][1]benzopyrano[2,3-e]isoindole (990) (6a R, 7S, 9a S, 12 R*, 13a S)-12-glycylamino-2, 3, 6, 6a, 7, 8, 9, 9a, 10, 11, 12, 13- dodecahydro-5-hydroxy-11-methoxyimino-6a,7,10,10-tetramethyl-13-dioxo-1H-benzo[8,8a][1]benzopyrano[2,3-e]isoindole (991) (6a R, 7S, 9a S, 12 R*, 13a S)-11-cyanoimino-12-ethoxy-2,3, 6, 6a, 7,8,9, 9a, 10, 11, 12, 13-dodecahydro-5-hydroxy-6a,7,10,10-tetramethyl-3-oxo-1H- benzo[8,8a][1]benzopyrano[2,3-e]isoindole (992) (6a R, 7S, 9a S, 12 R*, 13a S)-2, 3, 6, 6a, 7, 8, 9, 9a, 10, 11, 12, 13-dodecahydro-5- hydroxy-12-methanesulfonyloxy-6a,7,10,10-tetramethyl-11-(1-oxa-4-azacyclohex-4- yl)imino-13-dioxo-1H-benzo[8,8a][1]benzopyrano[2,3-e]isoindole (993) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-13-dioxo-12-phenylsulfinyl-1H- benzo[8,8a][1]benzopyrano[2,3-e]isoindole (994) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-13-dioxo-12-(3-pyridyl)carbonyloxy-1H- benzo[8,8a][1]benzopyrano[2,3-e]isoindole (995) (1R*, 6a R, 7S, 9a S, 12 S*, 13a S)-11-cyanoimino-2, 3, 6, 6a, 7, 8, 9, 9a, 10, 11, 12, 13-dodecahydro-1,5-dihydroxy-12-methanesulfonyloxy-6a,7,10,10-tetramethyl-3-oxo-1H- benzo[8,8a][1]benzopyrano[2,3-e]isoindole (996) (1R*, 6a R, 7S, 9a S, 12 S*, 13a S)-12-chloro-2, 3, 6, 6a, 7, 8, 9, 9a, 10, 11, 12, 13- dodecahydro-1,5-dihydroxy-6a,7,10,10-tetramethyl-3-oxo-11-ureidoimino-1H- benzo[8,8a][1]benzopyrano[2,3-e]isoindole (997) (1R*, 6a R, 7S, 9a S, 12 S*, 13a S)-12-amino-2, 3, 6, 6a, 7, 8, 9, 9a, 10, 11, 12, 13- dodecahydro-1,5-dihydroxy-6a,7,10,10-tetramethyl-3,11-dioxo-1H- benzo[8,8a][1]benzopyrano[2,3-e]isoindole (998) (1R*, 6a R, 7S, 9a S, 12 S*, 13a S)-11-cyanoimino-2, 3, 6, 6a, 7, 8, 9, 9a, 10, 11, 12, 13-dodecahydro-5-hydroxy-1-methyl-6a,7,10,10-tetramethyl-12-methylthio-3-oxo-1H- benzo[8,8a][1]benzopyrano[2,3-e]isoindole (999) (6a R, 7S, 9a S, 12 R*, 13a S)-12-ethoxy-2, 3, 6, 6a, 7, 8, 9, 9a, 10, 11, 12, 13- dodecahydro-5-hydroxy-6a,7,10,10-tetramethyl-11-(1-oxa-4-azacyclohex-4-yl)imino-3-oxo- 1H-benzo[8,8a][1]benzopyrano[2,3-e]isoindole (1000) (6a R, 7S, 9a S, 12 R*, 13a S)-12-benzoyloxy-11-hydrazono-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (1001) (1R*, 6a R, 7S, 9a S, 12 S*, 13a S)-12-carboxymethyloxy-11-hydrazono-2, 3, 6, 6a, 7, 8, 9, 9a, 10, 11, 12, 13-dodecahydro-5-hydroxy-1-methyl-6a,7,10,10-tetramethyl-3-oxo- 1H-benzo[8,8a][1]benzopyrano[2,3-e]isoindole (1002) (6a R, 7S, 9a S, 12 R*, 13a S)-12-chloro-2, 3, 6, 6a, 7, 8, 9, 9a, 10, 11, 12, 13- dodecahydro-5-hydroxy-6a,7,10,10-tetramethyl-11 -(1-oxa-4-azacyclohex-4-yl)imino-3-oxo- 1H-benzo[8,8a][1]benzopyrano[2,3-e]isoindole (1003) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-12-methylthio-11-(1-oxa-4- azacyclohex-4-yl)imino-3-oxo-1H-benzo[8,8a][1]benzopyrano[2,3-e]isoindole (1004) (6a R, 7S, 9a S, 12 R*, 13a S)-12-bromo-2, 3, 6, 6a, 7, 8, 9, 9a, 10, 11, 12, 13- dodecahydro-5-hydroxy-11-hydroxyimino-6a,7,10,10-tetramethyl-3-oxo-1H- benzo[8,8a][1]benzopyrano[2,3-e]isoindole (1005) (1R*, 6a R, 7S, 9a S, 12 S*, 13a S)-12-acetylamino-2, 3, 6, 6a, 7, 8, 9, 9a, 10, 11, 12, 13-dodecahydro-1,5-dihydroxy-6a,7,10,10-tetramethyl-11-(1-oxa-4-azacyclohex-4- yl)imino-3-oxo-1H-benzo[8,8a][1]benzopyrano[2,3-e]isoindole (1006) (1R*, 6a R, 7S, 9a S, 12 S*, 13a S)-1-acetoxy-11-cyanoimino-2, 3, 6, 6a, 7, 8, 9, 9a, 10, 11, 12, 13-dodecahydro-5-hydroxy-6a,7,10,10-tetramethyl-12-methylamino-3-oxo-1H- benzo[8,8a][1]benzopyrano[2,3-e]isoindole (1007) (6a R, 7S, 9a S, 12 R*, 13a S)-12-carbamoyloxy-2, 3, 6, 6a, 7, 8, 9, 9a, 10, 11, 12, 13-dodecahydro-5-hydroxy-11-hydroxyimino-6a,7,10,10-tetramethyl-13-dioxo-1H- benzo[8,8a][1]benzopyrano[2,3-e]isoindole (1008) (1R*, 6a R, 7S, 9a S, 12 S*, 13a S)-12-carbamoyloxy-2, 3, 6, 6a, 7, 8, 9, 9a, 10, 11, 12, 13-dodecahydro-5-hydroxy-1-methyl-6a,7,10,10-

(1009) (1R*, 6a R, 7S, 9a S, 12 S*, 13a S)-12-benzyloxycarbonylamino-11-cyanoimino-2, 3, 6, 6a, 7, 8, 9, 9a, 10, 11, 12, 13-dodecahydro-5-hydroxy-1-methyl-6a,7,10,10-tetramethyl- 3-oxo-1H-benzo[8,8a][1]benzopyrano[2,3-e]isoindole (1010) (1R*, 6a R, 7S, 9a S, 12 S*, 13a S)-1-acetoxy-12-acetylamino-2, 3, 6, 6a, 7, 8, 9, 9a, 10, 11, 12, 13-dodecahydro-5-hydroxy-11-methoxyimino-6a,7,10,10-tetramethyl-3-oxo-1H- benzo[8,8a][1]benzopyrano[2,3-e]isoindole (1011) (1R*, 6a R, 7S, 9a S, 12 S*, 13a S)-12-acetoxy-2, 3, 6, 6a, 7, 8, 9, 9a, 10, 11, 12, 13- dodecahydro-5-hydroxy-11-hydroxyimino-1-methyl-6a,7,10,10-tetramethyl-3-oxo-1H- benzo[8,8a][1]benzopyrano[2,3-e]isoindole (1012) (6a R, 7S, 9a S, 12 R*, 13a S)-2, 3, 6, 6a, 7, 8, 9, 9a, 10, 11, 12, 13-dodecahydro-5- hydroxy-imino-12-methanesulfonylamino-6a,7,10,10-tetramethyl-13-dioxo-1H- benzo[8,8a][1]benzopyrano[2,3-e]isoindole (1013) (1R*, 6a R, 7S, 9a S, 12 S*, 13a S)-2, 3, 6, 6a, 7, 8, 9, 9a, 10, 11, 12, 13- dodecahydro-5-hydroxy-1-methyl-6a,7,10,10-tetramethyl-3,11-dioxo-12-(3- pyridyl)carbonyloxy-1H-benzo[8,8a][1]benzopyrano[2,3-e]isoindole (1014) (1R*, 6a R, 7S, 9a S, 12 S*, 13a S)-12-amino-2, 3, 6, 6a, 7, 8, 9, 9a, 10, 11, 12, 13- dodecahydro-1,5-dihydroxy-6a,7,10,10-tetramethyl-11-(1-oxa-4-azacyclohex-4-yl)imino-3- oxo-1H-benzo[8,8a][1]benzopyrano[2,3-e]isoindole (1015) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-3-oxo-12-(3-pyridyl)carbonyloxy-1H- benzo[8,8a][1]benzopyrano[2,3-e]isoindole (1016) (6a R, 7S, 9a S, 12 R*, 13a S)-12-glycylamino-2, 3, 6, 6a, 7, 8, 9, 9a, 10, 11, 12, 13- dodecahydro-5-hydroxy-11-hydroxyimino-6a,7,10,10-tetramethyl-13-dioxo-1H-benzo[8,8a][1]benzopyrano[2,3-e]isoindole (1017) (6a R, 7S, 9a S, 12 R*, 13a S)-12-ethoxy-2, 3, 6, 6a, 7, 8, 9, 9a, 10, 11, 12, 13- dodecahydro-5-hydroxy-11-methoxyimino-6a,7,10,10-tetramethyl-13-dioxo-1H-benzo[8,8a][1]benzopyrano[2,3-e]isoindole (1018) (1R*, 6a R, 7S, 9a S, 12 S*, 13a S)-11-cyanoimino-2, 3, 6, 6a, 7, 8, 9, 9a, 10, 11, 12, 13-dodecahydro-1,5-dihydroxy-6a,7,10,10-tetramethyl-3-oxo-12-phenylthio-1H- benzo[8,8a][1]benzopyrano[2,3-e]isoindole (1019) (1R*, 6a R, 7S, 9a S, 12 S*, 13a S)-12-benzoylamino-2, 3, 6, 6a, 7, 8, 9, 9a, 10, 11, 12, 13-dodecahydro-1,5-dihydroxy-11-methoxyimino-6a,7,10,10-tetramethyl-3-oxo-1H- benzo[8,8a][1]benzopyrano[2,3-e]isoindole (1020) (6a R, 7S, 9a S, 12 R*, 13a S)-12-bromo-11-hydrazono-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (1021) (6a R, 7S, 9a S, 12 R*, 13a S)-2, 3, 6, 6a, 7, 8, 9, 9a, 10, 11, 12, 13-dodecahydro-5- hydroxy-12-(2-hydroxy)ethoxy-6a,7,10,10-tetramethyl-11-(1-oxa-4-azacyclohex-4- yl)imino-3-oxo-1H-benzo[8,8a][1]benzopyrano[2,3-e]isoindole (1022) (1R*, 6a R, 7S, 9a S, 12 S*, 13a S)-1-acetoxy-2, 3, 6, 6a, 7, 8, 9, 9a, 10, 11, 12, 13- dodecahydro-5,12-dihydroxy-6a,7,10,10-tetramethyl-3,11-dioxo-1H- benzo[8,8a][1]benzopyrano[2,3-e]isoindole (1023) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-12-methylsulfinyl-13-dioxo-1H- benzo[8,8a][1]benzopyrano[2,3-e]isoindole (1024) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-11-(1-oxa-4-azacyclohex-4-yl)imino-3- oxo-12-(3-pyridyl)carbonyloxy-1H-benzo[8,8a][1]benzopyrano[2,3-e]isoindole (1025) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-3-oxo-12-phenylsulfinyl-1H- benzo[8,8a][1]benzopyrano[2,3-e]isoindole (1026) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-3-oxo-12-phenylsulfonylamino-11- ureidoimino-1H-benzo[8,8a][1]benzopyrano[2,3-e]isoindole (1027) (1R*, 6a R, 7S, 9a S, 12 S*, 13a S)-1-acetoxy-11-hydrazono-2, 3, 6, 6a, 7, 8, 9, 9a, 10, 11, 12, 13-dodecahydro-5-hydroxy-6a,7,10,10-tetramethyl-3-oxo-12-phenylsulfonyl- 1H-benzo[8,8a][1]benzopyrano[2,3-e]isoindole (1028) (6a R, 7S, 9a S, 12 R*, 13a S)-2, 3, 6, 6a, 7, 8, 9, 9a, 10, 11, 12, 13-dodecahydro-5- dihydroxyphosphinyloxy-12-mercapto-6a,7,10,10-tetramethyl-3,11-dioxo-1H- benzo[8,8a][1]benzopyrano[2,3-e]isoindole (1029) (1R*, 6a R, 7S, 9a S, 12 S*, 13a S)-12-bromo-2, 3, 6, 6a, 7, 8, 9, 9a, 10, 11, 12, 13- dodecahydro-5-hydroxy-1-methyl-6a,7,10,10-tetramethyl-11-(1-oxa-4-azacyclohex-4- yl)imino-3-oxo-1H-benzo[8,8a][1]benzopyrano[2,3-e]isoindole (1030) (1R*, 6a R, 7S, 9a S, 12 S*, 13a S)-12-benzoyloxy-2, 3, 6, 6a, 7, 8, 9, 9a, 10, 11, 12, 13-dodecahydro-1,5-dihydroxy-6a,7,10,10-tetramethyl-11-(1-oxa-4-azacyclohex-4- yl)imino-3-oxo-1H-benzo[8,8a][1]benzopyrano[2,3-e]isoindole (1031) (6a R, 7S, 9a S, 12 R*, 13a S)-11-cyanoimino-2, 3, 6, 6a, 7, 8, 9, 9a, 10, 11, 12, 13- dodecahydro-5-hydroxy-12-methanesulfonyloxy-6a,7,10,10-tetramethyl-13-dioxo-1H- benzo[8,8a][1]benzopyrano[2,3-e]isoindole (1032) (1R*, 6a R, 7S, 9a S, 12 S*, 13a S)-12-bromo-11-hydrazono-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (1033) (6a R, 7S, 9a S, 12 R*, 13a S)-2, 3, 6, 6a, 7, 8, 9, 9a, 10, 11, 12, 13-dodecahydro-5- hydroxy-12-methoxy-6a,7,10,10-tetramethyl-1,3,11-trioxo-1H- benzo[8,8a][1]benzopyrano[2,3-e]isoindole (1034) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-3,11-dioxo-12-phenoxy-1H- benzo[8,8a][1]benzopyrano[2,3-e]isoindole (1035) (1R*, 6a R, 7S, 9a S, 12 S*, 13a S)-12-glycylamino-11-hydrazono-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (1036) (6a R, 7S, 9a S, 12 R*, 13a S)-12-benzyloxycarbonylamino-2, 3, 6, 6a, 7, 8, 9, 9a, 10, 11, 12, 13-dodecahydro-5-hydroxy-11-methoxyimino-6a,7,10,10-tetramethyl-3-oxo-1H- benzo[8,8a][1]benzopyrano[2,3-e]isoindole (1037) (1R*, 6a R, 7S, 9a S, 12 S*, 13a S)-12-bromo-2, 3, 6, 6a, 7, 8, 9, 9a, 10, 11, 12, 13- dodecahydro-5-hydroxy-11-methoxyimino-1-methyl-6a,7,10,10-tetramethyl-3-oxo-1H- benzo[8,8a][1]benzopyrano[2,3-e]isoindole (1038) (1R*, 6a R, 7S, 9a S, 12 S*, 13a S)-12-chloro-11-hydrazono-2, 3, 6, 6a, 7, 8, 9, 9a, 10, 11, 12, (1039) (6a R, 7S, 9a S, 12 R*, 13a S)-2, 3, 6, 6a, 7, 8, 9, 9a, 10, 11, 12, 13-dodecahydro-5- hydroxy-11-methoxyimino-6a,7,10,10-tetramethyl-3-oxo-12-phenoxy-1H- benzo[8,8a][1]benzopyrano[2,3-e]isoindole (1040) (1R*, 6a R, 7S, 9a S, 12 S*, 13a S)-12-bromo-2, 3, 6, 6a, 7, 8, 9, 9a, 10, 11, 12, 13- dodecahydro-5-hydroxy-11-hydroxyimino-1-methyl-6a,7,10,10-tetramethyl-3-oxo-1H- benzo[8,8a][1]benzopyrano[2,3-e]isoindole (1041) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-methoxy-6a,7,10,10-tetramethyl-3-oxo-11-ureidoimino-1H- benzo[8,8a][1]benzopyrano[2,3-e]isoindole (1042) (1R*, 6a R, 7S, 9a S, 12 S*, 13a S)-12-acetoxy-11-cyanoimino-2, 3, 6, 6a, 7, 8, 9, 9a, 10, 11, 12, 13-dodecahydro-1,5-dihydroxy-6a,7,10,10-tetramethyl-3-oxo-1H- benzo[8,8a][1]benzopyrano[2,3-e]isoindole (1043) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-12-methylamino-1,3,11-trioxo-1H- benzo[8,8a][1]benzopyrano[2,3-e]isoindole (1044) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-12-methylthio-3,11-dioxo-1H-benzo[8,8a][1]benzopyrano[2,3-e]isoindole (1045) (1R*, 6a R, 7S, 9a S, 12 S*, 13a S)-12-glycylamino-2, 3, 6, 6a, 7, 8, 9, 9a, 10, 11, 12, 13-dodecahydro-1,5-dihydroxy-6a,7,10,10-tetramethyl-11-(1-oxa-4-azacyclohex-4- yl)imino-3-oxo-1H-benzo[8,8a][1]benzopyrano[2,3-e]isoindole (1046) (1R*, 6a R, 7S, 9a S, 12 S*, 13a S)-12-benzyloxycarbonylamino-2, 3, 6, 6a, 7, 8, 9, 9a, 10, 11, 12, 13-dodecahydro-5-hydroxy-1-methyl-6a,7,10,10-tetramethyl-3,11-dioxo-1H- benzo[8,8a][1]benzopyrano[2,3-e]isoindole (1047) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-12-mercapto-6a,7,10,10-tetramethyl-11-(1-oxa-4-azacyclohex-4- yl)imino-3-oxo-1H-benzo[8,8a][1]benzopyrano[2,3-e]isoindole (1048) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-13-dioxo-12-phenoxy-1H- benzo[8,8a][1]benzopyrano[2,3-e]isoindole (1049) (6a R, 7S, 9a S, 12 R*, 13a S)-12-ethoxy-2, 3, 6, 6a, 7, 8, 9, 9a, 10, 11, 12, 13- dodecahydro-5-hydroxy-6a,7,10,10-tetramethyl-13-dioxo-11-ureidoimino-1H- benzo[8,8a][1]benzopyrano[2,3-e]isoindole (1050) (6a R, 7S, 9a S, 12 R*, 13a S)-12-azido-2, 3, 6, 6a, 7, 8, 9, 9a, 10, 11, 12, 13- dodecahydro-5-hydroxy-6a,7,10,10-tetramethyl-3,11-dioxo-1H- benzo[8,8a][1]benzopyrano[2,3-e]isoindole (1051) (1R*, 6a R, 7S, 9a S, 12 S*, 13a S)-2, 3, 6, 6a, 7, 8, 9, 9a, 10, 11, 12, 13- dodecahydro-5,12-dihydroxy-1-methyl-6a,7,10,10-tetramethyl-11-(1-oxa-4-azacyclohex-4- yl)imino-3-oxo-1H-benzo[8,8a][1]benzopyrano[2,3-e]isoindole (1052) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-12-methylamino-13-dioxo-1H-benzo[8,8a][1]benzopyrano[2,3-e]isoindole (1053) (1R*, 6a R, 7S, 9a S, 12 S*, 13a S)-1-acetoxy-12-bromo-2, 3, 6, 6a, 7, 8, 9, 9a, 10, 11, 12, 13-dodecahydro-5-hydroxy-6a,7,10,10-tetramethyl-11-(1-oxa-4- azacyclohex-4- yl)imino-3-oxo-1H-benzo[8,8a][1]benzopyrano[2,3-e]isoindole (1054) (1R*, 6a R, 7S, 9a S, 12 S*, 13a S)-12-amino-2, 3, 6, 6a, 7, 8, 9, 9a, 10, 11, 12, 13- dodecahydro-1,5-dihydroxy-11-methoxyimino-6a,7,10,10-tetramethyl-3-oxo-1H- benzo[8,8a][1]benzopyrano[2,3-e]isoindole (1055) (1R*, 6a R, 7S, 9a S, 12 S*, 13a S)-12-benzoylamino-2, 3, 6, 6a, 7, 8, 9, 9a, 10, 11, 12, 13-dodecahydro-1,5-dihydroxy-11-hydroxyimino-6a,7,10,10-tetramethyl-3-oxo-1H- benzo[8,8a][1]benzopyrano[2,3-e]isoindole (1056) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-13-dioxo-12-phenoxy-11-ureidoimino-1H- benzo[8,8a][1]benzopyrano[2,3-e]isoindole (1057) (1R*, 6a R, 7S, 9a S, 12 S*, 13a S)-12-bromo-2, 3, 6, 6a, 7, 8, 9, 9a, 10, 11, 12, 13- dodecahydro-1,5-dihydroxy-6a,7,10,10-tetramethyl-3-oxo-11-ureidoimino-1H- benzo[8,8a][1]benzopyrano[2,3-e]isoindole (1058) (6a R, 7S, 9a S, 12 R*, 13a S)-12-chloro-2, 3, 6, 6a, 7, 8, 9, 9a, 10, 11, 12, 13- dodecahydro-5-hydroxy-11-methoxyimino-6a,7,10,10-tetramethyl-13-dioxo-1H- benzo[8,8a][1]benzopyrano[2,3-e]isoindole (1059) (1R*, 6a R, 7S, 9a S, 12 S*, 13a S)-1-acetoxy-11-hydrazono-2, 3, 6, 6a, 7, 8, 9, 9a, 10, 11, 12, 13-dodecahydro-5-hydroxy-12-(2-hydroxy)ethoxy-6a,7,10,10-tetramethyl-3- oxo-1H-benzo[8,8a][1]benzopyrano[2,3-e]isoindole (1060) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-hydroxyimino-6a,7,10,10-tetramethyl-3-oxo-12-(3-pyridyl)carbonyloxy-1H-benzo[8,8a][1]benzopyrano[2,3-e]isoindole (1061) (1R*, 6a R, 7S, 9a S, 12 S*, 13a S)-1-acetoxy-12-benzoyloxy-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (1062) (6a R, 7S, 9a S, 12 R*, 13a S)-12-benzoylamino-2, 3, 6, 6a, 7, 8, 9, 9a, 10, 11, 12, 13-dodecahydro-5-hydroxy-6a,7,10,10-tetramethyl-13-dioxo-11-ureidoimino-1H- benzo[8,8a][1]benzopyrano[2,3-e]isoindole (1063) (1R*, 6a R, 7S, 9a S, 12 S*, 13a S)-12-benzyloxycarbonylamino-2, 3, 6, 6a, 7, 8, 9, 9a, 10, 11, 12, 13-dodecahydro-1,5-dihydroxy-6a,7,10,10-tetramethyl-3-oxo-11- ureidoimino-1H-benzo[8,8a][1]benzopyrano[2,3-e]isoindole (1064) (6a R, 7S, 9a S, 12 R*, 13a S)-11-hydrazono-2, 3, 6, 6a, 7, 8, 9, 9a, 10, 11, 12, 13- dodecahydro-5,12-dihydroxy-6a,7,10,10-tetramethyl-3-oxo-1H- benzo[8,8a][1]benzopyrano[2,3-e]isoindole (1065) (1R*, 6a R, 7S, 9a S, 12 S*, 13a S)-11-hydrazono-2, 3, 6, 6a, 7, 8, 9, 9a, 10, 11, 12, 13-dodecahydro-1,5-dihydroxy-6a,7,10,10-tetramethyl-12-methylsulfinyl-3-oxo-1H- benzo[8,8a][1]benzopyrano[2,3-e]isoindole (1066) (1R*, 6a R, 7S, 9a S, 12 S*, 13a S)-1-acetoxy-12-azido-2, 3, 6, 6a, 7, 8, 9, 9a, 10, 11, 12, 13-dodecahydro-5-hydroxy-6a,7,10,10-tetramethyl-3-oxo-11-ureidoimino-1H- benzo[8,8a][1]benzopyrano[2,3-e]isoindole (1067) (6a R, 7S, 9a S, 12 R*, 13a S)-11-cyanoimino-2, 3, 6, 6a, 7, 8, 9, 9a, 10, 11, 12, 13- dodecahydro-5-hydroxy-6a,7,10,10-tetramethyl-13-dioxo-12-phenylsulfonyl-1H- benzo[8,8a][1]benzopyrano[2,3-e]isoindole (1068) (6a R, 7S, 9a S, 12 R*, 13a S)-11-cyanoimino-2, 3, 6, 6a, 7, 8, 9, 9a, 10, 11, 12, 13- dodecahydro-5-hydroxy- 6a,7,10,10-tetramethyl-3-oxo-12-phenylsulfonyl-1H-benzo[8,8a][1]benzopyrano[2,3-e]isoindole (1069) (6a R, 7S, 9a S, 12 R*, 13a S)-12-chloro-2, 3, 6, 6a, 7, 8, 9, 9a, 10, 11, 12, 13- dodecahydro-5-hydroxy-6a,7,10,10-tetramethyl-3-oxo-11-ureidoimino-1H- benzo[8,8a][1]benzopyrano[2,3-e]isoindole (1070) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-1,3,11-trioxo-12-phenylsulfinyl-1H- benzo[8,8a][1]benzopyrano[2,3-e]isoindole (1071) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-12-methylsulfinyl-3-oxo-1H-benzo[8,8a][1]benzopyrano[2,3-e]isoindole (1072) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-methoxyimino-6a,7,10,10-tetramethyl-3-oxo-12-phenylsulfonyloxy-1H-benzo[8,8a][1]benzopyrano[2,3-e]isoindole (1073) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-hydroxyimino-6a,7,10,10-tetramethyl-12-methylthio-3-oxo-1H- benzo[8,8a][1]benzopyrano[2,3-e]isoindole (1074) (6a R, 7S, 9a S, 12 R*, 13a S)-2, 3, 6, 6a, 7, 8, 9, 9a, 10, 11, 12, 13-dodecahydro-5- dihydroxyphosphinyloxy-6a,7,10,10-tetramethyl-12-methylsulfinyl-1,3,11-trioxo-1H- benzo[8,8a][1]benzopyrano[2,3-e]isoindole (1075) (6a R, 7S, 9a S, 12 R*, 13a S)-12-azido-2, 3, 6, 6a, 7, 8, 9, 9a, 10, 11, 12, 13- dodecahydro-5-hydroxy-6a,7,10,10-tetramethyl-1,3,11-trioxo-1H- benzo[8,8a][1]benzopyrano[2,3-e]isoindole (1076) (1R*, 6a R, 7S, 9a S, 12 S*, 13a S)-12-acetoxy-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (1077) (1R*, 6a R, 7S, 9a S, 12 S*, 13a S)-12-ethoxy-2, 3, 6, 6a, 7, 8, 9, 9a, 10, 11, 12, 13- dodecahydro-1,5-dihydroxy-6a,7,10,10-tetramethyl-3,11-dioxo-1H- benzo[8,8a][1]benzopyrano[2,3-e]isoindole (1078) (1R*, 6a R, 7S, 9a S, 12 S*, 13a S)-12-benzoyloxy-11-cyanoimino-2, 3, 6, 6a, 7, 8, 9, 9a, 10, 11, 12, 13-dodecahydro-5-hydroxy-1-methyl-6a,7,10,10-tetramethyl-3-oxo-1H- benzo[8,8a][1]benzopyrano[2,3-e]isoindole (1079) (1R*, 6a R, 7S, 9a S, 12 S*, 13a S)-1-acetoxy-12-benzoylamino-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (1080) (6a R, 7S, 9a S, 12 R*, 13a S)-12-acetoxy-11-cyanoimino-2, 3, 6, 6a, 7, 8, 9, 9a, 10, 11, 12, 13-dodecahydro-5-hydroxy-6a,7,10,10-tetramethyl-3-oxo-1H- benzo[8,8a][1]benzopyrano[2,3-e]isoindole (1081) (6a R, 7S, 9a S, 12 R*, 13a S)-11-hydroxyimino-2, 3, 6, 6a, 7, 8, 9, 9a, 10, 11, 12, 13-dodecahydro-5,12-dihydroxy-6a,7,10,10-tetramethyl-3-oxo-1H- benzo[8,8a][1]benzopyrano[2,3-e]isoindole (1082) (6a R, 7S, 9a S, 12 R*, 13a S)-11-cyanoimino-2, 3, 6, 6a, 7, 8, 9, 9a, 10, 11, 12, 13- dodecahydro-5,12-dihydroxy-6a,7,10,10-tetramethyl-3-oxo-1H- benzo[8,8a][1]benzopyrano[2,3-e]isoindole (1083) (1R*, 6a R, 7S, 9a S, 12 S*, 13a S)-1-acetoxy-12-benzyloxycarbonylamino-2, 3, 6, 6a, 7, 8, 9, 9a, 10, 11, 12, 13-dodecahydro-5-hydroxy-6a,7,10,10-tetramethyl-11-(1-oxa-4- azacyclohex-4-yl)imino-3-oxo-1H-benzo[8,8a][1]benzopyrano[2,3-e]isoindole (1084) (1R*, 6a R, 7S, 9a S, 12 S*, 13a S)-12-benzyloxycarbonylamino-2, 3, 6, 6a, 7, 8, 9, 9a, 10, 11, 12, 13-dodecahydro-1,5-dihydroxy-6a,7,10,10-tetramethyl-11-(1-oxa-4- azacyclohex-4-yl)imino-3-oxo-1H-benzo[8,8a][1]benzopyrano[2,3-e]isoindole (1085) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-12-methylsulfinyl-11-(1-oxa-4-azacyclohex-4-yl)imino-13- dioxo-1H-benzo[8,8a][1]benzopyrano[2,3-e]isoindole (1086) (6a R, 7S, 9a S, 12 R*, 13a S)-2, 3, 6, 6a, 7, 8, 9, 9a, 10, 11, 12, 13-dodecahydro-5- hydroxy-11-hydroxyimino-12-methanesulfonyloxy-6a,7,10,10-tetramethyl-3-oxo-1H- benzo[8,8a][1]benzopyrano[2,3-e]isoindole (1087) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-3-oxo-12-phenylsulfonyloxy-1H- benzo[8,8a][1]benzopyrano[2,3-e]isoindole (1088) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-3-oxo-12-phenylsulfonyloxy-11-ureidoimino-1H-benzo[8,8a][1]benzopyrano[2,3-e]isoindole (1089) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-methoxyimino-6a,7,10,10-tetramethyl-3-oxo-12-phenylsulfonylamino-1H-benzo[8,8a][1]benzopyrano[2,3-e]isoindole (1090) (6a R, 7S, 9a S, 12 R*, 13a S)-12-benzyloxycarbonylamino-11-hydrazono-2, 3, 6, 6a, 7, 8, 9, 9a, 10, 11, 12, 13-dodecahydro-5-hydroxy-6a,7,10,10-tetramethyl-13-dioxo-1H- benzo[8,8a][1]benzopyrano[2,3-e]isoindole (1091) (6a R, 7S, 9a S, 12 R*, 13a S)-12-benzoylamino-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (1092) (6a R, 7S, 9a S, 12 R*, 13a S)-12-bromo-2, 3, 6, 6a, 7, 8, 9, 9a, 10; 11, 12, 13- dodecahydro-5-hydroxy-6a,7,10,10-tetramethyl-1,3,11-trioxo-1H- benzo[8,8a][1]benzopyrano[2,3-e]isoindole (1093) (1R*, 6a R, 7S, 9a S, 12 S*, 13a S)-2, 3, 6, 6a, 7, 8, 9, 9a, 10, 11, 12, 13- dodecahydro-1,5-dihydroxy-11-methoxyimino-6a,7,10,10-tetramethyl-12-methylthio-3-oxo-1H-benzo[8,8a][1]benzopyrano[2,3-e]isoindole (1094) (6a R, 7S, 9a S, 12 R*, 13a S)-12-carboxymethyloxy-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (1095) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-3-oxo-12-phenylthio-11-ureidoimino-1H- benzo[8,8a][1]benzopyrano[2,3-e]isoindole (1096) (6a R, 7S, 9a S, 12 R*, 13a S)-12-acetylamino-2, 3, 6, 6a, 7, 8, 9, 9a,10, 11, 12, 13- dodecahydro-5-dihydroxyphosphinyloxy-6a,7,10,10-tetramethyl-1,3,11-trioxo-1H- benzo[8,8a][1]benzopyrano[2,3-e]isoindole (1097) (1R*, 6a R, 7S, 9a S, 12 S*, 13a S)-1-acetoxy-12-acetylamino-2, 3, 6, 6a, 7, 8, 9, 9a, 10, 11, 12, 13-dodecahydro-5-hydroxy-6a,7,10,10-tetramethyl-3-oxo-11-ureidoimino-1H- benzo[8,8a][1]benzopyrano[2,3-e]isoindole (1098) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-methoxyimino-6a,7,10,10-tetramethyl-12-methylamino-3-oxo- 1H-benzo[8,8a][1]benzopyrano[2,3-e]isoindole (1099) (6a R, 7S, 9a S, 12 R*, 13a S)-2, 3, 6, 6a, 7, 8, 9, 9a, 10, 11, 12, 13-dodecahydro-5- hydroxy-6a,7,10,10-tetramethyl-1,3,11-trioxo-12-phenylsulfonyl-1H- benzo[8,8a][1]benzopyrano[2,3-e]isoindole (1100) (1R*, 6a R, 7S, 9a S, 12 S*, 13a S)-1-acetoxy-12-benzoylamino-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (1101) (1R*, 6a R, 7S, 9a S, 12 S*, 13a S)-2, 3, 6, 6a, 7, 8, 9, 9a, 10, 11, 12, 13- dodecahydro-1,5-dihydroxy-11-methoxyimino-6a,7,10,10-tetramethyl-3-oxo-12-(3-pyridyl)carbonyloxy-1H-benzo[8,8a][1]benzopyrano[2,3-e]isoindole (1102) (6a R, 7S, 9a S, 12 R*, 13a S)-2, 3, 6, 6a, 7, 8, 9, 9a, 10, 11, 12, 13-dodecahydro-5- hydroxy-11-hydroxyimino-6a,7,10,10-tetramethyl-12-methylthio-3-oxo-1H- benzo[8,8a][1]benzopyrano[2,3-e]isoindole (1103) (1R*, 6a R, 7S, 9a S, 12 S*, 13a S)-1-acetoxy-11-hydrazono-2, 3, 6, 6a, 7, 8, 9, 9a, 10, 11, 12, 13-dodecahydro-5-hydroxy-6a,7,10,10-tetramethyl-12-methylamino-3-oxo-1H- benzo[8,8a][1]benzopyrano[2,3-e]isoindole (1104) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-12-methylthio-3-oxo-11-ureidoimino-1H- benzo[8,8a][1]benzopyrano[2,3-e]isoindole (1105) (1R*, 6a R, 7S, 9a S, 12 S*, 13a S)-2, 3, 6, 6a, 7, 8, 9, 9a, 10, 11, 12, 13- dodecahydro-1,5-dihydroxy-6a,7,10,10-tetramethyl-3,11-dioxo-12-phenylthio-1H- benzo[8,8a][1]benzopyrano[2,3-e]isoindole (1106) (6a R, 7S, 9a S, 12 R*, 13a S)-11-hydrazono-2, 3, 6, 6a, 7, 8, 9, 9a, 10, 11, 12, 13- dodecahydro-5-hydroxy-6a,7,10,10-tetramethyl-12-methylthio-13-dioxo-1H-benzo[8,8a][1]benzopyrano[2,3-e]isoindole (1107) (1R*, 6a R, 7S, 9a S, 12 S*, 13a S)-1-acetoxy-12-azido-2, 3, 6, 6a, 7, 8, 9, 9a, 10, 11, 12, 13-dodecahydro-5-hydroxy-6a,7,10,10-tetramethyl-3,11-dioxo-1H- benzo[8,8a][1]benzopyrano[2,3-e]isoindole (1108) (1R*, 6a R, 7S, 9a S, 12 S*, 13a S)-1-acetoxy-11-cyanoimino-2, 3, 6, 6a, 7, 8, 9, 9a, 10, 11, 12, 13-dodecahydro-5-hydroxy-12-mercapto-6a,7,10,10-tetramethyl-3-oxo-1H- benzo[8,8a][1]benzopyrano[2,3-e]isoindole (1109) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-6a,7,10,10-tetramethyl-12-methylsulfinyl-3-oxo-11-ureidoimino- 1H-benzo[8,8a][1]benzopyrano[2,3-e]isoindole (1110) (1R*, 6a R, 7S, 9a S, 12 S*, 13a S)-1-acetoxy-2, 3, 6, 6a, 7, 8, 9, 9a, 10, 11, 12, 13- dodecahydro-5-hydroxy-11-hydroxyimino-6a,7,10,10-tetramethyl-12-methylsulfinyl-3-oxo- 1H-benzo[8,8a][1]benzopyrano[2,3-e]isoindole The biological activities of the compounds prepared in the Examples were tested as follows.

Test 1: Anti-Viral Activity

1) Anti-Viral Activity Against Influenza A Virus

Influenza A/WSN/33 strain was propagated in growing hen's eggs, and its infection titer was determined. MDBK cells (derived from bovine kidney) were put in each well on 96-well microtest tubes, and incubated overnight in 100 $\mu$l each of Eagle's Minimal Essential Medium (E-MEM) supplemented by 10% fetal bovine serum under 5% $CO_2$ at 37° C. Each of the samples to be tested was dissolved in dimethylsulfoxide, diluted appropriately with the above medium, and added to each of the above wells in 50 $\mu$l volume. Then, 50 $\mu$l of virus diluted with the above medium was added (multiplicity of infection=1) to the well, followed by incubation for 3 days under 5% $CO_2$ at 37° C. To each well was added 30 $\mu$l of a dimethylthiazolyldiphenyltetrazolium bromide (MTT) solution (5 mg/ml), followed by incubation for one hour at 37° C. The supernatant was discarded. After addition of 150 $\mu$l of 10% Triton X-100 isopropanol solution, the mixture was shaken for one hour. The inhibition of cytotoxic effect of the viral infection was then determined by measuring the amount of reduced MTT on the basis of the absorbance at 560 nm with reference to that at 690 nm, and expressed as $IC_{50}$ which is defined as the concentration of the compound capable of inhibiting the cytotoxicity of the virus by 50%.

2) Cytotoxicity Test

As in the measurement of anti-viral activity, samples were added to the cells, and incubated with 50 $\mu$l of culture medium instead of the viral dilution. The results are expressed as $CC_{50}$ which is defined as the concentration of the compound at which 50% of the cells are killed due to the toxicity of the compound. The results are shown in the following Table 14.

TABLE 14

Anti-viral activities against influenza A virus*

| Compound | $IC_{50}$ (mcg/ml) | $CC_{50}$ (mcg/ml) | Compound | $IC_{50}$ (mcg/ml) | $CC_{50}$ (mcg/ml) |
| --- | --- | --- | --- | --- | --- |
| (2) | 0.001 | 25 | (47c) | 0.01 | >10 |
| (28a) | 0.02 | 10–20 | (47d) | 0.003 | 5–10 |
| (28b) | 0.02 | 2.5 | (47e) | 0.025 | >10 |
| (28e) | 0.03 | >10 | (50a) | 0.004 | >40 |
| (28f) | 0.02 | >10 | (50b) | 0.01 | >10 |
| (30a) | 0.002 | >40 | (50c) | 0.05 | 5–10 |
| (30b) | 0.04 | 20 | (50d) | 0.0016 | >10 |
| (30c) | 0.04 | 20 | (50e) | 0.0016–0.0032 | >10 |
| (32a) | 0.001–0.002 | 20 | (50f) | 0.01 | 5 |
| (32b) | 0.04 | 10 | (51a) | 0.0016 | >10 |
| (32c) | 0.04–0.08 | 5 | (51b) | 0.003 | 5–10 |
| (34a) | 0.04 | >10 | (51d) | 0.005 | >10 |
| (35a) | 0.001 | 10 | (51f) | 0.05 | 25 |
| (35b) | 0.002–0.004 | 10 | (53a) | 0.04–0.08 | >10 |
| (13b) | 0.02 | 5 | (53b) | 0.08 | >10 |
| (13d) | 0.02–0.06 | 10 | (59a) | 0.001 | >10 |
| (41a) | 0.002 | 5 | (59b) | 0.001 | >10 |
| (42) | 0.002 | 5 | (64) | 0.001 | >10 |
| (43a) | 0.001–0.002 | 40 | (67a) | 0.016 | 6.3–12.5 |
| (47a) | 0.02 | >10 | (67b) | 0.032 | 25–50 |
| (47b) | 0.02 | >10 | (70) | 0.008 | 12.5–25 |

*viral strain: Influenza virus A/WSN/33 (H1N1); Cell: MDBK

3) Anti-Viral Activities Against Subtypes of Influenza A and B

In this experiment, the following viral strains were used: A/WSN/33; A/Kumamoto/5/67; A/Osaka/5/70; A/91N796 and B/91N759

MDCK cells (derived from dog kidney) were cultured on 12-well plates using E-MEM supplemented by 10% fetal bovine serum. To each well was added 250 $\mu$l each of a viral dilution prepared by 10-fold serial dilution with E-MEM, followed by incubation for one hour under 5% $CO_2$ at 37° C. After removal of the viral solution, one ml of E-MEM containing 0.8% agarose, 0.5% bovine serum albumin and 2 $\mu$g/ml trypsin, and an appropriately diluted test compound was added. The plate was inverted, and incubated for 3 days under 5% $CO_2$ at 37° C. The number of plaques formed was counted, and the $IC_{50}$ value, which is the concentration of the compound at which the number of plaques decreases by 50% compared to that of control which lacks the test compound, was determined. As in the above section 2), $CC_{50}$ values for MDCK cells were determined. The results are shown in the following Table 15.

TABLE 15

| Compound/virus | Anti-influenza virus activities *) | | | | | $CC_{50}$ (mcg/ml) |
| --- | --- | --- | --- | --- | --- | --- |
| | $IC_{50}$ (mcg/ml) | | | | | |
| | (1) | (2) | (3) | (4) | (5) | |
| SQ-02-S5(2) | 0.001–0.01 | 0.1–1 | 0.1–1 | 1 | 1 | 25 |
| SQ-02-S5-OX1(11) | 0.001–0.01 | 0.01–0.1 | 0.1–1 | 1 | 0.1 | 25–30 |
| SQ-02-S5-OX2(12) | 0.001–0.01 | 0.01–0.1 | 1–10 | 1 | 0.1–1 | 25–50 |

*) Cell: MDCK

Viral Strains:
(1): A/WSN/33 (H1N1)
(2): A/Kumamoto/5/67 (H2N2)
(3): A/Osaka/5/70 (H3N2)
(4): A/91N796 (H3N2)
(5): B/91N759

Industrial Applicability

The Compounds (I) of the present invention have anti-viral activity, especially against influenza A and B viruses, and are useful as pharmaceuticals. In addition, the method of the present invention can contribute to a development of novel compounds having anti-viral activity.

We claim:

1. A compound of the formula (I):

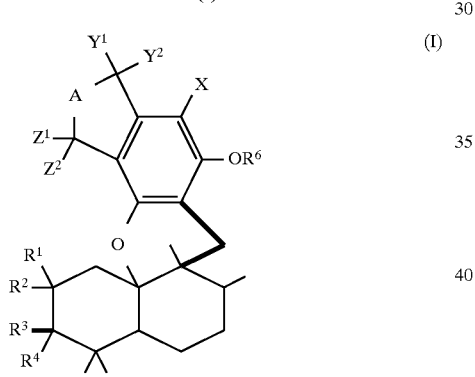

wherein $R^1$ is hydrogen; and $R^2$ is hydrogen, a halogen, azido, an optionally substituted lower alkyl, an optionally substituted lower alkylcarbonyl an optionally substituted arylcarbonyl, an optionally substituted heteroarylcarbonyl, —$OR^7$ (wherein $R^7$ is hydrogen, an optionally substituted lower alkyl, an optionally substituted lower alkylcarbonyl, an optionally substituted arylcarbonyl, an optionally substituted heteroarylcarbonyl, an optionally substituted lower alkylsulfonyl, an optionally substituted arylsulfonyl, an optionally substituted heteroarylsulfonyl, —$SO_3H$, an optionally substituted aryl, an optionally substituted aralkyl, a carbamoyl, or —$PO_3H_2$), $S(O)_nR^{13}$ (wherein $R^{13}$ is hydrogen, an optionally substituted lower alkyl, or an optionally substituted aryl, and n is 0, 1, or 2), or —$NHR^8$ (wherein $R^8$ is hydrogen, an optionally substituted lower alkyl, an optionally substituted lower alkylcarbonyl, an optionally substituted lower alkylsulfonyl, an optionally substituted arylcarbonyl an optionally substituted aralkyloxycarbonyl, an optionally substituted arylsulfonyl, an optionally substituted heteroarylsulfonyl, or an optionally substituted carbamoyl); or $R^1$ and $R^2$ taken together may form oxo or =$NR^9$ (wherein $R^9$ is hydroxy, a lower alkoxy, an optionally substituted aralkyl, an optionally substituted arylsulfonylamino, or —$NHCONH_2$);

$R^3$ is hydrogen; and $R^4$ is hydrogen, a halogen, —$OR^{10}$ (wherein $R^{10}$ is hydrogen, an optionally substituted lower alkyl, an optionally substituted lower alkylcarbonyl, an optionally substituted arylcarbonyl, an optionally substituted heteroarylcarbonyl, an optionally substituted lower alkylsulfonyl, an optionally substituted arylsulfonyl, an optionally substituted heteroarylsulfonyl, —$SO_3H$, or —$PO_3H_2$), $SR^{14}$ (wherein $R^{14}$ is hydrogen, an optionally substituted lower alkyl, or an optionally substituted aryl), or —$NHR^{11}$ (wherein $R^{11}$ is hydrogen, an optionally substituted lower alkyl, an optionally substituted lower alkylcarbonyl, an optionally substituted lower alkylsulfonyl, an optionally substituted arylsulfonyl, an optionally substituted heteroarylsulfonyl, or an optionally substituted carbamoyl); or $R^3$ and $R^4$ taken together may form oxo or =$NR^{12}$ (wherein $R^{12}$ is hydroxy, cyano, amino, an optionally substituted lower alkoxy, an optionally substituted aralkyl, an optionally substituted arylsulfonylamino, an optionally substituted aliphatic heterocyclic group, or —NHCONH);

or $R^2$ and $R^4$ taken together may form a single bond or —O—;

A is =$NR^5$ wherein $R^5$ is hydrogen, an optionally substituted lower alkyl, an optionally substituted lower alkylcarbonyl, an optionally substituted lower alkylsulfonyl or an optionally substituted arylsulfonyl;

$R^6$ is hydrogen, an optionally substituted lower alkyl, an optionally substituted lower alkylcarbonyl, or —$PO_3H_2$;

X is hydrogen or a halogen;

$Y^1$ and $Y^2$ are both hydrogens, or taken together may form oxo or an optionally substituted imino;

$Z^1$ and $Z^2$ are both hydrogens, or taken together may form oxo, or $Z^1$ is hydrogen and $Z^2$ is hydroxy, an optionally substituted lower alkyl, or an optionally substituted lower alkoxy, or a pharmaceutically acceptable salt or a hydrate thereof.

2. The compound of claim 1, wherein A is =NH.

3. The compound of claim 1, wherein $Y^1$ and $Y^2$ taken together may form oxo.

4. The compound of claim 1, wherein $Z^1$ and $Z^2$ are both hydrogens.

5. The compound of claim 1, wherein $R^1$ is hydrogen.

6. The compound of claim 1, wherein $R^3$ is hydrogen, and $R^4$ is $OR^{10}$ ($R^{10}$ is as defined above).

7. The compound of claim 1, wherein $R^3$ and $R^4$ taken together may form =$NR^{12}$ ($R^{12}$ is as defined above) or oxo.

8. The compound of claim 1, wherein $R^2$ is —$OR^7$ or —$NHR^8$ (wherein $R^7$ and $R^8$ are as defined above).

9. The compound of claim 1, wherein $Z^1$ is hydrogen, and $Z^2$ is hydroxy, an optionally substituted lower alkyl, or an optionally substituted lower alkoxy.

10. The compound of claim 1, wherein $R^6$ is hydrogen or —$PO_3H_2$.

11. The compound of claim 1, wherein A is NH; $R^1$, X, and $Z^1$ are both hydrogens; $R^2$ is —$OR^7$ or —$NHR^8$ ($R^7$ and $R^8$ are as defined above); $R^3$ and $R^4$ taken together may form oxo or =$NR^{12}$ ($R^{12}$ is as defined above); $R^6$ is hydrogen or —$PO_3H_2$; and $Y^1$ and $Y^2$ taken together may form oxo.

12. A pharmaceutical composition comprising a compound of claim 1 and a pharmaceutically acceptable carrier.

13. An antiviral agent comprising the compound of claim 1.

14. A process for preparing the compound of claim 1, which comprises cultivating in a medium a microorganism belonging to the Stachybotrys genus capable of producing a compound of claim 1, separating and purifying the compound produced from the resultant culture, and, if desired, chemically modifying the same.

* * * * *